United States Patent
Hunziker et al.

(10) Patent No.: US 11,446,156 B2
(45) Date of Patent: Sep. 20, 2022

(54) EXPANDABLE INTERVERTEBRAL IMPLANT, INSERTER INSTRUMENT, AND RELATED METHODS

(71) Applicant: Medos International Sarl, Le Locle (CH)

(72) Inventors: Markus Hunziker, Aargau (CH); Didier Gonzalez, Binnigen (CH)

(73) Assignee: Medos International Sarl

( * ) Notice: Subject to any disclaimer, the term of this patent is extended or adjusted under 35 U.S.C. 154(b) by 0 days.

(21) Appl. No.: 16/662,074

(22) Filed: Oct. 24, 2019

(65) Prior Publication Data
US 2020/0129307 A1    Apr. 30, 2020

Related U.S. Application Data

(60) Provisional application No. 62/751,501, filed on Oct. 26, 2018, provisional application No. 62/750,472, filed on Oct. 25, 2018.

(51) Int. Cl.
*A61F 2/44*    (2006.01)
*A61F 2/46*    (2006.01)
(Continued)

(52) U.S. Cl.
CPC ............ *A61F 2/4455* (2013.01); *A61F 2/447* (2013.01); *A61F 2/4611* (2013.01);
(Continued)

(58) Field of Classification Search
CPC .......... A61F 2/44; A61F 2/4455; A61F 2/557; A61F 2002/30579; A61F 2002/30405
See application file for complete search history.

(56) References Cited

U.S. PATENT DOCUMENTS 1,802,560 A    4/1931   Kerwin
1,924,695 A    8/1933   Olson
(Continued)

FOREIGN PATENT DOCUMENTS

AU    2006279558 A1    2/2007
AU    2005314079 B2    7/2012
(Continued)

OTHER PUBLICATIONS

POROCOAT(R) Porous Coating, 1 Page, https://emea.depuysynthese.com/hcp/hip/products/qs/porocoat-porous-coatingemea Accessed on Jul. 31, 2017.
(Continued)

*Primary Examiner* — Bruce E Snow
(74) *Attorney, Agent, or Firm* — BakerHostetler

(57) ABSTRACT

An expandable intervertebral implant includes a first endplate and a endplate, a first wedge member and a second wedge member spaced from the first wedge member that couple the first and second plates together. The first and second wedge members configured to move between a first collapsed position and a second expansion position. The implant includes an actuation member coupled to the first wedge member and the second wedge member. The first and second wedge members can be coupled to the upper and lower endplates at guide members that are asymmetric. An instrument can be coupled to the implant so as to provide a force to the actuation member that causes the wedge members to move between the collapsed position and the expansion position. The instrument can include a drive shaft and a toggle member that is configured to move the drive shaft between a first position whereby the drive shaft is configured to drive an attachment pin into the implant, and a second position whereby the drive shaft is aligned to drive the actuation member to rotate.

18 Claims, 26 Drawing Sheets

(51) Int. Cl.
*A61F 2/30* (2006.01)
*A61F 2/28* (2006.01)

(52) U.S. Cl.
CPC .......... *A61F 2002/2835* (2013.01); *A61F 2002/30266* (2013.01); *A61F 2002/30405* (2013.01); *A61F 2002/30579* (2013.01); *A61F 2002/4627* (2013.01); *A61F 2002/4629* (2013.01)

(56) References Cited

U.S. PATENT DOCUMENTS

| | | | |
|---|---|---|---|
| 1,965,653 A | 7/1934 | Kennedy |
| 2,077,804 A | 4/1937 | Gordon |
| 2,115,250 A | 4/1938 | Bruson |
| 2,121,193 A | 6/1938 | Gustav |
| 2,170,111 A | 8/1939 | Bruson |
| 2,173,655 A | 9/1939 | Neracher et al. |
| 2,229,024 A | 1/1941 | Bruson |
| 2,243,717 A | 5/1941 | Elias |
| 2,381,050 A | 8/1945 | Hardinge |
| 2,388,056 A | 10/1945 | Nathan |
| 2,485,531 A | 10/1949 | William et al. |
| 2,489,870 A | 11/1949 | Dzus |
| 2,570,465 A | 10/1951 | Lundholm |
| 2,677,369 A | 5/1954 | Knowles |
| 2,706,701 A | 4/1955 | Hans et al. |
| 2,710,277 A | 6/1955 | Shelanski et al. |
| 2,826,532 A | 3/1958 | Hosmer |
| 2,900,305 A | 8/1959 | Siggia |
| 2,977,315 A | 3/1961 | Scheib et al. |
| 3,091,237 A | 5/1963 | Skinner |
| 3,112,743 A | 12/1963 | Cochran et al. |
| 3,115,804 A | 12/1963 | Arthur |
| 3,228,828 A | 1/1966 | Romano |
| 3,312,139 A | 4/1967 | Di Cristina |
| 3,486,505 A | 12/1969 | Morrison |
| 3,489,143 A | 1/1970 | Halloran |
| 3,648,294 A | 3/1972 | Shahrestani |
| 3,698,391 A | 10/1972 | Mahony |
| 3,717,655 A | 2/1973 | Godefroi et al. |
| 3,760,802 A | 9/1973 | Fischer et al. |
| 3,800,788 A | 4/1974 | White |
| 3,805,775 A | 4/1974 | Fischer et al. |
| 3,811,449 A | 5/1974 | Gravlee et al. |
| 3,842,825 A | 10/1974 | Wagner |
| 3,848,601 A | 11/1974 | Ma et al. |
| 3,855,638 A | 12/1974 | Pilliar |
| 3,867,728 A | 2/1975 | Stubstad et al. |
| 3,875,595 A | 4/1975 | Froning |
| 3,889,665 A | 6/1975 | Ling et al. |
| 3,964,480 A | 6/1976 | Froning |
| 3,986,504 A | 10/1976 | Avila |
| 4,013,071 A | 3/1977 | Rosenberg |
| 4,052,988 A | 10/1977 | Doddi et al. |
| 4,091,806 A | 5/1978 | Aginsky |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,175,555 A | 11/1979 | Herbert |
| 4,205,399 A | 6/1980 | Jamiolkowski et al. |
| 4,236,512 A | 12/1980 | Aginsky |
| 4,249,435 A | 2/1981 | Smith et al. |
| 4,262,665 A | 4/1981 | Roalstad et al. |
| 4,262,676 A | 4/1981 | Jamshidi |
| 4,274,163 A | 6/1981 | Malcom et al. |
| 4,275,717 A | 6/1981 | Bolesky |
| 4,312,337 A | 1/1982 | Donohue |
| 4,312,353 A | 1/1982 | Shahbabian |
| 4,313,434 A | 2/1982 | Segal |
| 4,341,206 A | 7/1982 | Perrett et al. |
| 4,349,921 A | 9/1982 | Kuntz |
| 4,350,151 A | 9/1982 | Scott |
| 4,351,069 A | 9/1982 | Ballintyn et al. |
| 4,352,883 A | 10/1982 | Lim |
| 4,369,790 A | 1/1983 | McCarthy |
| 4,399,814 A | 8/1983 | Pratt et al. |
| 4,401,112 A | 8/1983 | Rezaian |
| 4,401,433 A | 8/1983 | Luther |
| 4,409,974 A | 10/1983 | Freedland |
| 4,440,921 A | 4/1984 | Allcock et al. |
| 4,449,532 A | 5/1984 | Storz |
| 4,451,256 A | 5/1984 | Weikl et al. |
| 4,456,005 A | 6/1984 | Lichty |
| 4,462,394 A | 7/1984 | Jacobs |
| 4,463,753 A | 8/1984 | Gustilo |
| 4,466,435 A | 8/1984 | Murray |
| 4,467,479 A | 8/1984 | Brody |
| 4,488,543 A | 12/1984 | Tornier |
| 4,488,549 A | 12/1984 | Lee et al. |
| 4,494,535 A | 1/1985 | Haig |
| 4,495,174 A | 1/1985 | Allcock et al. |
| 4,532,660 A | 8/1985 | Field |
| 4,537,185 A | 8/1985 | Stednitz |
| 4,538,612 A | 9/1985 | Patrick, Jr. |
| 4,542,539 A | 9/1985 | Rowe et al. |
| 4,545,374 A | 10/1985 | Jacobson |
| 4,562,598 A | 1/1986 | Kranz |
| 4,573,448 A | 3/1986 | Kambin |
| 4,595,006 A | 6/1986 | Burke et al. |
| 4,601,710 A | 7/1986 | Moll |
| 4,625,722 A | 12/1986 | Murray |
| 4,625,725 A | 12/1986 | Davison et al. |
| 4,627,434 A | 12/1986 | Murray |
| 4,628,945 A | 12/1986 | Johnson, Jr. |
| 4,629,450 A | 12/1986 | Suzuki et al. |
| 4,630,616 A | 12/1986 | Tretinyak |
| 4,632,101 A | 12/1986 | Freedland |
| 4,640,271 A | 2/1987 | Lower |
| 4,641,640 A | 2/1987 | Griggs |
| 4,645,503 A | 2/1987 | Lin et al. |
| 4,646,741 A | 3/1987 | Smith |
| 4,651,717 A | 3/1987 | Jakubczak |
| 4,653,489 A | 3/1987 | Tronzo |
| 4,665,906 A | 5/1987 | Jervis |
| 4,667,663 A | 5/1987 | Miyata |
| 4,686,973 A | 8/1987 | Frisch |
| 4,686,984 A | 8/1987 | Bonnet |
| 4,688,561 A | 8/1987 | Reese |
| 4,697,584 A | 10/1987 | Haynes |
| 4,706,670 A | 11/1987 | Andersen et al. |
| 4,714,469 A | 12/1987 | Kenna |
| 4,714,478 A | 12/1987 | Fischer |
| 4,721,103 A | 1/1988 | Freedland |
| 4,723,544 A | 2/1988 | Moore et al. |
| 4,743,256 A | 5/1988 | Brantigan |
| 4,743,257 A | 5/1988 | Toermaelae et al. |
| 4,759,766 A | 7/1988 | Buettner-Janz et al. |
| 4,760,843 A | 8/1988 | Fischer et al. |
| 4,772,287 A | 9/1988 | Ray et al. |
| 4,790,304 A | 12/1988 | Rosenberg |
| 4,790,817 A | 12/1988 | Luther |
| 4,796,612 A | 1/1989 | Reese |
| 4,802,479 A | 2/1989 | Haber et al. |
| 4,815,909 A | 3/1989 | Simons |
| 4,827,917 A | 5/1989 | Brumfield |
| 4,834,069 A | 5/1989 | Umeda |
| 4,834,757 A | 5/1989 | Brantigan |
| 4,838,282 A | 6/1989 | Strasser et al. |
| 4,858,601 A | 8/1989 | Glisson |
| 4,862,891 A | 9/1989 | Smith |
| 4,863,476 A | 9/1989 | Shepperd |
| 4,870,153 A | 9/1989 | Matzner et al. |
| 4,871,366 A | 10/1989 | Von et al. |
| 4,873,976 A | 10/1989 | Schreiber |
| 4,878,915 A | 11/1989 | Brantigan |
| 4,880,622 A | 11/1989 | Allcock et al. |
| 4,888,022 A | 12/1989 | Huebsch |
| 4,888,024 A | 12/1989 | Powlan |
| 4,889,119 A | 12/1989 | Jamiolkowski et al. |
| 4,892,550 A | 1/1990 | Huebsch |
| 4,896,662 A | 1/1990 | Noble |
| 4,898,186 A | 2/1990 | Ikada et al. |

(56) References Cited

U.S. PATENT DOCUMENTS

| | | |
|---|---|---|
| 4,898,577 A | 2/1990 | Badger et al. |
| 4,903,692 A | 2/1990 | Reese |
| 4,904,261 A | 2/1990 | Dove et al. |
| 4,911,718 A | 3/1990 | Lee et al. |
| 4,917,554 A | 4/1990 | Bronn |
| 4,932,969 A | 6/1990 | Frey et al. |
| 4,940,467 A | 7/1990 | Tronzo |
| 4,941,466 A | 7/1990 | Romano |
| 4,946,378 A | 8/1990 | Hirayama et al. |
| 4,959,064 A | 9/1990 | Engelhardt |
| 4,961,740 A | 10/1990 | Ray et al. |
| 4,963,144 A | 10/1990 | Huene |
| 4,966,587 A | 10/1990 | Baumgart |
| 4,968,317 A | 11/1990 | Toermaelae et al. |
| 4,969,888 A | 11/1990 | Scholten et al. |
| 4,978,334 A | 12/1990 | Toye et al. |
| 4,978,349 A | 12/1990 | Frigg |
| 4,981,482 A | 1/1991 | Ichikawa |
| 4,988,351 A | 1/1991 | Paulos et al. |
| 4,994,027 A | 2/1991 | Farrell |
| 4,995,200 A | 2/1991 | Eberhart |
| 5,002,557 A | 3/1991 | Hasson |
| 5,006,121 A | 4/1991 | Hafeli |
| 5,011,484 A | 4/1991 | Breard |
| 5,013,315 A | 5/1991 | Barrows |
| 5,013,316 A | 5/1991 | Goble et al. |
| 5,015,247 A | 5/1991 | Michelson |
| 5,015,255 A | 5/1991 | Kuslich |
| 5,019,082 A | 5/1991 | Frey et al. |
| 5,030,233 A | 7/1991 | Ducheyne |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,062,849 A | 11/1991 | Schelhas |
| 5,071,435 A | 12/1991 | Fuchs et al. |
| 5,071,437 A | 12/1991 | Arthurd |
| 5,080,662 A | 1/1992 | Paul |
| 5,084,043 A | 1/1992 | Hertzmann et al. |
| 5,092,891 A | 3/1992 | Kummer et al. |
| 5,098,241 A | 3/1992 | Aldridge et al. |
| 5,098,433 A | 3/1992 | Freedland |
| 5,098,435 A | 3/1992 | Stednitz et al. |
| 5,102,413 A | 4/1992 | Poddar |
| 5,108,404 A | 4/1992 | Scholten et al. |
| 5,114,407 A | 5/1992 | Burbank |
| 5,116,336 A | 5/1992 | Frigg |
| 5,120,171 A | 6/1992 | Lasner |
| 5,122,130 A | 6/1992 | Keller |
| 5,122,133 A | 6/1992 | Evans |
| 5,122,141 A | 6/1992 | Simpson et al. |
| 5,123,926 A | 6/1992 | Pisharodi |
| 5,133,719 A | 7/1992 | Winston |
| 5,133,755 A | 7/1992 | Brekke |
| 5,134,477 A | 7/1992 | Knauer et al. |
| 5,139,486 A | 8/1992 | Moss |
| 5,147,366 A | 9/1992 | Arroyo et al. |
| 5,158,543 A | 10/1992 | Lazarus |
| 5,163,939 A | 11/1992 | Winston |
| 5,163,989 A | 11/1992 | Campbell et al. |
| 5,167,663 A | 12/1992 | Brumfield |
| 5,167,664 A | 12/1992 | Hodorek |
| 5,169,400 A | 12/1992 | Muehling et al. |
| 5,169,402 A | 12/1992 | Elloy |
| 5,171,278 A | 12/1992 | Pisharodi |
| 5,171,279 A | 12/1992 | Mathews |
| 5,171,280 A | 12/1992 | Baumgartner |
| 5,176,651 A | 1/1993 | Allgood et al. |
| 5,176,683 A | 1/1993 | Kimsey et al. |
| 5,176,692 A | 1/1993 | Wilk et al. |
| 5,176,697 A | 1/1993 | Hasson et al. |
| 5,178,501 A | 1/1993 | Carstairs |
| 5,183,052 A | 2/1993 | Terwilliger |
| 5,183,464 A | 2/1993 | Dubrul |
| 5,188,118 A | 2/1993 | Terwilliger |
| 5,192,327 A | 3/1993 | Brantigan |
| 5,195,506 A | 3/1993 | Hulfish |
| 5,201,742 A | 4/1993 | Hasson |
| 5,217,462 A | 6/1993 | Asnis et al. |
| 5,217,475 A | 6/1993 | Kuber |
| 5,217,486 A | 6/1993 | Rice et al. |
| 5,224,952 A | 7/1993 | Deniega et al. |
| 5,228,441 A | 7/1993 | Lundquist |
| 5,234,431 A | 8/1993 | Keller |
| 5,241,972 A | 9/1993 | Bonati |
| 5,242,410 A | 9/1993 | Melker |
| 5,242,447 A | 9/1993 | Borzone |
| 5,242,448 A | 9/1993 | Pettine et al. |
| 5,242,879 A | 9/1993 | Abe et al. |
| 5,246,441 A | 9/1993 | Ross et al. |
| 5,250,049 A | 10/1993 | Michael |
| 5,250,061 A | 10/1993 | Michelson |
| 5,257,632 A | 11/1993 | Turkel et al. |
| 5,263,953 A | 11/1993 | Bagby |
| 5,269,797 A | 12/1993 | Bonati et al. |
| 5,280,782 A | 1/1994 | Wilk |
| 5,285,795 A | 2/1994 | Ryan et al. |
| 5,286,001 A | 2/1994 | Rafeld |
| 5,290,243 A | 3/1994 | Chodorow et al. |
| 5,290,312 A | 3/1994 | Kojimoto et al. |
| 5,300,074 A | 4/1994 | Frigg |
| 5,303,718 A | 4/1994 | Krajicek |
| 5,304,142 A | 4/1994 | Liebl et al. |
| 5,306,307 A | 4/1994 | Senter et al. |
| 5,306,308 A | 4/1994 | Gross et al. |
| 5,306,309 A | 4/1994 | Wagner et al. |
| 5,306,310 A | 4/1994 | Siebels |
| 5,308,327 A | 5/1994 | Heaven et al. |
| 5,308,352 A | 5/1994 | Koutrouvelis |
| 5,312,410 A | 5/1994 | Miller et al. |
| 5,312,417 A | 5/1994 | Wilk |
| 5,314,477 A | 5/1994 | Marnay |
| 5,320,644 A | 6/1994 | Baumgartner |
| 5,322,505 A | 6/1994 | Krause et al. |
| 5,324,261 A | 6/1994 | Amundson et al. |
| 5,330,429 A | 7/1994 | Noguchi et al. |
| 5,331,975 A | 7/1994 | Bonutti |
| 5,334,184 A | 8/1994 | Bimman |
| 5,334,204 A | 8/1994 | Clewett et al. |
| 5,342,365 A | 8/1994 | Waldman |
| 5,342,382 A | 8/1994 | Brinkerhoff et al. |
| 5,344,252 A | 9/1994 | Kakimoto |
| 5,361,752 A | 11/1994 | Moll et al. |
| 5,364,398 A | 11/1994 | Chapman et al. |
| 5,370,646 A | 12/1994 | Reese et al. |
| 5,370,647 A | 12/1994 | Graber et al. |
| 5,370,661 A | 12/1994 | Branch |
| 5,370,697 A | 12/1994 | Baumgartner |
| 5,372,660 A | 12/1994 | Davidson et al. |
| 5,374,267 A | 12/1994 | Siegal |
| 5,382,248 A | 1/1995 | Jacobson et al. |
| 5,383,932 A | 1/1995 | Wilson et al. |
| 5,385,151 A | 1/1995 | Scarfone et al. |
| 5,387,213 A | 2/1995 | Breard et al. |
| 5,387,215 A | 2/1995 | Fisher |
| 5,390,683 A | 2/1995 | Pisharodi |
| 5,395,317 A | 3/1995 | Kambin |
| 5,395,371 A | 3/1995 | Miller et al. |
| 5,397,364 A | 3/1995 | Kozak et al. |
| 5,401,269 A | 3/1995 | Buettner-Janz et al. |
| 5,407,430 A | 4/1995 | Peters |
| 5,410,016 A | 4/1995 | Hubbell et al. |
| 5,415,661 A | 5/1995 | Holmes |
| 5,423,816 A | 6/1995 | Lin |
| 5,423,817 A | 6/1995 | Lin |
| 5,423,850 A | 6/1995 | Berger |
| 5,424,773 A | 6/1995 | Saito |
| 5,425,773 A | 6/1995 | Boyd et al. |
| 5,431,658 A | 7/1995 | Moskovich |
| 5,441,538 A | 8/1995 | Bonutti |
| 5,443,514 A | 8/1995 | Steffee |
| 5,449,359 A | 9/1995 | Groiso |
| 5,449,361 A | 9/1995 | Preissman |
| 5,452,748 A | 9/1995 | Simmons et al. |

(56) References Cited

U.S. PATENT DOCUMENTS

| | | |
|---|---|---|
| 5,454,365 A | 10/1995 | Bonutti |
| 5,454,790 A | 10/1995 | Dubrul |
| 5,454,815 A | 10/1995 | Geisser et al. |
| 5,454,827 A | 10/1995 | Aust et al. |
| 5,456,686 A | 10/1995 | Klapper et al. |
| 5,458,641 A | 10/1995 | Ramirez Jimenez |
| 5,458,643 A | 10/1995 | Oka |
| 5,462,563 A | 10/1995 | Shearer et al. |
| 5,464,427 A | 11/1995 | Curtis et al. |
| 5,464,929 A | 11/1995 | Bezwada et al. |
| 5,468,245 A | 11/1995 | Vargas, III |
| 5,470,333 A | 11/1995 | Ray |
| 5,472,426 A | 12/1995 | Bonati et al. |
| 5,474,539 A | 12/1995 | Costa et al. |
| 5,480,400 A | 1/1996 | Berger |
| 5,484,437 A | 1/1996 | Michelson |
| 5,486,190 A | 1/1996 | Green |
| 5,496,318 A | 3/1996 | Howland et al. |
| 5,498,265 A | 3/1996 | Asnis et al. |
| 5,501,695 A | 3/1996 | Anspach et al. |
| 5,505,710 A | 4/1996 | Dorsey, III |
| 5,507,816 A | 4/1996 | Bullivant |
| 5,509,923 A | 4/1996 | Middleman et al. |
| 5,512,037 A | 4/1996 | Russell et al. |
| 5,514,143 A | 5/1996 | Bonutti et al. |
| 5,514,153 A | 5/1996 | Bonutti |
| 5,514,180 A | 5/1996 | Heggeness et al. |
| 5,520,690 A | 5/1996 | Errico et al. |
| 5,520,896 A | 5/1996 | De et al. |
| 5,522,398 A | 6/1996 | Goldenberg et al. |
| 5,522,790 A | 6/1996 | Moll et al. |
| 5,522,846 A | 6/1996 | Bonutti |
| 5,522,895 A | 6/1996 | Mikos |
| 5,522,899 A | 6/1996 | Michelson |
| 5,527,312 A | 6/1996 | Ray |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,534,029 A | 7/1996 | Shima |
| 5,534,030 A | 7/1996 | Navarro et al. |
| 5,536,127 A | 7/1996 | Pennig |
| 5,538,009 A | 7/1996 | Byrne et al. |
| 5,540,688 A | 7/1996 | Navas |
| 5,540,693 A | 7/1996 | Fisher |
| 5,540,711 A | 7/1996 | Kieturakis et al. |
| 5,545,164 A | 8/1996 | Howland |
| 5,545,222 A | 8/1996 | Bonutti |
| 5,549,610 A | 8/1996 | Russell et al. |
| 5,549,679 A | 8/1996 | Kuslich |
| 5,554,191 A | 9/1996 | Lahille et al. |
| 5,556,431 A | 9/1996 | Buttner-Janz |
| 5,558,674 A | 9/1996 | Heggeness et al. |
| D374,287 S | 10/1996 | Goble |
| 5,562,736 A | 10/1996 | Ray et al. |
| 5,562,738 A | 10/1996 | Boyd et al. |
| 5,564,926 A | 10/1996 | Per-Ingvar |
| 5,569,248 A | 10/1996 | Mathews |
| 5,569,251 A | 10/1996 | Baker et al. |
| 5,569,290 A | 10/1996 | McAfee |
| 5,569,548 A | 10/1996 | Koike et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,591,168 A | 1/1997 | Judet et al. |
| 5,593,409 A | 1/1997 | Michelson |
| 5,595,751 A | 1/1997 | Bezwada et al. |
| 5,597,579 A | 1/1997 | Bezwada et al. |
| 5,601,556 A | 2/1997 | Pisharodi |
| 5,601,561 A | 2/1997 | Terry et al. |
| 5,601,572 A | 2/1997 | Middleman et al. |
| 5,607,687 A | 3/1997 | Bezwada et al. |
| 5,609,634 A | 3/1997 | Voydeville |
| 5,609,635 A | 3/1997 | Michelson |
| 5,613,950 A | 3/1997 | Yoon |
| 5,618,142 A | 4/1997 | Sonden et al. |
| 5,618,314 A | 4/1997 | Harwin et al. |
| 5,618,552 A | 4/1997 | Bezwada et al. |
| 5,620,698 A | 4/1997 | Bezwada et al. |
| 5,624,447 A | 4/1997 | Myers |
| 5,626,613 A | 5/1997 | Schmieding |
| 5,628,751 A | 5/1997 | Sander et al. |
| 5,628,752 A | 5/1997 | Asnis et al. |
| 5,632,746 A | 5/1997 | Middleman et al. |
| 5,639,276 A | 6/1997 | Weinstock et al. |
| 5,643,320 A | 7/1997 | Lower et al. |
| 5,645,589 A | 7/1997 | Li |
| 5,645,596 A | 7/1997 | Kim et al. |
| 5,645,597 A | 7/1997 | Krapiva |
| 5,645,599 A | 7/1997 | Samani |
| 5,645,850 A | 7/1997 | Bezwada et al. |
| 5,647,857 A | 7/1997 | Anderson et al. |
| 5,648,088 A | 7/1997 | Bezwada et al. |
| 5,649,931 A | 7/1997 | Bryant et al. |
| 5,653,763 A | 8/1997 | Errico et al. |
| 5,658,335 A | 8/1997 | Allen |
| 5,662,683 A | 9/1997 | Kay |
| 5,665,095 A | 9/1997 | Jacobson et al. |
| 5,665,122 A | 9/1997 | Kambin |
| 5,667,508 A | 9/1997 | Errico et al. |
| 5,669,915 A | 9/1997 | Caspar et al. |
| 5,669,926 A | 9/1997 | Aust et al. |
| 5,674,294 A | 10/1997 | Bainville et al. |
| 5,674,295 A | 10/1997 | Ray et al. |
| 5,674,296 A | 10/1997 | Bryan et al. |
| 5,676,701 A | 10/1997 | Yuan et al. |
| 5,679,723 A | 10/1997 | Cooper et al. |
| 5,681,263 A | 10/1997 | Flesch |
| 5,683,465 A | 11/1997 | Shinn et al. |
| 5,693,100 A | 12/1997 | Pisharodi |
| 5,695,513 A | 12/1997 | Johnson et al. |
| 5,697,977 A | 12/1997 | Pisharodi |
| 5,698,213 A | 12/1997 | Jamiolkowski et al. |
| 5,700,239 A | 12/1997 | Yoon |
| 5,700,583 A | 12/1997 | Jamiolkowski et al. |
| 5,702,391 A | 12/1997 | Lin |
| 5,702,449 A | 12/1997 | McKay |
| 5,702,450 A | 12/1997 | Bisserie |
| 5,702,453 A | 12/1997 | Rabbe et al. |
| 5,702,454 A | 12/1997 | Baumgartner |
| 5,707,359 A | 1/1998 | Bufalini |
| 5,713,870 A | 2/1998 | Yoon |
| 5,713,903 A | 2/1998 | Sander et al. |
| 5,716,415 A | 2/1998 | Steffee |
| 5,716,416 A | 2/1998 | Lin |
| 5,720,753 A | 2/1998 | Sander et al. |
| 5,725,531 A | 3/1998 | Shapiro |
| 5,725,541 A | 3/1998 | Anspach et al. |
| 5,725,588 A | 3/1998 | Errico et al. |
| 5,728,097 A | 3/1998 | Mathews |
| 5,728,116 A | 3/1998 | Rosenman |
| 5,735,853 A | 4/1998 | Olerud |
| 5,741,253 A | 4/1998 | Michelson |
| 5,741,282 A | 4/1998 | Anspach et al. |
| 5,743,881 A | 4/1998 | Demco |
| 5,743,912 A | 4/1998 | Lahille et al. |
| 5,743,914 A | 4/1998 | Skiba |
| 5,749,879 A | 5/1998 | Middleman et al. |
| 5,749,889 A | 5/1998 | Bacich et al. |
| 5,752,969 A | 5/1998 | Cunci et al. |
| 5,755,797 A | 5/1998 | Baumgartner |
| 5,755,798 A | 5/1998 | Papavero et al. |
| 5,756,127 A | 5/1998 | Grisoni et al. |
| 5,762,500 A | 6/1998 | Lazarof |
| 5,762,629 A | 6/1998 | Kambin |
| 5,766,252 A | 6/1998 | Henry et al. |
| 5,772,661 A | 6/1998 | Michelson |
| 5,772,662 A | 6/1998 | Chapman et al. |
| 5,772,678 A | 6/1998 | Thomason et al. |
| 5,776,156 A | 7/1998 | Shikhman |
| 5,782,800 A | 7/1998 | Yoon |
| 5,782,832 A | 7/1998 | Larsen et al. |
| 5,782,865 A | 7/1998 | Grotz |

(56) References Cited

U.S. PATENT DOCUMENTS

| | | |
|---|---|---|
| 5,788,703 A | 8/1998 | Mittelmeier et al. |
| 5,792,044 A | 8/1998 | Foley et al. |
| 5,797,909 A | 8/1998 | Michelson |
| 5,800,549 A | 9/1998 | Bao |
| 5,807,275 A | 9/1998 | Jamshidi |
| 5,807,327 A | 9/1998 | Green et al. |
| 5,810,721 A | 9/1998 | Mueller et al. |
| 5,810,821 A | 9/1998 | Vandewalle |
| 5,810,866 A | 9/1998 | Yoon |
| 5,814,084 A | 9/1998 | Grivas et al. |
| 5,820,628 A | 10/1998 | Middleman et al. |
| 5,823,979 A | 10/1998 | Mezo |
| 5,824,084 A | 10/1998 | Muschler |
| 5,824,093 A | 10/1998 | Ray et al. |
| 5,824,094 A | 10/1998 | Serhan et al. |
| 5,827,289 A | 10/1998 | Reiley et al. |
| 5,833,657 A | 11/1998 | Reinhardt et al. |
| 5,836,948 A | 11/1998 | Zucherman et al. |
| 5,837,752 A | 11/1998 | Shastri et al. |
| 5,846,259 A | 12/1998 | Berthiaume |
| 5,848,986 A | 12/1998 | Lundquist et al. |
| 5,849,004 A | 12/1998 | Bramlet |
| 5,851,212 A | 12/1998 | Zirps et al. |
| 5,851,216 A | 12/1998 | Allen |
| 5,857,995 A | 1/1999 | Thomas et al. |
| 5,859,150 A | 1/1999 | Jamiolkowski et al. |
| 5,860,973 A | 1/1999 | Michelson |
| 5,860,977 A | 1/1999 | Zucherman et al. |
| 5,865,846 A | 2/1999 | Bryan et al. |
| 5,865,848 A | 2/1999 | Baker |
| 5,871,485 A | 2/1999 | Rao et al. |
| 5,873,854 A | 2/1999 | Wolvek |
| 5,876,404 A | 3/1999 | Zucherman et al. |
| 5,888,220 A | 3/1999 | Felt et al. |
| 5,888,221 A | 3/1999 | Gelbard |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,850 A | 4/1999 | Cachia |
| 5,893,889 A | 4/1999 | Harrington |
| 5,893,890 A | 4/1999 | Pisharodi |
| 5,895,428 A | 4/1999 | Berry |
| 5,902,231 A | 5/1999 | Foley et al. |
| 5,904,690 A | 5/1999 | Middleman et al. |
| 5,904,696 A | 5/1999 | Rosenman |
| 5,908,422 A | 6/1999 | Bresina |
| 5,916,228 A | 6/1999 | Ripich et al. |
| 5,916,267 A | 6/1999 | Prakit |
| 5,919,235 A | 7/1999 | Husson et al. |
| 5,925,056 A | 7/1999 | Thomas et al. |
| 5,925,074 A | 7/1999 | Gingras et al. |
| 5,928,235 A | 7/1999 | Friedl |
| 5,928,244 A | 7/1999 | Tovey et al. |
| 5,931,870 A | 8/1999 | Cuckler et al. |
| 5,935,129 A | 8/1999 | McDevitt et al. |
| 5,947,999 A | 9/1999 | Groiso |
| 5,948,000 A | 9/1999 | Larsen et al. |
| 5,954,635 A | 9/1999 | Foley et al. |
| 5,954,722 A | 9/1999 | Bono |
| 5,954,747 A | 9/1999 | Clark |
| 5,957,902 A | 9/1999 | Teves |
| 5,957,924 A | 9/1999 | Toermaelae et al. |
| 5,961,554 A | 10/1999 | Janson et al. |
| 5,964,730 A | 10/1999 | Williams et al. |
| 5,964,761 A | 10/1999 | Kambin |
| 5,967,783 A | 10/1999 | Ura |
| 5,967,970 A | 10/1999 | Cowan et al. |
| 5,968,044 A | 10/1999 | Nicholson et al. |
| 5,968,098 A | 10/1999 | Winslow |
| 5,972,015 A | 10/1999 | Scribner et al. |
| 5,972,385 A | 10/1999 | Liu et al. |
| 5,976,139 A | 11/1999 | Bramlet |
| 5,976,146 A | 11/1999 | Ogawa et al. |
| 5,976,186 A | 11/1999 | Bao |
| 5,976,187 A | 11/1999 | Richelsoph |
| 5,980,522 A | 11/1999 | Koros et al. |
| 5,984,927 A | 11/1999 | Wenstrom et al. |
| 5,984,966 A | 11/1999 | Kiema et al. |
| 5,985,307 A | 11/1999 | Hanson et al. |
| 5,989,255 A | 11/1999 | Pepper et al. |
| 5,989,291 A | 11/1999 | Ralph et al. |
| 5,993,459 A | 11/1999 | Larsen et al. |
| 5,997,510 A | 12/1999 | Schwemberger |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke |
| 6,007,519 A | 12/1999 | Rosselli |
| 6,007,566 A | 12/1999 | Wenstrom, Jr. |
| 6,007,580 A | 12/1999 | Lehto et al. |
| 6,010,508 A | 1/2000 | Bradley |
| 6,010,513 A | 1/2000 | Toermaelae et al. |
| 6,012,494 A | 1/2000 | Balazs |
| 6,015,410 A | 1/2000 | Toermaelae et al. |
| 6,015,436 A | 1/2000 | Helmut |
| 6,019,762 A | 2/2000 | Cole |
| 6,019,792 A | 2/2000 | Cauthen |
| 6,019,793 A | 2/2000 | Perren et al. |
| 6,022,350 A | 2/2000 | Ganem |
| 6,022,352 A | 2/2000 | Vandewalle |
| 6,030,162 A | 2/2000 | Huebner |
| 6,030,364 A | 2/2000 | Durgin et al. |
| 6,030,401 A | 2/2000 | Marino |
| 6,033,406 A | 3/2000 | Mathews |
| 6,033,412 A | 3/2000 | Losken et al. |
| 6,036,701 A | 3/2000 | Rosenman |
| 6,039,740 A | 3/2000 | Olerud |
| 6,039,761 A | 3/2000 | Li et al. |
| 6,039,763 A | 3/2000 | Shelokov |
| 6,045,552 A | 4/2000 | Zucherman et al. |
| 6,045,579 A | 4/2000 | Hochschuler et al. |
| 6,048,309 A | 4/2000 | Flom et al. |
| 6,048,342 A | 4/2000 | Zucherman et al. |
| 6,048,346 A | 4/2000 | Reiley et al. |
| 6,048,360 A | 4/2000 | Khosravi et al. |
| 6,049,026 A | 4/2000 | Muschler |
| 6,053,922 A | 4/2000 | Krause et al. |
| 6,053,935 A | 4/2000 | Brenneman et al. |
| 6,056,763 A | 5/2000 | Parsons |
| 6,063,121 A | 5/2000 | Xavier et al. |
| 6,066,142 A | 5/2000 | Serbousek et al. |
| 6,066,154 A | 5/2000 | Reiley et al. |
| 6,066,175 A | 5/2000 | Henderson et al. |
| 6,068,630 A | 5/2000 | Zucherman et al. |
| 6,068,648 A | 5/2000 | Cole et al. |
| 6,071,982 A | 6/2000 | Wise et al. |
| 6,073,051 A | 6/2000 | Sharkey et al. |
| 6,074,390 A | 6/2000 | Zucherman et al. |
| 6,080,155 A | 6/2000 | Michelson |
| 6,080,158 A | 6/2000 | Lin |
| 6,080,193 A | 6/2000 | Hochschuler et al. |
| 6,083,225 A | 7/2000 | Winslow et al. |
| 6,083,244 A | 7/2000 | Lubbers et al. |
| 6,090,112 A | 7/2000 | Zucherman et al. |
| 6,090,143 A | 7/2000 | Meriwether et al. |
| 6,096,038 A | 8/2000 | Michelson |
| 6,096,080 A | 8/2000 | Nicholson et al. |
| 6,099,531 A | 8/2000 | Bonutti |
| 6,102,914 A | 8/2000 | Bulstra et al. |
| 6,102,950 A | 8/2000 | Vaccaro |
| 6,106,557 A | 8/2000 | Robioneck et al. |
| 6,110,210 A | 8/2000 | Norton et al. |
| 6,113,624 A | 9/2000 | Bezwada et al. |
| 6,113,637 A | 9/2000 | Gill et al. |
| 6,113,638 A | 9/2000 | Williams et al. |
| 6,113,640 A | 9/2000 | Toermaelae et al. |
| 6,117,174 A | 9/2000 | Nolan |
| 6,119,044 A | 9/2000 | Kuzma |
| 6,120,508 A | 9/2000 | Gruenig et al. |
| 6,123,705 A | 9/2000 | Michelson |

(56) References Cited

U.S. PATENT DOCUMENTS

| | | |
|---|---|---|
| 6,123,711 A | 9/2000 | Winters |
| 6,126,660 A | 10/2000 | Dietz |
| 6,126,661 A | 10/2000 | Faccioli et al. |
| 6,126,663 A | 10/2000 | Hair |
| 6,126,686 A | 10/2000 | Badylak et al. |
| 6,126,689 A | 10/2000 | Brett |
| 6,127,597 A | 10/2000 | Beyar et al. |
| 6,129,762 A | 10/2000 | Li |
| 6,129,763 A | 10/2000 | Chauvin et al. |
| 6,132,435 A | 10/2000 | Young |
| 6,136,031 A | 10/2000 | Middleton |
| 6,139,558 A | 10/2000 | Wagner |
| 6,139,579 A | 10/2000 | Steffee et al. |
| 6,146,384 A | 11/2000 | Lee et al. |
| 6,146,387 A | 11/2000 | Trott et al. |
| 6,146,420 A | 11/2000 | McKay |
| 6,146,421 A | 11/2000 | Gordon et al. |
| 6,147,135 A | 11/2000 | Yuan et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,179 A | 12/2000 | Simonson |
| 6,159,211 A | 12/2000 | Boriani et al. |
| 6,159,244 A | 12/2000 | Suddaby |
| 6,161,350 A | 12/2000 | Espinosa |
| 6,162,234 A | 12/2000 | Freedland et al. |
| 6,162,236 A | 12/2000 | Osada |
| 6,162,252 A | 12/2000 | Kuras et al. |
| 6,165,218 A | 12/2000 | Husson et al. |
| 6,165,486 A | 12/2000 | Marra et al. |
| 6,168,595 B1 | 1/2001 | Durham et al. |
| 6,168,597 B1 | 1/2001 | Biedermann et al. |
| 6,171,610 B1 | 1/2001 | Vacanti et al. |
| 6,174,337 B1 | 1/2001 | Keenan |
| 6,175,758 B1 | 1/2001 | Kambin |
| 6,176,882 B1 | 1/2001 | Biedermann et al. |
| 6,179,794 B1 | 1/2001 | Burras |
| 6,179,873 B1 | 1/2001 | Zientek |
| 6,183,471 B1 | 2/2001 | Zucherman et al. |
| 6,183,472 B1 | 2/2001 | Lutz |
| 6,183,474 B1 | 2/2001 | Bramlet et al. |
| 6,183,517 B1 | 2/2001 | Suddaby |
| 6,187,043 B1 | 2/2001 | Ledergerber |
| 6,187,048 B1 | 2/2001 | Milner et al. |
| 6,190,387 B1 | 2/2001 | Zucherman et al. |
| 6,190,414 B1 | 2/2001 | Young et al. |
| 6,193,757 B1 | 2/2001 | Foley et al. |
| 6,197,033 B1 | 3/2001 | Haid et al. |
| 6,197,041 B1 | 3/2001 | Shichman et al. |
| 6,197,065 B1 | 3/2001 | Martin et al. |
| 6,197,325 B1 | 3/2001 | MacPhee et al. |
| 6,200,322 B1 | 3/2001 | Branch et al. |
| 6,203,565 B1 | 3/2001 | Bonutti et al. |
| 6,206,826 B1 | 3/2001 | Mathews et al. |
| 6,206,922 B1 | 3/2001 | Zdeblick et al. |
| D439,980 S | 4/2001 | Reiley et al. |
| 6,213,957 B1 | 4/2001 | Milliman et al. |
| 6,214,368 B1 | 4/2001 | Lee et al. |
| 6,217,509 B1 | 4/2001 | Foley et al. |
| 6,217,579 B1 | 4/2001 | Koros |
| 6,221,082 B1 | 4/2001 | Marino et al. |
| 6,224,603 B1 | 5/2001 | Marino |
| 6,224,631 B1 | 5/2001 | Kohrs |
| 6,224,894 B1 | 5/2001 | Jamiolkowski et al. |
| 6,228,058 B1 | 5/2001 | Dennis et al. |
| 6,231,606 B1 | 5/2001 | Graf et al. |
| 6,235,030 B1 | 5/2001 | Zucherman et al. |
| 6,235,043 B1 | 5/2001 | Reiley et al. |
| 6,238,397 B1 | 5/2001 | Zucherman et al. |
| 6,238,491 B1 | 5/2001 | Davidson et al. |
| 6,241,733 B1 | 6/2001 | Nicholson et al. |
| 6,241,734 B1 | 6/2001 | Scribner et al. |
| 6,241,769 B1 | 6/2001 | Nicholson et al. |
| 6,245,107 B1 | 6/2001 | Ferree |
| 6,248,108 B1 | 6/2001 | Toermaelae et al. |
| 6,248,110 B1 | 6/2001 | Reiley et al. |
| 6,248,131 B1 | 6/2001 | Felt et al. |
| 6,251,111 B1 | 6/2001 | Barker et al. |
| 6,251,140 B1 | 6/2001 | Marino et al. |
| 6,258,093 B1 | 7/2001 | Edwards et al. |
| 6,261,289 B1 | 7/2001 | Levy |
| 6,264,676 B1 | 7/2001 | Gellman et al. |
| 6,264,695 B1 | 7/2001 | Stoy |
| 6,267,763 B1 | 7/2001 | Castro |
| 6,267,765 B1 | 7/2001 | Taylor et al. |
| 6,267,767 B1 | 7/2001 | Strobel et al. |
| 6,277,149 B1 | 8/2001 | Boyle et al. |
| 6,280,444 B1 | 8/2001 | Zucherman et al. |
| 6,280,456 B1 | 8/2001 | Scribner et al. |
| 6,280,474 B1 | 8/2001 | Cassidy et al. |
| 6,280,475 B1 | 8/2001 | Bao |
| 6,287,313 B1 | 9/2001 | Sasso |
| 6,290,724 B1 | 9/2001 | Marino |
| 6,293,909 B1 | 9/2001 | Chu et al. |
| 6,293,952 B1 | 9/2001 | Brosens et al. |
| D449,691 S | 10/2001 | Reiley et al. |
| 6,296,644 B1 | 10/2001 | Saurat et al. |
| 6,296,647 B1 | 10/2001 | Robioneck et al. |
| 6,302,914 B1 | 10/2001 | Michelson |
| 6,306,136 B1 | 10/2001 | Baccelli |
| 6,306,177 B1 | 10/2001 | Felt et al. |
| D450,676 S | 11/2001 | Huttner |
| 6,312,443 B1 | 11/2001 | Stone |
| 6,319,254 B1 | 11/2001 | Giet et al. |
| 6,319,272 B1 | 11/2001 | Brenneman et al. |
| 6,331,312 B1 | 12/2001 | Lee et al. |
| 6,332,882 B1 | 12/2001 | Zucherman et al. |
| 6,332,883 B1 | 12/2001 | Zucherman et al. |
| 6,332,894 B1 | 12/2001 | Stalcup et al. |
| 6,332,895 B1 | 12/2001 | Suddaby |
| 6,342,074 B1 | 1/2002 | Simpson |
| 6,346,092 B1 | 2/2002 | Leschinsky |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,361,557 B1 | 3/2002 | Gittings et al. |
| 6,364,828 B1 | 4/2002 | Yeung et al. |
| 6,364,897 B1 | 4/2002 | Bonutti |
| 6,368,325 B1 | 4/2002 | McKinley et al. |
| 6,368,350 B1 | 4/2002 | Erickson et al. |
| 6,368,351 B1 | 4/2002 | Glenn et al. |
| 6,371,971 B1 | 4/2002 | Tsugita et al. |
| 6,371,989 B1 | 4/2002 | Chauvin et al. |
| 6,375,681 B1 | 4/2002 | Truscott |
| 6,375,682 B1 | 4/2002 | Fleischmann et al. |
| 6,375,683 B1 | 4/2002 | Crozet et al. |
| 6,379,355 B1 | 4/2002 | Zucherman et al. |
| 6,379,363 B1 | 4/2002 | Herrington et al. |
| 6,387,130 B1 | 5/2002 | Stone et al. |
| 6,398,793 B1 | 6/2002 | McGuire |
| 6,402,750 B1 | 6/2002 | Atkinson et al. |
| 6,409,766 B1 | 6/2002 | Brett |
| 6,409,767 B1 | 6/2002 | Perice et al. |
| 6,413,278 B1 | 7/2002 | Marchosky |
| 6,416,551 B1 | 7/2002 | Keller |
| 6,419,641 B1 | 7/2002 | Mark et al. |
| 6,419,676 B1 | 7/2002 | Zucherman et al. |
| 6,419,677 B2 | 7/2002 | Zucherman et al. |
| 6,419,704 B1 | 7/2002 | Ferree |
| 6,419,705 B1 | 7/2002 | Erickson |
| 6,419,706 B1 | 7/2002 | Graf |
| 6,423,061 B1 | 7/2002 | Bryant |
| 6,423,067 B1 | 7/2002 | Eisermann |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,425,920 B1 | 7/2002 | Hamada |
| 6,428,541 B1 | 8/2002 | Boyd et al. |
| 6,428,556 B1 | 8/2002 | Chin |
| 6,436,101 B1 | 8/2002 | Hamada |
| 6,436,140 B1 | 8/2002 | Liu et al. |

(56) References Cited

U.S. PATENT DOCUMENTS

| | | |
|---|---|---|
| 6,436,143 B1 | 8/2002 | Ross et al. |
| 6,440,138 B1 | 8/2002 | Reiley et al. |
| 6,440,154 B2 | 8/2002 | Gellman et al. |
| 6,440,169 B1 | 8/2002 | Elberg et al. |
| 6,443,989 B1 | 9/2002 | Jackson |
| 6,447,518 B1 | 9/2002 | Krause et al. |
| 6,447,527 B1 | 9/2002 | Thompson et al. |
| 6,447,540 B1 | 9/2002 | Fontaine et al. |
| 6,450,989 B2 | 9/2002 | Dubrul |
| 6,451,019 B1 | 9/2002 | Zucherman et al. |
| 6,451,020 B1 | 9/2002 | Zucherman et al. |
| 6,454,806 B1 | 9/2002 | Cohen et al. |
| 6,454,807 B1 | 9/2002 | Jackson |
| 6,458,134 B1 | 10/2002 | Songer et al. |
| 6,461,359 B1 | 10/2002 | Tribus et al. |
| 6,468,277 B1 | 10/2002 | Justin et al. |
| 6,468,279 B1 | 10/2002 | Reo |
| 6,468,309 B1 | 10/2002 | Lieberman |
| 6,468,310 B1 | 10/2002 | Ralph et al. |
| 6,471,724 B2 | 10/2002 | Zdeblick et al. |
| 6,475,226 B1 | 11/2002 | Belef et al. |
| 6,478,029 B1 | 11/2002 | Boyd et al. |
| 6,478,796 B2 | 11/2002 | Zucherman et al. |
| 6,478,805 B1 | 11/2002 | Marino et al. |
| 6,482,235 B1 | 11/2002 | Lambrecht et al. |
| 6,485,491 B1 | 11/2002 | Farris et al. |
| 6,485,518 B1 | 11/2002 | Cornwall et al. |
| D467,657 S | 12/2002 | Scribner |
| 6,488,693 B2 | 12/2002 | Gannoe et al. |
| 6,488,710 B2 | 12/2002 | Besselink |
| 6,489,309 B1 | 12/2002 | Singh et al. |
| 6,491,626 B1 | 12/2002 | Stone et al. |
| 6,491,695 B1 | 12/2002 | Roggenbuck |
| 6,491,714 B1 | 12/2002 | Bennett |
| 6,491,724 B1 | 12/2002 | Ferree |
| 6,494,860 B2 | 12/2002 | Rocamora et al. |
| 6,494,883 B1 | 12/2002 | Ferree |
| 6,494,893 B2 | 12/2002 | Dubrul |
| 6,498,421 B1 | 12/2002 | Oh et al. |
| 6,500,178 B2 | 12/2002 | Zucherman et al. |
| 6,500,205 B1 | 12/2002 | Michelson |
| 6,506,192 B1 | 1/2003 | Gertzman et al. |
| 6,508,839 B1 | 1/2003 | Lambrecht et al. |
| 6,511,471 B2 | 1/2003 | Rosenman et al. |
| 6,511,481 B2 | 1/2003 | Von et al. |
| 6,512,958 B1 | 1/2003 | Swoyer et al. |
| D469,871 S | 2/2003 | Sand |
| 6,514,256 B2 | 2/2003 | Zucherman et al. |
| 6,517,543 B1 | 2/2003 | Berrevoets et al. |
| 6,517,580 B1 | 2/2003 | Ramadan et al. |
| 6,520,907 B1 | 2/2003 | Foley et al. |
| 6,520,991 B2 | 2/2003 | Huene |
| D472,323 S | 3/2003 | Sand |
| 6,527,774 B2 | 3/2003 | Lieberman |
| 6,527,803 B1 | 3/2003 | Crozet et al. |
| 6,527,804 B1 | 3/2003 | Gauchet et al. |
| 6,530,930 B1 | 3/2003 | Marino et al. |
| 6,533,791 B1 | 3/2003 | Betz et al. |
| 6,533,797 B1 | 3/2003 | Stone et al. |
| 6,533,818 B1 | 3/2003 | Weber et al. |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,547,823 B2 | 4/2003 | Scarborough et al. |
| 6,551,319 B2 | 4/2003 | Lieberman |
| 6,551,322 B1 | 4/2003 | Lieberman |
| 6,554,831 B1 | 4/2003 | Rivard et al. |
| 6,554,833 B2 | 4/2003 | Levy et al. |
| 6,554,852 B1 | 4/2003 | Oberlander |
| 6,558,389 B2 | 5/2003 | Clark et al. |
| 6,558,390 B2 | 5/2003 | Cragg |
| 6,558,424 B2 | 5/2003 | Thalgott |
| 6,562,046 B2 | 5/2003 | Sasso |
| 6,562,049 B1 | 5/2003 | Norlander et al. |
| 6,562,072 B1 | 5/2003 | Fuss et al. |
| 6,562,074 B2 | 5/2003 | Gerbec et al. |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,579,293 B1 | 6/2003 | Chandran |
| 6,579,320 B1 | 6/2003 | Gauchet et al. |
| 6,579,321 B1 | 6/2003 | Gordon et al. |
| 6,582,390 B1 | 6/2003 | Sanderson |
| 6,582,431 B1 | 6/2003 | Ray |
| 6,582,433 B2 | 6/2003 | Yun |
| 6,582,437 B2 | 6/2003 | Dorchak et al. |
| 6,582,441 B1 | 6/2003 | He et al. |
| 6,582,453 B1 | 6/2003 | Tran et al. |
| 6,582,466 B1 | 6/2003 | Gauchet |
| 6,582,467 B1 | 6/2003 | Teitelbaum et al. |
| 6,582,468 B1 | 6/2003 | Gauchet |
| 6,585,730 B1 | 7/2003 | Foerster |
| 6,585,740 B2 | 7/2003 | Schlapfer et al. |
| 6,589,240 B2 | 7/2003 | Hinchliffe |
| 6,589,249 B2 | 7/2003 | Sater et al. |
| 6,592,553 B2 | 7/2003 | Zhang et al. |
| 6,592,624 B1 | 7/2003 | Fraser et al. |
| 6,592,625 B2 | 7/2003 | Cauthen |
| 6,595,998 B2 | 7/2003 | Johnson et al. |
| 6,596,008 B1 | 7/2003 | Kambin |
| 6,599,294 B2 | 7/2003 | Fuss et al. |
| 6,599,297 B1 | 7/2003 | Carlsson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,607,558 B2 | 8/2003 | Kuras |
| 6,610,066 B2 | 8/2003 | Dinger et al. |
| 6,610,091 B1 | 8/2003 | Reiley |
| 6,610,094 B2 | 8/2003 | Husson |
| 6,613,050 B1 | 9/2003 | Wagner et al. |
| 6,613,054 B2 | 9/2003 | Scribner et al. |
| 6,616,678 B2 | 9/2003 | Nishtala et al. |
| 6,620,196 B1 | 9/2003 | Trieu |
| 6,623,505 B2 | 9/2003 | Scribner et al. |
| 6,626,943 B2 | 9/2003 | Eberlein et al. |
| 6,626,944 B1 | 9/2003 | Jean |
| 6,629,998 B1 | 10/2003 | Lin |
| 6,632,224 B2 | 10/2003 | Cachia et al. |
| 6,632,235 B2 | 10/2003 | Weikel et al. |
| 6,635,059 B2 | 10/2003 | Randall et al. |
| 6,635,060 B2 | 10/2003 | Hanson et al. |
| 6,635,362 B2 | 10/2003 | Zheng |
| RE38,335 E | 11/2003 | Aust et al. |
| D482,787 S | 11/2003 | Reiss |
| 6,641,564 B1 | 11/2003 | Krads |
| 6,641,582 B1 | 11/2003 | Hanson et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,248 B2 | 11/2003 | Casutt |
| 6,648,890 B2 | 11/2003 | Culbert et al. |
| 6,648,893 B2 | 11/2003 | Dudasik |
| 6,648,917 B2 | 11/2003 | Gerbec et al. |
| 6,652,527 B2 | 11/2003 | Zucherman et al. |
| 6,652,592 B1 | 11/2003 | Grooms et al. |
| D483,495 S | 12/2003 | Sand |
| 6,655,962 B1 | 12/2003 | Kennard |
| 6,656,178 B1 | 12/2003 | Veldhuizen et al. |
| 6,656,180 B2 | 12/2003 | Stahurski |
| 6,660,004 B2 | 12/2003 | Barker et al. |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm et al. |
| 6,669,698 B1 | 12/2003 | Tromanhauser et al. |
| 6,669,729 B2 | 12/2003 | Chin |
| 6,669,732 B2 | 12/2003 | Serhan et al. |
| 6,673,074 B2 | 1/2004 | Shluzas |
| 6,676,663 B2 | 1/2004 | Higueras et al. |
| 6,676,664 B1 | 1/2004 | Al-Assir |
| 6,676,665 B2 | 1/2004 | Foley et al. |
| 6,679,833 B2 | 1/2004 | Smith et al. |

(56) References Cited

U.S. PATENT DOCUMENTS

| | | | |
|---|---|---|---|
| 6,679,915 B1 | 1/2004 | Cauthen |
| 6,682,535 B2 | 1/2004 | Hoogland |
| 6,682,561 B2 | 1/2004 | Songer et al. |
| 6,682,562 B2 | 1/2004 | Mart et al. |
| 6,685,706 B2 | 2/2004 | Padget et al. |
| 6,685,742 B1 | 2/2004 | Jackson |
| 6,689,125 B1 | 2/2004 | Keith et al. |
| 6,689,152 B2 | 2/2004 | Balceta et al. |
| 6,689,168 B2 | 2/2004 | Lieberman |
| 6,692,499 B2 | 2/2004 | Toermaelae et al. |
| 6,692,563 B2 | 2/2004 | Zimmermann |
| 6,695,842 B2 | 2/2004 | Zucherman et al. |
| 6,695,851 B2 | 2/2004 | Zdeblick et al. |
| 6,699,246 B2 | 3/2004 | Zucherman et al. |
| 6,699,247 B2 | 3/2004 | Zucherman et al. |
| 6,706,070 B1 * | 3/2004 | Wagner ............... A61F 2/4455 623/17.15 |
| 6,709,458 B2 | 3/2004 | Michelson |
| 6,712,819 B2 | 3/2004 | Zucherman et al. |
| 6,716,216 B1 | 4/2004 | Boucher et al. |
| 6,716,247 B2 | 4/2004 | Michelson |
| 6,716,957 B2 | 4/2004 | Tunc |
| 6,719,760 B2 | 4/2004 | Dorchak et al. |
| 6,719,761 B1 | 4/2004 | Reiley et al. |
| 6,719,773 B1 | 4/2004 | Boucher et al. |
| 6,719,796 B2 | 4/2004 | Cohen et al. |
| 6,723,096 B1 | 4/2004 | Dorchak et al. |
| 6,723,126 B1 | 4/2004 | Berry |
| 6,723,127 B2 | 4/2004 | Ralph et al. |
| 6,723,128 B2 | 4/2004 | Uk |
| 6,726,691 B2 | 4/2004 | Osorio et al. |
| D490,159 S | 5/2004 | Sand |
| 6,730,126 B2 | 5/2004 | Boehm et al. |
| 6,733,093 B2 | 5/2004 | Deland et al. |
| 6,733,460 B2 | 5/2004 | Ogura |
| 6,733,532 B1 | 5/2004 | Gauchet et al. |
| 6,733,534 B2 | 5/2004 | Sherman |
| 6,733,535 B2 | 5/2004 | Michelson |
| 6,733,635 B1 | 5/2004 | Ozawa et al. |
| 6,740,090 B1 | 5/2004 | Cragg et al. |
| 6,740,093 B2 | 5/2004 | Hochschuler et al. |
| 6,740,117 B2 | 5/2004 | Ralph et al. |
| D492,032 S | 6/2004 | Muller et al. |
| 6,743,166 B2 | 6/2004 | Berci et al. |
| 6,743,255 B2 | 6/2004 | Ferree |
| 6,746,451 B2 | 6/2004 | Middleton et al. |
| 6,749,560 B1 | 6/2004 | Konstorum |
| 6,752,831 B2 | 6/2004 | Sybert et al. |
| 6,755,837 B2 | 6/2004 | Ebner |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,758,847 B2 | 7/2004 | Maguire |
| 6,758,861 B2 | 7/2004 | Ralph et al. |
| 6,758,862 B2 | 7/2004 | Berry et al. |
| 6,761,720 B1 | 7/2004 | Senegas |
| 6,764,491 B2 | 7/2004 | Frey et al. |
| 6,764,514 B1 | 7/2004 | Li et al. |
| D495,417 S | 8/2004 | Doelling et al. |
| 6,770,075 B2 | 8/2004 | Howland |
| 6,773,460 B2 | 8/2004 | Jackson |
| 6,780,151 B2 | 8/2004 | Grabover et al. |
| 6,783,530 B2 | 8/2004 | Levy |
| 6,790,210 B1 | 9/2004 | Cragg et al. |
| 6,793,656 B1 | 9/2004 | Mathews |
| 6,793,678 B2 | 9/2004 | Hawkins |
| 6,793,679 B2 | 9/2004 | Michelson |
| 6,796,983 B1 | 9/2004 | Zucherman et al. |
| 6,805,685 B2 | 10/2004 | Taylor |
| 6,805,695 B2 | 10/2004 | Keith et al. |
| 6,805,697 B1 | 10/2004 | Helm et al. |
| 6,805,714 B2 | 10/2004 | Sutcliffe |
| 6,808,526 B1 | 10/2004 | Magerl et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,824,565 B2 | 11/2004 | Muhanna et al. |
| 6,830,589 B2 | 12/2004 | Erickson |
| 6,835,205 B2 | 12/2004 | Atkinson et al. |
| 6,835,206 B2 | 12/2004 | Jackson |
| 6,835,208 B2 | 12/2004 | Marchosky |
| 6,840,941 B2 | 1/2005 | Rogers et al. |
| 6,840,944 B2 | 1/2005 | Suddaby |
| 6,852,126 B2 | 2/2005 | Ahlgren |
| 6,852,127 B2 | 2/2005 | Varga et al. |
| 6,852,129 B2 | 2/2005 | Gerbec et al. |
| 6,855,167 B2 | 2/2005 | Shimp et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,215 B2 | 4/2005 | Taras et al. |
| 6,878,167 B2 | 4/2005 | Ferree |
| 6,881,228 B2 | 4/2005 | Zdeblick et al. |
| 6,881,229 B2 | 4/2005 | Khandkar et al. |
| 6,883,520 B2 | 4/2005 | Lambrecht et al. |
| 6,887,243 B2 | 5/2005 | Culbert |
| 6,887,248 B2 | 5/2005 | McKinley et al. |
| 6,890,333 B2 | 5/2005 | Von et al. |
| 6,893,464 B2 | 5/2005 | Kiester |
| 6,893,466 B2 | 5/2005 | Trieu |
| 6,899,716 B2 | 5/2005 | Cragg |
| 6,899,719 B2 | 5/2005 | Reiley et al. |
| 6,899,735 B2 | 5/2005 | Coates et al. |
| D506,828 S | 6/2005 | Layne et al. |
| 6,902,566 B2 | 6/2005 | Zdcherman et al. |
| 6,905,512 B2 | 6/2005 | Paes et al. |
| 6,908,465 B2 | 6/2005 | Von et al. |
| 6,908,506 B2 | 6/2005 | Zimmermann |
| 6,916,323 B2 | 7/2005 | Kitchens |
| 6,921,403 B2 | 7/2005 | Cragg et al. |
| 6,923,810 B1 | 8/2005 | Michelson |
| 6,923,811 B1 | 8/2005 | Carl et al. |
| 6,923,813 B2 | 8/2005 | Phillips et al. |
| 6,923,814 B1 | 8/2005 | Hildebrand et al. |
| 6,929,606 B2 | 8/2005 | Ritland |
| 6,929,647 B2 | 8/2005 | Cohen |
| 6,936,071 B1 | 8/2005 | Marnay et al. |
| 6,936,072 B2 | 8/2005 | Lambrecht et al. |
| 6,942,668 B2 | 9/2005 | Padget et al. |
| 6,945,973 B2 | 9/2005 | Bray |
| 6,945,975 B2 | 9/2005 | Dalton |
| 6,946,000 B2 | 9/2005 | Senegas et al. |
| 6,949,100 B1 | 9/2005 | Venturini |
| 6,949,108 B2 | 9/2005 | Holmes |
| 6,951,561 B2 | 10/2005 | Warren et al. |
| 6,952,129 B2 | 10/2005 | Lin et al. |
| 6,953,477 B2 | 10/2005 | Berry |
| 6,955,691 B2 | 10/2005 | Chae et al. |
| 6,962,606 B2 | 11/2005 | Michelson |
| 6,964,674 B1 | 11/2005 | Matsuura et al. |
| 6,964,686 B2 | 11/2005 | Gordon |
| 6,966,910 B2 | 11/2005 | Ritland |
| 6,966,912 B2 | 11/2005 | Michelson |
| 6,969,404 B2 | 11/2005 | Ferree |
| 6,969,405 B2 | 11/2005 | Suddaby |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,979,352 B2 | 12/2005 | Reynolds |
| 6,979,353 B2 | 12/2005 | Bresina |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,004,971 B2 | 2/2006 | Serhan et al. |
| 7,008,431 B2 | 3/2006 | Simonson |
| 7,008,453 B1 | 3/2006 | Michelson |
| 7,014,633 B2 | 3/2006 | Cragg |
| 7,018,089 B2 | 3/2006 | Wenz et al. |
| 7,018,412 B2 | 3/2006 | Ferreira et al. |
| 7,018,415 B1 | 3/2006 | McKay |

(56) References Cited

U.S. PATENT DOCUMENTS

| | | |
|---|---|---|
| 7,018,416 B2 | 3/2006 | Hanson et al. |
| 7,018,453 B2 | 3/2006 | Klein et al. |
| 7,022,138 B2 | 4/2006 | Mashburn |
| 7,025,746 B2 | 4/2006 | Tal |
| 7,025,787 B2 | 4/2006 | Bryan et al. |
| 7,029,473 B2 | 4/2006 | Zucherman et al. |
| 7,029,498 B2 | 4/2006 | Boehm et al. |
| 7,037,339 B2 | 5/2006 | Houfburg |
| 7,041,107 B2 | 5/2006 | Pohjonen et al. |
| 7,044,954 B2 | 5/2006 | Reiley et al. |
| 7,048,694 B2 | 5/2006 | Mark et al. |
| 7,048,736 B2 | 5/2006 | Robinson et al. |
| 7,060,068 B2 | 6/2006 | Tromanhauser et al. |
| 7,060,073 B2 | 6/2006 | Frey et al. |
| 7,063,701 B2 | 6/2006 | Michelson |
| 7,063,702 B2 | 6/2006 | Michelson |
| 7,063,703 B2 | 6/2006 | Reo |
| 7,063,725 B2 | 6/2006 | Foley |
| 7,066,960 B1 | 6/2006 | Dickman |
| 7,066,961 B2 | 6/2006 | Michelson |
| 7,069,087 B2 | 6/2006 | Sharkey et al. |
| 7,070,598 B2 | 7/2006 | Lim et al. |
| 7,070,601 B2 | 7/2006 | Culbert et al. |
| 7,074,203 B1 | 7/2006 | Johanson et al. |
| 7,074,226 B2 | 7/2006 | Roehm et al. |
| 7,081,120 B2 | 7/2006 | Li et al. |
| 7,081,122 B1 | 7/2006 | Reiley et al. |
| 7,083,650 B2 | 8/2006 | Moskowitz et al. |
| 7,087,053 B2 | 8/2006 | Vanney |
| 7,087,055 B2 | 8/2006 | Lim et al. |
| 7,087,083 B2 | 8/2006 | Pasquet et al. |
| 7,089,063 B2 | 8/2006 | Lesh et al. |
| 7,094,239 B1 | 8/2006 | Michelson |
| 7,094,257 B2 | 8/2006 | Mujwid et al. |
| 7,094,258 B2 | 8/2006 | Lambrecht et al. |
| 7,101,375 B2 | 9/2006 | Zucherman et al. |
| 7,114,501 B2 | 10/2006 | Johnson et al. |
| 7,115,128 B2 | 10/2006 | Michelson |
| 7,115,163 B2 | 10/2006 | Zimmermann |
| 7,118,572 B2 | 10/2006 | Bramlet et al. |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,125,424 B2 | 10/2006 | Banick et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson et al. |
| 7,153,306 B2 | 12/2006 | Ralph et al. |
| 7,153,307 B2 | 12/2006 | Scribner et al. |
| D536,096 S | 1/2007 | Hoogland et al. |
| 7,156,874 B2 | 1/2007 | Paponneau et al. |
| 7,156,875 B2 | 1/2007 | Michelson |
| 7,156,876 B2 | 1/2007 | Moumene et al. |
| 7,156,877 B2 | 1/2007 | Lotz et al. |
| 7,163,558 B2 | 1/2007 | Senegas et al. |
| 7,166,107 B2 | 1/2007 | Anderson |
| 7,172,612 B2 | 2/2007 | Ishikawa |
| 7,179,293 B2 | 2/2007 | McKay |
| 7,179,294 B2 | 2/2007 | Eisermann et al. |
| 7,189,242 B2 | 3/2007 | Boyd et al. |
| 7,201,751 B2 | 4/2007 | Zucherman et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,220,281 B2 | 5/2007 | Lambrecht et al. |
| 7,223,227 B2 | 5/2007 | Pflueger |
| 7,223,292 B2 | 5/2007 | Messerli et al. |
| 7,226,481 B2 | 6/2007 | Kuslich |
| 7,226,483 B2 | 6/2007 | Gerber et al. |
| 7,235,101 B2 | 6/2007 | Berry et al. |
| 7,238,204 B2 | 7/2007 | Le et al. |
| 7,241,297 B2 | 7/2007 | Shaolian et al. |
| 7,244,273 B2 | 7/2007 | Pedersen et al. |
| 7,250,060 B2 | 7/2007 | Trieu |
| 7,252,671 B2 | 8/2007 | Scribner et al. |
| 7,267,683 B2 | 9/2007 | Sharkey et al. |
| 7,267,687 B2 | 9/2007 | McGuckin, Jr. |
| 7,270,679 B2 | 9/2007 | Istephanous et al. |
| 7,276,062 B2 | 10/2007 | McDaniel et al. |
| 7,282,061 B2 | 10/2007 | Sharkey et al. |
| 7,291,173 B2 | 11/2007 | Richelsoph et al. |
| 7,300,440 B2 | 11/2007 | Zdeblick et al. |
| 7,306,628 B2 | 12/2007 | Zucherman et al. |
| 7,309,357 B2 | 12/2007 | Kim |
| 7,311,713 B2 | 12/2007 | Johnson et al. |
| 7,316,714 B2 | 1/2008 | Gordon et al. |
| 7,318,840 B2 | 1/2008 | McKay |
| 7,320,689 B2 | 1/2008 | Keller |
| 7,320,708 B1 | 1/2008 | Bernstein |
| 7,322,962 B2 | 1/2008 | Forrest |
| 7,326,211 B2 | 2/2008 | Padget et al. |
| 7,326,248 B2 | 2/2008 | Michelson |
| 7,335,203 B2 | 2/2008 | Winslow et al. |
| 7,351,262 B2 | 4/2008 | Bindseil et al. |
| 7,361,140 B2 | 4/2008 | Ries et al. |
| 7,371,238 B2 | 5/2008 | Soboleski et al. |
| 7,377,942 B2 | 5/2008 | Berry |
| 7,383,639 B2 | 6/2008 | Malandain |
| 7,400,930 B2 | 7/2008 | Sharkey et al. |
| 7,406,775 B2 | 8/2008 | Funk et al. |
| 7,410,501 B2 | 8/2008 | Michelson |
| 7,413,576 B2 | 8/2008 | Sybert et al. |
| 7,422,594 B2 | 9/2008 | Zander |
| 7,434,325 B2 | 10/2008 | Foley et al. |
| 7,442,211 B2 | 10/2008 | De et al. |
| 7,445,636 B2 | 11/2008 | Michelson |
| 7,445,637 B2 | 11/2008 | Taylor |
| 7,470,273 B2 | 12/2008 | Dougherty-Shah |
| D584,812 S | 1/2009 | Ries |
| 7,473,256 B2 | 1/2009 | Assell et al. |
| 7,473,268 B2 | 1/2009 | Zucherman et al. |
| 7,476,251 B2 | 1/2009 | Zucherman et al. |
| 7,485,134 B2 | 2/2009 | Simonson |
| 7,488,326 B2 | 2/2009 | Elliott |
| 7,491,237 B2 | 2/2009 | Randall et al. |
| 7,500,991 B2 | 3/2009 | Bartish et al. |
| 7,503,920 B2 | 3/2009 | Siegal |
| 7,503,933 B2 | 3/2009 | Michelson |
| 7,507,241 B2 | 3/2009 | Levy et al. |
| 7,517,363 B2 | 4/2009 | Rogers et al. |
| 7,520,888 B2 | 4/2009 | Trieu |
| 7,547,317 B2 | 6/2009 | Cragg |
| 7,556,629 B2 | 7/2009 | Von et al. |
| 7,556,651 B2 | 7/2009 | Humphreys et al. |
| 7,569,054 B2 | 8/2009 | Michelson |
| 7,569,074 B2 | 8/2009 | Eisermann et al. |
| 7,572,279 B2 | 8/2009 | Jackson |
| 7,575,580 B2 | 8/2009 | Lim et al. |
| 7,575,599 B2 | 8/2009 | Villiers et al. |
| 7,578,820 B2 | 8/2009 | Moore et al. |
| 7,588,574 B2 | 9/2009 | Assell et al. |
| 7,601,173 B2 | 10/2009 | Messerli et al. |
| 7,608,083 B2 | 10/2009 | Lee et al. |
| 7,618,458 B2 | 11/2009 | Biedermann et al. |
| 7,621,950 B1 | 11/2009 | Globerman et al. |
| 7,621,960 B2 | 11/2009 | Boyd et al. |
| 7,625,377 B2 | 12/2009 | Veldhuizen et al. |
| 7,625,378 B2 | 12/2009 | Foley |
| 7,625,394 B2 | 12/2009 | Molz et al. |
| 7,637,905 B2 | 12/2009 | Saadat et al. |
| 7,641,657 B2 | 1/2010 | Cragg |
| 7,641,670 B2 | 1/2010 | Davison et al. |
| 7,641,692 B2 | 1/2010 | Bryan et al. |
| 7,647,123 B2 | 1/2010 | Sharkey et al. |
| 7,648,523 B2 | 1/2010 | Mirkovic et al. |
| 7,655,010 B2 | 2/2010 | Serhan et al. |
| 7,666,186 B2 | 2/2010 | Harp |
| 7,666,266 B2 | 2/2010 | Izawa et al. |

(56) References Cited

U.S. PATENT DOCUMENTS

| | | |
|---|---|---|
| 7,670,354 B2 | 3/2010 | Davison et al. |
| 7,670,374 B2 | 3/2010 | Schaller |
| 7,674,265 B2 | 3/2010 | Smith et al. |
| 7,674,273 B2 | 3/2010 | Davison et al. |
| 7,682,370 B2 | 3/2010 | Pagliuca et al. |
| 7,682,400 B2 | 3/2010 | Zwirkoski |
| 7,691,120 B2 | 4/2010 | Shluzas et al. |
| 7,691,147 B2 | 4/2010 | Guetlin et al. |
| 7,699,878 B2 | 4/2010 | Pavlov et al. |
| 7,703,727 B2 | 4/2010 | Selness |
| 7,704,280 B2 | 4/2010 | Lechmann et al. |
| 7,717,944 B2 | 5/2010 | Foley et al. |
| 7,722,530 B2 | 5/2010 | Davison |
| 7,722,612 B2 | 5/2010 | Sala et al. |
| 7,722,674 B1 | 5/2010 | Grotz |
| 7,727,263 B2 | 6/2010 | Cragg |
| 7,731,751 B2 | 6/2010 | Butler et al. |
| 7,740,633 B2 | 6/2010 | Assell et al. |
| 7,744,599 B2 | 6/2010 | Cragg |
| 7,744,650 B2 | 6/2010 | Lindner et al. |
| 7,749,270 B2 | 7/2010 | Peterman |
| 7,762,995 B2 | 7/2010 | Eversull et al. |
| 7,763,025 B2 | 7/2010 | Ainsworth |
| 7,763,028 B2 | 7/2010 | Lim et al. |
| 7,763,038 B2 | 7/2010 | Todd |
| 7,763,055 B2 | 7/2010 | Foley |
| 7,766,930 B2 | 8/2010 | DiPoto et al. |
| 7,771,473 B2 | 8/2010 | Thramann |
| 7,771,479 B2 | 8/2010 | Humphreys et al. |
| 7,785,368 B2 | 8/2010 | Schaller |
| 7,789,914 B2 | 9/2010 | Michelson |
| 7,794,463 B2 | 9/2010 | Cragg |
| 7,799,032 B2 | 9/2010 | Assell et al. |
| 7,799,033 B2 | 9/2010 | Assell et al. |
| 7,799,036 B2 | 9/2010 | Davison et al. |
| 7,799,080 B2 | 9/2010 | Doty |
| 7,799,081 B2 | 9/2010 | McKinley |
| 7,799,083 B2 | 9/2010 | Smith et al. |
| 7,803,161 B2 | 9/2010 | Foley et al. |
| D626,233 S | 10/2010 | Cipoletti et al. |
| 7,814,429 B2 | 10/2010 | Buffet et al. |
| 7,819,921 B2 | 10/2010 | Grotz |
| 7,824,410 B2 | 11/2010 | Simonson et al. |
| 7,824,429 B2 | 11/2010 | Culbert et al. |
| 7,824,445 B2 | 11/2010 | Biro et al. |
| 7,828,807 B2 | 11/2010 | Lehuec et al. |
| 7,837,734 B2 | 11/2010 | Zucherman et al. |
| 7,846,183 B2 | 12/2010 | Blain |
| 7,846,206 B2 | 12/2010 | Oglaza et al. |
| 7,850,695 B2 | 12/2010 | Pagliuca et al. |
| 7,850,733 B2 | 12/2010 | Baynham et al. |
| 7,854,766 B2 | 12/2010 | Moskowitz et al. |
| 7,857,832 B2 | 12/2010 | Culbert et al. |
| 7,857,840 B2 | 12/2010 | Krebs et al. |
| 7,862,590 B2 | 1/2011 | Lim et al. |
| 7,862,595 B2 | 1/2011 | Foley et al. |
| 7,867,259 B2 | 1/2011 | Foley et al. |
| 7,874,980 B2 | 1/2011 | Sonnenschein et al. |
| 7,875,077 B2 | 1/2011 | Humphreys et al. |
| 7,879,098 B1 | 2/2011 | Simmons, Jr. |
| 7,887,589 B2 | 2/2011 | Glenn et al. |
| 7,892,171 B2 | 2/2011 | Davison et al. |
| 7,892,249 B2 | 2/2011 | Davison et al. |
| 7,901,438 B2 | 3/2011 | Culbert et al. |
| 7,901,459 B2 | 3/2011 | Hodges et al. |
| 7,909,870 B2 | 3/2011 | Kraus |
| 7,909,874 B2 | 3/2011 | Zielinski |
| 7,918,874 B2 | 4/2011 | Siegal |
| 7,922,719 B2 | 4/2011 | Ralph et al. |
| 7,922,729 B2 | 4/2011 | Michelson |
| 7,931,674 B2 | 4/2011 | Zucherman et al. |
| 7,931,689 B2 | 4/2011 | Hochschuler et al. |
| 7,935,051 B2 | 5/2011 | Miles et al. |
| 7,938,832 B2 | 5/2011 | Culbert et al. |
| 7,942,903 B2 | 5/2011 | Moskowitz et al. |
| 7,947,078 B2 | 5/2011 | Siegal |
| 7,951,199 B2 | 5/2011 | Miller |
| 7,955,391 B2 | 6/2011 | Schaller |
| 7,959,675 B2 | 6/2011 | Gately |
| 7,963,967 B1 | 6/2011 | Woods |
| 7,963,993 B2 | 6/2011 | Schaller |
| 7,967,864 B2 | 6/2011 | Schaller |
| 7,967,865 B2 | 6/2011 | Schaller |
| 7,985,231 B2 | 7/2011 | Sankaran |
| 7,993,403 B2 | 8/2011 | Foley et al. |
| 7,998,176 B2 | 8/2011 | Culbert |
| 8,007,535 B2 | 8/2011 | Hudgins et al. |
| 8,012,212 B2 | 9/2011 | Link et al. |
| 8,021,424 B2 | 9/2011 | Beger et al. |
| 8,021,426 B2 | 9/2011 | Segal et al. |
| 8,025,697 B2 | 9/2011 | Mcclellan et al. |
| 8,034,109 B2 | 10/2011 | Zwirkoski |
| 8,034,110 B2 | 10/2011 | Garner et al. |
| 8,038,703 B2 | 10/2011 | Dobak et al. |
| 8,043,293 B2 | 10/2011 | Warnick |
| 8,043,381 B2 | 10/2011 | Hestad et al. |
| 8,052,754 B2 | 11/2011 | Froehlich |
| 8,057,544 B2 | 11/2011 | Schaller |
| 8,057,545 B2 | 11/2011 | Hughes et al. |
| 8,062,375 B2 | 11/2011 | Glerum et al. |
| 8,075,621 B2 | 12/2011 | Michelson |
| 8,097,036 B2 | 1/2012 | Cordaro et al. |
| 8,100,978 B2 | 1/2012 | Bass |
| 8,105,382 B2 | 1/2012 | Olmos et al. |
| 8,109,972 B2 | 2/2012 | Zucherman et al. |
| 8,109,977 B2 | 2/2012 | Culbert et al. |
| 8,114,088 B2 | 2/2012 | Miller |
| 8,118,871 B2 | 2/2012 | Gordon |
| 8,128,700 B2 | 3/2012 | DeLurio et al. |
| 8,128,702 B2 | 3/2012 | Zucherman et al. |
| 8,133,232 B2 | 3/2012 | Levy et al. |
| 8,147,549 B2 | 4/2012 | Metcalf et al. |
| 8,177,812 B2 | 5/2012 | Sankaran |
| 8,187,327 B2 | 5/2012 | Edidin et al. |
| 8,187,332 B2 | 5/2012 | McLuen |
| 8,192,495 B2 | 6/2012 | Simpson et al. |
| 8,202,322 B2 | 6/2012 | Doty |
| 8,206,423 B2 | 6/2012 | Siegal |
| 8,216,312 B2 | 7/2012 | Gray |
| 8,216,314 B2 | 7/2012 | Richelsoph |
| 8,216,317 B2 | 7/2012 | Thibodeau |
| 8,221,501 B2 | 7/2012 | Eisermann et al. |
| 8,221,502 B2 | 7/2012 | Branch, Jr. |
| 8,221,503 B2 | 7/2012 | Garcia et al. |
| 8,231,675 B2 | 7/2012 | Rhoda |
| 8,231,681 B2 | 7/2012 | Castleman et al. |
| 8,236,029 B2 | 8/2012 | Siegal |
| 8,236,058 B2 | 8/2012 | Fabian et al. |
| 8,241,328 B2 | 8/2012 | Siegal |
| 8,241,358 B2 | 8/2012 | Butler et al. |
| 8,241,361 B2 | 8/2012 | Link |
| 8,241,364 B2 | 8/2012 | Hansell et al. |
| 8,246,622 B2 | 8/2012 | Siegal et al. |
| 8,257,440 B2 | 9/2012 | Gordon et al. |
| 8,257,442 B2 | 9/2012 | Edie et al. |
| 8,262,666 B2 | 9/2012 | Baynham et al. |
| 8,262,736 B2 | 9/2012 | Michelson |
| 8,267,939 B2 | 9/2012 | Cipoletti et al. |
| 8,267,965 B2 | 9/2012 | Gimbel et al. |
| 8,273,128 B2 | 9/2012 | Oh et al. |
| 8,273,129 B2 | 9/2012 | Baynham et al. |
| 8,287,599 B2 | 10/2012 | McGuckin, Jr. |
| 8,292,959 B2 | 10/2012 | Webb et al. |
| 8,303,663 B2 | 11/2012 | Jimenez et al. |
| 8,317,866 B2 | 11/2012 | Palmatier et al. |
| 8,323,345 B2 | 12/2012 | Sledge |
| 8,328,812 B2 | 12/2012 | Siegal et al. |
| 8,328,852 B2 | 12/2012 | Zehavi et al. |
| 8,337,559 B2 | 12/2012 | Hansell et al. |
| 8,343,193 B2 | 1/2013 | Johnson et al. |
| 8,343,222 B2 | 1/2013 | Cope |
| 8,353,961 B2 | 1/2013 | McClintock et al. |
| 8,361,154 B2 | 1/2013 | Reo |
| 8,366,777 B2 | 2/2013 | Matthis et al. |

(56) References Cited

U.S. PATENT DOCUMENTS

| | | |
|---|---|---|
| 8,377,098 B2 | 2/2013 | Landry et al. |
| 8,382,842 B2 | 2/2013 | Greenhalgh et al. |
| 8,394,129 B2 | 3/2013 | Morgenstern et al. |
| 8,398,712 B2 | 3/2013 | De et al. |
| 8,398,713 B2 | 3/2013 | Weiman |
| 8,403,990 B2 | 3/2013 | Dryer et al. |
| 8,409,282 B2 | 4/2013 | Kim |
| 8,409,290 B2 | 4/2013 | Zamani et al. |
| 8,409,291 B2 | 4/2013 | Blackwell et al. |
| 8,414,650 B2 | 4/2013 | Bertele et al. |
| 8,425,559 B2 | 4/2013 | Tebbe et al. |
| 8,435,298 B2 | 5/2013 | Weiman |
| 8,454,617 B2 | 6/2013 | Schaller et al. |
| 8,454,698 B2 | 6/2013 | De et al. |
| 8,465,524 B2 | 6/2013 | Siegal |
| 8,470,043 B2 | 6/2013 | Schaller et al. |
| 8,480,715 B2 | 7/2013 | Gray |
| 8,480,742 B2 | 7/2013 | Pisharodi |
| 8,480,748 B2 | 7/2013 | Poulos |
| 8,486,109 B2 | 7/2013 | Siegal |
| 8,486,148 B2 | 7/2013 | Butler et al. |
| 8,491,591 B2 | 7/2013 | Sebastian |
| 8,491,653 B2 | 7/2013 | Zucherman et al. |
| 8,491,657 B2 | 7/2013 | Attia et al. |
| 8,491,659 B2 | 7/2013 | Weiman |
| 8,506,635 B2 | 8/2013 | Palmatier et al. |
| 8,518,087 B2 | 8/2013 | Lopez et al. |
| 8,518,120 B2 | 8/2013 | Glerum et al. |
| 8,523,909 B2 | 9/2013 | Hess |
| 8,523,944 B2 | 9/2013 | Jimenez et al. |
| 8,535,380 B2 | 9/2013 | Greenhalgh et al. |
| 8,545,567 B1 | 10/2013 | Krueger |
| 8,551,092 B2 | 10/2013 | Morgan et al. |
| 8,551,173 B2 | 10/2013 | Lechmann et al. |
| 8,556,978 B2 | 10/2013 | Schaller |
| 8,556,979 B2 | 10/2013 | Glerum et al. |
| 8,568,481 B2 | 10/2013 | Olmos et al. |
| 8,579,977 B2 | 11/2013 | Fabian |
| 8,579,981 B2 | 11/2013 | Lim et al. |
| 8,591,583 B2 | 11/2013 | Schaller et al. |
| 8,591,585 B2 | 11/2013 | McLaughlin et al. |
| 8,597,330 B2 | 12/2013 | Siegal |
| 8,597,333 B2 | 12/2013 | Morgenstern et al. |
| 8,597,360 B2 | 12/2013 | McLuen et al. |
| 8,603,168 B2 | 12/2013 | Gordon et al. |
| 8,603,170 B2 | 12/2013 | Cipoletti et al. |
| 8,603,177 B2 | 12/2013 | Gray |
| 8,623,091 B2 | 1/2014 | Suedkamp et al. |
| 8,628,576 B2 | 1/2014 | Triplett et al. |
| 8,628,577 B1 | 1/2014 | Jimenez |
| 8,628,578 B2 | 1/2014 | Miller et al. |
| 8,632,595 B2 | 1/2014 | Weiman |
| 8,636,746 B2 | 1/2014 | Jimenez et al. |
| 8,641,764 B2 | 2/2014 | Gately |
| 8,663,329 B2 | 3/2014 | Ernst |
| 8,663,331 B2 | 3/2014 | McClellan et al. |
| 8,668,740 B2 | 3/2014 | Rhoda et al. |
| 8,672,977 B2 | 3/2014 | Siegal et al. |
| 8,679,161 B2 | 3/2014 | Malandain et al. |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,751 B2 | 4/2014 | Ashley et al. |
| 8,702,757 B2 | 4/2014 | Thommen et al. |
| 8,702,798 B2 | 4/2014 | Matthis et al. |
| 8,709,086 B2 | 4/2014 | Glerum |
| 8,709,088 B2 | 4/2014 | Kleiner et al. |
| 8,715,351 B1 | 5/2014 | Pinto |
| 8,721,723 B2 | 5/2014 | Hansell et al. |
| 8,728,160 B2 | 5/2014 | Globerman et al. |
| 8,728,166 B2 | 5/2014 | Schwab |
| 8,740,954 B2 | 6/2014 | Ghobrial et al. |
| 8,753,398 B2 | 6/2014 | Gordon et al. |
| 8,758,349 B2 | 6/2014 | Germain et al. |
| 8,758,441 B2 | 6/2014 | Hovda et al. |
| 8,764,806 B2 | 7/2014 | Abdou |
| 8,771,360 B2 | 7/2014 | Jimenez et al. |
| 8,777,993 B2 | 7/2014 | Siegal et al. |
| 8,778,025 B2 | 7/2014 | Ragab et al. |
| 8,795,366 B2 | 8/2014 | Varela |
| 8,795,374 B2 | 8/2014 | Chee |
| 8,801,787 B2 | 8/2014 | Schaller |
| 8,801,792 B2 | 8/2014 | De et al. |
| 8,808,376 B2 | 8/2014 | Schaller |
| 8,828,085 B1 | 9/2014 | Jensen |
| 8,845,638 B2 | 9/2014 | Siegal et al. |
| 8,845,728 B1 | 9/2014 | Abdou |
| 8,845,731 B2 | 9/2014 | Weiman |
| 8,845,732 B2 | 9/2014 | Weiman |
| 8,845,733 B2 | 9/2014 | O'Neil et al. |
| 8,845,734 B2 | 9/2014 | Weiman |
| 8,852,242 B2 | 10/2014 | Morgenstern et al. |
| 8,852,243 B2 | 10/2014 | Morgenstern et al. |
| 8,852,279 B2 | 10/2014 | Weiman |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,900,235 B2 | 12/2014 | Siegal |
| 8,900,307 B2 | 12/2014 | Hawkins et al. |
| 8,906,098 B2 | 12/2014 | Siegal |
| 8,920,506 B2 | 12/2014 | McGuckin, Jr. |
| 8,926,704 B2 | 1/2015 | Glerum et al. |
| 8,936,641 B2 | 1/2015 | Cain |
| 8,940,049 B1 | 1/2015 | Jimenez et al. |
| 8,940,050 B2 | 1/2015 | Laurence et al. |
| 8,940,052 B2 | 1/2015 | Lechmann et al. |
| 8,961,609 B2 | 2/2015 | Schaller |
| 8,968,408 B2 | 3/2015 | Schaller et al. |
| 8,979,860 B2 | 3/2015 | Voellmicke et al. |
| 8,979,929 B2 | 3/2015 | Schaller |
| 8,986,387 B1 | 3/2015 | To et al. |
| 8,986,388 B2 | 3/2015 | Siegal et al. |
| 8,986,389 B2 | 3/2015 | Lim et al. |
| 9,005,291 B2 | 4/2015 | Loebl et al. |
| 9,017,408 B2 | 4/2015 | Siegal et al. |
| 9,017,413 B2 | 4/2015 | Siegal et al. |
| 9,039,767 B2 | 5/2015 | Raymond et al. |
| 9,039,771 B2 | 5/2015 | Glerum et al. |
| 9,044,334 B2 | 6/2015 | Siegal et al. |
| 9,044,338 B2 | 6/2015 | Schaller |
| 9,060,876 B1 | 6/2015 | To et al. |
| 9,066,808 B2 | 6/2015 | Schaller |
| 9,078,767 B1 | 7/2015 | McLean |
| 9,089,428 B2 | 7/2015 | Bertele et al. |
| 9,095,446 B2 | 8/2015 | Landry et al. |
| 9,095,447 B2 | 8/2015 | Barreiro et al. |
| 9,101,488 B2 | 8/2015 | Malandain |
| 9,101,489 B2 | 8/2015 | Protopsaltis et al. |
| 9,101,491 B2 | 8/2015 | Rodgers et al. |
| 9,101,492 B2 | 8/2015 | Mangione et al. |
| 9,107,766 B1 | 8/2015 | McLean et al. |
| 9,119,730 B2 | 9/2015 | Glerum et al. |
| 9,237,956 B1 | 1/2016 | Jensen |
| 9,254,138 B2 | 2/2016 | Siegal et al. |
| 9,259,326 B2 | 2/2016 | Schaller |
| 9,271,846 B2 | 3/2016 | Lim et al. |
| 9,277,928 B2 | 3/2016 | Morgenstern Lopez |
| 9,282,979 B2 | 3/2016 | O'Neil et al. |
| 9,283,092 B2 | 3/2016 | Siegal et al. |
| 9,295,562 B2 | 3/2016 | Lechmann et al. |
| 9,314,348 B2 | 4/2016 | Emstad |
| 9,320,610 B2 | 4/2016 | Alheidt et al. |
| 9,320,615 B2 | 4/2016 | Suedkamp et al. |
| 9,326,866 B2 | 5/2016 | Schaller et al. |
| 9,333,091 B2 | 5/2016 | DiMauro |
| 9,358,123 B2 | 6/2016 | Remington et al. |
| 9,387,087 B2 | 7/2016 | Tyber |
| 9,402,732 B2 | 8/2016 | Gabelberger |
| 9,402,739 B2 | 8/2016 | Weiman et al. |
| 9,408,712 B2 | 8/2016 | Siegal et al. |
| 9,414,923 B2 | 8/2016 | Studer et al. |
| 9,414,934 B2 | 8/2016 | Cain |
| 9,414,936 B2 | 8/2016 | Miller et al. |

(56) References Cited

U.S. PATENT DOCUMENTS

| | | |
|---|---|---|
| 9,433,510 B2 | 9/2016 | Lechmann et al. |
| 9,439,776 B2 | 9/2016 | DiMauro et al. |
| 9,439,777 B2 | 9/2016 | DiMauro |
| 9,445,825 B2 | 9/2016 | Belaney et al. |
| 9,445,918 B1 | 9/2016 | Lin et al. |
| 9,445,919 B2 | 9/2016 | Palmatier et al. |
| 9,463,099 B2 | 10/2016 | Levy et al. |
| 9,474,623 B2 | 10/2016 | Cain |
| 9,492,288 B2 | 11/2016 | Wagner et al. |
| 9,510,954 B2 | 12/2016 | Glerum et al. |
| 9,522,070 B2 | 12/2016 | Flower et al. |
| 9,532,884 B2 | 1/2017 | Siegal et al. |
| 9,566,167 B2 | 2/2017 | Barrus et al. |
| 9,579,215 B2 | 2/2017 | Suedkamp et al. |
| 9,592,129 B2 | 3/2017 | Slivka et al. |
| 9,597,197 B2 | 3/2017 | Lechmann et al. |
| 9,662,223 B2 | 5/2017 | Matthis et al. |
| 9,662,224 B2 | 5/2017 | Weiman et al. |
| 9,675,470 B2 | 6/2017 | Packer et al. |
| 9,717,601 B2 | 8/2017 | Miller |
| 9,724,207 B2 | 8/2017 | DiMauro et al. |
| 9,730,803 B2 | 8/2017 | DiMauro et al. |
| 9,730,806 B2 | 8/2017 | Capote |
| 9,750,552 B2 | 9/2017 | Stephan et al. |
| 9,750,618 B1 | 9/2017 | Daffinson et al. |
| 9,788,962 B2 | 10/2017 | Gabelberger |
| 9,788,963 B2 | 10/2017 | Aquino et al. |
| 9,788,971 B1 | 10/2017 | Stein |
| 9,801,639 B2 | 10/2017 | O'Neil et al. |
| 9,801,640 B2 | 10/2017 | O'Neil et al. |
| 9,801,729 B2 | 10/2017 | DiMauro et al. |
| 9,801,734 B1 | 10/2017 | Stein et al. |
| 9,808,351 B2 | 11/2017 | Kelly et al. |
| 9,808,353 B2 | 11/2017 | Suddaby et al. |
| 9,814,589 B2 | 11/2017 | DiMauro |
| 9,814,590 B2 | 11/2017 | Serhan et al. |
| 9,833,334 B2 | 12/2017 | Voellmicke et al. |
| 9,839,528 B2 | 12/2017 | Weiman et al. |
| 9,839,530 B2 | 12/2017 | Hawkins et al. |
| 9,848,991 B2 | 12/2017 | Boehm et al. |
| 9,872,779 B2 | 1/2018 | Miller et al. |
| 9,895,236 B2 | 2/2018 | Voellmicke et al. |
| 9,907,670 B2 | 3/2018 | Deridder et al. |
| 9,924,978 B2 | 3/2018 | Thommen et al. |
| 9,925,060 B2 | 3/2018 | DiMauro et al. |
| 9,931,223 B2 | 4/2018 | Cain |
| 9,931,226 B2 | 4/2018 | Kurtaliaj et al. |
| 9,937,053 B2 | 4/2018 | Melkent et al. |
| 9,949,769 B2 | 4/2018 | Serhan et al. |
| 9,962,272 B1 | 5/2018 | Daffinson et al. |
| 9,974,664 B2 | 5/2018 | Emerick et al. |
| 9,980,823 B2 | 5/2018 | Matthis et al. |
| 9,980,825 B2 | 5/2018 | Nichols et al. |
| 9,993,350 B2 | 6/2018 | Cain |
| 10,004,607 B2 | 6/2018 | Weiman |
| 10,058,433 B2 | 8/2018 | Lechmann et al. |
| 10,085,843 B2 | 10/2018 | DiMauro |
| 10,092,417 B2 | 10/2018 | Weiman |
| 10,137,009 B2 | 11/2018 | Weiman |
| 10,143,569 B2 | 12/2018 | Weiman |
| 10,166,117 B1 | 1/2019 | Daffinson et al. |
| 10,219,915 B1 | 3/2019 | Stein |
| 10,238,500 B2 | 3/2019 | Rogers et al. |
| 10,265,191 B2 | 4/2019 | Lim et al. |
| 10,307,254 B2 | 6/2019 | Levy et al. |
| 10,363,142 B2 | 7/2019 | McClintock et al. |
| 10,376,372 B2 | 8/2019 | Serhan et al. |
| 10,398,563 B2 | 9/2019 | Engstrom |
| 10,398,566 B2 * | 9/2019 | Olmos .................. A61F 2/447 |
| 10,405,986 B2 | 9/2019 | Kelly et al. |
| 10,405,989 B2 | 9/2019 | O'Neil et al. |
| 10,420,651 B2 | 9/2019 | Serhan et al. |
| 10,426,632 B2 | 10/2019 | Butler et al. |
| 10,433,971 B2 | 10/2019 | DiMauro et al. |
| 10,433,974 B2 | 10/2019 | O'Neil |
| 10,433,977 B2 | 10/2019 | Lechmann et al. |
| 10,449,056 B2 | 10/2019 | Cain |
| 10,449,058 B2 | 10/2019 | Lechmann et al. |
| 10,470,894 B2 | 11/2019 | Foley et al. |
| 10,492,918 B2 | 12/2019 | DiMauro |
| 10,492,924 B2 | 12/2019 | Stein et al. |
| 10,500,062 B2 | 12/2019 | Marchek et al. |
| 10,512,489 B2 | 12/2019 | Serhan et al. |
| 10,537,436 B2 | 1/2020 | Maguire et al. |
| 10,548,741 B2 | 2/2020 | Suedkamp et al. |
| 10,555,817 B2 | 2/2020 | DiMauro et al. |
| 10,575,959 B2 | 3/2020 | DiMauro et al. |
| 10,583,013 B2 | 3/2020 | DiMauro et al. |
| 10,583,015 B2 | 3/2020 | Olmos et al. |
| 10,639,164 B2 | 5/2020 | DiMauro et al. |
| 10,639,166 B2 | 5/2020 | Weiman |
| 10,682,241 B2 | 6/2020 | Glerum et al. |
| 10,743,914 B2 | 8/2020 | Lopez et al. |
| 10,758,371 B2 | 9/2020 | Hessler et al. |
| 10,842,644 B2 | 11/2020 | Weiman et al. |
| 10,888,433 B2 | 1/2021 | Frasier et al. |
| 10,966,840 B2 | 4/2021 | Voellmicke et al. |
| 10,973,652 B2 | 4/2021 | Hawkins et al. |
| 11,051,954 B2 | 7/2021 | Greenhalgh et al. |
| 11,103,362 B2 | 8/2021 | Butler et al. |
| 2001/0011174 A1 | 8/2001 | Reiley et al. |
| 2001/0012950 A1 | 8/2001 | Nishtala et al. |
| 2001/0016741 A1 | 8/2001 | Burkus et al. |
| 2001/0016775 A1 | 8/2001 | Scarborough et al. |
| 2001/0027320 A1 | 10/2001 | Sasso |
| 2001/0032020 A1 | 10/2001 | Besselink |
| 2001/0037126 A1 | 11/2001 | Stack et al. |
| 2001/0039452 A1 | 11/2001 | Zucherman et al. |
| 2001/0039453 A1 | 11/2001 | Gresser et al. |
| 2001/0049529 A1 | 12/2001 | Cachia et al. |
| 2001/0049530 A1 | 12/2001 | Culbert et al. |
| 2001/0049531 A1 | 12/2001 | Reiley et al. |
| 2001/0056302 A1 | 12/2001 | Boyer et al. |
| 2002/0001476 A1 | 1/2002 | Nagamine et al. |
| 2002/0010070 A1 | 1/2002 | Cales et al. |
| 2002/0016583 A1 | 2/2002 | Cragg |
| 2002/0026195 A1 | 2/2002 | Layne et al. |
| 2002/0026244 A1 | 2/2002 | Tried |
| 2002/0029084 A1 | 3/2002 | Paul et al. |
| 2002/0032462 A1 | 3/2002 | Houser et al. |
| 2002/0032483 A1 | 3/2002 | Nicholson et al. |
| 2002/0035400 A1 | 3/2002 | Bryan et al. |
| 2002/0037799 A1 | 3/2002 | Li et al. |
| 2002/0045904 A1 | 4/2002 | Fuss et al. |
| 2002/0045942 A1 | 4/2002 | Ham |
| 2002/0045943 A1 | 4/2002 | Uk |
| 2002/0055740 A1 | 5/2002 | Lieberman |
| 2002/0055781 A1 | 5/2002 | Sazy |
| 2002/0058947 A1 | 5/2002 | Hochschuler et al. |
| 2002/0068974 A1 | 6/2002 | Kuslich et al. |
| 2002/0068976 A1 | 6/2002 | Jackson |
| 2002/0068977 A1 | 6/2002 | Jackson |
| 2002/0072801 A1 | 6/2002 | Michelson |
| 2002/0077700 A1 | 6/2002 | Marga et al. |
| 2002/0077701 A1 | 6/2002 | Kuslich |
| 2002/0082584 A1 | 6/2002 | Rosenman et al. |
| 2002/0082608 A1 | 6/2002 | Reiley et al. |
| 2002/0087152 A1 | 7/2002 | Mikus et al. |
| 2002/0087163 A1 | 7/2002 | Dixon et al. |
| 2002/0091387 A1 | 7/2002 | Hoogland |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0120335 A1 | 8/2002 | Angelucci et al. |
| 2002/0128713 A1 | 9/2002 | Ferree |
| 2002/0128715 A1 | 9/2002 | Bryan et al. |
| 2002/0128716 A1 | 9/2002 | Cohen et al. |
| 2002/0138078 A1 | 9/2002 | Chappuis |
| 2002/0138146 A1 | 9/2002 | Jackson |
| 2002/0143331 A1 | 10/2002 | Zucherman et al. |
| 2002/0143334 A1 | 10/2002 | Hoffmann et al. |
| 2002/0143335 A1 | 10/2002 | Von et al. |
| 2002/0151895 A1 | 10/2002 | Soboleski et al. |

(56) References Cited

U.S. PATENT DOCUMENTS

| | | |
|---|---|---|
| 2002/0151976 A1 | 10/2002 | Foley et al. |
| 2002/0156482 A1 | 10/2002 | Scribner et al. |
| 2002/0161444 A1 | 10/2002 | Choi |
| 2002/0165612 A1 | 11/2002 | Gerber et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson et al. |
| 2002/0183778 A1 | 12/2002 | Reiley et al. |
| 2002/0183848 A1 | 12/2002 | Ray et al. |
| 2002/0191487 A1 | 12/2002 | Sand |
| 2002/0193883 A1 | 12/2002 | Wironen |
| 2002/0198526 A1 | 12/2002 | Shaolian et al. |
| 2003/0004575 A1 | 1/2003 | Erickson |
| 2003/0004576 A1 | 1/2003 | Thalgott |
| 2003/0006942 A1 | 1/2003 | Searls et al. |
| 2003/0014112 A1 | 1/2003 | Ralph et al. |
| 2003/0014113 A1 | 1/2003 | Ralph et al. |
| 2003/0014116 A1 | 1/2003 | Ralph et al. |
| 2003/0018390 A1 | 1/2003 | Husson |
| 2003/0023305 A1 | 1/2003 | McKay |
| 2003/0028250 A1 | 2/2003 | Reiley et al. |
| 2003/0028251 A1 | 2/2003 | Mathews |
| 2003/0032963 A1 | 2/2003 | Reiss et al. |
| 2003/0040796 A1 | 2/2003 | Ferree |
| 2003/0040799 A1 | 2/2003 | Boyd et al. |
| 2003/0045937 A1 | 3/2003 | Ginn |
| 2003/0045939 A1 | 3/2003 | Casutt |
| 2003/0050644 A1 | 3/2003 | Boucher et al. |
| 2003/0063582 A1 | 4/2003 | Mizell et al. |
| 2003/0065330 A1 | 4/2003 | Zucherman et al. |
| 2003/0065396 A1 | 4/2003 | Michelson |
| 2003/0069582 A1 | 4/2003 | Culbert |
| 2003/0069593 A1 | 4/2003 | Tremulis et al. |
| 2003/0069642 A1 | 4/2003 | Ralph et al. |
| 2003/0073998 A1 | 4/2003 | Pagliuca et al. |
| 2003/0074063 A1 | 4/2003 | Gerbec et al. |
| 2003/0074075 A1 | 4/2003 | Thomas et al. |
| 2003/0078667 A1 | 4/2003 | Asas et al. |
| 2003/0083642 A1 | 5/2003 | Boyd et al. |
| 2003/0083688 A1 | 5/2003 | Simonson |
| 2003/0108588 A1 | 6/2003 | Chen et al. |
| 2003/0130664 A1 | 7/2003 | Boucher et al. |
| 2003/0130739 A1 | 7/2003 | Gerbec et al. |
| 2003/0135275 A1 | 7/2003 | Garcia et al. |
| 2003/0139648 A1 | 7/2003 | Foley et al. |
| 2003/0139812 A1 | 7/2003 | Garcia et al. |
| 2003/0139813 A1 | 7/2003 | Messerli et al. |
| 2003/0153874 A1 | 8/2003 | Tal |
| 2003/0171812 A1 | 9/2003 | Grunberg et al. |
| 2003/0187431 A1 | 10/2003 | Simonson |
| 2003/0187445 A1 | 10/2003 | Keith et al. |
| 2003/0187506 A1 | 10/2003 | Ross et al. |
| 2003/0191414 A1 | 10/2003 | Reiley et al. |
| 2003/0191489 A1 | 10/2003 | Reiley et al. |
| 2003/0191531 A1 | 10/2003 | Berry et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin |
| 2003/0204261 A1 | 10/2003 | Eisermann et al. |
| 2003/0208122 A1 | 11/2003 | Melkent et al. |
| 2003/0208136 A1 | 11/2003 | Mark et al. |
| 2003/0208203 A1 | 11/2003 | Lim et al. |
| 2003/0208220 A1 | 11/2003 | Worley et al. |
| 2003/0208270 A9 | 11/2003 | Michelson |
| 2003/0220643 A1 | 11/2003 | Ferree |
| 2003/0220648 A1 | 11/2003 | Osorio et al. |
| 2003/0220695 A1 | 11/2003 | Sevrain |
| 2003/0229350 A1 | 12/2003 | Kay |
| 2003/0229372 A1 | 12/2003 | Reiley et al. |
| 2003/0233096 A1 | 12/2003 | Osorio et al. |
| 2003/0233102 A1 | 12/2003 | Nakamura et al. |
| 2003/0233145 A1 | 12/2003 | Landry et al. |
| 2003/0233146 A1 | 12/2003 | Grinberg et al. |
| 2004/0002761 A1 | 1/2004 | Rogers et al. |
| 2004/0006391 A1 | 1/2004 | Reiley |
| 2004/0008949 A1 | 1/2004 | Liu et al. |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0010318 A1 | 1/2004 | Ferree |
| 2004/0019354 A1 | 1/2004 | Johnson et al. |
| 2004/0019359 A1 | 1/2004 | Worley et al. |
| 2004/0024408 A1 | 2/2004 | Burkus et al. |
| 2004/0024409 A1 | 2/2004 | Sand et al. |
| 2004/0024410 A1 | 2/2004 | Olson et al. |
| 2004/0024463 A1 | 2/2004 | Thomas et al. |
| 2004/0024465 A1 | 2/2004 | Lambrecht et al. |
| 2004/0030387 A1 | 2/2004 | Landry et al. |
| 2004/0034343 A1 | 2/2004 | Gillespie et al. |
| 2004/0034429 A1 | 2/2004 | Lambrecht et al. |
| 2004/0049190 A1 | 3/2004 | Biedermann et al. |
| 2004/0049203 A1 | 3/2004 | Scribner et al. |
| 2004/0049223 A1 | 3/2004 | Nishtala et al. |
| 2004/0049270 A1 | 3/2004 | Gewirtz |
| 2004/0054412 A1 | 3/2004 | Gerbec et al. |
| 2004/0059333 A1 | 3/2004 | Carl et al. |
| 2004/0059337 A1 | 3/2004 | Hanson et al. |
| 2004/0059339 A1 | 3/2004 | Roehm et al. |
| 2004/0059350 A1 | 3/2004 | Gordon et al. |
| 2004/0059418 A1 | 3/2004 | McKay et al. |
| 2004/0064144 A1 | 4/2004 | Johnson et al. |
| 2004/0068269 A1 | 4/2004 | Bonati et al. |
| 2004/0073213 A1 | 4/2004 | Serhan et al. |
| 2004/0073308 A1 | 4/2004 | Kuslich et al. |
| 2004/0073310 A1 | 4/2004 | Moumene et al. |
| 2004/0082953 A1 | 4/2004 | Petit |
| 2004/0083000 A1 | 4/2004 | Keller et al. |
| 2004/0087947 A1 | 5/2004 | Lim et al. |
| 2004/0088055 A1 | 5/2004 | Hanson et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0093083 A1 | 5/2004 | Branch et al. |
| 2004/0097924 A1 | 5/2004 | Lambrecht et al. |
| 2004/0097930 A1 | 5/2004 | Justis et al. |
| 2004/0097932 A1 | 5/2004 | Ray et al. |
| 2004/0097941 A1 | 5/2004 | Weiner et al. |
| 2004/0097973 A1 | 5/2004 | Loshakove et al. |
| 2004/0098131 A1 | 5/2004 | Bryan et al. |
| 2004/0102774 A1 | 5/2004 | Trieu |
| 2004/0102784 A1 | 5/2004 | Pasquet et al. |
| 2004/0102846 A1 | 5/2004 | Keller et al. |
| 2004/0106925 A1 | 6/2004 | Brads |
| 2004/0106940 A1 | 6/2004 | Shaolian et al. |
| 2004/0111161 A1 | 6/2004 | Trieu |
| 2004/0116997 A1 | 6/2004 | Taylor et al. |
| 2004/0117019 A1 | 6/2004 | Trieu et al. |
| 2004/0117022 A1 | 6/2004 | Marnay et al. |
| 2004/0127906 A1 | 7/2004 | Culbert et al. |
| 2004/0127990 A1 | 7/2004 | Bartish et al. |
| 2004/0127991 A1 | 7/2004 | Ferree |
| 2004/0133124 A1 | 7/2004 | Bates et al. |
| 2004/0133229 A1 | 7/2004 | Lambrecht et al. |
| 2004/0133279 A1 | 7/2004 | Krueger et al. |
| 2004/0133280 A1 | 7/2004 | Trieu |
| 2004/0138748 A1 | 7/2004 | Boyer et al. |
| 2004/0143284 A1 | 7/2004 | Chin |
| 2004/0143332 A1 | 7/2004 | Krueger et al. |
| 2004/0143734 A1 | 7/2004 | Buer et al. |
| 2004/0147129 A1 | 7/2004 | Rolfson |
| 2004/0147877 A1 | 7/2004 | Heuser |
| 2004/0147950 A1 | 7/2004 | Mueller et al. |
| 2004/0148027 A1 | 7/2004 | Errico et al. |
| 2004/0153064 A1 | 8/2004 | Foley et al. |
| 2004/0153065 A1 | 8/2004 | Lim |
| 2004/0153115 A1 | 8/2004 | Reiley et al. |
| 2004/0153156 A1 | 8/2004 | Cohen et al. |
| 2004/0153160 A1 | 8/2004 | Carrasco |
| 2004/0158206 A1 | 8/2004 | Aboul-Hosn et al. |
| 2004/0158258 A1 | 8/2004 | Bonati et al. |

(56) References Cited

U.S. PATENT DOCUMENTS

| | | |
|---|---|---|
| 2004/0162617 A1 | 8/2004 | Zucherman et al. |
| 2004/0162618 A1 | 8/2004 | Mujwid et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0172133 A1 | 9/2004 | Gerber et al. |
| 2004/0172134 A1 | 9/2004 | Berry |
| 2004/0176775 A1 | 9/2004 | Burkus et al. |
| 2004/0186052 A1 | 9/2004 | Iyer et al. |
| 2004/0186471 A1 | 9/2004 | Trieu |
| 2004/0186482 A1 | 9/2004 | Kolb et al. |
| 2004/0186528 A1 | 9/2004 | Ries et al. |
| 2004/0186570 A1 | 9/2004 | Rapp |
| 2004/0186573 A1 | 9/2004 | Ferree |
| 2004/0186577 A1 | 9/2004 | Ferree |
| 2004/0193271 A1 | 9/2004 | Fraser et al. |
| 2004/0193277 A1 | 9/2004 | Long et al. |
| 2004/0199162 A1 | 10/2004 | Von et al. |
| 2004/0210231 A1 | 10/2004 | Boucher et al. |
| 2004/0210310 A1 | 10/2004 | Trieu |
| 2004/0215343 A1 | 10/2004 | Hochschdler et al. |
| 2004/0215344 A1 | 10/2004 | Hochschdler et al. |
| 2004/0220580 A1 | 11/2004 | Johnson et al. |
| 2004/0220668 A1 | 11/2004 | Eisermann et al. |
| 2004/0220669 A1 | 11/2004 | Studer |
| 2004/0220672 A1 | 11/2004 | Shadduck |
| 2004/0225292 A1 | 11/2004 | Sasso et al. |
| 2004/0225296 A1 | 11/2004 | Reiss et al. |
| 2004/0225361 A1 | 11/2004 | Glenn et al. |
| 2004/0230191 A1 | 11/2004 | Frey et al. |
| 2004/0230309 A1 | 11/2004 | DiMauro et al. |
| 2004/0243229 A1 | 12/2004 | Mdlund et al. |
| 2004/0243239 A1 | 12/2004 | Taylor |
| 2004/0243241 A1 | 12/2004 | Istephanous et al. |
| 2004/0249377 A1 | 12/2004 | Kaes et al. |
| 2004/0249461 A1 | 12/2004 | Ferree |
| 2004/0249466 A1 | 12/2004 | Liu et al. |
| 2004/0254520 A1 | 12/2004 | Porteous et al. |
| 2004/0254575 A1 | 12/2004 | Obenchain et al. |
| 2004/0254643 A1 | 12/2004 | Jackson |
| 2004/0254644 A1 | 12/2004 | Taylor |
| 2004/0260297 A1 | 12/2004 | Padget et al. |
| 2004/0260300 A1 | 12/2004 | Gorensek et al. |
| 2004/0260397 A1 | 12/2004 | Lambrecht et al. |
| 2004/0266257 A1 | 12/2004 | Ries et al. |
| 2004/0267271 A9 | 12/2004 | Scribner et al. |
| 2004/0267367 A1 | 12/2004 | O'Neil |
| 2005/0004578 A1 | 1/2005 | Lambrecht et al. |
| 2005/0010292 A1 | 1/2005 | Carrasco |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0019365 A1 | 1/2005 | Frauchiger et al. |
| 2005/0021041 A1 | 1/2005 | Michelson |
| 2005/0033289 A1 | 2/2005 | Warren et al. |
| 2005/0033295 A1 | 2/2005 | Wisnewski |
| 2005/0033434 A1 | 2/2005 | Berry |
| 2005/0033440 A1 | 2/2005 | Lambrecht et al. |
| 2005/0038431 A1 | 2/2005 | Bartish et al. |
| 2005/0038515 A1 | 2/2005 | Kunzler |
| 2005/0038517 A1 | 2/2005 | Garrison et al. |
| 2005/0043737 A1 | 2/2005 | Reiley et al. |
| 2005/0043796 A1 | 2/2005 | Grant et al. |
| 2005/0043800 A1 | 2/2005 | Paul et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0065610 A1 | 3/2005 | Pisharodi |
| 2005/0069571 A1 | 3/2005 | Slivka et al. |
| 2005/0070908 A1 | 3/2005 | Cragg |
| 2005/0070911 A1 | 3/2005 | Carrison et al. |
| 2005/0070913 A1 | 3/2005 | Milbocker et al. |
| 2005/0071011 A1 | 3/2005 | Ralph et al. |
| 2005/0080443 A1 | 4/2005 | Fallin et al. |
| 2005/0080488 A1 | 4/2005 | Schultz |
| 2005/0085912 A1 | 4/2005 | Arnin et al. |
| 2005/0090443 A1 | 4/2005 | Michael |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0096745 A1 | 5/2005 | Andre et al. |
| 2005/0102202 A1 | 5/2005 | Linden et al. |
| 2005/0107880 A1 | 5/2005 | Shimp et al. |
| 2005/0113916 A1 | 5/2005 | Branch |
| 2005/0113917 A1 | 5/2005 | Chae et al. |
| 2005/0113918 A1 | 5/2005 | Messerli et al. |
| 2005/0113919 A1 | 5/2005 | Cragg et al. |
| 2005/0113927 A1 | 5/2005 | Malek |
| 2005/0113928 A1 | 5/2005 | Cragg et al. |
| 2005/0118228 A1 | 6/2005 | Trieu |
| 2005/0118550 A1 | 6/2005 | Achille |
| 2005/0119657 A1 | 6/2005 | Goldsmith |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Feitelbaum et al. |
| 2005/0125061 A1 | 6/2005 | Zucherman et al. |
| 2005/0125062 A1 | 6/2005 | Biedermann et al. |
| 2005/0125066 A1 | 6/2005 | McAfee |
| 2005/0130929 A1 | 6/2005 | Boyd |
| 2005/0131267 A1 | 6/2005 | Falmadge |
| 2005/0131268 A1 | 6/2005 | Falmadge |
| 2005/0131269 A1 | 6/2005 | Falmadge |
| 2005/0131406 A1 | 6/2005 | Reiley et al. |
| 2005/0131409 A1 | 6/2005 | Chervitz et al. |
| 2005/0131411 A1 | 6/2005 | Culbert |
| 2005/0131536 A1 | 6/2005 | Eisermann et al. |
| 2005/0131538 A1 | 6/2005 | Chervitz et al. |
| 2005/0131540 A1 | 6/2005 | Trieu |
| 2005/0131541 A1 | 6/2005 | Trieu |
| 2005/0137595 A1 | 6/2005 | Hoffmann et al. |
| 2005/0137602 A1 | 6/2005 | Assell et al. |
| 2005/0142211 A1 | 6/2005 | Wenz |
| 2005/0143734 A1 | 6/2005 | Cachia et al. |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149030 A1 | 7/2005 | Serhan et al. |
| 2005/0149034 A1 | 7/2005 | Assell et al. |
| 2005/0149191 A1 | 7/2005 | Cragg et al. |
| 2005/0149194 A1 | 7/2005 | Ahlgren |
| 2005/0149197 A1 | 7/2005 | Cadthen |
| 2005/0154396 A1 | 7/2005 | Foley et al. |
| 2005/0154463 A1 | 7/2005 | Trieu |
| 2005/0154467 A1 | 7/2005 | Peterman et al. |
| 2005/0165398 A1 | 7/2005 | Reiley |
| 2005/0165406 A1 | 7/2005 | Assell et al. |
| 2005/0165420 A1 | 7/2005 | Cha |
| 2005/0165484 A1 | 7/2005 | Ferree |
| 2005/0165485 A1 | 7/2005 | Trieu |
| 2005/0171539 A1 | 8/2005 | Braun et al. |
| 2005/0171541 A1 | 8/2005 | Boehm et al. |
| 2005/0171552 A1 | 8/2005 | Johnson et al. |
| 2005/0171608 A1 | 8/2005 | Peterman et al. |
| 2005/0171610 A1 | 8/2005 | Humphreys et al. |
| 2005/0177173 A1 | 8/2005 | Aebi et al. |
| 2005/0177235 A1 | 8/2005 | Baynham et al. |
| 2005/0177240 A1 | 8/2005 | Blain |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0182418 A1 | 8/2005 | Boyd et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |

(56) References Cited

U.S. PATENT DOCUMENTS

| | | |
|---|---|---|
| 2005/0197702 A1 | 9/2005 | Coppes et al. |
| 2005/0197707 A1 | 9/2005 | Trieu et al. |
| 2005/0203512 A1 | 9/2005 | Hawkins et al. |
| 2005/0216018 A1 | 9/2005 | Sennett |
| 2005/0216026 A1 | 9/2005 | Brads |
| 2005/0216081 A1 | 9/2005 | Taylor |
| 2005/0216087 A1 | 9/2005 | Zucherman et al. |
| 2005/0222681 A1 | 10/2005 | Richley et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251142 A1 | 11/2005 | Hoffmann et al. |
| 2005/0251149 A1 | 11/2005 | Wenz |
| 2005/0251260 A1 | 11/2005 | Gerber et al. |
| 2005/0256525 A1 | 11/2005 | Culbert et al. |
| 2005/0256576 A1 | 11/2005 | Moskowitz et al. |
| 2005/0261682 A1 | 11/2005 | Ferree |
| 2005/0261684 A1 | 11/2005 | Shaolian et al. |
| 2005/0261695 A1 | 11/2005 | Cragg et al. |
| 2005/0261769 A1 | 11/2005 | Moskowitz et al. |
| 2005/0261781 A1 | 11/2005 | Sennett et al. |
| 2005/0267471 A1 | 12/2005 | Biedermann et al. |
| 2005/0273166 A1 | 12/2005 | Sweeney |
| 2005/0273173 A1 | 12/2005 | Gordon et al. |
| 2005/0277938 A1 | 12/2005 | Parsons |
| 2005/0278023 A1 | 12/2005 | Zwirkoski |
| 2005/0278026 A1 | 12/2005 | Gordon et al. |
| 2005/0278027 A1 | 12/2005 | Hyde |
| 2005/0278029 A1 | 12/2005 | Trieu |
| 2005/0283238 A1 | 12/2005 | Reiley |
| 2005/0283244 A1 | 12/2005 | Gordon et al. |
| 2005/0287071 A1 | 12/2005 | Wenz |
| 2006/0004326 A1 | 1/2006 | Collins et al. |
| 2006/0004456 A1 | 1/2006 | McKay |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009851 A1 | 1/2006 | Collins et al. |
| 2006/0015105 A1 | 1/2006 | Warren et al. |
| 2006/0015119 A1 | 1/2006 | Plassky et al. |
| 2006/0020284 A1 | 1/2006 | Foley et al. |
| 2006/0022180 A1 | 2/2006 | Selness |
| 2006/0030850 A1 | 2/2006 | Keegan et al. |
| 2006/0030872 A1 | 2/2006 | Culbert et al. |
| 2006/0030933 A1 | 2/2006 | Delegge et al. |
| 2006/0030943 A1 | 2/2006 | Peterman |
| 2006/0032621 A1 | 2/2006 | Martin et al. |
| 2006/0036241 A1 | 2/2006 | Siegal |
| 2006/0036244 A1 | 2/2006 | Spitler et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036261 A1 | 2/2006 | McDonnell |
| 2006/0036273 A1 | 2/2006 | Siegal |
| 2006/0036323 A1 | 2/2006 | Carl et al. |
| 2006/0036324 A1 | 2/2006 | Sachs et al. |
| 2006/0041258 A1 | 2/2006 | Galea |
| 2006/0041314 A1 | 2/2006 | Millard |
| 2006/0045904 A1 | 3/2006 | Aronson |
| 2006/0058790 A1 | 3/2006 | Carl et al. |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0064101 A1 | 3/2006 | Arramon |
| 2006/0064102 A1 | 3/2006 | Ebner |
| 2006/0064171 A1 | 3/2006 | Trieu |
| 2006/0064172 A1 | 3/2006 | Trieu |
| 2006/0069436 A1 | 3/2006 | Sutton et al. |
| 2006/0069439 A1 | 3/2006 | Zucherman et al. |
| 2006/0069440 A1 | 3/2006 | Zucherman et al. |
| 2006/0074429 A1 | 4/2006 | Ralph et al. |
| 2006/0079908 A1 | 4/2006 | Lieberman |
| 2006/0084867 A1 | 4/2006 | Tremblay et al. |
| 2006/0084977 A1 | 4/2006 | Lieberman |
| 2006/0084988 A1 | 4/2006 | Kim |
| 2006/0085002 A1 | 4/2006 | Trieu et al. |
| 2006/0085009 A1 | 4/2006 | Truckai et al. |
| 2006/0085010 A1 | 4/2006 | Lieberman |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100622 A1 | 5/2006 | Jackson |
| 2006/0100706 A1 | 5/2006 | Shadduck et al. |
| 2006/0100707 A1 | 5/2006 | Stinson et al. |
| 2006/0106381 A1 | 5/2006 | Ferree et al. |
| 2006/0106397 A1 | 5/2006 | Lins |
| 2006/0106459 A1 | 5/2006 | Truckai et al. |
| 2006/0111715 A1 | 5/2006 | Jackson |
| 2006/0111728 A1 | 5/2006 | Abdou |
| 2006/0111785 A1 | 5/2006 | O'Neil |
| 2006/0119629 A1 | 6/2006 | An et al. |
| 2006/0122609 A1 | 6/2006 | Mirkovic et al. |
| 2006/0122610 A1 | 6/2006 | Culbert et al. |
| 2006/0122701 A1 | 6/2006 | Kiester |
| 2006/0122703 A1 | 6/2006 | Aebi et al. |
| 2006/0122704 A1 | 6/2006 | Vresilovic et al. |
| 2006/0129244 A1 | 6/2006 | Ensign |
| 2006/0136062 A1 | 6/2006 | DiNello et al. |
| 2006/0136064 A1 | 6/2006 | Sherman |
| 2006/0142759 A1 | 6/2006 | Amin et al. |
| 2006/0142765 A9 | 6/2006 | Dixon et al. |
| 2006/0142776 A1 | 6/2006 | Iwanari |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149229 A1 | 7/2006 | Kwak et al. |
| 2006/0149237 A1 | 7/2006 | Markworth et al. |
| 2006/0149252 A1 | 7/2006 | Markworth et al. |
| 2006/0149379 A1 | 7/2006 | Kuslich et al. |
| 2006/0149380 A1 | 7/2006 | Lotz et al. |
| 2006/0149385 A1 | 7/2006 | McKay |
| 2006/0155379 A1 | 7/2006 | Heneveld et al. |
| 2006/0161162 A1 | 7/2006 | Lambrecht et al. |
| 2006/0161166 A1 | 7/2006 | Johnson et al. |
| 2006/0167547 A1 | 7/2006 | Suddaby |
| 2006/0167553 A1 | 7/2006 | Cauthen et al. |
| 2006/0173545 A1 | 8/2006 | Cauthen et al. |
| 2006/0178743 A1 | 8/2006 | Carter |
| 2006/0178745 A1 | 8/2006 | Bartish et al. |
| 2006/0178746 A1 | 8/2006 | Bartish et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnin et al. |
| 2006/0190085 A1 | 8/2006 | Cauthen |
| 2006/0195102 A1 | 8/2006 | Malandain |
| 2006/0195103 A1 | 8/2006 | Padget et al. |
| 2006/0195191 A1 | 8/2006 | Sweeney et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |

(56) References Cited

U.S. PATENT DOCUMENTS

| | | |
|---|---|---|
| 2006/0206207 A1 | 9/2006 | Dryer et al. |
| 2006/0212118 A1 | 9/2006 | Abernathie |
| 2006/0217711 A1 | 9/2006 | Stevens et al. |
| 2006/0229627 A1 | 10/2006 | Hunt et al. |
| 2006/0229629 A1 | 10/2006 | Manzi et al. |
| 2006/0235403 A1 | 10/2006 | Blain |
| 2006/0235412 A1 | 10/2006 | Blain |
| 2006/0235423 A1 | 10/2006 | Cantu |
| 2006/0235521 A1 | 10/2006 | Zucherman et al. |
| 2006/0235531 A1 | 10/2006 | Buettner-Janz |
| 2006/0241643 A1 | 10/2006 | Lim et al. |
| 2006/0241663 A1 | 10/2006 | Rice et al. |
| 2006/0241770 A1 | 10/2006 | Rhoda et al. |
| 2006/0247634 A1 | 11/2006 | Warner et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0253120 A1 | 11/2006 | Anderson et al. |
| 2006/0253201 A1 | 11/2006 | McLuen |
| 2006/0254784 A1 | 11/2006 | Hartmann et al. |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265075 A1 | 11/2006 | Baumgartner et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow et al. |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal et al. |
| 2006/0293662 A1 | 12/2006 | Boyer et al. |
| 2006/0293663 A1 | 12/2006 | Walkenhorst et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010826 A1 | 1/2007 | Rhoda et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010886 A1 | 1/2007 | Banick et al. |
| 2007/0010889 A1 | 1/2007 | Francis |
| 2007/0016191 A1 | 1/2007 | Culbert et al. |
| 2007/0032703 A1 | 2/2007 | Sankaran et al. |
| 2007/0032790 A1 | 2/2007 | Aschmann et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0043440 A1 | 2/2007 | William et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055236 A1 | 3/2007 | Hudgins et al. |
| 2007/0055237 A1 | 3/2007 | Edidin et al. |
| 2007/0055246 A1 | 3/2007 | Zucherman et al. |
| 2007/0055264 A1 | 3/2007 | Parmigiani |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0055377 A1 | 3/2007 | Hanson et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0067035 A1 | 3/2007 | Falahee |
| 2007/0068329 A1 | 3/2007 | Phan et al. |
| 2007/0073292 A1 | 3/2007 | Kohm et al. |
| 2007/0073399 A1 | 3/2007 | Zipnick et al. |
| 2007/0078436 A1 | 4/2007 | Leung et al. |
| 2007/0078463 A1 | 4/2007 | Malandain |
| 2007/0093689 A1 | 4/2007 | Steinberg |
| 2007/0093897 A1 | 4/2007 | Gerbec et al. |
| 2007/0093899 A1 | 4/2007 | Dutoit et al. |
| 2007/0093901 A1 | 4/2007 | Grotz et al. |
| 2007/0093906 A1 | 4/2007 | Hudgins et al. |
| 2007/0118132 A1 | 5/2007 | Culbert et al. |
| 2007/0118222 A1 | 5/2007 | Lang |
| 2007/0118223 A1 | 5/2007 | Allard et al. |
| 2007/0123868 A1 | 5/2007 | Culbert et al. |
| 2007/0123891 A1 | 5/2007 | Ries et al. |
| 2007/0123892 A1 | 5/2007 | Ries et al. |
| 2007/0123986 A1 | 5/2007 | Schaller |
| 2007/0129730 A1 | 6/2007 | Woods et al. |
| 2007/0135922 A1 | 6/2007 | Trieu |
| 2007/0142843 A1 | 6/2007 | Dye |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0161992 A1 | 7/2007 | Kwak et al. |
| 2007/0162005 A1 | 7/2007 | Peterson et al. |
| 2007/0162127 A1 | 7/2007 | Peterman et al. |
| 2007/0162132 A1 | 7/2007 | Messerli |
| 2007/0162138 A1 | 7/2007 | Heinz |
| 2007/0167945 A1 | 7/2007 | Lange et al. |
| 2007/0168036 A1 | 7/2007 | Ainsworth et al. |
| 2007/0168038 A1 | 7/2007 | Trieu |
| 2007/0173939 A1 | 7/2007 | Kim et al. |
| 2007/0173940 A1 | 7/2007 | Hestad et al. |
| 2007/0178222 A1 | 8/2007 | Storey et al. |
| 2007/0179612 A1 | 8/2007 | Johnson et al. |
| 2007/0179615 A1 | 8/2007 | Heinz et al. |
| 2007/0179616 A1 | 8/2007 | Braddock et al. |
| 2007/0179618 A1 | 8/2007 | Trieu et al. |
| 2007/0185578 A1 | 8/2007 | O'Neil et al. |
| 2007/0191953 A1 | 8/2007 | Trieu |
| 2007/0191954 A1 | 8/2007 | Hansell et al. |
| 2007/0191959 A1 | 8/2007 | Hartmann et al. |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0198089 A1 | 8/2007 | Moskowitz et al. |
| 2007/0203491 A1 | 8/2007 | Pasquet et al. |
| 2007/0208423 A1 | 9/2007 | Messerli et al. |
| 2007/0208426 A1 | 9/2007 | Trieu |
| 2007/0213717 A1 | 9/2007 | Trieu et al. |
| 2007/0213737 A1 | 9/2007 | Schermerhorn et al. |
| 2007/0213826 A1 | 9/2007 | Smith et al. |
| 2007/0219634 A1 | 9/2007 | Greenhalgh et al. |
| 2007/0225706 A1 | 9/2007 | Clark et al. |
| 2007/0225726 A1 | 9/2007 | Dye et al. |
| 2007/0225807 A1 | 9/2007 | Phan et al. |
| 2007/0225815 A1 | 9/2007 | Keith et al. |
| 2007/0233074 A1 | 10/2007 | Anderson et al. |
| 2007/0233076 A1 | 10/2007 | Tried |
| 2007/0233083 A1 | 10/2007 | Abdou |
| 2007/0233089 A1 | 10/2007 | DiPoto et al. |
| 2007/0233130 A1 | 10/2007 | Suddaby |
| 2007/0233244 A1 | 10/2007 | Lopez et al. |
| 2007/0233254 A1 | 10/2007 | Grotz et al. |

(56) References Cited

U.S. PATENT DOCUMENTS

| | | |
|---|---|---|
| 2007/0250167 A1 | 10/2007 | Bray et al. |
| 2007/0260245 A1 | 11/2007 | Malandain et al. |
| 2007/0260255 A1 | 11/2007 | Haddock et al. |
| 2007/0260314 A1 | 11/2007 | Biyani |
| 2007/0270823 A1 | 11/2007 | Tried et al. |
| 2007/0270954 A1 | 11/2007 | Wu |
| 2007/0270957 A1 | 11/2007 | Heinz |
| 2007/0270968 A1 | 11/2007 | Baynham et al. |
| 2007/0276373 A1 | 11/2007 | Malandain |
| 2007/0276375 A1 | 11/2007 | Rapp |
| 2007/0276497 A1 | 11/2007 | Anderson |
| 2007/0282443 A1 | 12/2007 | Globerman et al. |
| 2007/0282449 A1 | 12/2007 | De et al. |
| 2007/0288091 A1 | 12/2007 | Braddock et al. |
| 2007/0299521 A1 | 12/2007 | Glenn et al. |
| 2008/0009877 A1 | 1/2008 | Sankaran et al. |
| 2008/0015694 A1 | 1/2008 | Tribus |
| 2008/0015701 A1 | 1/2008 | Garcia et al. |
| 2008/0021556 A1 | 1/2008 | Edie |
| 2008/0021557 A1 | 1/2008 | Trieu |
| 2008/0021558 A1 | 1/2008 | Thramann |
| 2008/0021559 A1 | 1/2008 | Thramann |
| 2008/0027437 A1 | 1/2008 | Johnson et al. |
| 2008/0027438 A1 | 1/2008 | Abdou |
| 2008/0027453 A1 | 1/2008 | Johnson et al. |
| 2008/0027454 A1 | 1/2008 | Johnson et al. |
| 2008/0027544 A1 | 1/2008 | Melkent |
| 2008/0027550 A1 | 1/2008 | Link et al. |
| 2008/0033440 A1 | 2/2008 | Moskowitz et al. |
| 2008/0045966 A1 | 2/2008 | Buttermann et al. |
| 2008/0051890 A1 | 2/2008 | Wadgh et al. |
| 2008/0051897 A1 | 2/2008 | Lopez et al. |
| 2008/0051902 A1 | 2/2008 | Dwyer |
| 2008/0058598 A1 | 3/2008 | Ries et al. |
| 2008/0058937 A1 | 3/2008 | Malandain et al. |
| 2008/0058944 A1 | 3/2008 | Duplessis et al. |
| 2008/0065082 A1 | 3/2008 | Chang et al. |
| 2008/0065219 A1 | 3/2008 | Dye |
| 2008/0071356 A1 | 3/2008 | Greenhalgh et al. |
| 2008/0071380 A1 | 3/2008 | Sweeney |
| 2008/0077148 A1 | 3/2008 | Ries et al. |
| 2008/0077150 A1 | 3/2008 | Nguyen |
| 2008/0077241 A1 | 3/2008 | Nguyen |
| 2008/0082172 A1 | 4/2008 | Jackson |
| 2008/0082173 A1 | 4/2008 | Delurio et al. |
| 2008/0097436 A1 | 4/2008 | Culbert et al. |
| 2008/0097454 A1 | 4/2008 | Deridder et al. |
| 2008/0097611 A1 | 4/2008 | Mastrorio et al. |
| 2008/0103601 A1 | 5/2008 | Biro et al. |
| 2008/0108990 A1 | 5/2008 | Mitchell et al. |
| 2008/0108996 A1 | 5/2008 | Padget et al. |
| 2008/0119935 A1 | 5/2008 | Alvarez |
| 2008/0125865 A1 | 5/2008 | Abdelgany |
| 2008/0132934 A1 | 6/2008 | Reiley et al. |
| 2008/0133012 A1 | 6/2008 | McGuckin |
| 2008/0133017 A1 | 6/2008 | Beyar et al. |
| 2008/0140085 A1 | 6/2008 | Gately et al. |
| 2008/0140207 A1 | 6/2008 | Olmos et al. |
| 2008/0147129 A1 | 6/2008 | Biedermann et al. |
| 2008/0147193 A1 | 6/2008 | Matthis et al. |
| 2008/0154377 A1 | 6/2008 | Voellmicke |
| 2008/0154379 A1 | 6/2008 | Steiner et al. |
| 2008/0161927 A1 | 7/2008 | Savage et al. |
| 2008/0167657 A1 | 7/2008 | Greenhalgh |
| 2008/0172128 A1 | 7/2008 | Perez-Cruet et al. |
| 2008/0177306 A1 | 7/2008 | Lamborne et al. |
| 2008/0177312 A1 | 7/2008 | Perez-Cruet et al. |
| 2008/0177388 A1 | 7/2008 | Patterson et al. |
| 2008/0183204 A1 | 7/2008 | Greenhalgh et al. |
| 2008/0188945 A1 | 8/2008 | Boyce et al. |
| 2008/0195096 A1 | 8/2008 | Frei |
| 2008/0195209 A1 | 8/2008 | Garcia et al. |
| 2008/0195210 A1 | 8/2008 | Milijasevic et al. |
| 2008/0208255 A1 | 8/2008 | Siegal |
| 2008/0208344 A1 | 8/2008 | Kilpela et al. |
| 2008/0221586 A1 | 9/2008 | Garcia-Bengochea et al. |
| 2008/0221687 A1 | 9/2008 | Viker |
| 2008/0228225 A1 | 9/2008 | Trautwein et al. |
| 2008/0229597 A1 | 9/2008 | Malandain |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243251 A1 | 10/2008 | Stad et al. |
| 2008/0243254 A1 | 10/2008 | Butler |
| 2008/0249622 A1 | 10/2008 | Gray |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0255618 A1 | 10/2008 | Fisher et al. |
| 2008/0262619 A1 | 10/2008 | Ray |
| 2008/0269904 A1 | 10/2008 | Voorhies |
| 2008/0281346 A1 | 11/2008 | Greenhalgh et al. |
| 2008/0281364 A1 | 11/2008 | Chirico et al. |
| 2008/0281425 A1 | 11/2008 | Thalgott et al. |
| 2008/0287981 A1 | 11/2008 | Culbert et al. |
| 2008/0287997 A1 | 11/2008 | Altarac et al. |
| 2008/0300685 A1 | 12/2008 | Carls et al. |
| 2008/0306537 A1 | 12/2008 | Culbert |
| 2008/0312743 A1 | 12/2008 | Vila et al. |
| 2008/0319477 A1 | 12/2008 | Justis et al. |
| 2009/0005870 A1 | 1/2009 | Hawkins et al. |
| 2009/0005873 A1 | 1/2009 | Slivka et al. |
| 2009/0018524 A1 | 1/2009 | Greenhalgh et al. |
| 2009/0030423 A1 | 1/2009 | Puno |
| 2009/0048631 A1 | 2/2009 | Bhatnagar et al. |
| 2009/0048678 A1 | 2/2009 | Saal et al. |
| 2009/0054898 A1 | 2/2009 | Gleason |
| 2009/0054911 A1 | 2/2009 | Mueller et al. |
| 2009/0054988 A1 | 2/2009 | Hess |
| 2009/0054991 A1 | 2/2009 | Biyani et al. |
| 2009/0062807 A1 | 3/2009 | Song |
| 2009/0069813 A1 | 3/2009 | Von et al. |
| 2009/0069895 A1 | 3/2009 | Sittings et al. |
| 2009/0076607 A1 | 3/2009 | Aalsma et al. |
| 2009/0076610 A1 | 3/2009 | Afzal |
| 2009/0088789 A1 | 4/2009 | O'Neil et al. |
| 2009/0099568 A1 | 4/2009 | Lowry et al. |
| 2009/0105712 A1 | 4/2009 | Dauster et al. |
| 2009/0105745 A1 | 4/2009 | Culbert |
| 2009/0112217 A1 | 4/2009 | Hester |
| 2009/0112320 A1 | 4/2009 | Kraus |
| 2009/0112324 A1 | 4/2009 | Refai et al. |
| 2009/0131986 A1 | 5/2009 | Lee et al. |
| 2009/0149857 A1 | 6/2009 | Culbert et al. |
| 2009/0164020 A1 | 6/2009 | Janowski et al. |
| 2009/0177281 A1 | 7/2009 | Swanson et al. |
| 2009/0177284 A1 | 7/2009 | Rogers et al. |
| 2009/0182429 A1 | 7/2009 | Humphreys et al. |
| 2009/0192613 A1 | 7/2009 | Wing et al. |
| 2009/0192614 A1 | 7/2009 | Beger et al. |
| 2009/0198339 A1 | 8/2009 | Kleiner et al. |
| 2009/0216234 A1 | 8/2009 | Farr et al. |
| 2009/0221967 A1 | 9/2009 | Thommen et al. |
| 2009/0222043 A1 | 9/2009 | Altarac et al. |
| 2009/0222096 A1 | 9/2009 | Trieu |
| 2009/0222099 A1 | 9/2009 | Liu et al. |
| 2009/0222100 A1 | 9/2009 | Cipoletti et al. |
| 2009/0234364 A1 | 9/2009 | Crook |
| 2009/0234389 A1 | 9/2009 | Chuang et al. |
| 2009/0234398 A1 | 9/2009 | Chirico et al. |
| 2009/0240333 A1 | 9/2009 | Trudeau et al. |
| 2009/0240334 A1 | 9/2009 | Richelsoph |
| 2009/0240335 A1 | 9/2009 | Arcenio et al. |
| 2009/0248159 A1 | 10/2009 | Aflatoon |
| 2009/0248163 A1 | 10/2009 | King et al. |
| 2009/0275890 A1 | 11/2009 | Leibowitz et al. |
| 2009/0276049 A1 | 11/2009 | Weiland |
| 2009/0276051 A1 | 11/2009 | Arramon et al. |
| 2009/0292361 A1 | 11/2009 | Lopez |
| 2009/0299479 A1 | 12/2009 | Jones et al. |
| 2010/0016905 A1 | 1/2010 | Greenhalgh et al. |
| 2010/0016968 A1 | 1/2010 | Moore |
| 2010/0030217 A1 | 2/2010 | Mitusina |
| 2010/0040332 A1 | 2/2010 | Van et al. |

(56) References Cited

U.S. PATENT DOCUMENTS

| | | |
|---|---|---|
| 2010/0042218 A1 | 2/2010 | Nebosky et al. |
| 2010/0049324 A1 | 2/2010 | Valdevit et al. |
| 2010/0070036 A1 | 3/2010 | Implicito |
| 2010/0076492 A1 | 3/2010 | Warner et al. |
| 2010/0076502 A1 | 3/2010 | Guyer et al. |
| 2010/0076559 A1 | 3/2010 | Bagga et al. |
| 2010/0082109 A1 | 4/2010 | Greenhalgh et al. |
| 2010/0094422 A1 | 4/2010 | Hansell et al. |
| 2010/0094424 A1 | 4/2010 | Woodburn et al. |
| 2010/0094426 A1 | 4/2010 | Grohowski et al. |
| 2010/0100098 A1 | 4/2010 | Norton et al. |
| 2010/0100183 A1 | 4/2010 | Prewett et al. |
| 2010/0106191 A1 | 4/2010 | Yue et al. |
| 2010/0114105 A1 | 5/2010 | Butters et al. |
| 2010/0114147 A1 | 5/2010 | Biyani |
| 2010/0125334 A1 | 5/2010 | Krueger |
| 2010/0174314 A1 | 7/2010 | Mirkovic et al. |
| 2010/0179594 A1 | 7/2010 | Theofilos et al. |
| 2010/0185290 A1 | 7/2010 | Compton et al. |
| 2010/0185292 A1 | 7/2010 | Hochschuler et al. |
| 2010/0191241 A1 | 7/2010 | Mccormack et al. |
| 2010/0191334 A1 | 7/2010 | Keller |
| 2010/0191336 A1 | 7/2010 | Greenhalgh |
| 2010/0204795 A1 | 8/2010 | Greenhalgh |
| 2010/0204796 A1 | 8/2010 | Bae et al. |
| 2010/0211107 A1 | 8/2010 | Muhanna |
| 2010/0211176 A1 | 8/2010 | Greenhalgh |
| 2010/0211182 A1 | 8/2010 | Zimmermann |
| 2010/0217269 A1 | 8/2010 | Landes |
| 2010/0222884 A1 | 9/2010 | Greenhalgh |
| 2010/0234849 A1 | 9/2010 | Bouadi |
| 2010/0234956 A1 | 9/2010 | Attia et al. |
| 2010/0241231 A1 | 9/2010 | Marino et al. |
| 2010/0249935 A1 | 9/2010 | Slivka et al. |
| 2010/0256768 A1 | 10/2010 | Lim et al. |
| 2010/0262240 A1 | 10/2010 | Chavatte et al. |
| 2010/0268231 A1 | 10/2010 | Kuslich et al. |
| 2010/0268338 A1 | 10/2010 | Melkent et al. |
| 2010/0274358 A1 | 10/2010 | Mueller et al. |
| 2010/0280619 A1 | 11/2010 | Yuan et al. |
| 2010/0286777 A1 | 11/2010 | Errico et al. |
| 2010/0286783 A1 | 11/2010 | Lechmann et al. |
| 2010/0292700 A1 | 11/2010 | Ries |
| 2010/0292796 A1 | 11/2010 | Greenhalgh et al. |
| 2010/0298938 A1 | 11/2010 | Humphreys et al. |
| 2010/0305700 A1 | 12/2010 | Ben-Arye et al. |
| 2010/0305704 A1 | 12/2010 | Messerli et al. |
| 2010/0324607 A1 | 12/2010 | Davis |
| 2010/0324683 A1 | 12/2010 | Reichen et al. |
| 2010/0331845 A1 | 12/2010 | Foley et al. |
| 2010/0331891 A1 | 12/2010 | Culbert et al. |
| 2011/0004216 A1 | 1/2011 | Amendola et al. |
| 2011/0004308 A1 | 1/2011 | Marino et al. |
| 2011/0004310 A1 | 1/2011 | Michelson |
| 2011/0009970 A1 | 1/2011 | Puno |
| 2011/0015747 A1 | 1/2011 | McManus et al. |
| 2011/0029082 A1 | 2/2011 | Hall |
| 2011/0029083 A1 | 2/2011 | Hynes et al. |
| 2011/0029085 A1 | 2/2011 | Hynes et al. |
| 2011/0029086 A1 | 2/2011 | Glazer et al. |
| 2011/0035011 A1 | 2/2011 | Cain |
| 2011/0040332 A1 | 2/2011 | Culbert et al. |
| 2011/0046674 A1 | 2/2011 | Calvosa et al. |
| 2011/0054538 A1 | 3/2011 | Zehavi et al. |
| 2011/0066186 A1 | 3/2011 | Boyer et al. |
| 2011/0071527 A1 | 3/2011 | Nelson et al. |
| 2011/0082552 A1 | 4/2011 | Wistrom et al. |
| 2011/0093074 A1 | 4/2011 | Glerum et al. |
| 2011/0093076 A1 | 4/2011 | Reo et al. |
| 2011/0098531 A1 | 4/2011 | To |
| 2011/0098628 A1 | 4/2011 | Yeung et al. |
| 2011/0098818 A1 | 4/2011 | Brodke et al. |
| 2011/0112586 A1 | 5/2011 | Guyer et al. |
| 2011/0130835 A1 | 6/2011 | Ashley et al. |
| 2011/0130838 A1 | 6/2011 | Morgenstern Lopez |
| 2011/0144692 A1 | 6/2011 | Saladin et al. |
| 2011/0144753 A1 | 6/2011 | Marchek et al. |
| 2011/0153020 A1 | 6/2011 | Abdelgany et al. |
| 2011/0159070 A1 | 6/2011 | Jin et al. |
| 2011/0160773 A1 | 6/2011 | Aschmann et al. |
| 2011/0160861 A1 | 6/2011 | Jimenez et al. |
| 2011/0160866 A1 | 6/2011 | Laurence et al. |
| 2011/0172716 A1 | 7/2011 | Glerum |
| 2011/0172774 A1 | 7/2011 | Varela |
| 2011/0190816 A1 | 8/2011 | Sheffer et al. |
| 2011/0190891 A1 | 8/2011 | Suh et al. |
| 2011/0230971 A1 | 9/2011 | Donner et al. |
| 2011/0238072 A1 | 9/2011 | Tyndall |
| 2011/0251690 A1 | 10/2011 | Berger et al. |
| 2011/0270261 A1 | 11/2011 | Mast et al. |
| 2011/0276142 A1 | 11/2011 | Niemiec et al. |
| 2011/0282453 A1 | 11/2011 | Greenhalgh et al. |
| 2011/0282459 A1 | 11/2011 | McClellan et al. |
| 2011/0301711 A1 | 12/2011 | Palmatier et al. |
| 2011/0301712 A1 | 12/2011 | Palmatier et al. |
| 2011/0307010 A1 | 12/2011 | Pradhan |
| 2011/0313465 A1 | 12/2011 | Warren et al. |
| 2011/0319899 A1 | 12/2011 | O'Neil et al. |
| 2011/0319997 A1 | 12/2011 | Glerum et al. |
| 2011/0319998 A1 | 12/2011 | O'Neil et al. |
| 2011/0320000 A1 | 12/2011 | O'Neil et al. |
| 2012/0004726 A1 | 1/2012 | Greenhalgh et al. |
| 2012/0004732 A1 | 1/2012 | Goel et al. |
| 2012/0006361 A1 | 1/2012 | Miyagi et al. |
| 2012/0010715 A1 | 1/2012 | Spann |
| 2012/0022654 A1 | 1/2012 | Farris et al. |
| 2012/0029636 A1 | 2/2012 | Ragab et al. |
| 2012/0029637 A1 | 2/2012 | Ragab et al. |
| 2012/0029639 A1 | 2/2012 | Blackwell et al. |
| 2012/0035730 A1 | 2/2012 | Spann |
| 2012/0059474 A1 | 3/2012 | Weiman |
| 2012/0059475 A1 | 3/2012 | Weiman |
| 2012/0071977 A1 | 3/2012 | Oglaza et al. |
| 2012/0071980 A1 | 3/2012 | Purcell et al. |
| 2012/0083887 A1 | 4/2012 | Purcell et al. |
| 2012/0083889 A1 | 4/2012 | Purcell et al. |
| 2012/0109319 A1 | 5/2012 | Perisic |
| 2012/0123546 A1 | 5/2012 | Medina |
| 2012/0136443 A1 | 5/2012 | Wenzel |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0191204 A1 | 7/2012 | Bae et al. |
| 2012/0197299 A1 | 8/2012 | Fabian, Jr. |
| 2012/0197403 A1 | 8/2012 | Merves |
| 2012/0197405 A1 | 8/2012 | Cuevas et al. |
| 2012/0203290 A1 | 8/2012 | Warren et al. |
| 2012/0203347 A1 | 8/2012 | Glerum et al. |
| 2012/0209383 A1 | 8/2012 | Tsuang et al. |
| 2012/0215262 A1 | 8/2012 | Culbert et al. |
| 2012/0215315 A1 | 8/2012 | Hochschuler et al. |
| 2012/0215316 A1 | 8/2012 | Mohr et al. |
| 2012/0226357 A1 | 9/2012 | Varela |
| 2012/0232552 A1 | 9/2012 | Morgenstern et al. |
| 2012/0232658 A1 | 9/2012 | Morgenstern et al. |
| 2012/0253395 A1 | 10/2012 | Linares |
| 2012/0253406 A1 | 10/2012 | Bae et al. |
| 2012/0265309 A1 | 10/2012 | Glerum et al. |
| 2012/0277795 A1 | 11/2012 | Von et al. |
| 2012/0277869 A1 | 11/2012 | Siccardi et al. |
| 2012/0277877 A1 | 11/2012 | Smith et al. |
| 2012/0290090 A1 | 11/2012 | Glerum et al. |
| 2012/0290097 A1 | 11/2012 | Cipoletti et al. |
| 2012/0310350 A1 | 12/2012 | Farris et al. |
| 2012/0310352 A1 | 12/2012 | DiMauro et al. |
| 2012/0323327 A1 | 12/2012 | McAfee |
| 2012/0323328 A1 | 12/2012 | Weiman |
| 2012/0323329 A1 | 12/2012 | Jimenez et al. |
| 2012/0330421 A1 | 12/2012 | Weiman |
| 2012/0330422 A1 | 12/2012 | Weiman |
| 2013/0006361 A1 | 1/2013 | Glerum et al. |

(56) References Cited

U.S. PATENT DOCUMENTS

| | | |
|---|---|---|
| 2013/0006362 A1 | 1/2013 | Biedermann et al. |
| 2013/0023937 A1 | 1/2013 | Biedermann et al. |
| 2013/0023993 A1 | 1/2013 | Weiman |
| 2013/0023994 A1 | 1/2013 | Glerum |
| 2013/0030536 A1 | 1/2013 | Rhoda et al. |
| 2013/0030544 A1 | 1/2013 | Studer |
| 2013/0053966 A1 | 2/2013 | Jimenez et al. |
| 2013/0060337 A1 | 3/2013 | Petersheim et al. |
| 2013/0073044 A1 | 3/2013 | Gamache |
| 2013/0079790 A1 | 3/2013 | Stein et al. |
| 2013/0085572 A1 | 4/2013 | Glerum et al. |
| 2013/0085574 A1 | 4/2013 | Sledge |
| 2013/0109925 A1 | 5/2013 | Horton et al. |
| 2013/0110240 A1 | 5/2013 | Hansell et al. |
| 2013/0116791 A1 | 5/2013 | Theofilos |
| 2013/0123924 A1 | 5/2013 | Butler et al. |
| 2013/0123927 A1 | 5/2013 | Malandain |
| 2013/0138214 A1 | 5/2013 | Greenhalgh et al. |
| 2013/0144387 A1 | 6/2013 | Walker et al. |
| 2013/0144388 A1 | 6/2013 | Emery et al. |
| 2013/0144391 A1 | 6/2013 | Siegal et al. |
| 2013/0150906 A1 | 6/2013 | Kerboul |
| 2013/0158663 A1 | 6/2013 | Miller et al. |
| 2013/0158664 A1 | 6/2013 | Palmatier et al. |
| 2013/0158667 A1 | 6/2013 | Tabor et al. |
| 2013/0158668 A1 | 6/2013 | Nichols et al. |
| 2013/0158669 A1 | 6/2013 | Sungarian et al. |
| 2013/0173004 A1 | 7/2013 | Greenhalgh et al. |
| 2013/0190875 A1 | 7/2013 | Shulock et al. |
| 2013/0190876 A1 | 7/2013 | Drochner et al. |
| 2013/0190877 A1 | 7/2013 | Medina |
| 2013/0197642 A1 | 8/2013 | Ernst |
| 2013/0197647 A1 | 8/2013 | Wolters et al. |
| 2013/0204371 A1 | 8/2013 | McLuen et al. |
| 2013/0211525 A1 | 8/2013 | McLuen et al. |
| 2013/0211526 A1 | 8/2013 | Alheidt et al. |
| 2013/0218276 A1 | 8/2013 | Fiechter et al. |
| 2013/0231747 A1 | 9/2013 | Olmos et al. |
| 2013/0238006 A1 | 9/2013 | O'Neil et al. |
| 2013/0253585 A1 | 9/2013 | Garcia et al. |
| 2013/0261746 A1 | 10/2013 | Linares et al. |
| 2013/0261747 A1 | 10/2013 | Geisert |
| 2013/0268077 A1 | 10/2013 | You et al. |
| 2013/0274883 A1 | 10/2013 | McLuen et al. |
| 2013/0310937 A1 | 11/2013 | Luiz |
| 2013/0310939 A1 | 11/2013 | Fabian et al. |
| 2013/0325128 A1 | 12/2013 | Perloff et al. |
| 2014/0018816 A1 | 1/2014 | Fenn et al. |
| 2014/0025169 A1 | 1/2014 | Lechmann et al. |
| 2014/0039622 A1 | 2/2014 | Glerum et al. |
| 2014/0039626 A1 | 2/2014 | Dale |
| 2014/0046333 A1 | 2/2014 | Johnson et al. |
| 2014/0046446 A1 | 2/2014 | Robinson |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0067073 A1 | 3/2014 | Hauck |
| 2014/0081267 A1 | 3/2014 | Orsak et al. |
| 2014/0086962 A1 | 3/2014 | Jin et al. |
| 2014/0094916 A1 | 4/2014 | Glerum et al. |
| 2014/0094917 A1 | 4/2014 | Salerni |
| 2014/0100662 A1 | 4/2014 | Patterson et al. |
| 2014/0107790 A1 | 4/2014 | Combrowski |
| 2014/0114414 A1 | 4/2014 | Abdou et al. |
| 2014/0114423 A1 | 4/2014 | Suedkamp et al. |
| 2014/0121774 A1 | 5/2014 | Glerum et al. |
| 2014/0128977 A1 | 5/2014 | Glerum et al. |
| 2014/0128980 A1 | 5/2014 | Kirschman |
| 2014/0135934 A1 | 5/2014 | Hansell et al. |
| 2014/0142706 A1 | 5/2014 | Hansell et al. |
| 2014/0148904 A1 | 5/2014 | Robinson |
| 2014/0163682 A1 | 6/2014 | Lott et al. |
| 2014/0163683 A1 | 6/2014 | Seifert et al. |
| 2014/0172103 A1 | 6/2014 | O'Neil et al. |
| 2014/0172105 A1 | 6/2014 | Frasier et al. |
| 2014/0172106 A1 | 6/2014 | To et al. |
| 2014/0180421 A1 | 6/2014 | Glerum et al. |
| 2014/0188225 A1 | 7/2014 | Dmuschewsky |
| 2014/0228959 A1 | 8/2014 | Niemiec et al. |
| 2014/0236296 A1 | 8/2014 | Wagner et al. |
| 2014/0243892 A1 | 8/2014 | Choinski |
| 2014/0243981 A1 | 8/2014 | Davenport et al. |
| 2014/0243982 A1 | 8/2014 | Miller |
| 2014/0249629 A1 | 9/2014 | Moskowitz et al. |
| 2014/0249630 A1 | 9/2014 | Weiman |
| 2014/0257484 A1 | 9/2014 | Flower et al. |
| 2014/0257486 A1 | 9/2014 | Alheidt |
| 2014/0257494 A1 | 9/2014 | Thorwarth et al. |
| 2014/0277139 A1 | 9/2014 | Vrionis et al. |
| 2014/0277204 A1 | 9/2014 | Sandhu |
| 2014/0277464 A1 | 9/2014 | Richter et al. |
| 2014/0277473 A1 | 9/2014 | Perrow |
| 2014/0277474 A1 | 9/2014 | Robinson et al. |
| 2014/0277476 A1 | 9/2014 | McLean et al. |
| 2014/0277481 A1 | 9/2014 | Lee et al. |
| 2014/0277507 A1 | 9/2014 | Baynham |
| 2014/0296983 A1 | 10/2014 | Fauth et al. |
| 2014/0303731 A1 | 10/2014 | Glerum |
| 2014/0303732 A1 | 10/2014 | Rhoda et al. |
| 2014/0324171 A1 | 10/2014 | Glerum et al. |
| 2014/0336764 A1 | 11/2014 | Masson et al. |
| 2014/0343678 A1 | 11/2014 | Suddaby et al. |
| 2015/0012097 A1 | 1/2015 | Ibarra et al. |
| 2015/0012098 A1 | 1/2015 | Eastlack et al. |
| 2015/0045894 A1 | 2/2015 | Hawkins et al. |
| 2015/0057755 A1 | 2/2015 | Suddaby et al. |
| 2015/0066145 A1 | 3/2015 | Rogers et al. |
| 2015/0088256 A1 | 3/2015 | Ballard |
| 2015/0094610 A1 | 4/2015 | Morgenstern et al. |
| 2015/0094812 A1 | 4/2015 | Cain |
| 2015/0094813 A1 | 4/2015 | Lechmann et al. |
| 2015/0094814 A1 | 4/2015 | Emerick et al. |
| 2015/0100128 A1 | 4/2015 | Glerum et al. |
| 2015/0112398 A1 | 4/2015 | Morgenstern et al. |
| 2015/0112437 A1 | 4/2015 | Davis et al. |
| 2015/0112438 A1 | 4/2015 | McLean |
| 2015/0157470 A1 | 6/2015 | Voellmicke et al. |
| 2015/0164655 A1 | 6/2015 | DiMauro |
| 2015/0173914 A1 | 6/2015 | DiMauro et al. |
| 2015/0173916 A1 | 6/2015 | Cain |
| 2015/0182347 A1 | 7/2015 | Robinson |
| 2015/0190242 A1 | 7/2015 | Blain et al. |
| 2015/0196400 A1 | 7/2015 | Dace |
| 2015/0196401 A1 | 7/2015 | DiMauro et al. |
| 2015/0202052 A1 | 7/2015 | DiMauro |
| 2015/0216671 A1 | 8/2015 | Cain |
| 2015/0216672 A1 | 8/2015 | Cain |
| 2015/0216673 A1 | 8/2015 | DiMauro |
| 2015/0223946 A1 | 8/2015 | Weiman et al. |
| 2015/0230929 A1 | 8/2015 | Lorio |
| 2015/0230932 A1 | 8/2015 | Schaller |
| 2015/0238324 A1 | 8/2015 | Nebosky et al. |
| 2015/0250606 A1 | 9/2015 | McLean |
| 2015/0272743 A1 | 10/2015 | Jimenez et al. |
| 2015/0305881 A1 | 10/2015 | Bal et al. |
| 2015/0320571 A1 | 11/2015 | Lechmann et al. |
| 2016/0000577 A1 | 1/2016 | Dimauro |
| 2016/0016309 A1 | 1/2016 | Swift et al. |
| 2016/0022437 A1 | 1/2016 | Kelly et al. |
| 2016/0022438 A1 | 1/2016 | Lamborne et al. |
| 2016/0038301 A1 | 2/2016 | Wickham |
| 2016/0038304 A1 | 2/2016 | Aquino et al. |
| 2016/0045333 A1 | 2/2016 | Baynham |
| 2016/0051373 A1 | 2/2016 | Faulhaber |
| 2016/0051374 A1 | 2/2016 | Faulhaber |
| 2016/0051376 A1 | 2/2016 | Serhan et al. |
| 2016/0058573 A1 | 3/2016 | Dimauro et al. |
| 2016/0067055 A1 | 3/2016 | Hawkins et al. |
| 2016/0074170 A1 | 3/2016 | Rogers et al. |
| 2016/0074175 A1 | 3/2016 | O'Neil |
| 2016/0081814 A1 | 3/2016 | Baynham |
| 2016/0089247 A1 | 3/2016 | Nichols et al. |
| 2016/0100954 A1 | 4/2016 | Rumi et al. |
| 2016/0106551 A1 | 4/2016 | Grimberg et al. |

(56) References Cited

U.S. PATENT DOCUMENTS

| | | |
|---|---|---|
| 2016/0113776 A1 | 4/2016 | Capote |
| 2016/0120660 A1 | 5/2016 | Melkent et al. |
| 2016/0120662 A1 | 5/2016 | Schaller |
| 2016/0128843 A1 | 5/2016 | Tsau et al. |
| 2016/0199195 A1 | 7/2016 | Hauck et al. |
| 2016/0199196 A1 | 7/2016 | Serhan et al. |
| 2016/0206440 A1 | 7/2016 | Deridder et al. |
| 2016/0220382 A1 | 8/2016 | Hawkins et al. |
| 2016/0228258 A1 | 8/2016 | Schaller et al. |
| 2016/0235455 A1 | 8/2016 | Wahl |
| 2016/0242929 A1 | 8/2016 | Voellmicke et al. |
| 2016/0256291 A1 | 9/2016 | Miller |
| 2016/0310296 A1 | 10/2016 | DiMauro et al. |
| 2016/0317313 A1 | 11/2016 | DiMauro |
| 2016/0317317 A1 | 11/2016 | Marchek et al. |
| 2016/0317714 A1 | 11/2016 | DiMauro et al. |
| 2016/0331541 A1 | 11/2016 | DiMauro et al. |
| 2016/0331546 A1 | 11/2016 | Lechmann et al. |
| 2016/0331548 A1 | 11/2016 | DiMauro et al. |
| 2016/0338854 A1 | 11/2016 | Serhan et al. |
| 2016/0367265 A1 | 12/2016 | Morgenstern Lopez |
| 2016/0367380 A1 | 12/2016 | DiMauro |
| 2016/0374821 A1 | 12/2016 | DiMauro et al. |
| 2017/0000622 A1 | 1/2017 | Thommen et al. |
| 2017/0035578 A1 | 2/2017 | DiMauro et al. |
| 2017/0056179 A1 | 3/2017 | Lorio |
| 2017/0071756 A1 | 3/2017 | Slivka et al. |
| 2017/0100177 A1 | 4/2017 | Kim |
| 2017/0100255 A1 | 4/2017 | Hleihil et al. |
| 2017/0100260 A1 | 4/2017 | Duffield et al. |
| 2017/0119542 A1 | 5/2017 | Logan et al. |
| 2017/0128226 A1 | 5/2017 | Faulhaber |
| 2017/0209284 A1 | 7/2017 | Overes et al. |
| 2017/0216045 A1 | 8/2017 | Dewey et al. |
| 2017/0266015 A1 | 9/2017 | Overes et al. |
| 2017/0290674 A1 | 10/2017 | Olmos et al. |
| 2017/0290675 A1 | 10/2017 | Olmos et al. |
| 2017/0290677 A1 | 10/2017 | Olmos et al. |
| 2017/0296352 A1 | 10/2017 | Richerme et al. |
| 2017/0304074 A1 | 10/2017 | DiMauro et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0028200 A1 | 2/2018 | O'Neil et al. |
| 2018/0036141 A1 | 2/2018 | Oneil et al. |
| 2018/0055649 A1 | 3/2018 | Kelly et al. |
| 2018/0071111 A1 | 3/2018 | Sharifi-Mehr et al. |
| 2018/0078379 A1 | 3/2018 | Serhan et al. |
| 2018/0116811 A1 | 5/2018 | Bernard et al. |
| 2018/0161171 A1 | 6/2018 | Frasier et al. |
| 2018/0161175 A1 | 6/2018 | Frasier et al. |
| 2018/0168819 A1 | 6/2018 | Voellmicke et al. |
| 2018/0193164 A1 | 7/2018 | Shoshtaev |
| 2018/0256360 A1 | 9/2018 | Cain |
| 2018/0256362 A1 | 9/2018 | Slivka et al. |
| 2018/0360616 A1 | 12/2018 | Luu |
| 2019/0008654 A1 | 1/2019 | Thommen |
| 2019/0021868 A1 | 1/2019 | Ludwig et al. |
| 2019/0083276 A1 | 3/2019 | DiMauro |
| 2019/0105171 A1 | 4/2019 | Rogers et al. |
| 2019/0117409 A1 | 4/2019 | Shoshtaev |
| 2019/0133785 A1 | 5/2019 | Georges |
| 2019/0142602 A1 | 5/2019 | Olmos et al. |
| 2019/0269521 A1 | 9/2019 | Shoshtaev |
| 2019/0336301 A1 | 11/2019 | Engstrom |
| 2019/0388238 A1 | 12/2019 | Lechmann et al. |
| 2020/0008950 A1 | 1/2020 | Serhan et al. |
| 2020/0015982 A1 | 1/2020 | O'Neil |
| 2020/0030114 A1 | 1/2020 | Cain |
| 2020/0060843 A1 | 2/2020 | Evans et al. |
| 2020/0078192 A1 | 3/2020 | Marchek et al. |
| 2020/0129308 A1 | 4/2020 | Suedkamp et al. |
| 2020/0297506 A1 | 9/2020 | Olmos et al. |
| 2020/0375754 A1 | 12/2020 | Cain |
| 2020/0375755 A1 | 12/2020 | Cain |
| 2020/0383799 A1 | 12/2020 | Cain |
| 2020/0405497 A1 | 12/2020 | Olmos et al. |
| 2020/0405500 A1 | 12/2020 | Cain |
| 2021/0000160 A1 | 1/2021 | Olmos et al. |
| 2021/0177619 A1 | 6/2021 | Voellmicke et al. |
| 2021/0353427 A1 * | 11/2021 | Butler .................... A61F 2/446 |

FOREIGN PATENT DOCUMENTS

| | | |
|---|---|---|
| CA | 2617872 A1 | 2/2007 |
| CN | 1177918 A | 4/1998 |
| CN | 1383790 A | 12/2002 |
| CN | 1819805 A | 8/2006 |
| CN | 101031260 A | 9/2007 |
| CN | 101087566 A | 12/2007 |
| CN | 101185594 A | 5/2008 |
| CN | 101631516 A | 1/2010 |
| CN | 101909548 A | 12/2010 |
| CN | 102164552 A | 8/2011 |
| CN | 103620249 A | 3/2014 |
| CN | 104023674 A | 9/2014 |
| CN | 104023675 A | 9/2014 |
| CN | 104042366 A | 9/2014 |
| CN | 104822332 A | 8/2015 |
| CN | 104921848 A | 9/2015 |
| CN | 104939876 A | 9/2015 |
| CN | 105025846 A | 11/2015 |
| CN | 105188582 A | 12/2015 |
| CN | 204971722 U | 1/2016 |
| CN | 105769391 A | 7/2016 |
| CN | 105769392 A | 7/2016 |
| CN | 107205829 A | 9/2017 |
| DE | 2804936 A1 | 8/1979 |
| DE | 3023353 A1 | 4/1981 |
| DE | 3801459 A1 | 8/1989 |
| DE | 3911610 A1 | 10/1990 |
| DE | 4012622 C1 | 7/1991 |
| DE | 9407806 U1 | 7/1994 |
| DE | 19710392 C1 | 7/1999 |
| DE | 19832798 C1 | 11/1999 |
| DE | 20101793 U1 | 5/2001 |
| DE | 202006005868 U1 | 6/2006 |
| DE | 202008001079 U1 | 3/2008 |
| DE | 10357960 B4 | 9/2015 |
| EP | 0077159 A1 | 4/1983 |
| EP | 0260044 A1 | 3/1988 |
| EP | 0270704 A1 | 6/1988 |
| EP | 0282161 A1 | 9/1988 |
| EP | 0433717 A1 | 6/1991 |
| EP | 0509084 A1 | 10/1992 |
| EP | 0525352 A1 | 2/1993 |
| EP | 0529275 A2 | 3/1993 |
| EP | 0609084 A2 | 8/1994 |
| EP | 0611557 A2 | 8/1994 |
| EP | 0621020 A1 | 10/1994 |
| EP | 0625336 A2 | 11/1994 |
| EP | 0678489 A1 | 10/1995 |
| EP | 0743045 A2 | 11/1996 |
| EP | 0853929 A2 | 7/1998 |
| EP | 1046376 A1 | 10/2000 |
| EP | 1157676 A1 | 11/2001 |
| EP | 1283026 A2 | 2/2003 |
| EP | 1290985 A2 | 3/2003 |
| EP | 1308132 A2 | 5/2003 |
| EP | 1374784 A1 | 1/2004 |
| EP | 1378205 A1 | 1/2004 |
| EP | 1405602 A1 | 4/2004 |
| EP | 1532949 A1 | 5/2005 |
| EP | 1541096 A1 | 6/2005 |
| EP | 1605836 A1 | 12/2005 |
| EP | 1385449 B1 | 7/2006 |
| EP | 1683593 A2 | 7/2006 |
| EP | 1698305 A1 | 9/2006 |
| EP | 1829486 A1 | 9/2007 |
| EP | 1843723 A1 | 10/2007 |
| EP | 1845874 A1 | 10/2007 |
| EP | 1924227 A2 | 5/2008 |
| EP | 1925272 | 5/2008 |
| EP | 2331023 A2 | 6/2011 |

(56) References Cited

FOREIGN PATENT DOCUMENTS

| | | |
|---|---|---|
| EP | 2368529 A1 | 9/2011 |
| EP | 2237748 B1 | 9/2012 |
| EP | 2641571 A1 | 9/2013 |
| EP | 2699065 A1 | 2/2014 |
| EP | 2705809 A1 | 3/2014 |
| EP | 2764851 A1 | 8/2014 |
| EP | 2777633 | 9/2014 |
| EP | 2645965 B1 | 8/2016 |
| EP | 3263072 A1 | 1/2018 |
| EP | 3366263 A1 | 8/2018 |
| FR | 2649311 A1 | 1/1991 |
| FR | 2699065 A1 | 6/1994 |
| FR | 2712486 A1 | 5/1995 |
| FR | 2718635 A1 | 10/1995 |
| FR | 2728778 A1 | 7/1996 |
| FR | 2730159 A1 | 8/1996 |
| FR | 2745709 A1 | 9/1997 |
| FR | 2800601 A1 | 5/2001 |
| FR | 2801189 A1 | 5/2001 |
| FR | 2808182 A1 | 11/2001 |
| FR | 2874814 A1 | 3/2006 |
| FR | 2913331 A1 | 9/2008 |
| FR | 2948277 | 1/2011 |
| FR | 3026294 | 4/2016 |
| GB | 2157788 A | 10/1985 |
| GB | 2173565 A | 10/1986 |
| JP | 64-052439 A | 2/1989 |
| JP | 06-500039 A | 1/1994 |
| JP | 06-319742 A | 11/1994 |
| JP | 07-502419 A | 3/1995 |
| JP | 07-184922 A | 7/1995 |
| JP | 07-213533 A | 8/1995 |
| JP | 10-085232 A | 4/1998 |
| JP | 11-089854 A | 4/1999 |
| JP | 2003-010197 A | 1/2003 |
| JP | 2003-126266 A | 5/2003 |
| JP | 2003-526457 A | 9/2003 |
| JP | 2006-501901 A | 1/2006 |
| JP | 2006-516456 | 7/2006 |
| JP | 2007-054666 A | 3/2007 |
| JP | 2007-530243 A | 11/2007 |
| JP | 2008-507363 A | 3/2008 |
| JP | 2008-126085 A | 6/2008 |
| JP | 2011-509766 A | 3/2011 |
| JP | 2011-520580 A | 7/2011 |
| JP | 2012-020153 A | 2/2012 |
| JP | 2012-508048 A | 4/2012 |
| JP | 4988203 B2 | 8/2012 |
| JP | 2013-508031 | 3/2013 |
| JP | 5164571 B2 | 3/2013 |
| JP | 2013-516206 A | 5/2013 |
| JP | 2014-502867 A | 2/2014 |
| JP | 2015-500707 A | 1/2015 |
| JP | 2015-525652 A | 9/2015 |
| JP | 2017-505196 A | 2/2017 |
| WO | 91/09572 A1 | 7/1991 |
| WO | 92/04423 A2 | 3/1992 |
| WO | 92/07594 A1 | 5/1992 |
| WO | 92/14423 A1 | 9/1992 |
| WO | 93/04634 A1 | 3/1993 |
| WO | 93/04652 A1 | 3/1993 |
| WO | 93/17669 A1 | 9/1993 |
| WO | 94/04100 A1 | 3/1994 |
| WO | 95/31158 | 11/1995 |
| WO | 96/28100 A1 | 9/1996 |
| WO | 97/00054 A1 | 1/1997 |
| WO | 97/26847 A1 | 7/1997 |
| WO | 98/34552 A1 | 8/1998 |
| WO | 98/34568 A1 | 8/1998 |
| WO | 99/02214 A1 | 1/1999 |
| WO | 99/26562 A1 | 6/1999 |
| WO | 99/42062 A1 | 8/1999 |
| WO | 99/52478 A1 | 10/1999 |
| WO | 99/53871 A1 | 10/1999 |
| WO | 99/60956 A1 | 12/1999 |
| WO | 99/62417 A1 | 12/1999 |
| WO | 99/63914 A1 | 12/1999 |
| WO | 00/12033 | 3/2000 |
| WO | 00/13620 A1 | 3/2000 |
| WO | 00/24343 A1 | 5/2000 |
| WO | 00/67652 | 5/2000 |
| WO | 00/44288 A1 | 8/2000 |
| WO | 00/53127 A1 | 9/2000 |
| WO | 00/67650 A1 | 11/2000 |
| WO | 00/67651 A1 | 11/2000 |
| WO | 00/74605 A1 | 12/2000 |
| WO | 00/76409 A1 | 12/2000 |
| WO | 01/01893 A1 | 1/2001 |
| WO | 01/01895 A1 | 1/2001 |
| WO | 01/10316 A1 | 2/2001 |
| WO | 01/12054 A2 | 2/2001 |
| WO | 01/17464 A1 | 3/2001 |
| WO | 01/80751 A1 | 11/2001 |
| WO | 01/95838 A1 | 12/2001 |
| WO | 02/03870 A1 | 1/2002 |
| WO | 02/17824 A2 | 3/2002 |
| WO | 02/17825 A2 | 3/2002 |
| WO | 02/30338 A1 | 4/2002 |
| WO | 02/43601 A2 | 6/2002 |
| WO | 02/43628 A1 | 6/2002 |
| WO | 02/45627 A1 | 6/2002 |
| WO | 02/47563 A1 | 6/2002 |
| WO | 02/71921 A2 | 9/2002 |
| WO | 02/85250 A2 | 10/2002 |
| WO | 03/02021 A1 | 1/2003 |
| WO | 03/05937 A1 | 1/2003 |
| WO | 03/07854 A1 | 1/2003 |
| WO | 03/20169 A2 | 3/2003 |
| WO | 03/21308 A2 | 3/2003 |
| WO | 03/22165 A1 | 3/2003 |
| WO | 03/28587 A2 | 4/2003 |
| WO | 03/43488 A2 | 5/2003 |
| WO | 03/03951 A1 | 6/2003 |
| WO | 2003/101308 A1 | 12/2003 |
| WO | 2004/008949 A2 | 1/2004 |
| WO | 03/59180 A2 | 3/2004 |
| WO | 2004/030582 A2 | 4/2004 |
| WO | 2004/034924 A2 | 4/2004 |
| WO | 2004/062505 A1 | 7/2004 |
| WO | 2004/064603 A2 | 8/2004 |
| WO | 2004/069033 A2 | 8/2004 |
| WO | 2004/078220 A2 | 9/2004 |
| WO | 2004/078221 A2 | 9/2004 |
| WO | 2004/080316 A1 | 9/2004 |
| WO | 2004/082526 A2 | 9/2004 |
| WO | 2004/098420 A2 | 11/2004 |
| WO | 2004/098453 A2 | 11/2004 |
| WO | 2004/108022 A1 | 12/2004 |
| WO | 2005/027734 A2 | 3/2005 |
| WO | 2005/032433 A2 | 4/2005 |
| WO | 2005/039455 A1 | 5/2005 |
| WO | 2005/051246 A2 | 6/2005 |
| WO | 2005/081877 A2 | 9/2005 |
| WO | 2005/094297 A2 | 10/2005 |
| WO | 2005/112834 A2 | 12/2005 |
| WO | 2005/112835 A2 | 12/2005 |
| WO | 2005/115261 A1 | 12/2005 |
| WO | 2006/017507 A2 | 2/2006 |
| WO | 2006/044920 A2 | 4/2006 |
| WO | 2006/047587 A2 | 5/2006 |
| WO | 2006/047645 A2 | 5/2006 |
| WO | 2006/058079 A2 | 6/2006 |
| WO | 2006/058281 A2 | 6/2006 |
| WO | 2006/060420 A1 | 6/2006 |
| WO | 2006/063083 A1 | 6/2006 |
| WO | 2006/065419 A2 | 6/2006 |
| WO | 2006/066228 A2 | 6/2006 |
| WO | 2006/072941 A2 | 7/2006 |
| WO | 2006/078972 A2 | 7/2006 |
| WO | 2006/081843 A1 | 8/2006 |
| WO | 2006/108067 A2 | 10/2006 |
| WO | 2006/118944 A1 | 11/2006 |
| WO | 2007/009107 A2 | 1/2007 |
| WO | 2007/022194 A2 | 2/2007 |

(56) References Cited

FOREIGN PATENT DOCUMENTS

| | | |
|---|---|---|
| WO | 2007/028098 A2 | 3/2007 |
| WO | 2007/048012 A2 | 4/2007 |
| WO | 2007/067726 A2 | 6/2007 |
| WO | 2007/084427 A2 | 7/2007 |
| WO | 2007/119212 A2 | 10/2007 |
| WO | 2007/124130 A2 | 11/2007 |
| WO | 2008/005627 A2 | 1/2008 |
| WO | 2008/011378 A1 | 1/2008 |
| WO | 2008/044057 A1 | 4/2008 |
| WO | 2008/064842 A2 | 6/2008 |
| WO | 2008/070863 A2 | 6/2008 |
| WO | 2008/103781 A2 | 8/2008 |
| WO | 2008/103832 A2 | 8/2008 |
| WO | 2009/064787 A2 | 5/2009 |
| WO | 2009/092102 A1 | 7/2009 |
| WO | 2009/124269 A1 | 10/2009 |
| WO | 2009/143496 A1 | 11/2009 |
| WO | 2009/147527 A2 | 12/2009 |
| WO | 2009/152919 A1 | 12/2009 |
| WO | 2010/011348 A1 | 1/2010 |
| WO | 2010/068725 A2 | 6/2010 |
| WO | 2010/075451 A1 | 7/2010 |
| WO | 2010/075555 A2 | 7/2010 |
| WO | 2010/088766 A1 | 8/2010 |
| WO | 2010/121002 A1 | 10/2010 |
| WO | 2010/136170 A1 | 12/2010 |
| WO | 2010/148112 A1 | 12/2010 |
| WO | 2011/013047 A2 | 2/2011 |
| WO | 2011/046459 A1 | 4/2011 |
| WO | 2011/046460 A1 | 4/2011 |
| WO | 2011/060087 A1 | 5/2011 |
| WO | 2011/079910 A2 | 7/2011 |
| WO | 2011/119617 A1 | 9/2011 |
| WO | 2011/142761 A1 | 11/2011 |
| WO | 2011/150350 A1 | 12/2011 |
| WO | 2012/009152 A1 | 1/2012 |
| WO | 2012/027490 A2 | 3/2012 |
| WO | 2012/028182 A1 | 3/2012 |
| WO | 2012/030331 A1 | 3/2012 |
| WO | 2012/089317 A1 | 7/2012 |
| WO | 2012/103254 A2 | 8/2012 |
| WO | 2012/122294 A1 | 9/2012 |
| WO | 2012/129197 A1 | 9/2012 |
| WO | 2012/135764 A1 | 10/2012 |
| WO | 2013/006669 A2 | 1/2013 |
| WO | 2013/023096 A1 | 2/2013 |
| WO | 2013/025876 A1 | 2/2013 |
| WO | 2013/043850 A2 | 3/2013 |
| WO | 2013/062903 A1 | 5/2013 |
| WO | 2013/082184 A1 | 6/2013 |
| WO | 2013/148176 A1 | 10/2013 |
| WO | 2013/149611 A1 | 10/2013 |
| WO | 2013/158294 A1 | 10/2013 |
| WO | 2013/173767 A1 | 11/2013 |
| WO | 2013/184946 A1 | 12/2013 |
| WO | 2014/014610 A1 | 1/2014 |
| WO | 2014/018098 A1 | 1/2014 |
| WO | 2014/026007 A1 | 2/2014 |
| WO | 2014/035962 A1 | 3/2014 |
| WO | 2014/088521 A2 | 6/2014 |
| WO | 2014/116891 A1 | 7/2014 |
| WO | 2014/144696 A1 | 9/2014 |
| WO | 2015/004660 A1 | 1/2015 |
| WO | 2015/013479 A2 | 1/2015 |
| WO | 2015/022039 A1 | 2/2015 |
| WO | 2015/048997 A1 | 4/2015 |
| WO | 2016/069796 A1 | 5/2016 |
| WO | 2016/118246 A1 | 7/2016 |
| WO | 2016/127139 A1 | 8/2016 |
| WO | 2017/040881 A1 | 3/2017 |
| WO | 2017/136620 A1 | 8/2017 |
| WO | 2018/078148 A1 | 5/2018 |

OTHER PUBLICATIONS

ProMap TM EMG Navigation Probe. Technical Brochure Spineology Inc, Dated May 2009.

Regan et al., Endoscopic thoracic fusion cage Atlas of Endoscopic Spine Surgery Quality Medical Publishing, Inc. 1995;350-354.

Shin, "Posterior Lumbar Interbody Fusion via a Unilateral Approach", Yonsei Medical Journal, 2006, pp. 319-325, vol. 47(3).

Siddiqui," The Positional Magnetic Resonance Imaging Changes in the Lumbar Spine Following Insertion of a Novel Interspinous Process Distraction Device", Spine, vol. 30, No. 23, pp. 2677-2682, 2005.

Slivka et al., In vitro compression testing of fiber-reinforced, bioabsorbable, porous implants. Synthetic Bioabsorbable Polymers for Implants. STP1396, pp. 124-135, ATSM International, Jul. 2000.

Sonic Accelerated Fracture Healing System/Exogen 3000. Premarket Approval. U.S. Food & Drug Administration. Date believed to be May 10, 2000. Retrieved Jul. 23, 2012 from <http://www.accessdata.fda.gov/scripts/cdrh/crdocs/cfPMA/pma.cfm?id=14736#>. 4 pages, 2012.

Spine Solutions Brochure—Prodisc 2001, 16 pages.

Stewart et al., Co-expression of the stro-1 anitgen and alkaline phosphatase in cultures of human bone and marrow cells. ASBMR 18th Annual Meeting. Bath Institute for Rheumatic Diseases, Bath, Avon, UK. Abstract No. P208, p. S142, 1996.

Timmer et al., In vitro degradation of polymeric networks of poly(propylene fumarate) and the crosslinking macromer poly(propylene fumarate)-diacrylate. Biomaterials. Feb. 2003;24(4):571-7.

U.S. Appl. No. 60/424,055, Method and apparatus for spinal fixation, filed Nov. 5, 2002.

U.S. Appl. No. 60/397,588, Method and apparatus for spinal fixation, filed Jul. 19, 2002.

U.S. Appl. No. 61/675,975, Expandable Implant, filed Jul. 26, 2012.

Provisional U.S. Appl. No. 60/942,998, Method and Apparatus for Spinal Stabilization, filed Jun. 8, 2007.

United States District Court, Central District of California, Case No. 1:10-CV-00849-LPS, *Nuvasive, Inc.*, vs., *Globus Medical, Inc.*, Videotaped Deposition of: Luiz Pimenta, M.D., May 9, 2012, 20 pages.

U.S. Appl. No. 14/640,220, filed Mar. 6, 2015, entitled Expandable Intervertebral Implant.

U.S. Appl. No. 14/685,358, filed Apr. 13, 2015, entitled Expandable Intervertebral Implant.

U.S. Appl. No. 14/685,402, filed Apr. 13, 2015, entitled Expandable Intervertebral Implant.

U.S. Appl. No. 14/790,866, filed Jul. 2, 2015, entitled Expandable Implant.

U.S. Appl. No. 11/464,782 (pending) to Schaller flied Aug. 15, 2006, entitled "Spinal Tissue Distraction Devices".

U.S. Appl. No. 11/464,790 (pending) to Schaller flied Aug. 15, 2006, entitled "Spinal Tissue Distraction Devices".

U.S. Appl. No. 11/464,793 (pending) to Schaller flied Aug. 15, 2006, entitled "Devices For Limiting The Movement Of Material Introduced Between Layers Of Spinal Tissue".

U.S. Appl. No. 11/464,807 (pending) to Schaller filed Aug. 15, 2006, entitled "Methods Of DistractinQ Tissue Layers Of The Human Spine".

U.S. Appl. No. 11/464,812 (pending) to Schaller flied Aug. 15, 2006, entitled "Methods Of Distracting Tissue Layers Of The Human Spine".

U.S. Appl. No. 11/464,815 (pending) to Schaller flied Aug. 15, 2006, entitled "Methods for Limiting the Movement of Material Introduced Between Layers of Spinal Tissue".

U.S. Appl. No. 60/689,570, filed Jun. 13, 2005; Inventor: Tzony Siegal, Title: Directional Drilling System.

U.S. Appl. No. 60/794,171, filed Apr. 21, 2006, entitled Method and Apparatus for Spinal Fixation.

U.S. Appl. No. 60/557,246, filed Mar. 29, 2004 entitled: Device and Methods to Reduce and Stabilize Broken Bones.

Vikram Talwar,"Insertion loads of the X STOP Interspinous Process Distraction System Designed to Treat Neurogenic Intermittent Claudication", Eur Spine J. (2006) 15: pp. 908-912.

(56) References Cited

OTHER PUBLICATIONS

Walsh et al., Preparation of porous composite implant materials by in situ polymerization of porous apatite containing epsilon-caprolactone or methyl methacrylate Biomaterials. Jun. 2001;22(11):1205-12.
Zimmer.com, Longer BAK/L Sterile Interbody Fusion Devices. Date believed to be 1997. Product Data Sheet.Zimmer. Retrieved Jul. 23, 2012 from <http:/ catalog.zimmer.com/contenUzpc/products/600/600/620/S20/S045. html>, 2 pages.
Zucherman, "A Multicenter, Prospective, Randomized Trial Evaluating the X STOP Interspinous Process Decompression System for the Treatment of Neurogenic Intermittent Claudication", SPINE, vol. 30, No. 12, pp. 1351-1358, 2005.
Alfen et al., "Developments in the area of Endoscopic Spine Surgery", European Musculoskeletal Review 2006, pp. 23-24, ThessysTM, Transforaminal Endoscopic Spine Systems, joi max Medical Solutions.
Brochure for PERPOS PLS System Surgical Technique by Interventional Spine, 2008, 8 pages.
Brooks et al., "Efficacy of Supplemental Posterior Transfacet Pedicle Device Fixation in the Setting of One- or Two-Level Anterior Lumbar Interbody Fusion", Retrieved Jun. 19, 2017, 6 pages.
Bruder et al., Identification and characterization of a cell surface differentiation antigen on human osteoprogenitor cells 42nd Annual Meeting of the Orthopaedic Research Society, p. 574, Feb. 19-22, 1996, Atlanta, Georgia.
Bruder et al., Monoclonal antibodies reactive with human osteogenic cell surface antigens. Bone. Sep. 1997;21(3):225-235.
Burkoth et al., A review of photocrosslinked polyanhydrides: in situ forming degradable networks. Biomaterials. Dec. 2000; 21 (23): 2395-2404.
Cambridge Scientific News, FDA Approves Cambridge Scientific, Inc.'s Orthopedic WISORB (TM) Malleolar Screw [online], Jul. 30, 2002 [retrieved on Oct. 14, 2003], Retrieved from the Internet <URL http://www.cambridgescientificinc.com>.
Carrino, John A., Roxanne Chan and Alexander R. Vaccaro, "Vertebral Augmentation: Vertebroplasty and Kyphoplasty", Seminars in Roentgenology, vol. 39, No. 1 (Jan.), 2004: pp. 68-84.
Cheng, B.C., Ph D., Biomechanical pullout strength and histology of Plasmapore Registered XP coated implants Ovine multi time point survival study Aesculap Implant Systems, LLC, 2013, 12 pages.
Chiang, "Biomechanical Comparison of Instrumented Posterior Lumbar Interbody Fusion with One or Two Cages by Finite Element Analysis", Spine, Sep. 2006, pages E682- E689, vol. 31(19), Lippincott Williams & Wilkins, Inc.
Chin, Kingsley R., M.D. "Eady Results of the Triage Medical Percutaneous Transfacet Pedicular BONE-LOK Compression Device for Lumbar Fusion", accessed online Jul. 10, 2017, 10 pages.
CN Office Action dated Apr. 24, 2020 for CN Application No. 201780040910.
Edeland, H.G., "Some Additional Suggestions For An Intervertebral Disc Prosthesis", J of Bio Medical Engr., vol. 7(1) pp. 57-62, Jan. 1985.
European Search Report EP03253921 dated Nov. 13, 2003, 4 pages.
Flemming et al., Monoclonal anitbody against adult marrow-derived mesenchymal stem cells recognizes developing vasculature in embryonic human skin. Developmental Dynamics. 1998;212:119-132.
Folman, Posterior Lumbar Interbody Fusion for Degenerative Disc Disease Using a Minimally Invasive B-Twin Expandable Spinal Spacer, Journal of Spinal Disorders & Techniques, 2003, pp. 455-460, vol. 16(5).
Gore, "Technique of Cervical Interbody Fusion", Clinical Orthopaedics and Related Research, Sep. 1984, pp. 191-195, No. 188.
Gray's Anatomy, Crown Publishers, Inc., 1977, pp. 33-54.
Ha, S. W. et al., Topographical characterization and microstructural interface analysis of vacuum-plasma-sprayed titanium and hydroxyapatite coatings on carbon fibre-reinforced poly(etheretherketone), J. Mater. Sci.: Materials in Medicine, 1997, v. 8, pp. 891-896.
Haas, Norbert P., New Products from AO Development [online], May 2002 [retrieved on Oct. 14, 2003], Retrieved from the Internet <URL: http://www.ao.asif.ch/development/pdf_tk_news_02.pdf>.
Hao et al., Investigation of nanocomposites based on semi-interpenetrating network of [L—poly (epsilon- caprolactone)]/[net-poly (epsilon-caprolactone)] and hydroxyapatite nanocrystals. Biomaterials Apr. 2003;24(9): 1531-9.
Harsha, A. P. et al., "Tribo performance of polyaryletherketone composites," Polymer Testing, 2002, v. 21, pp. 697-709.
Haynesworth et al., Cell surface antigens on human marrow-derived mesenchymal cells are detected by monoclonal antibodies. Bone. 1992;13(1):69-80.
Hitchon et al., Comparison of the biomechanics of hydroxyapatite and polymethylmethacrylate vertebroplasty in a cadaveric spinal compression fracture model. J Neurosurg. Oct. 2001; 95(2 Suppl): 215-20.
Hoogland et al., "Total Lumar Intervertebral Disc Replacement: Testing a New Articulating Space in Human Cadaver Spines-241", Annual ORS, Dallas, TX, Feb. 21-23, 1978, 8 pages.
https://emea.depuysynthes.com/hcp/hip/products/qs/porocoat-porous-coating-emea, Porocoat (Registered) Porous Coating, Depuy Synthes, webpage, accessed Jul. 5, 2016.
Hunt, "Expandable Cage Placement Via a Posterolateral Approach in Lumbar Spine Reconstructions", Journal of Neurosurgery: Spine, Sep. 2006, pp. 271-274, vol. 5.
International Patent Application No. PCT/US2013/029014, International Search Report dated Jul. 1, 2013, 2 pages.
Iprenburg et al., "Transforaminal Endoscopic Surgery in Lumbar Disc Herniation in an Economic Crisis—The TESSYS Method", US Musculoskeletal, 2008, p. 47-49.
Joshi, Ajeya P., M.D. and Paul A. Glazer, M.D., "Vertebroplasty: Current Concepts and Outlook for the Future", 2003, (5 pages), From: http://www.orthojournalhms.org/html/pdfs/manuscript-15.pdf.
Kambin et al., "Percutaneous Lateral Discectomy of the Lumbar Spine: A Preliminary Report", Clin. Orthop,: 1983, 174: 127-132.
Kandziora, Frank, et al., "Biomechanical Analysis of Biodegradable Interbody Fusion Cages Augmented with Poly (propylene Glycol-co-Fumaric Acid)," SPINE, 27(15): 1644-1651 (2002).
King., "Internal Fixation for Lumbosacral Fusion, The Journal of Bone and Joint Surgery", J. Bone Joint Surg. Am., 1948; 30: 560-578.
Kotsias, A., Clinical trial of titanium-coated PEEL cages anterior cervical discectomy and fusion. [Klinishe Untersuching zum Einsatz von titanbeschichteten Polyetheretherketon- Implantaten bei der cervikalen interkorporalen fusion] Doctoral thesis. Department of Medicine, Charite, University of Medicine Berlin, 2014, 73 pages. (German Tanguage document/Engl. summary).
Krbec, "Replacement of the Vertebral Body with an Expansion Implant (Synex)", Acta Chir Orthop Traumatol Cech, 2002, pp. 158-162, vol. 69(3).
Kroschwitz et al., eds., Hydrogels. Concise Encyclopedia of Polymer Science and Engineering. Wiley and Sons, pp. 458-459, 1990.
Lendlein et al., AB-polymer networks based on oligo(epsilon-caprolactone) segments showing shape-memory properties. Proc Natl Acad Sci US A Jan. 3, 20010;98(3):842-7. Epub Jan. 2, 20013.
Link SB Charite Brochure—Intervertebral Prosthesis 1988, 29 pages.
Mahar et al., "Biomechanical Comparison of Novel Percutaneous Transfacet Device and a Traditional Posterior System for Single Level Fusion", Journal of Spinal Disorders & Techniques, Dec. 2006, vol. 19, No. 8, pp. 591-594.
Malberg. M.I., MD; Pimenta, L., Md; Millan, M.M., MD, 9th International Meeting on Advanced Spine Techniques, May 23-25, 2002, Montreux, Switzerland. Paper #54, Paper #60, and E-Poster#54, 5 pages.
McAfee et al., Minimally invasive anterior retroperitoneal approach to the lumbar spine: Emphasis on the lateral BAK. SPINE 1998;23(13):1476-84.

(56) References Cited

OTHER PUBLICATIONS

Medco Forum, "Percutaneous Lumbar Fixation Via PERPOS PLS System Interventional Spine", Sep. 2008, vol. 15, No. 37.
Medco Forum, "Percutaneous Lumbar Fixation via PERPOS System From Interventional Spine", Oct. 2007, vol. 14, No. 49.
Mendez et al., Self-curing acrylic formulations containing PMMA/PCL composites: properties and antibiotic release behavior. J Biomed Mater Res. Jul. 2002; 61 (1 ):66-74.
Morgenstern, "Transforaminal Endoscopic Stenosis Surgery—A Comparative Study of Laser and Reamed Foraminoplasty", in European Musculoskeletal Review, Issue 1,2009.
Nguyen, H. X., et al., "Poly(Aryl-Ether-Ether-Ketone) and Its Advanced Composites: A Review," Polymer Composites, Apr. 1987, v. 8, p. 57.
Niosi, Christina A., "Biomechanical Characterization of the three-dimentinoal kinematic behavior of the Dynesys dynamic stabilization system: an in vitro study", Eur Spine J. (2006) 15: pp. 913-922.
OSTEOSET Registered DBM Pellets (Important Medical Information) [online], Nov. 2002 [retrieved on Oct. 14, 2003] Retrieved from the Internet <URL: http://www.wmt.com/Literature>.
Paul D. Fuchs, "The use of an interspinous implant in conjunction with a graded facetectomy procedure", Spine vol. 30, No. 11, pp. 1266-1272, 2005.
Polikeit, "The Importance of the Endplate for Interbody Cages in the Lumbar Spine", Eur. Spine J., 2003, pp. 556-561, vol. 12.
Allcock, "Polyphosphazenes"; The Encyclopedia of Polymer Science; 1988; pp. 31-41; vol. 13; Wiley Intersciences, John Wiley & Sons.
Cohn, "Biodegradable PEO/PLA Block Copolymers"; Journal of Biomedical Materials Research; 1988; pp. 993-1009 vol. 22; John Wiley & Sons, Inc.
Cohn, "Polymer Preprints"; Journal of Biomaterials Research; 1989; p. 498; Biomaterials Research Labortatory, Casal Institute of Applied Chemistry, Israel.
Heller, "Poly (Otrho Esters)"; Handbook of Biodegradable Polymers; edited by Domb; et al.; Hardwood Academic Press; 1997; pp. 99-118.
Japanese Office Action for Application No. 2013-542047, dated Sep. 8, 2015 (12 pages).
Japanese Office Action for Application No. 2016-135826, dated Jun. 6, 2017, (7 pages).
Kemnitzer, "Degradable Polymers Derived From the Amino Acid L-Tyrosine"; 1997; pp. 251-272; edited by Domb, et al., Hardwood Academic Press.
Khoo, "Minimally Invasive Correction of Grade I and II Isthmic Spondylolisthesis using AxiaLIF for L5/S1 Fusion", pp. 1-7, Rev B Sep. 15, 2008.
Khoo, Axilif address spongy from the caudal approach. Minimally Invasive Correction of Grage I and II Isthmic Spondylolisthesis using AsiaLiF for L5/S1 Fusion, pp. 45-0123 Rev B Sep. 15, 2008.
U.S. Appl. No. 61/009,546, filed Dec. 28, 2007 Rodgers.
U.S. Appl. No. 61/140,926, filed Dec. 26, 2008 Spann.
U.S. Appl. No. 61/178,315, filed May 14, 2009 Spann.
U.S. Appl. No. 09/558,057, filed Apr. 26, 2000 entitled Bone Fixation System.
Vandorpe, "Biodegradable Polyphosphazenes for Biomedical Applications"; Handbook of Biodegradable Polymers 1997; pp. 161-182; Hardwood Academic Press.

* cited by examiner

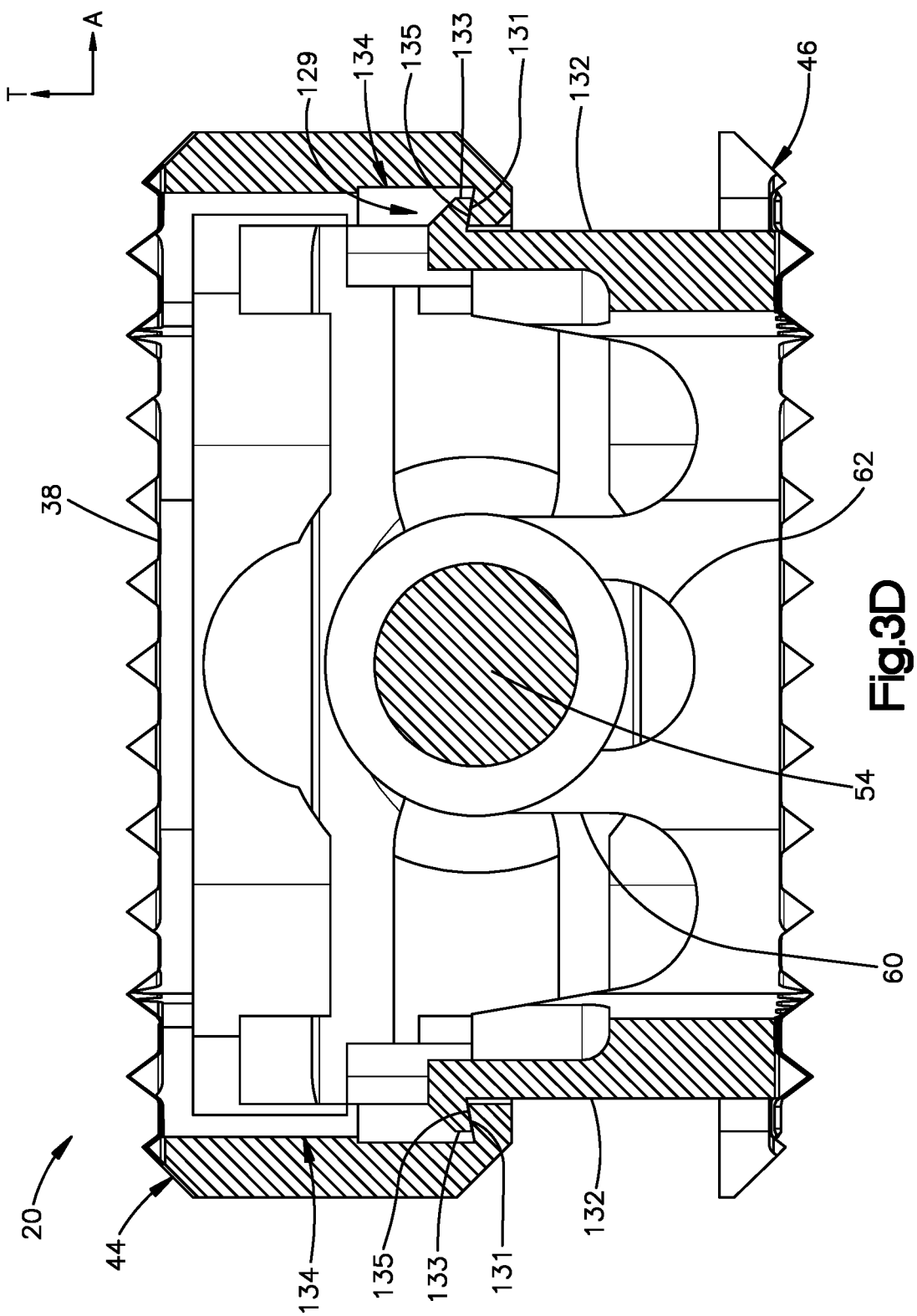

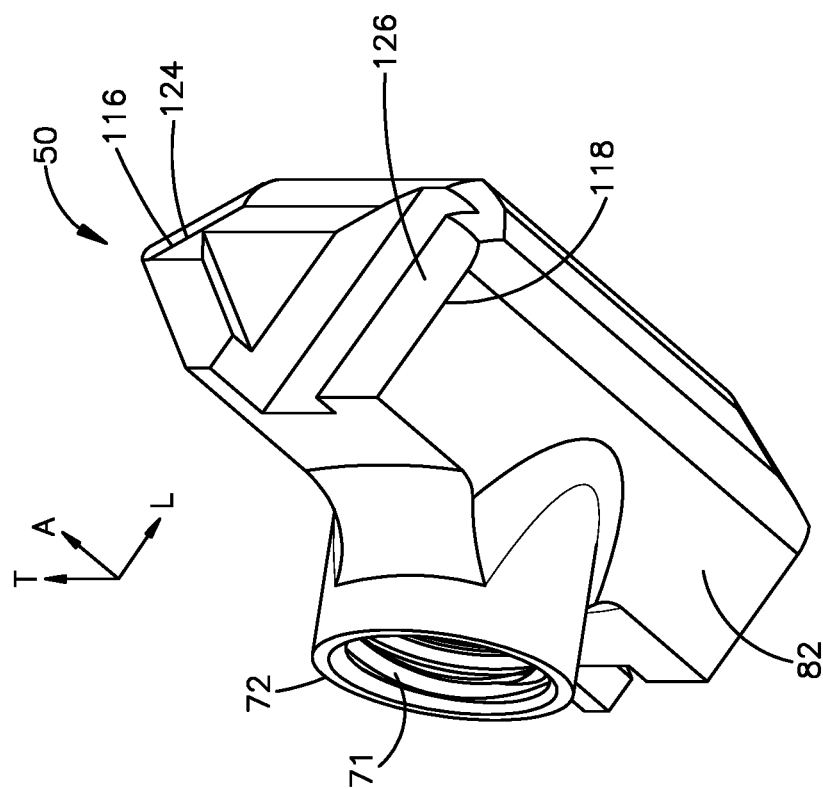
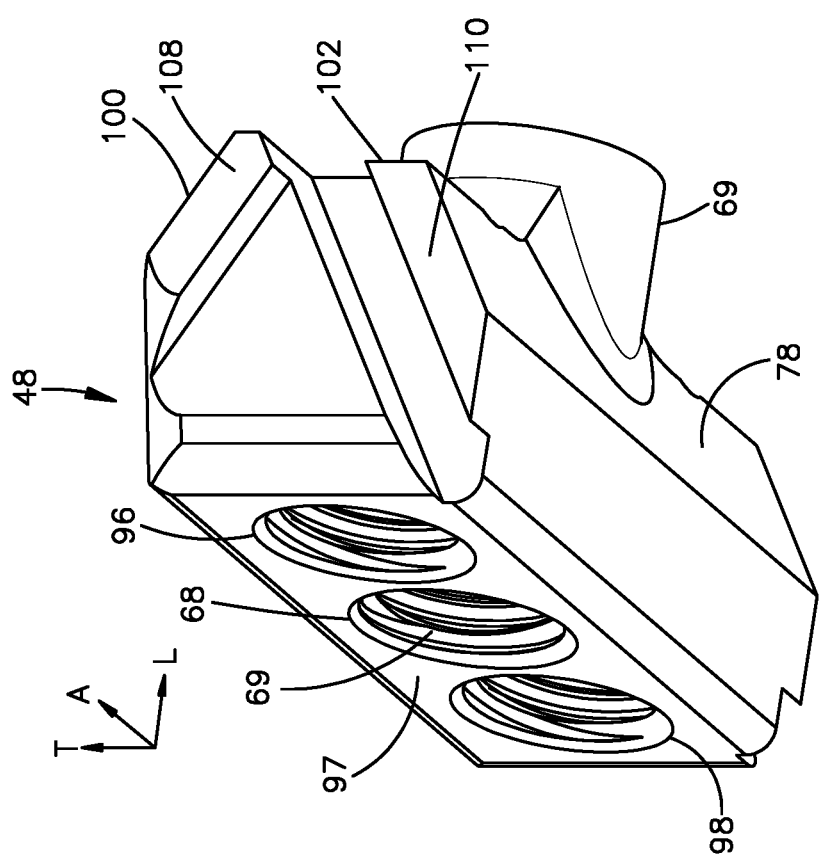

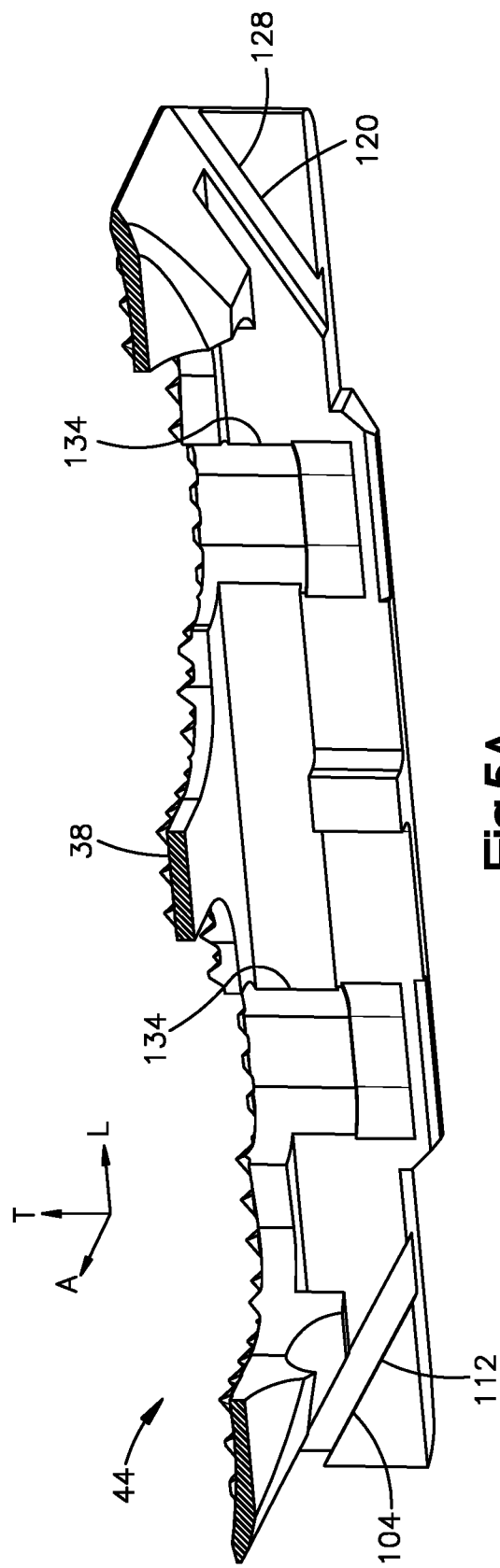
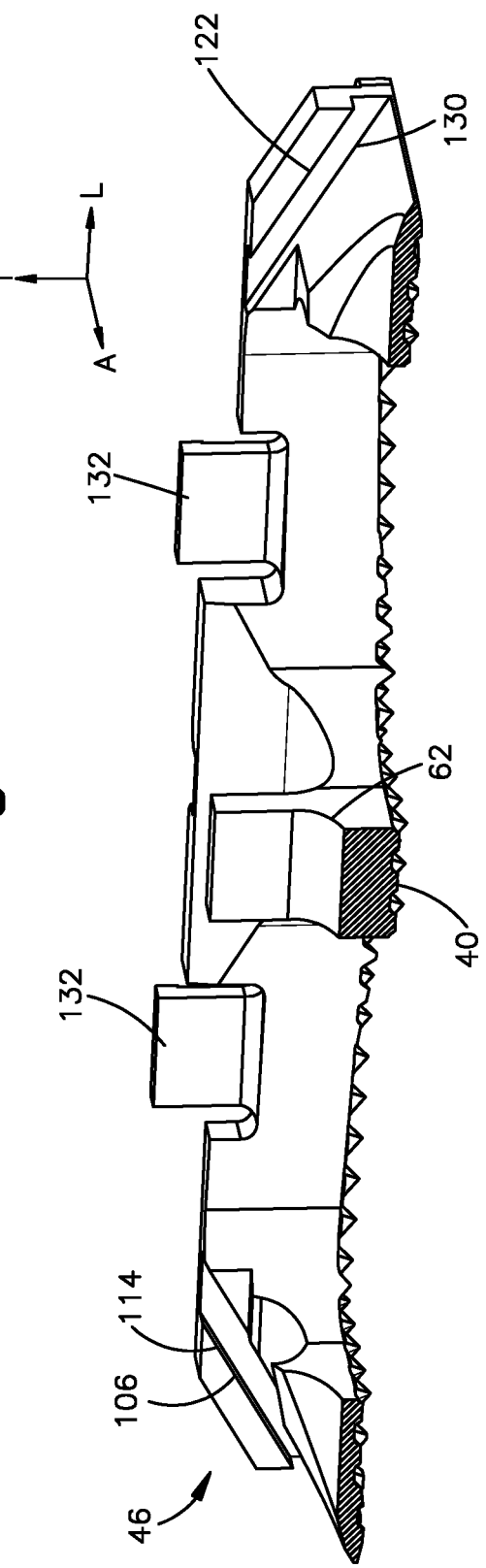

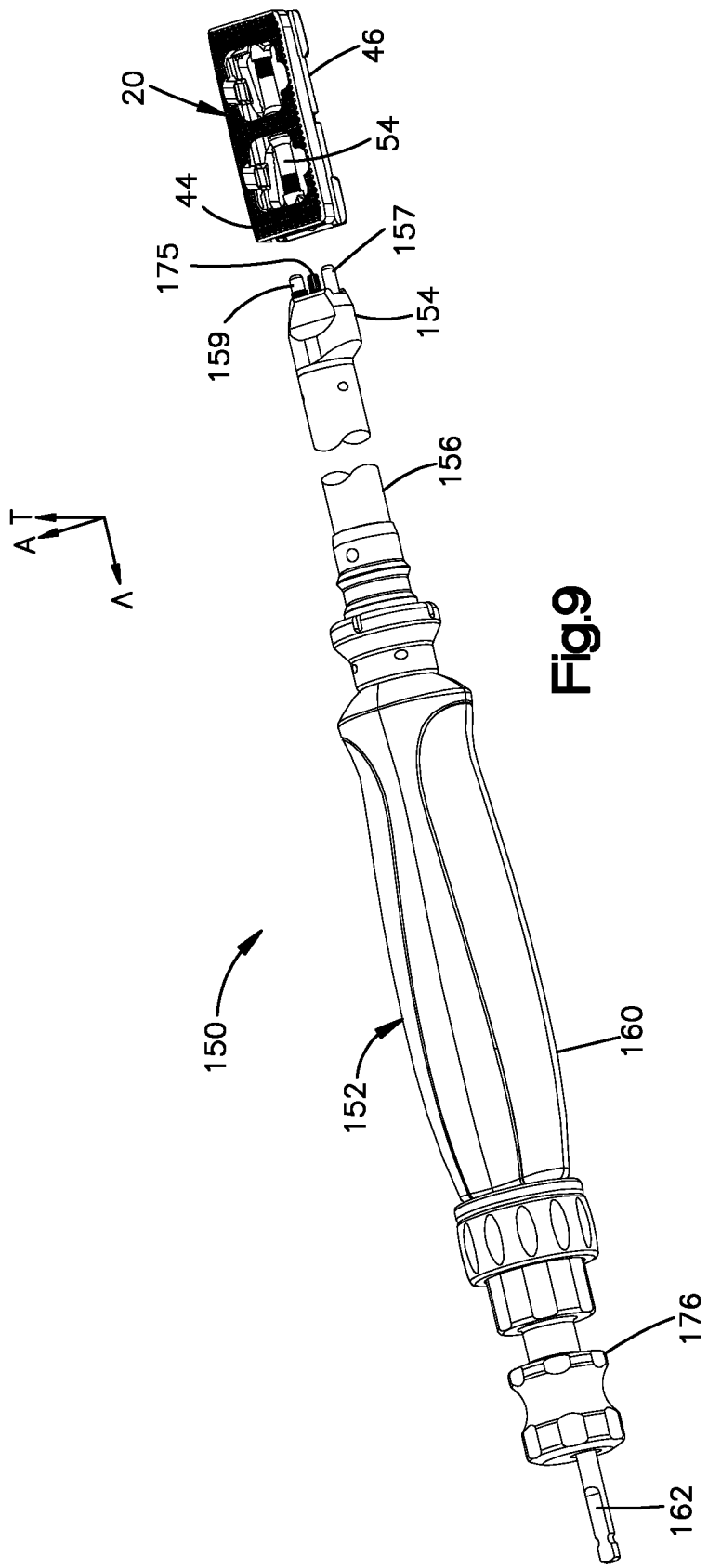

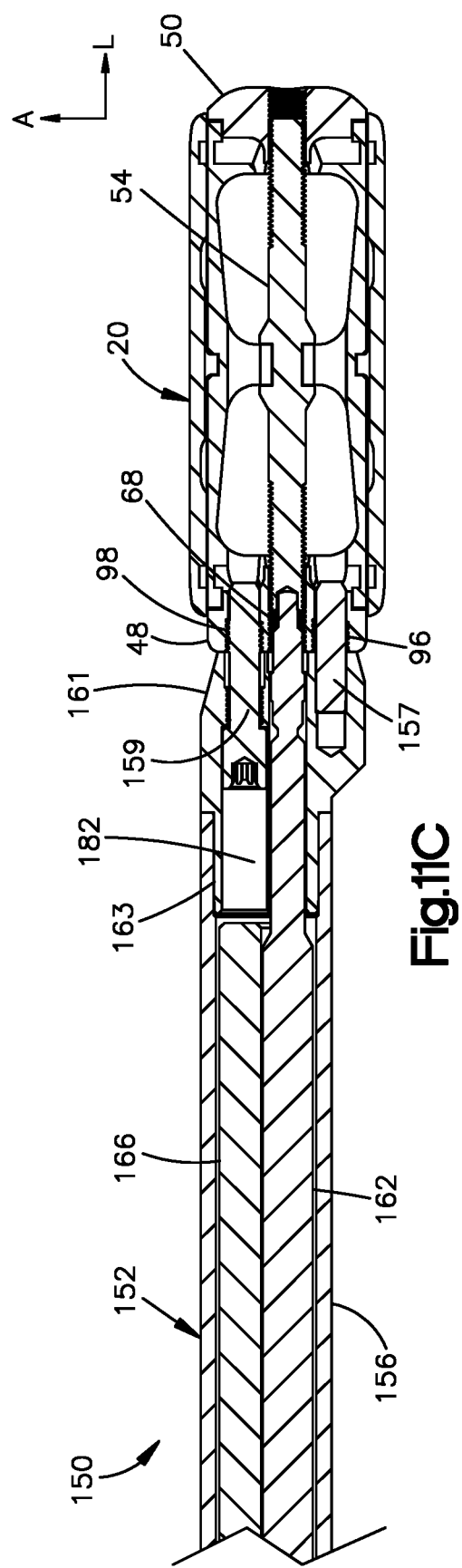
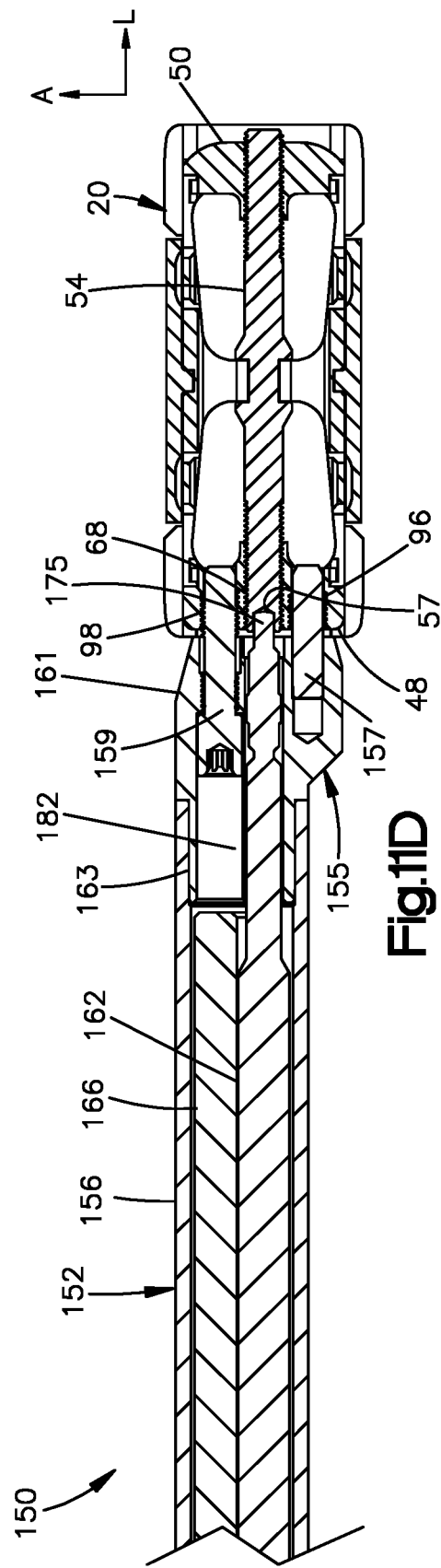
Fig.11C
Fig.11D

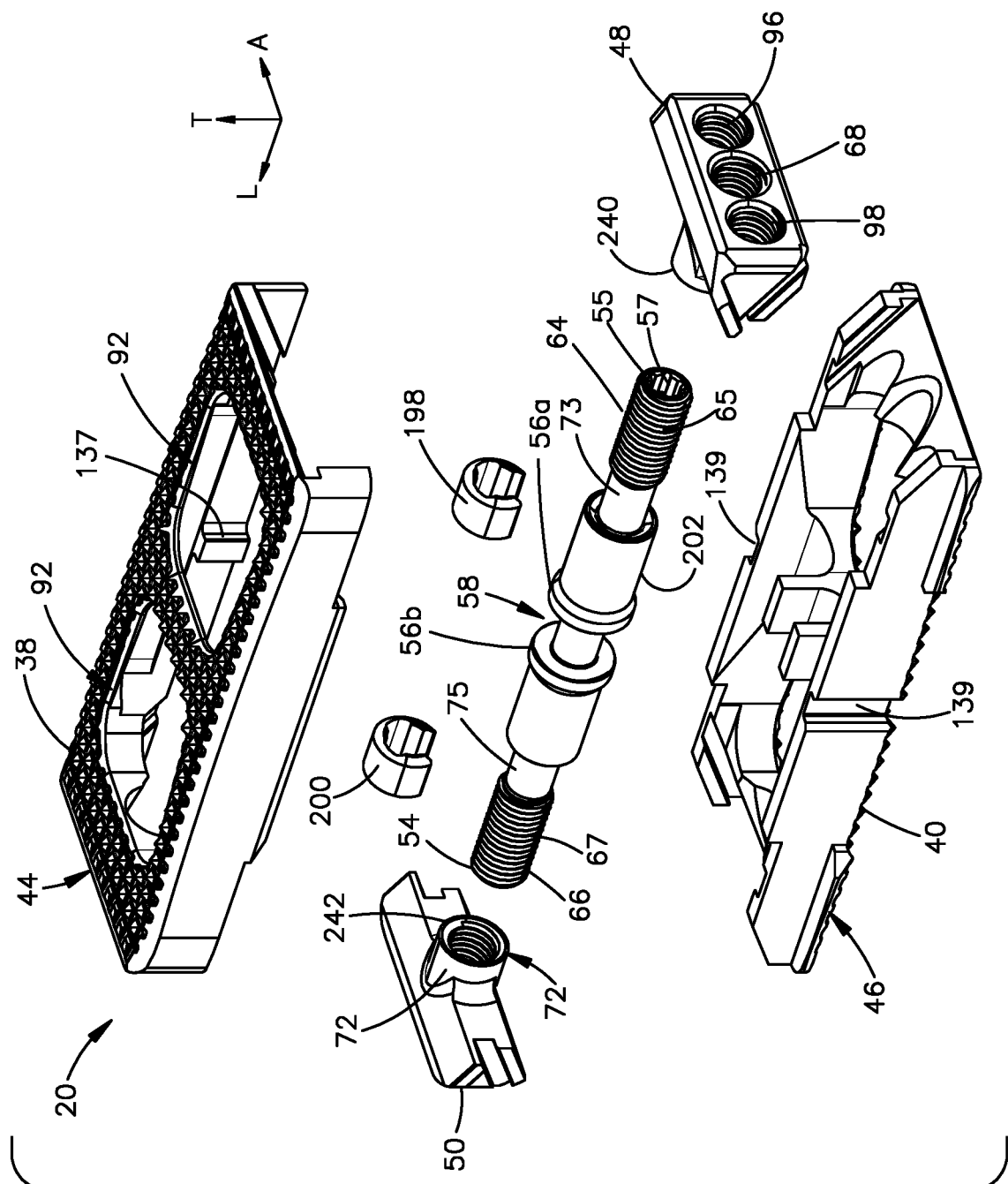

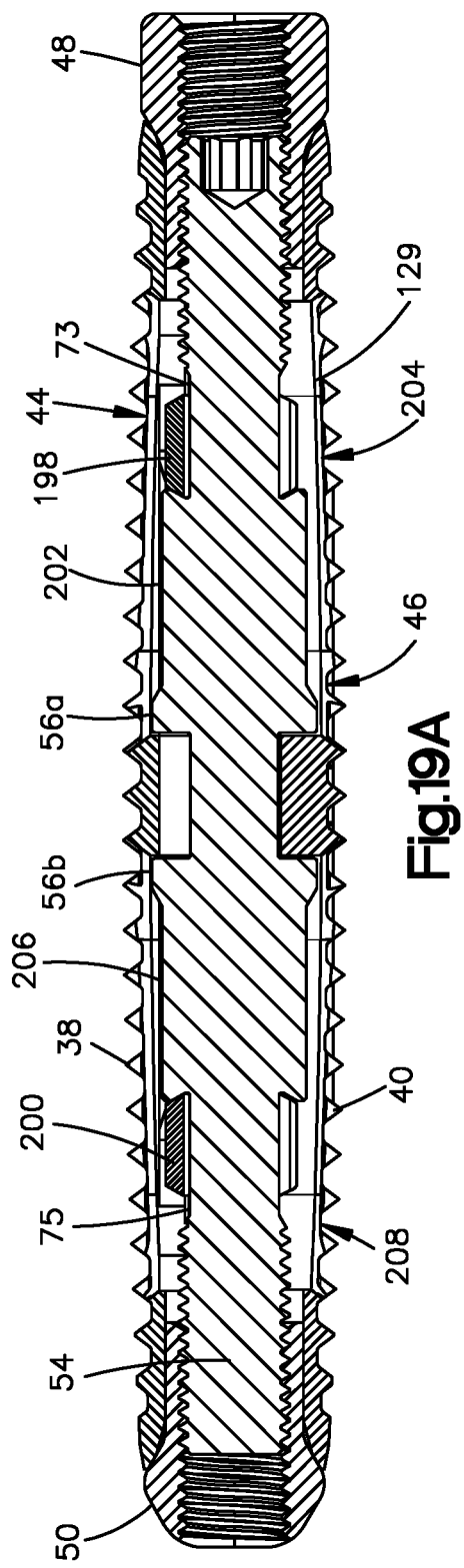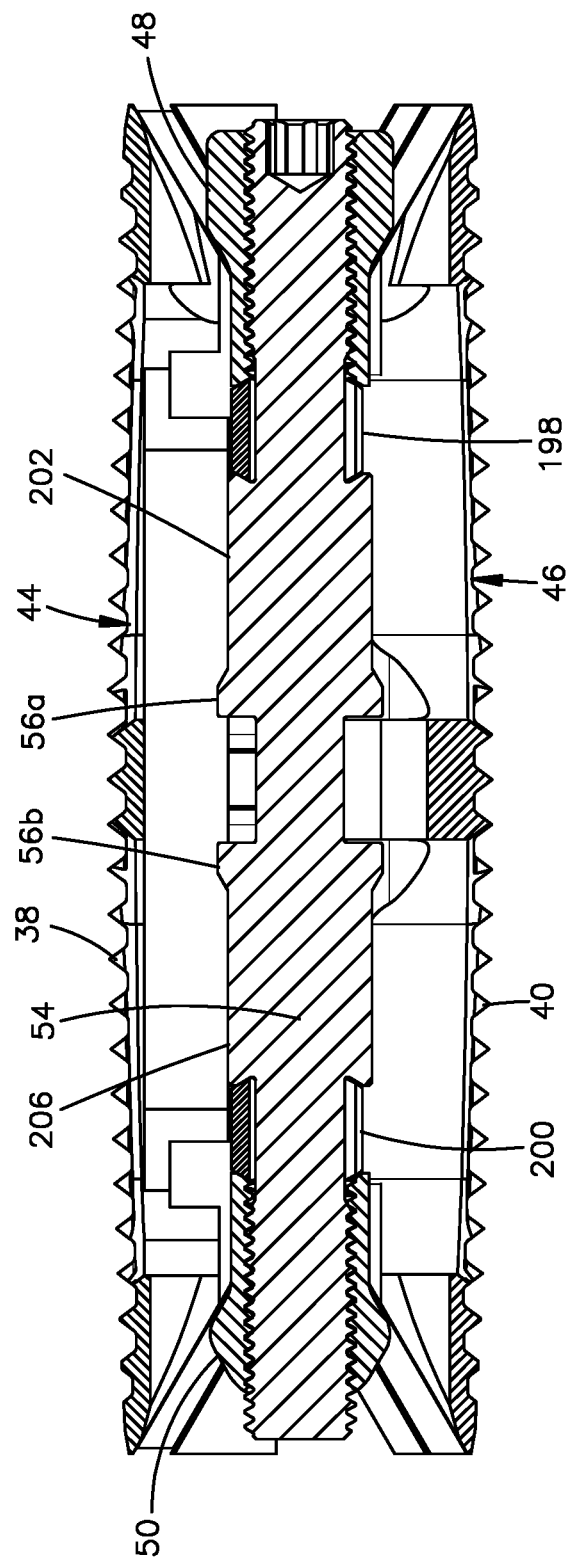

EXPANDABLE INTERVERTEBRAL IMPLANT, INSERTER INSTRUMENT, AND RELATED METHODS

CROSS-REFERENCE TO RELATED APPLICATIONS

This claims priority to U.S. Patent Application Ser. No. 62/751,501 filed Oct. 26, 2018, and to U.S. Patent Application Ser. No. 62/750,472 filed Oct. 25, 2018, the disclosure of each of which is hereby incorporated by reference as if set forth in its entirety herein.

TECHNICAL FIELD

The present invention relates to an expandable intervertebral implant, system, kit and method.

BACKGROUND

The human spine is comprised of a series of vertebral bodies separated by intervertebral discs. The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1.beta. and TNF-.alpha. as well as matrix metalloproteinases ("MMPs"). These cytokines and MMPs help regulate the metabolism of the nucleus pulposus cells.

In some instances of degenerative disc disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of proinflammatory cytokines and/or MMPs that may cause nerve irritation and pain.

As DDD progresses, toxic levels of the cytokines and MMPs present in the nucleus pulposus begin to degrade the extracellular matrix. In particular, the MMPs (as mediated by the cytokines) begin cleaving the water-retaining portions of the proteoglycans, thereby reducing their water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices".

One proposed method of managing these problems is to remove the problematic disc and replace it with a device that restores disc height and allows for bone growth between the adjacent vertebrae. These devices are commonly called fusion devices, or "interbody fusion devices". Current spinal fusion procedures include transforaminal lumbar interbody fusion (TLIF), posterior lumbar interbody fusion (PLIF), and extreme lateral interbody fusion (XLIF) procedures. However, implants having textured, toothed upper and lower vertebral engagement teeth can suffer from mechanical interference between the teeth and the bony endplates during implantation. Expandable fusion devices are configured to be implanted into the intervertebral space in a collapsed configuration, and subsequently expanded in the intervertebral space to achieve height restoration.

SUMMARY

In one example, an expandable implant can be configured to be inserted in an intervertebral space defined between a first vertebral body and a second vertebral body. The implant can include an upper endplate defining an upper bone contacting surface, the upper endplate having an upper guide member. The implant can further include a lower endplate defining a lower bone contacting surface opposite the upper bone contacting surface along a transverse direction, the lower endplate having a lower guide member. The implant can further define an insertion end and a trailing end opposite the insertion end along a longitudinal direction that is perpendicular to the transverse direction. The implant can further include at least one expansion member that defines a ramped engagement surface configured to bear against an engagement surface of one of the upper and lower endplates so as to move the expandable implant from a collapsed configuration to an expanded configuration as the expansion member moves in an expansion direction with respect to the upper and lower endplate. The expandable implant can define a first height from the upper bone contacting surface to the lower bone contacting surface along in the collapsed configuration. The expandable implant defines a second height from the upper bone contacting surface to the lower bone contacting surface in the collapsed configuration, and the second height is greater than the first height. The expansion member can define an upper guide member and a lower guide member configured to the upper guide member of the upper endplate and the lower guide member of the lower endplate, respectively, so as to guide movement of the upper and lower endplates away from each other as the expansion member moves in the expansion direction. The upper guide members of both the expansion member and the upper endplate can be asymmetrical with respect to the lower guide members of both the expansion member and the lower endplate about a midplane that is oriented perpendicular to the transverse direction.

BRIEF DESCRIPTION OF THE DRAWINGS

The foregoing summary, as well as the following detailed description of illustrative embodiments of the intervertebral implant of the present application, will be better understood when read in conjunction with the appended drawings. For the purposes of illustrating the expandable intervertebral implant of the present application, there is shown in the drawings illustrative embodiments. It should be understood, however, that the application is not limited to the precise arrangements and instrumentalities shown. In the drawings:

FIG. 3D is another sectional side elevation view of the expandable intervertebral implant illustrated in FIG. 2B;

FIG. 4A is a perspective view of a first wedge member of the expandable intervertebral implant illustrated in FIG. 3A;

FIG. 4B is a perspective view of a second wedge member of the expandable intervertebral implant illustrated in FIG. 3A;

FIG. 5A is a sectional side elevation view of an upper endplate of the expandable intervertebral implant illustrated in FIG. 3A;

FIG. 5B is a sectional side elevation view of a lower endplate of the expandable intervertebral implant illustrated in FIG. 3A;

FIG. 9 is a perspective view of an implant assembly, including the expandable intervertebral implant illustrated in FIG. 2A and an instrument;

FIG. 11C is a sectional top plan view similar to FIG. 11B, but showing the drive shaft coupled to an actuator shaft of the implant;

FIG. 11D is a sectional top plan view similar to FIG. 11C, but after the drive shaft has rotated the actuator shaft of the implant so as to expand the implant;

FIG. 18 is an exploded perspective view of an expandable intervertebral implant of another example;

FIG. 19A is a perspective view of the expandable intervertebral implant illustrated in FIG. 18, shown in a collapsed configuration;

FIG. 19B is a perspective view of the expandable intervertebral implant illustrated in FIG. 19A, shown in an expanded configuration;

DETAILED DESCRIPTION OF ILLUSTRATIVE EMBODIMENTS

Figure 1:
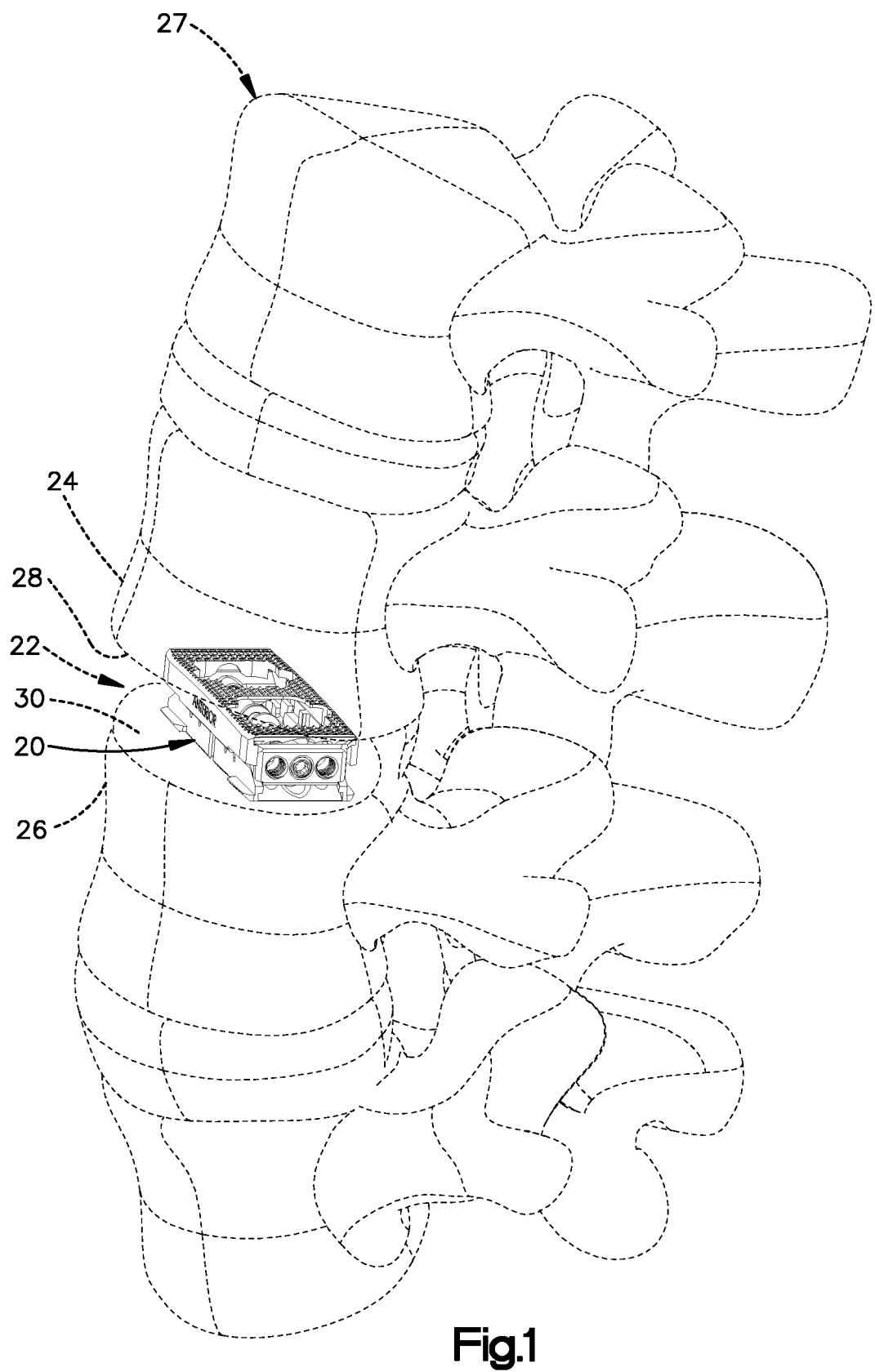
FIG. 1 is a perspective view of an expandable intervertebral implant disposed in an intervertebral space.

Referring initially to FIG. 1, an expandable intervertebral implant 20 is configured to be inserted into an intervertebral space 22. The intervertebral space 22 can be defined by a superior vertebral body 24 and an adjacent inferior vertebral body 26 of a human spine 27. The superior vertebral body 24 defines superior vertebral surface 28. The inferior vertebral body 26 defines an inferior vertebral surface 30. The vertebral bodies 24 and 26 can be anatomically adjacent. It should be understood, however, that the intervertebral implant can alternatively be configured to fit in an intervertebral space 22 that is defined by superior and inferior vertebral bodies that remain after a corpectomy has been performed so as to remove one or more vertebral bodies between the superior and inferior vertebral bodies. The intervertebral space 22 is shown in FIG. 1 after a discectomy, whereby the intervertebral disc material has been removed or at least partially removed to prepare the intervertebral space 22 to receive the intervertebral implant 20. The intervertebral space 22 can be defined in the lumbar region of the spine 27, or alternatively in the cervical region or the thoracic region.

As will be appreciated from the description below, the intervertebral implant 20 is configured to be inserted into the intervertebral space 22 along a lateral anatomical approach. In one example, the intervertebral implant 20 is configured to be inserted into the intervertebral space 22 in a collapsed configuration (see FIG. 2A), and subsequently expanded in the intervertebral space 22 to an expanded configuration (FIG. 2B) so as to achieve appropriate height restoration. The intervertebral space 22 can be disposed anywhere along the spine as desired. For instance, the intervertebral space 22 can be disposed at the lumbar region of the spine. Alternatively, the intervertebral space 22 can be disposed at the thoracic region of the spine. Alternatively still, the intervertebral space 22 can be disposed at the cervical region of the spine.

The intervertebral implant 20 is described herein as extending horizontally along a longitudinal direction "L" and a lateral direction "A", and transversely along a transverse direction "T". Unless otherwise specified herein, the terms "longitudinal," "lateral," and "transverse" are used to describe the orthogonal directional components of various implant components and implant component axes. The longitudinal direction L can be perpendicular to the transverse direction T. The lateral direction A can be perpendicular to the longitudinal direction L and the transverse direction T. It should be appreciated that while the longitudinal and lateral directions are illustrated as extending along horizontal directions, and that the transverse direction T is illustrated as extending along a vertical direction, the directions may differ during use depending on the orientation of the implant. For instance, when the implant 20 is inserted into an intervertebral space, such as the intervertebral space 22, the transverse direction T extends generally along the superior-inferior (or caudal-cranial) direction, while the horizontal plane defined by the longitudinal direction L and lateral direction A lies generally in the anatomical plane defined by the anterior-posterior direction, and the medial-lateral direction. In particular, the lateral direction A can extend generally along the anterior-posterior direction. The longitudinal direction L can extend generally along the medial-lateral direction.

Figure 2A:
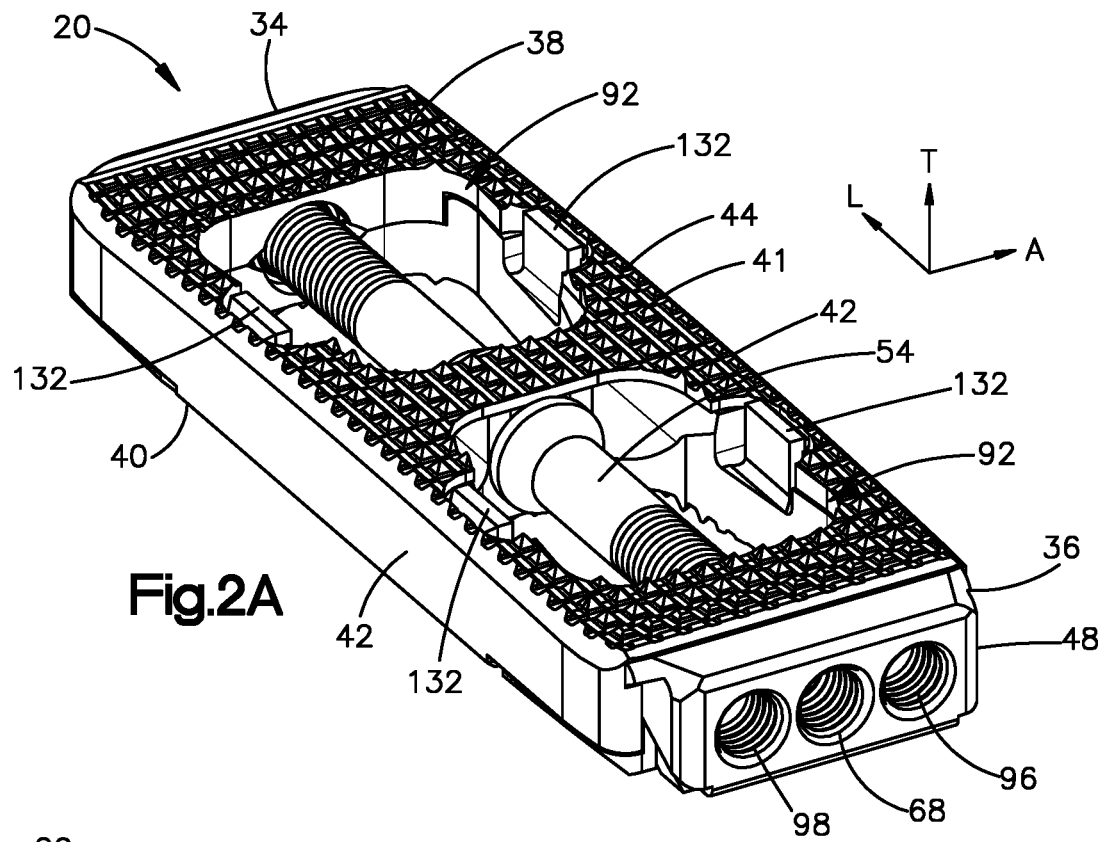
FIG. 2A is a perspective view of the expandable intervertebral implant illustrated in FIG. 1, shown in a collapsed configuration.
Figure 2B:
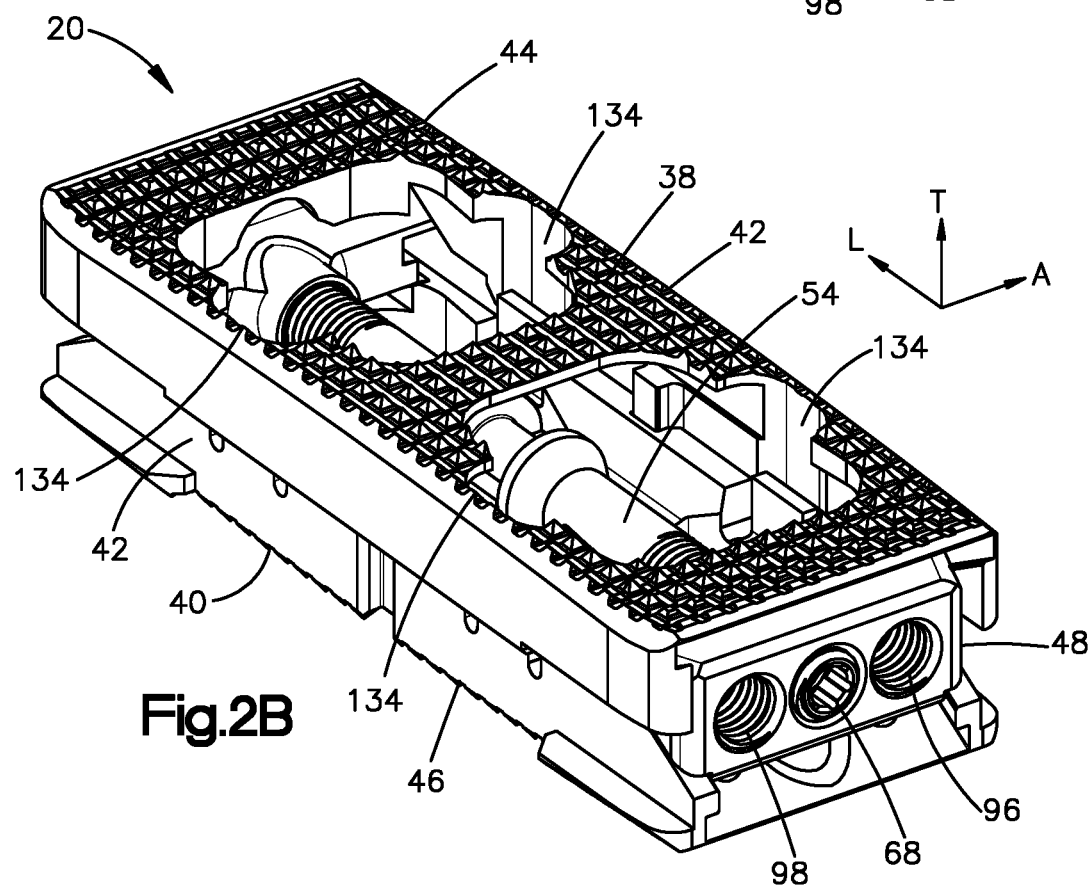
FIG. 2B is a perspective view of the expandable intervertebral implant illustrated in FIG. 2A, shown in an expanded configuration.

Referring now also to FIGS. 2A-2B, the expandable intervertebral implant 20 defines a leading end 34 and a trailing end 36 opposite the leading end 34 along a longitudinal direction L. The longitudinal direction L can generally extend along an insertion direction into the intervertebral space 22. Thus, the longitudinal direction L can be said to extend along the anatomical medial-lateral direction after the intervertebral implant 20 has been inserted into the intervertebral space 22 along the insertion direction. In particular, the leading end 34 can be said to be spaced from the trailing end 36 in the insertion direction. The leading end 34 can be tapered so as to facilitate insertion into the intervertebral space 22. The trailing end 36 is spaced from the leading end 34 in a direction that is opposite the insertion direction. The leading end 34 can also be said to define a distal end, and the trailing end 36 can be said to define a proximal end that is opposite the distal end. Thus, the expandable implant 20 can be said to define a distal direction from the trailing end 36 to the leading end 34 along the longitudinal direction L. The expandable implant 20 can also be said to define a proximal direction from the leading end 34 to the trailing end 36 along the longitudinal direction L. Thus, the distal direction can be coincident with the insertion direction. The proximal direction can be coincident with the direction opposite the insertion direction.

The intervertebral implant 20 can further define opposed side surfaces 42 that are opposite each other along a lateral direction A. The lateral direction A can be oriented perpendicular to the longitudinal direction L. The lateral direction A can be said to define a width of the implant. The width can be measured along the anatomical anterior-posterior direction after the intervertebral implant 20 has been inserted into the intervertebral space 22.

Figure 2C:
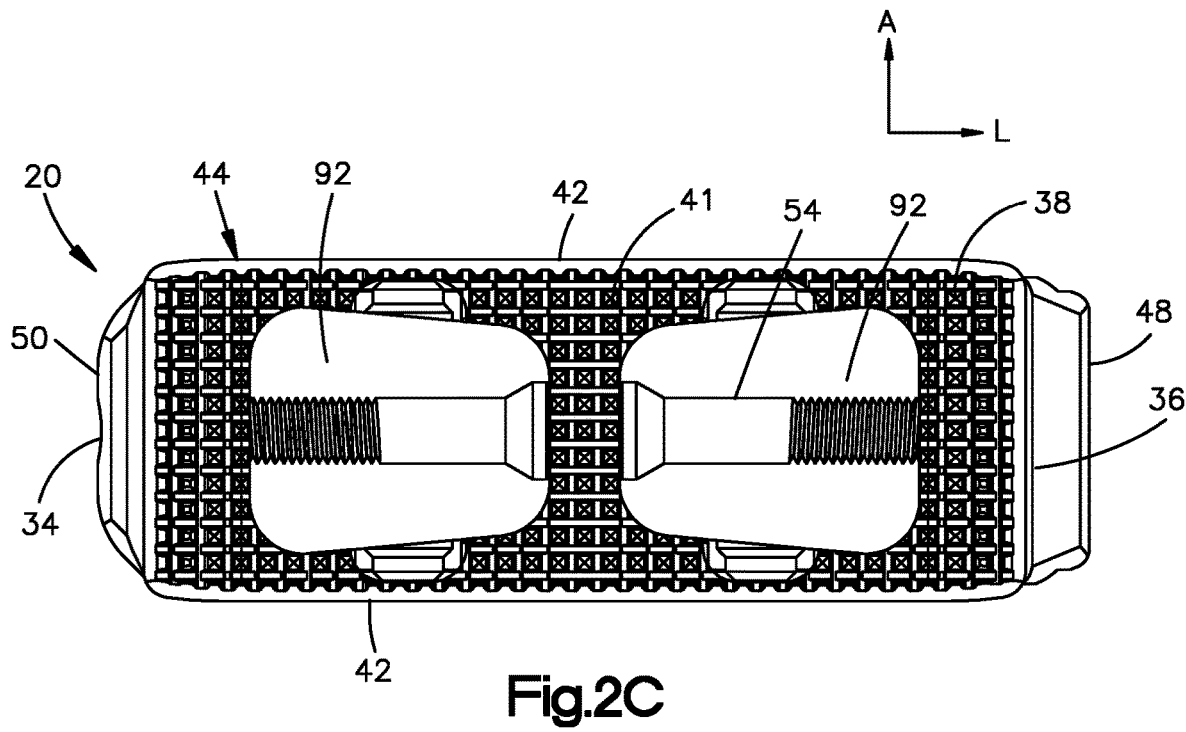
FIG. 2C is a top plan view of the expandable intervertebral implant illustrated in FIG. 2A.
Figure 2D:
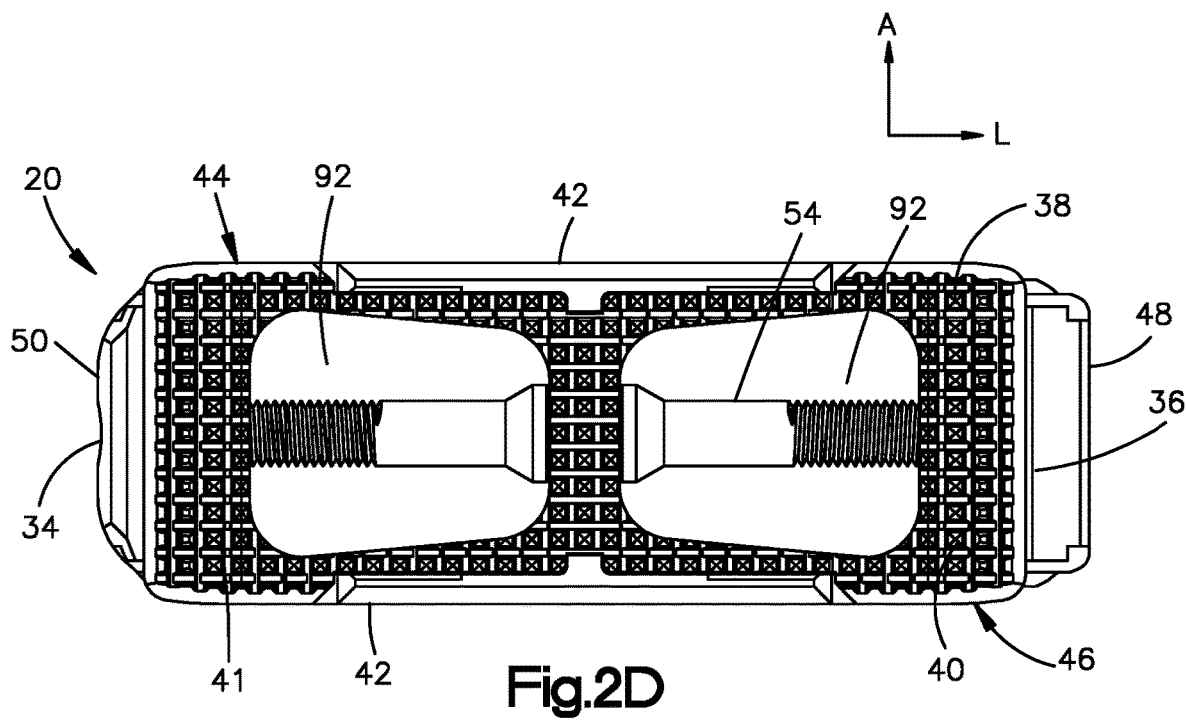
FIG. 2D is a bottom plan view of the expandable intervertebral implant illustrated in FIG. 2A.

Referring also to FIGS. 2C-2D, the intervertebral implant 20 can define an upper surface 38 that is configured to engage and contact the superior vertebral surface 28, and a lower surface 40 that is configured to engage and contact the inferior vertebral surface 30. Thus, the upper surface 38 can be referred to as an upper or superior vertebral bone contacting surface, and the lower surface 40 can be referred to as a lower or inferior vertebral bone contacting surface. The upper and lower surfaces 38 and 40 are spaced from each other along a transverse direction T that is oriented perpendicular to the longitudinal direction L. The transverse direction T can define a height of the intervertebral implant 20. The height can be measured along the anatomical caudal-cranial direction after the intervertebral implant 20 has been inserted into the intervertebral space 22. The height of the intervertebral implant 20 can be measured along the transverse direction T from the upper surface 38 to the lower surface 40. As used herein, the term "superior" and derivatives thereof refer to a direction from the lower surface 40 toward the upper surface 38. As used herein, the term "inferior" and derivatives thereof refer to a direction from the upper surface 38 toward the lower surface 40.

Further, the leading end 34 can be tapered along the transverse direction T. Thus, the upper and lower surfaces 38 and 40 can be tapered toward each other along the transverse direction T at the leading end 34 as they extend along the insertion direction. The side surfaces 42 can be tapered toward each other along the lateral direction A at the leading end 34 as they extend along the insertion direction.

The upper and lower bone contacting surfaces 38 and 40 can define a texture 41 configured to grip the respective vertebral body. The texture 41 can be configured as desired, and can include teeth, spikes, ridges, cones, barbs, indentations, knurls, or the like. The texture 41 can extend along a portion or an entirety of each of the upper and lower bone contacting surfaces 38 and 40. For instance, the upper and lower bone contacting surfaces 38 and 40 can include specific patterns of textured and non-textured portions. Further, as illustrated in FIGS. 3B-3C, at least a portion of each of the upper and lower bone contacting surfaces 38 and 40 can be convex. For instance, in one example, at least a portion of each of the upper and lower bone contacting surfaces 38 and 40 can be convex in a plane that is defined by the longitudinal direction L and the transverse direction T. Alternatively, the upper and lower bone contacting surfaces 38 and 40 can be substantially planar.

Figure 3A:
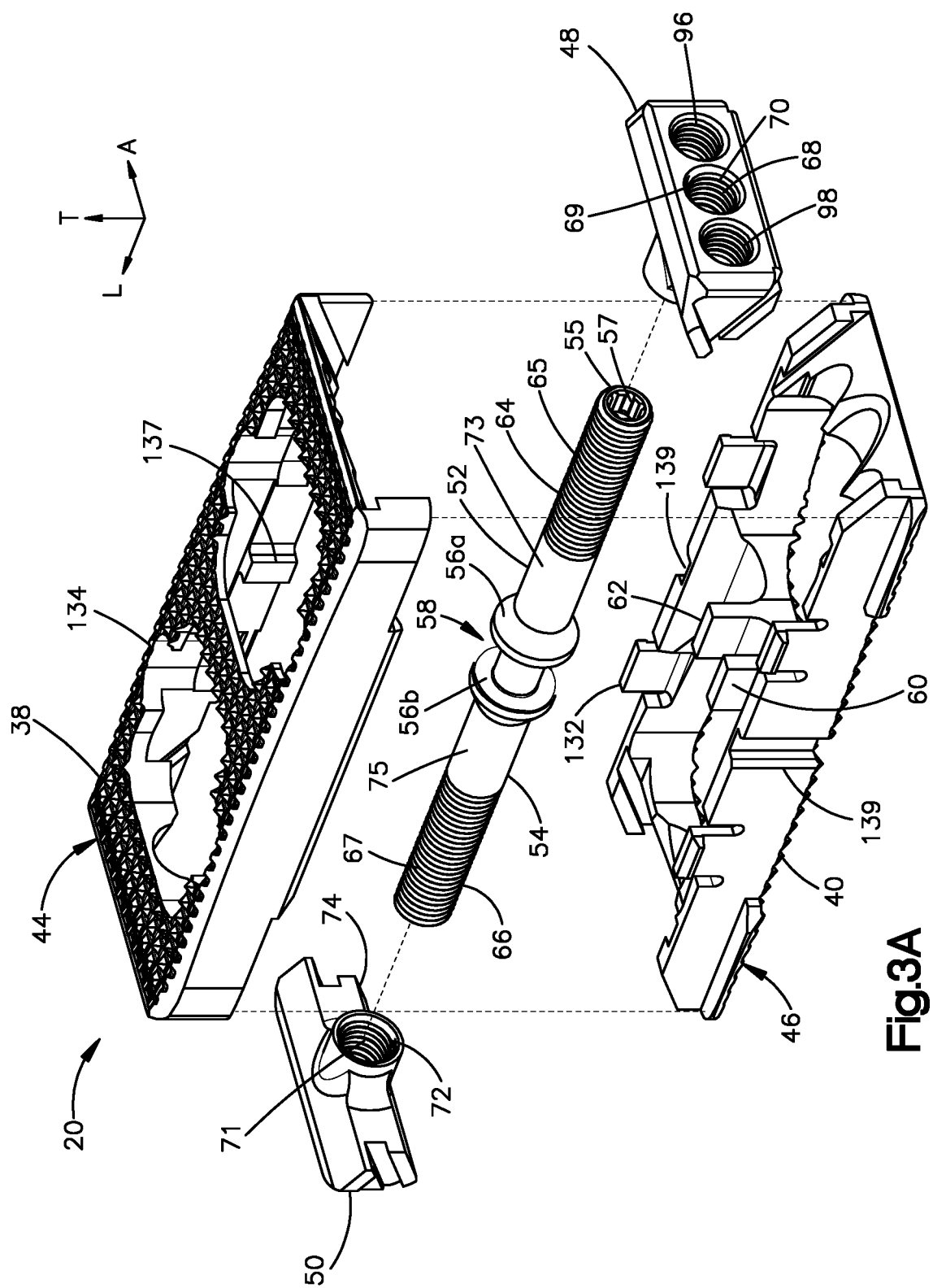
FIG. 3A is an exploded perspective view of the expandable intervertebral implant illustrated in FIG. 2A.
Figure 3B:
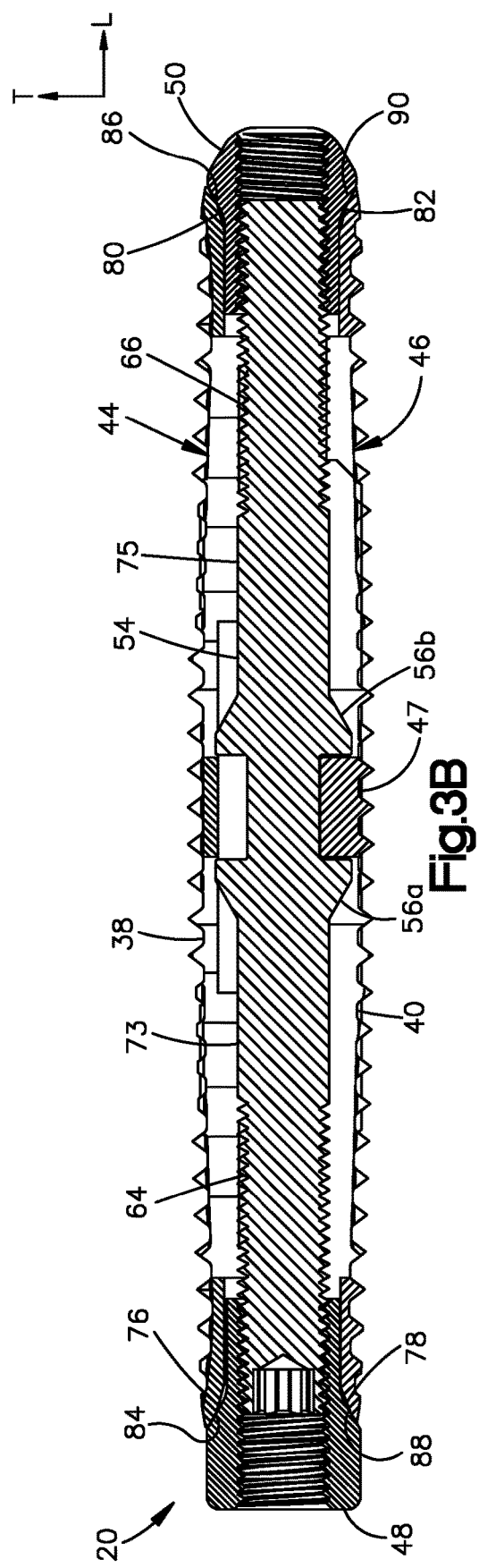
FIG. 3B is a sectional side elevation view of the expandable intervertebral implant illustrated in FIG. 2A.
Figure 3C:
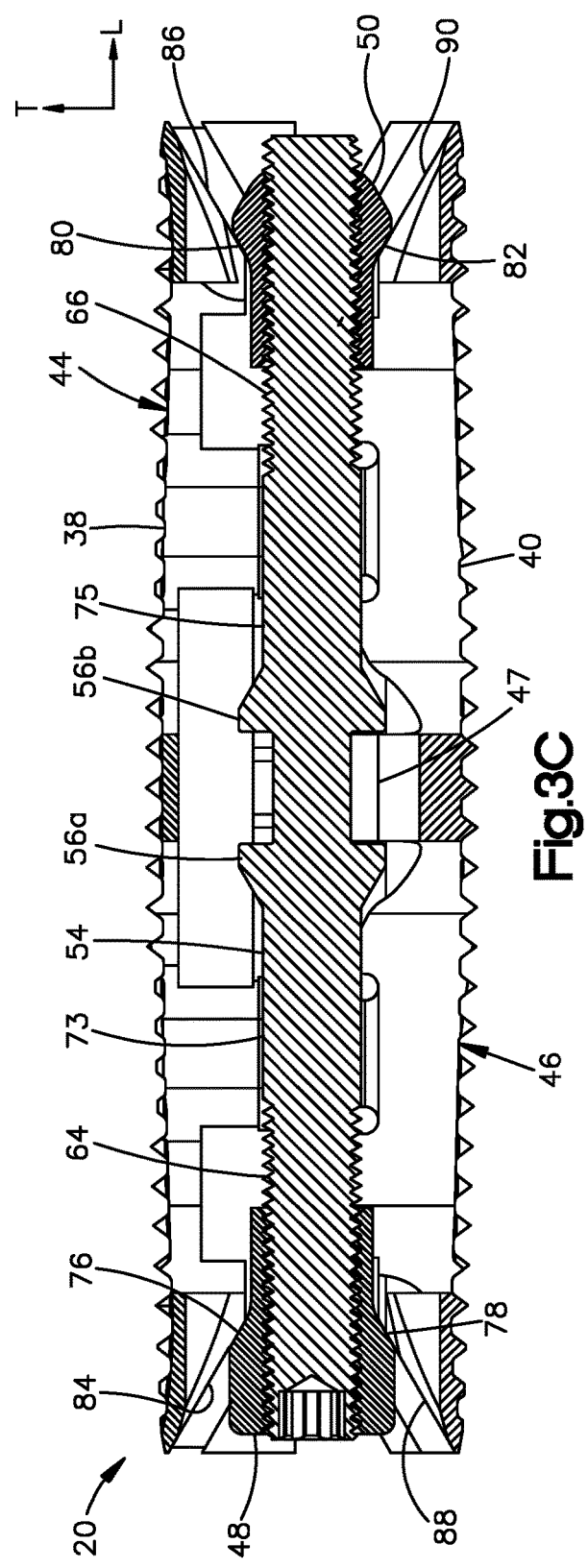
FIG. 3C is a sectional side elevation view of the expandable intervertebral implant illustrated in FIG. 2B.
Figure 6A:
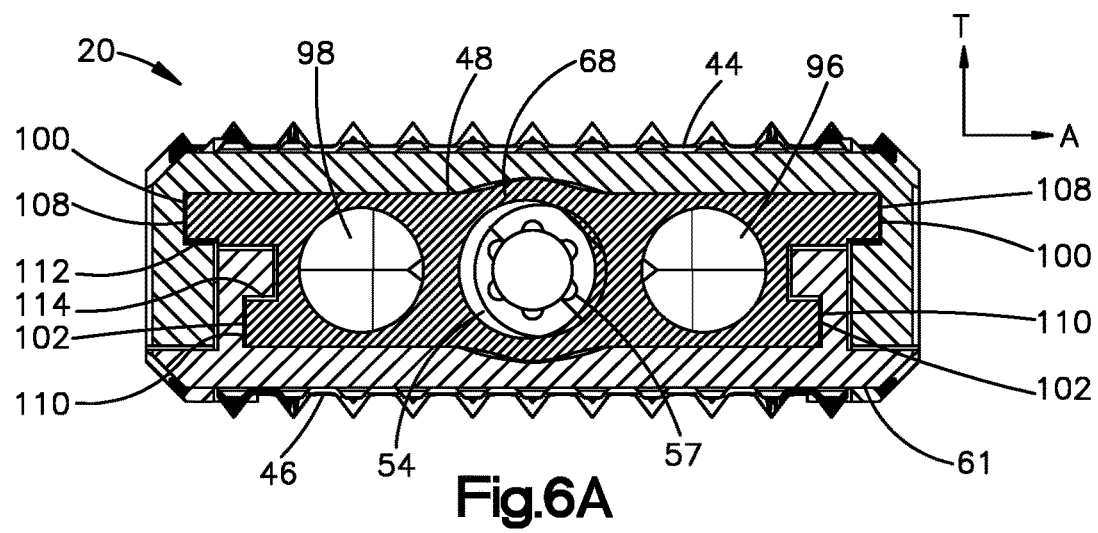
FIG. 6A is a sectional end elevation view of the expandable intervertebral implant illustrated in FIG. 2A.
Figure 6B:
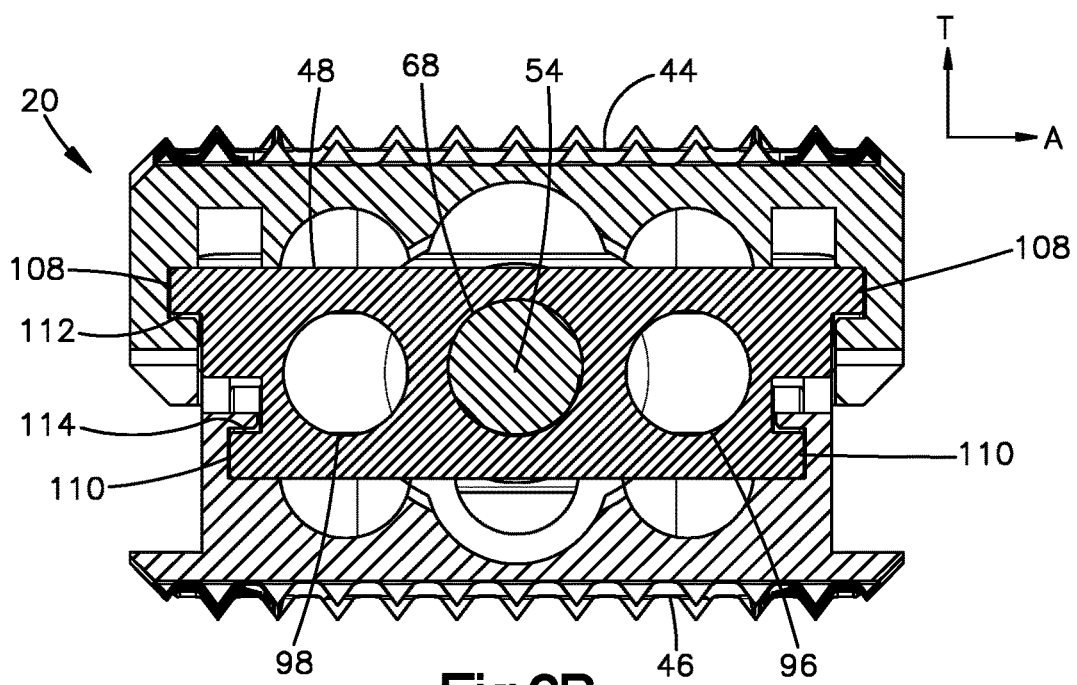
FIG. 6B is a sectional end elevation view of the expandable intervertebral implant illustrated in FIG. 2B.

Referring now to FIGS. 3A-3C, the intervertebral implant 20 includes a first or upper endplate 44 a second or lower endplate 46 that is opposite the upper endplate 44 along the transverse direction T. An upward direction and derivatives thereof can be defined along a direction from the lower endplate 46 to the upper endplate 44. A lower or downward direction and derivatives thereof can be defined along a direction from the upper endplate 44 to the lower endplate 46. The upper endplate 44 can define the upper surface 38. The lower endplate 46 can define the lower surface 40. Further, at least one of the endplates 44 and 46 can define the side surfaces 42. For instance, as will be described in more detail below, the endplates 44 and 46 can combine to define the side surfaces 42 when the expandable implant 20 is in the expanded configuration. The endplates 44 and 46 can define the side surfaces 42 when the implant 20 is in the expanded configuration. Further still, the endplates 44 and 46 can combine so as to define the leading end 34. The endplates 44 and 46 can further combine so as to define the trailing end 36 when the implant 20 is in the expanded configuration. When the expandable implant 20 is in the collapsed configuration, the endplates 44 and 46 can nest with each other. When the implant 20 is fully collapsed, one of the endplates 44 and 46 can define the side surfaces 42.

The intervertebral implant 20 can further include at least one expansion member that is movable between a collapsed position (FIG. 3B) and an expansion position (FIG. 3C). For instance, the at least one expansion member is movable in an expansion direction from the collapsed position to the expansion position. The at least one expansion member is further movable in a collapse direction from the expansion position to the collapsed position. The expansion direction and the collapse direction can be oriented along the longitudinal direction L. When the at least one expansion member moves in the expansion direction, the at least one expansion member moves the intervertebral implant to the expanded configuration. When the at least one expansion member moves in the collapse direction, the at least one expansion member moves the intervertebral implant 20 to the collapsed configuration. Thus, the at least one expansion member is configured to move the implant 20 between the collapsed configuration and the expanded configuration. The implant 20 has a first height in the collapsed configuration and a second height in the expanded configuration. The second height H2 is greater than the first height. The implant 20 is configured to be maintained in the expanded configuration when it is implanted in the intervertebral space and thus when it experiences anatomical loads along the transverse direction T.

As will be appreciated from the description below, when the intervertebral implant 20 is in the collapsed configuration, movement of the at least one expansion member in the expansion direction causes the at least one expansion member to urge at least one of the upper endplate 44 and the lower endplate 46 away from the other of the upper endplate 44 and the lower endplate 46 along the transverse direction T, thereby moving the intervertebral implant 20 to the expanded configuration. For instance, the at least one expansion member can be configured to urge each of the upper endplate 44 and the lower endplate 46 to move away from the other of the upper endplate 44 and the lower endplate 46 along the transverse direction T. The intervertebral implant 20 can be constructed such that when the implant is in a fully expanded configuration, the at least one expansion member is unable to cause the intervertebral implant 20 to further expand along the transverse direction T. In one example, the at least one expansion member is unable to move further in the expansion direction when the intervertebral implant is in the fully expanded configuration.

When the intervertebral implant 20 is in the expanded configuration, movement of the at least one expansion member in the collapse direction causes the at least one expansion member to urge at least one of the upper endplate 44 and the lower endplate 46 toward from the other of the upper endplate 44 and the lower endplate 46 along the transverse direction T, thereby moving the intervertebral implant 20 to the collapsed configuration. For instance, the at least one expansion member can be configured to urge each of the upper endplate 44 and the lower endplate 46 to move toward the other of the upper endplate 44 and the lower endplate 46 along the transverse direction T. The intervertebral implant 20 can be constructed such that when the implant is in a fully collapsed configuration, the at least one expansion member is unable to move further to the collapsed position so as to cause the intervertebral implant 20 to further collapse along the transverse direction T. In one example, the at least one expansion member is unable to move further in the collapse direction when the intervertebral implant 20 is in the fully collapsed configuration.

With continuing reference to FIGS. 3A-3C, the at least one expansion member can include a pair of expansion members. Further, the at least one expansion member can be configured as at least one wedge member. The at least one wedge member can include a pair of wedge members. For instance, the at least one wedge member can include a first wedge member 48 and a second wedge member 50. Thus the at least one expansion member can include a first expansion member that can be configured as the first wedge member 48, and a second expansion member that can be configured as a second wedge member 50. It should be appreciated, of course, that the first and second expansion members can be configured in any suitable manner as desired other than wedge members.

The and second wedge members 48 and 50 can be positioned between the upper and lower endplates 44 and 46 along the transverse direction T. The first wedge member 48 can be disposed proximal with respect to the second wedge member 50. Conversely, the second wedge member 50 can be said to be disposed distal with respect to the first wedge member 48. Further, the distal end of the second wedge member 50 can define the tapered leading end of the implant 20 when the implant is in the collapsed configuration. Thus, the first wedge member 48 can be referred to as a proximal wedge member, and the second wedge member 50 can be referred to as a distal wedge member. The first and second wedge members 48 and 50 can move toward each other in the expansion direction. Conversely, the first and second wedge members 48 and 50 can move away from each other in the collapse direction.

The intervertebral implant 20 can include an actuator 52 that is coupled to the at least one wedge member. The actuator 52 can be configured to selectively drive the at least one wedge member in the expansion direction and the collapse direction. In particular, the actuator can be coupled to each of the first and second wedge members 48 and 50. The actuator 52 can be configured to drive the first and second wedge members 48 and 50 toward each other along the longitudinal direction L. Further, the actuator 52 can be configured to drive the first and second wedge members 48 and 50 away from each other along the longitudinal direction L.

In one example, the actuator 52 can be configured as a rotatable actuator shaft 54. The actuator shaft 54 can be rotatably supported by at least one of the upper endplate 44 and the lower endplate 46 at a coupling 47. Further, the actuator shaft 54 can be fixed with respect to translation of the actuator shaft 54 along the longitudinal direction L relative to the endplates 44 and 46. In particular, the coupling 47 is configured to translatably fix the actuator shaft 54 relative to the endplates 44 and 46. The first and second wedge members 48 and 50 can be disposed on opposite sides of the coupling 47 with respect to the longitudinal direction L. In one example, the length of the actuator shaft 54 along the longitudinal direction L can be no greater than, such as less than, the respectively lengths of the upper and lower endplates 44 and 46 along the longitudinal direction.

The endplates, wedge members, and actuator shaft can be made of any suitable material as desired. For instance, the endplates and wedge members can be formed of a polyaryletherketone (PAEK) including polyether ether ketone (PEEK), polyetherketoneketone (PEKK), or any other suitable biocompatible polymeric material. The actuator shaft 54 can be formed from a biocompatible polymeric material or metallic alloy, such as titanium or steel. It should be appreciated that the any suitable material can be used to form the implant components as described herein. For instance, an entirety of the implant can be made from a titanium alloy. For instance, an entirety of the implant can be made from a titanium-aluminium-niobium (TAN) alloy.

In one example, the actuator shaft 54 can include at least one flange 56 that is configured to engage at least one of the upper endplate 44 and the lower endplate 46. The at least one flange 56 can include first and second flanges 56a and 56b, respectively, that are spaced from each other along the longitudinal direction L so as to define a recess 58 therebetween. At least one of the upper endplate 44 and the lower endplate 46 can define a projection 60 sized to fit in the recess 58 so as to define the coupling 47. The projection 60 can be configured as a cradle 62 that is received in the recess 58. The cradle 62 can define a mechanical interference with the flanges 56a-b both with respect to proximal and distal translation of the actuator shaft 54 relative to the endplates 44 and 46. The cradle 62 can have a sufficient height along the transverse direction T so as to extend in the recess 58 and define the interference both when the implant 20 is in the collapsed configuration and when the implant 20 is in the expanded configuration. In one example, the cradle 62 can be defined by the lower endplate 46. The upper endplate 44 can be fixed to the lower endplate 46 with respect to relative movement along the longitudinal direction L. The first and second flanges 56a-b are rotatable along a central axis of the actuator shaft 54 with respect to the cradle 62, and thus with respect to the endplates 44 and 46. The central axis can be oriented along the longitudinal direction L. It should be appreciated, of course, that the actuator shaft 54 can be translatably fixed to the endplates 44 and 46, and rotatable with respect to the endplates 44 and 46 in any suitable alternative embodiment as desired. For instance, the actuator shaft 54 can include a flange that is received in a recess of one or both of the upper endplate 44 and the lower endplate 46.

The first and second wedge members 48 and 50 can each threadedly mate with the actuator shaft 54. Rotation of the actuator shaft 54 in a first direction of rotation drives the first and second wedge members 48 and 50 to move in the expansion direction. Rotation of the actuator shaft 54 in a second direction opposite the first direction drives the first and second wedge members 48 and 50 to move in the collapse direction. The actuator shaft 54 defines a proximal end 55 that defines a coupling member 57 configured to couple to a drive shaft. The drive shaft can include a complementary drive member that is configured to engage the coupling member 57 of the actuator shaft 54 so as to drive the actuator shaft 54 to selectively rotate in the first direction of rotation and the second direction of rotation. In one example, the coupling member 57 of the actuator shaft 54 can be configured as a socket. The drive member of the drive shaft can be configured as a projection that is received in the socket. The projection and the socket can each define a hex head, a Phillips head, a flat head, a start head, or the like. Alternatively, the drive member of the drive shaft can be configured as a socket, and the coupling member of the 57 of the actuator shaft 54 can be configured as a projection that is configured to be received by the socket of the drive member.

The actuator shaft 54 can define a first threaded portion 64 that includes a first external thread 65, and a second threaded portion 66 that includes a second external thread 67. The at least one flange 56 can be disposed between the first threaded portion 64 and the second threaded portion 66 with respect to the longitudinal direction L. The first threaded portion 64 can be referred to as a proximal threaded portion disposed proximal of the at least one flange 56. The second threaded portion 66 can be referred to as a distal threaded portion that is disposed distal of the at least one flange 56. The first and second threaded portions 64 and 66 can define respective first and second external thread patterns that are oriented in opposite directions.

The actuator shaft 54 can further define a first unthreaded portion 73 that extends between the first threaded portion 64 and the first flange 56a. For instance, the first unthreaded portion 73 can extend from the first threaded portion 64 to the first flange 56a. The first unthreaded portion 73 can define an outer diameter that is equal to the minor diameter of the first threaded portion 64. Alternatively, the first threaded portion 64 can extend to the first flange 56a. Similarly, the actuator shaft 54 can further define a second unthreaded portion 75 that extends between the second threaded portion 66 and the second flange 56b. For instance, the second unthreaded portion 75 can extend from the second threaded portion 66 to the second flange 56b. The second unthreaded portion 75 can define an outer diameter that is equal to the minor diameter of the second threaded portion 66. In one example, the outer diameter of the second unthreaded portion 75 can be substantially equal to the outer diameter of the first unthreaded portion 73. Alternatively, the second threaded portion 66 can extend to the second flange 56b.

The first and second wedge members 48 and 50 are configured to threadedly mate with the first and second threaded portions 64 and 66, respectively, of the actuator shaft 54. In one example, the first wedge member 48 can include a first wall 69 that defines a first bore 68 sized to receive the first threaded portion 64. The first bore 68 can extend through the first wedge member 48 along the longitudinal direction L. The first wedge member 48 can define a first internal thread 70 in the first bore 68 that mates with the first external thread 65 when the first threaded portion 64 has been received in the first bore 68. The second wedge member 50 can include a second wall 71 that defines a second bore 72 sized to receive the second threaded portion 64. The second bore 72 can extend through the second wedge member 50 along the longitudinal direction L. The second wedge member 50 can define a second internal thread 74 in the second bore 72 that mates with the second external thread 67 when the second threaded portion 66 has been received in the second bore 72. Thus, the first internal thread 70 and the second internal thread 74 can define respective first and second internal thread patterns that are oriented in opposite directions.

The first internal thread pattern can be oriented in the same direction as the first external thread pattern. The second internal thread pattern can be oriented in the same direction as the second external thread pattern. Thus, when the actuator shaft 54 rotates about the central axis, the first and second wedge members 48 and 50 translate along the actuator shaft 54. As described above, when the actuator shaft 54 rotates in the first direction of rotation, the first and second wedge members 48 and 50 translate along the actuator shaft 54 toward each other. When the actuator shaft 54 rotates in the second direction of rotation, the first and second wedge members 48 and 50 translate along the actuator shaft 54 away from each other. The first and second internal thread patterns and the first and second external thread patterns can have the same thread pitch, such that the first and second wedge members 48 and 50 can translate along the actuator shaft 54 at the same rate. It should be appreciated, of course, that the thread pitches can be different such that the first and second wedge members 48 and 50 translate along the actuator shaft 54 at respective different rates as desired.

Referring now to FIGS. 3B-4B, each of the first and second wedge member 48 and 50 can define a respective at least one engagement surface that bears against a respective at least one of the upper endplate 44 and the lower endplate 46 when the wedge members move in the expansion direction. As will be appreciated from the description below, the at least one engagement surface can push the at least one of the upper endplate 44 and the lower endplate 46 away from the other of the upper endplate 44 and the lower endplate 46 along the transverse direction T as the wedge members 48 and 50 travel in the expansion direction.

In one example, the first wedge member 48 defines a first upper engagement surface 76 and a first lower engagement surface 78 opposite the first upper engagement surface 76 along the transverse direction T. The first upper engagement surface 76 can be configured as a ramped engagement surface. Similarly, the first lower engagement surface 78 can be configured as a ramped engagement surface. The first upper engagement surface 76 can flare downward as it extends in the expansion direction of the first wedge member 48. The expansion direction of the first wedge member 48 can be toward the coupling 47, and thus toward the second wedge member 50. The first lower engagement surface 78 can flare upward as it extends in the expansion direction of the first wedge member 48. For instance, the first upper engagement surface 76 and the first lower engagement surface 78 can have a linear taper. Alternatively, the first upper engagement surface 76 and the first lower engagement surface 78 can have a curved taper. The first upper engagement surface 76 and the first lower engagement surface 78 can be sloped substantially equal and opposite each other. The first wall 69, and thus the first bore 68, can extend out with respect to the first upper engagement surface 76 and the first lower engagement surface 78 in the expansion direction.

In one example, the second wedge member 50 defines a second upper engagement surface 80 and a second lower engagement surface 82 opposite the second upper engagement surface 80 along the transverse direction T. The second upper engagement surface 80 can be configured as a ramped engagement surface. Similarly, the second lower engagement surface 82 can be configured as a ramped engagement surface. For instance, the second upper engagement surface 80 can flare downward as it extends in the expansion direction of the second wedge member 50. The expansion direction of the second wedge member 50 can be toward the coupling 47, and thus toward the first wedge member 48. The second lower engagement surface 80 can flare upward as it extends in the expansion direction of the second wedge member 50. For instance, the second upper engagement surface 80 and the second lower engagement surface 82 can have a linear taper. Alternatively, the second upper engagement surface 80 and the second lower engagement surface 82 can have a curved taper. The second upper engagement surface 80 and the second lower engagement surface 82 can be sloped substantially equal and opposite each other. Further, the first and second upper engagement surfaces 76 and 80 can be sloped substantially equal and opposite each other. Further, the first and second lower engagement surfaces 78 and 82 can be sloped equal and opposite each other. The second wall 71, and thus the second bore 72, can extend out with respect to the second upper engagement surface 80 and the second lower engagement surface 82 in the expansion direction.

With continuing reference to FIGS. 3B-3C, the upper endplate 44 can define a first upper engagement surface 84 that is configured to engage the first upper engagement surface 76 of the first wedge member 48. For instance, the first upper engagement surface 84 of the upper endplate 44 is configured to ride along the first upper engagement surface 76 of the first wedge member 48, and vice versa, as the first wedge member 48 moves in both the expansion direction and the collapse direction. In one example, the first upper engagement surface 84 of the upper endplate 44 can be in surface contact with the first upper engagement surface 76 of the first wedge member 48. The first upper engagement surface 84 of the upper endplate 44 can flare down toward the lower endplate 46 as it extends in the expansion direction of the first wedge member 48. For instance, the first upper engagement surface 84 of the upper endplate 44 can have a linear taper. Alternatively, the first upper engagement surface 84 of the upper endplate 44 can have a curved taper. The first upper engagement surface 84 of the upper endplate 44 can be sloped equal to the first upper engagement surface 76 of the first wedge member 48.

The upper endplate 44 can further define a second upper engagement surface 86 that is configured to engage the second upper engagement surface 80 of the second wedge member 50. For instance, the second upper engagement surface 86 of the upper endplate 44 is configured to ride along the second upper engagement surface 80 of the second wedge member 48, and vice versa, as the second wedge member 50 moves in both the expansion direction and the collapse direction. In one example, the second upper engagement surface 86 of the upper endplate 44 can be in surface contact with the second upper engagement surface 80 of the second wedge member 50. The second upper engagement surface 86 of the upper endplate 44 can flare down toward the lower endplate 46 as it extends in the expansion direction of the second wedge member 50. For instance, the second upper engagement surface 86 of the upper endplate 44 can have a linear taper. Alternatively, the second upper engagement surface 86 of the upper endplate 44 can have a curved taper. The second upper engagement surface 86 of the upper endplate 44 can be sloped equal to the second upper engagement surface 80 of the second wedge member 50. Further, the first and second upper engagement surfaces 84 and 86 of the upper endplate can be sloped substantially equal and opposite each other. The term "substantially" and "approximately" as used herein can include the stated shape, direction, dimension, or other parameter along with variations due to factors such as manufacturing tolerance, and in one example can account for variations up to +/−10% of the stated shape, direction, dimension, or other parameter.

The lower endplate 46 can define a first lower engagement surface 88 that is configured to engage the first lower engagement surface 78 of the first wedge member 48. For instance, the first lower engagement surface 88 of the lower endplate 46 is configured to ride along the first lower engagement surface 78 of the first wedge member 48, and vice versa, as the first wedge member 48 moves in both the expansion direction and the collapse direction. In one example, the first lower engagement surface 88 of the lower endplate 46 can be in surface contact with the first lower engagement surface 78 of the first wedge member 48. The first lower engagement surface 88 of the lower endplate 46 can flare up toward the upper endplate 44 as it extends in the expansion direction of the first wedge member 48. For instance, the first lower engagement surface 88 of the lower endplate 46 can have a linear taper. Alternatively, the first lower engagement surface 88 of the lower endplate 46 can have a curved taper. The first lower engagement surface 88 of the lower endplate 46 can be sloped equal to the first lower engagement surface 78 of the first wedge member 48.

The lower endplate 46 can further define a second lower engagement surface 90 that is configured to engage the second lower engagement surface 82 of the second wedge member 50. For instance, the second lower engagement surface 90 of the lower endplate 46 is configured to ride along the second lower engagement surface 82 of the second wedge member 50, and vice versa, as the second wedge member 50 moves in both the expansion direction and the collapse direction. In one example, the second lower engagement surface 90 of the lower endplate 46 can be in surface contact with the second lower engagement surface 82 of the second wedge member 50. The second lower engagement surface 90 of the lower endplate 46 can flare up toward the upper endplate 44 as it extends in the expansion direction of the second wedge member 50. For instance, the second lower engagement surface 90 of the lower endplate 46 can have a linear taper. Alternatively, the second lower engagement surface 90 of the lower endplate 46 can have a curved taper. The second lower engagement surface 90 of the lower endplate 46 can be sloped equal to the second lower engagement surface 82 of the second wedge member 50. Further, the first and second lower engagement surfaces 88 and 90 of the second endplate 46 can be sloped substantially equal and opposite each other.

Thus, it can be said that the intervertebral implant 20 includes at least one wedge member that is configured to ride along a complementary engagement surface of at least one or both of the upper endplate 44 and the lower endplate 46 as the at least one wedge member moves in the expansion direction and the collapse direction. The at least one wedge member can include the first and second wedge members 48 and 50. The first and second wedge members 48 and 50 can push the upper and lower endplates 44 and 46 away from each other along the transverse direction as they travel in the expansion direction. The engagement surfaces 76 and 78 of the first wedge member 48, the engagement surfaces 80 and 82 of the second wedge member 50, the engagement surfaces 84 and 86 the upper endplate 44, and the engagement surfaces 88 and 90 of the lower endplate 46 can all be referred to as ramp surfaces.

As illustrated in FIG. 2C-2D, the upper and lower endplates 44 and 46 can include bone graft apertures 92 that extend therethrough along the transverse direction T. The endplates 44 and 46 can be configured to receive bone graft material that can fuse to the respective vertebral body through the respective bone graft apertures 92.

Referring now to FIGS. 4A-6B, the first wedge member 48 and the upper and lower endplates 44 and 46 can include respective complementary guide members that guide the movement of the upper and lower endplates 44 and 46 away from and toward each other, respectively, as the first wedge member 48 moves in the expansion direction and the collapse direction. The guide members of the first and second wedge members 48 and 50 can further apply a force to the guide members of the upper and lower endplates that draw the upper and lower endplates toward each other as the wedge members 48 and 50 move in the collapse direction. As will be appreciated from the description below, the guide members can be ramped and sloped equal to respective pairs of the engagement surfaces.

In particular, the first wedge member 48 defines a first upper guide member 100 and a first lower guide member 102. At least a portion of the first upper guide member 100 and at least a portion of the first lower guide member 102 can be aligned with each other along a plane that is oriented along the lateral direction A and the transverse direction T. The first upper guide member 100 can be disposed upward with respect to the first lower guide member 102. The upper endplate 44 defines a first upper guide member 104 that is configured to engage the first upper guide member 100 of the first wedge member 48. The lower endplate 46 defines a first lower guide member 106 that is configured to engage the first lower guide member 100 of the first wedge member 48. The first upper guide member 104 of the upper endplate 44 can be disposed upward with respect to the first lower guide member 106 of the lower endplate 46.

As will be appreciated from the description below, the first upper guide member 100 and the first lower guide member 102 of the first wedge member 48 can be asymmetrical with respect to each other about a first centrally disposed midplane that is oriented along the longitudinal direction L and the lateral direction A. The midplane can thus be oriented perpendicular to the transverse direction T. Further, the midplane can be positioned equidistantly between the upper guide members and the lower guide members. In one example, the midplane can include the central axis of the actuator shaft 54.

Further, the first upper guide member 104 of the upper endplate 44 and the first lower guide member 106 of the lower endplate 46 can be asymmetrical with respect to each other about a second centrally disposed midplane that is oriented along the longitudinal direction L and the lateral direction A. The first and second centrally disposed midplanes can be coincident with each other. Thus, the second midplane can be oriented perpendicular to the transverse direction T. Further, the second midplane can be positioned equidistantly between the upper guide members and the lower guide members. In one example, the second midplane can include the central axis of the actuator shaft 54.

In one example, one of the upper end lower guide members of the first wedge member 48 can define at least one outer projection, and the other of the upper and lower guide members of the first wedge member 48 can define at least one inner projection. The at least one inner projection can be inwardly offset with respect to the at least one outer projection along the lateral direction A. Similarly, one of the first guide members of the upper and lower endplates 44 and 46 can define an outer channel that is configured to slidably received the outer projection of the first wedge member 48. The other of the first guide members of the upper and lower endplates 44 and 46 can define an inner channel that is configured to slidably receive the inner projection of the first wedge member 48. Thus, the complementary guide members of the first wedge member 48 and the upper and lower endplates 44 and 46 can define tongue-in-groove, or T-shaped, guidance engagements.

In one example, the first upper guide member 100 of the first wedge member 48 can be configured as at least one first outer projection 108 that extends out along the lateral direction A. For instance, the first upper guide member 100 of the first wedge member 48 can be configured as first and second outer projections 108 that extend out along the lateral direction A away from each other. The first and second outer projections 108 can be aligned with each other along the lateral direction A. The outer projections 108 of the first wedge member 48 can define respective upper surfaces that are coplanar with the first upper engagement surface 76 (see FIGS. 3B-3C) of the first wedge member 48. In one example, the first lower guide member 102 of the first wedge member 48 can be configured as at least one first inner projection 110 that is inwardly offset with respect to the at least one outer projection 108 along the lateral direction A. For instance, the first lower guide member 102 can be configured as first and second inner projections 110 that are inwardly recessed with respect to the outer projections 108 along the lateral direction A. The inner projections 110 can extend away from each other, and can be aligned with each other along the lateral direction A. The inner projections of the 110 of the first wedge member 48 can define respective lower surfaces that are coplanar with the first lower engagement surface 78 (see FIGS. 3B-3C) of the first wedge member 48. It should be appreciated, of course, that the first upper guide member 100 of the first wedge member 48 can alternatively be configured as the at least one inner projection, and the first lower guide member 102 of the first wedge member 48 can alternatively be configured as the at least one outer projection. Further, the first outer projections 108 can also be referred to as first upper projections 108, and the first inner projections 110 can also be referred to as first lower projections 110.

The first upper guide member 104 of the upper endplate 44 can be configured as at least one channel 112 that is sized to slidably receive the at least one projection 108. The at least one channel 112 can be configured as first and second channels 112 that are recessed along the lateral direction A toward the respective side surfaces of the implant. The channels 112 can be recessed in respective directions away each other. The first and second channels 112 are configured to slidably receive the first and second projections 108. The first and second projections 108 can be elongate along the direction of extension of the respective channels 112. The channels 112 can extend through the proximal facing surface of the upper endplate 44. The projections 108 and the channels 112 can flare downward as they extend in the expansion direction of the first wedge member 48. The channels 112 can be referred to as outer channels.

The first lower guide member 106 of the lower endplate 46 can be configured as at least one channel 114 that is sized to slidably receive the at least one inner projection 110 of the first wedge member 48. The at least one channel 114 can be referred to as an inner channel that is inwardly offset with respect to the at least one outer channel 112 of the upper endplate 44. The at least one inner channel 114 can be configured as first and second inner channels 114 that are recessed along respective directions away from each other. The first and second inner channels 114 can slidably receive respective ones of the first and second inner projections 110. The projections 110 and the channels 114 can flare upward as they extend in the expansion direction of the first wedge member 48. The channels 114 can extend through the proximal facing surface of the lower endplate 46.

With continuing reference to FIGS. 4A-6B, the second wedge member 50 and the upper and lower endplates 44 and 46 can include respective complementary guide members that guide the movement of the upper and lower endplates 44 and 46 away from and toward each other, respectively, as the second wedge member 50 moves in the expansion direction and the collapse direction. In particular, the second wedge member 50 defines a second upper guide member 116 and a second lower guide member 118. At least a portion of the second upper guide member 116 and at least a portion of the second lower guide member 118 can be aligned with each other in a plane that is oriented along the lateral direction A and the transverse direction T. The second upper guide member 116 can be disposed upward with respect to the second lower guide member 118. The upper endplate 44 defines a second upper guide member 120 that is configured to engage the second upper guide member 116 of the second wedge member 50. The lower endplate 46 defines a second lower guide member 122 that is configured to engage the second lower guide member 118 of the second wedge member 50. The second upper guide member 120 of the upper endplate 44 can be disposed upward with respect to the second lower guide member 122 of the lower endplate 46.

As will be appreciated from the description below, the second upper guide member 116 and the second lower guide member 118 of the second wedge member 50 can be asymmetrical with respect to each other about a third centrally disposed midplane that is oriented along the longitudinal direction L and the lateral direction A. The third centrally disposed midplane can be coincident with the first centrally disposed plane. Further, the second upper guide member 120 of the upper endplate 44 and the second lower guide member 122 of the lower endplate 46 can be asymmetrical with respect to each other about a fourth centrally disposed midplane that is oriented along the longitudinal direction L and the lateral direction A. The third and fourth centrally disposed planes can be coincident with each other. In one example, one of the upper end lower guide members of the second wedge member 50 can define at least one outer projection, and the other of the upper and lower guide members of the second wedge member 50 can define at least one inner projection. The at least one inner projection can be inwardly offset from the at least one outer projection along the lateral direction A. Similarly, one of the second guide members of the upper and lower endplates 44 and 46 can define at least one inner channel that is configured to slidably receive the at least one inner projection of the second wedge member 50. The other of the second guide members of the upper and lower endplates 44 and 46 can define at least one inner channel that is configured to slidably receive the at least one inner projection of the second wedge member 50. Thus, the complementary guide members of the second wedge member 50 and the upper and lower endplates 44 and 46 can define tongue-in-groove, or T-shaped, guidance engagements.

In one example, the second upper guide member 116 of the second wedge member 50 can be configured as at least one second outer projection 124 that extends out along the lateral direction A. For instance, the second upper guide member 116 of the second wedge member 50 can be configured as first and second outer projections 124 that extend out along the lateral direction A away from each other. The first and second outer projections 124 can be aligned with each other along the lateral direction A. The first and second outer projections 124 of the second wedge member 50 can define respective upper surfaces that are coplanar with the second upper engagement surface 80 (see FIGS. 3B-3C) of the second wedge member 50. In one example, the second lower guide member 118 of the second wedge member 50 can be configured as at least one second inner projection 126 that extend outward along the lateral direction A. For instance, the second lower guide member 118 can be configured as first and second inner projections 126 that extend outward other along the lateral direction A away from each other. The inner projections 126 can be inwardly offset with respect to the outer projections 124 along the lateral direction A. Further, the inner projections can be aligned with each other along the lateral direction A. The first and second inner projections 126 of the second wedge member 50 can define respective lower surfaces that are coplanar with the second lower engagement surface 82 (see FIGS. 3B-3C) of the second wedge member 50. It should be appreciated, of course, that the second upper guide member 116 of the second wedge member 50 can alternatively be configured as the at least one inner projection, and the second lower guide member 118 of the second wedge member 50 can alternatively be configured as the at least one outer projection.

The second upper guide member 120 of the upper endplate 44 can be configured as at least one channel 128 that is sized to slidably receive the at least one projection 124. The at least one channel 128 can thus be referred to as an outer channel. Further, the at least one channel 128 can be configured as first and second outer channels 128 that are recessed outward along the lateral direction A toward the respective side surfaces of the implant 20. Accordingly, the first and second outer channels 128 can be recessed along a direction away from each other. The first and second outer channels 128 are configured to slidably receive the first and second outer projections 124. The outer channels 128 can extend through the distal facing surface of the upper endplate 44. The projections 124 and the channels 128 can flare downward as they extend in the expansion direction of the second wedge member 50.

The second lower guide member 122 of the lower endplate 46 can be configured as at least one inner channel 130 that is sized to slidably receive the at least one inner projection 126 of the second wedge member 50. The at least one inner channel 130 can be inwardly recessed along the lateral direction A with respect to the at least one outer channel 128. The at least one inner channel 130 can be configured as first and second inner 130 that are recessed laterally outward away from each other. The first and second inner channels 130 can slidably receive respective ones of the first and second inner projections 126. The first and second inner projections 126 can be elongate along the direction of the first and second inner channels 130, respectively. The inner channels 130 and the inner projections 126 can flare upward as they extend in the expansion direction of the second wedge member 50. The inner channels 130 can extend out from the distal facing surface of the lower endplate 46. The second outer projections 124 can also be referred to second upper projections 124, and the second inner projections 126 can also be referred to as second lower projections 126.

It should thus be appreciated that the guide members of the first and second wedge members 48 and 50 can engage the guide members of the upper and lower endplates 44 and 46 so as to prevent the wedge members 48 and 50 from becoming decoupled from the upper and lower endplates 44 and 46 along the transverse direction T. In this regard, it should be appreciated that the upper end lower endplates 44 and 46 can abut each other along the transverse direction T when the implant 20 is in the fully collapsed configuration. The guide members of the first and second wedge members 48 and 50 can be engaged with the guide members of the upper and lower endplates 44 and 46 when the implant 20 is in the fully collapsed configuration. Thus, the wedge members 48 and 50 are prevented from fully backing out of the engagement members of the upper and lower endplates 44 and 46. Further, the intervertebral implant 20 can be constructed such that the first and second wedge members 48 and 50 do not extend past the upper and lower endplates 44 and 46 along the longitudinal direction L. Thus, no part of the first wedge member 48 extends proximally past the proximal end of the upper and lower endplates 44 and 46. Further, no part of the second wedge member 50 extends distally past the distal end of the upper and lower endplates 44 and 46. For instance, the entirety of the first wedge member 50 can be recessed distally with respect to the proximal ends of the endplates 44 and 46 both when the implant 20 is in the collapsed configuration and when the implant 20 is in the expanded configuration. Similarly, the entirety of the second wedge member 50 can be recessed proximally with respect to the distal ends of the endplates 44 and 46 both when the implant 20 is in the collapsed configuration and when the implant 20 is in the expanded configuration. The implant 20 can further include a stop member that prevents the wedge members 48 and 50 from continuing to move in the expansion direction once the implant has reached the fully expanded configuration.

As described above, the upper end lower endplates 44 and 46 can abut each other along the transverse direction T when the implant 20 is in the fully collapsed configuration. In particular, one of the upper and lower endplates 44 and 46 can nest within the other of the upper and lower endplates 44 and 46 when the intervertebral implant 20 is in the collapsed configuration. In one example, the lower endplate 46 can nest within the upper endplate 44. That is, the side walls and end walls of the lower endplate 46 can fit inside the side walls and end walls of the upper endplate 44 until a horizontal plate member 61 that defines the lower surface 40 abuts the lower end of the side walls of the upper endplate 44. In particular, an inner surface of the horizontal plate member 61 that is opposite the lower surface 40 abuts the lower end of the side walls of the upper endplate 44. The inner surface of the horizontal plate member 61 of the lower endplate 46 can also abut the lower end of the end walls of the upper endplate 44.

Accordingly, the intervertebral implant 20 can achieve a low profile in the collapsed configuration. For instance, the implant 20 can have a height in a range from approximately 5 mm to approximately 10 mm at its geometric center, such as approximately 7 mm, when the implant 20 is in the fully collapsed configuration. It should be appreciated that the height of the implant 20 in the fully collapsed configuration can be any suitable height as desired, such as from approximately 10 mm to approximately 15 mm. Thus, the implant be inserted into the intervertebral space with minimal or no mechanical interference between at least one or both of the surfaces 38 and 40 and the bony vertebral endplates of the vertebrae. The height of the implant 20 in the fully expanded configuration can be greater than the height of the implant 20 in the fully collapsed configuration by any suitable difference distance as desired. For instance, the difference distance can be in a range from approximately 2 mm to approximately 15 mm, including from approximately 4 mm to approximately 8 mm, including approximately 5 mm. At the tapered leading end, the height of the implant 20 can be less than the height of the implant at the geometric center by any suitable reduction distance as desired. In one example, the reduction distance can be in a range greater than 0 mm up to approximately 5 mm, which can include up to approximately 4 mm, up to approximately 3 mm, up to approximately 2 mm, and up to approximately 1 mm.

It should thus be appreciated that the endplate whose at least one guide member is configured as an inner channel can nest within the endplate whose at least one guide member is configured as an outer channel. In this regard, an inner surface of a horizontal plate member of the upper endplate 44 that is opposite the lower surface 38 can alternatively abuts the upper end of the side walls of the lower endplate 46. The inner surface of the horizontal plate member of the upper endplate 44 can also abut the upper end of the end walls of the lower endplate 46. It should be appreciated that one or both of the guide members of each of the wedge members 48 and 50 can be alternatively configured as channels, and one or both of the guide members of each of the endplates 44 and 46 can alternatively be configured as projections that are slidably received in the channels in the manner described herein.

Referring again to FIGS. 2A-2B, one of the upper and lower endplates 44 and 46 can define at least one upstanding alignment rib 137, and the other of the upper and lower endplates 44 and 46 can define at least one alignment channel 139 that is positioned and sized to receive the alignment rib so as to guide movement of the endplates 44 and 46 toward and away from each other, respectively, along the transverse direction T. The alignment rib 137 and the alignment channel 139 can be oriented along the transverse direction T. In one example, the upper endplate 44 can define the at least one alignment rib 137, and the lower endplate 46 can define the at least one alignment channel 139. For instance, the upper endplate 44 can include first and second alignment ribs 137 that are spaced from each other along the lateral direction A. The alignment ribs 137 can further be aligned with each other along the lateral direction A. Similarly, the lower endplate 46 can define first and second alignment channels 139 that are spaced from each other along the lateral direction A. The alignment channels 139 can further be aligned with each other along the lateral direction A. It should be appreciated, of course, that the implant 20 can be alternatively constructed such that the lower endplate 46 includes the at least one alignment rib 137, and the upper endplate 44 includes the at least one alignment channel 139.

In one example, the projections 137 can extend inward along the lateral direction A from the laterally inner surface of each of the side walls of the upper endplate 44. The lower endplate 46 can include at least one recess 139, such as first and second recesses at each side wall of the lower endplate 46. In particular, the recesses 139 can extend inward into the outer surface of the side walls of the lower endplate 46 along the lateral direction A. The recesses 139 can extend vertically through the lower endplate 46. It should be appreciated, of course, that the projections 137 and recesses 139 can be alternatively positioned as desired. The recesses 139 can be sized and positioned to slidably receive respective ones of the projections 137 as the implant 20 moves between the collapsed configuration and the expanded configuration.

Referring also to FIG. 3D, the implant 20 can include an expansion limiter 129 that prevents the endplates 44 and 46 from further moving away from each other along the transverse direction T once the implant 20 has been fully expanded to the fully expanded configuration. The expansion limiter 129 can include at least one first stop surface 131 of one of the upper and lower endplates 44 and 46, and at least one second stop surface 135 of the upper and lower endplates 44 and 46. The first and second stop surfaces 131 and 135 can be configured to contact each other when the implant 20 is in the fully expanded configuration, thereby preventing the endplates 44 and 46 from further moving apart from each other.

For instance, in one example, one of the upper and lower endplates 44 and 46 can define at least one limiter tab 132, and the other of the upper and lower endplates 44 and 46 can define at least one limiter channel 134. The limiter channel 134 is sized to receive at least a portion of the limiter tab 132 as the implant 20 moves between the expanded configuration and the collapsed configuration. The limiter tabs 132 of one of the upper and lower endplates 44 and 46 can include the first stop surface 131 that is configured to engage the complementary second stop surface 135 of the other of the upper and lower endplates 44 and 46 when the implant 20 is in the fully expanded configuration. The first stop surface 131 can ride in the limiter channel 134 as the implant 20 moves between the collapsed configuration and the expanded configuration. In one example, the lower endplate 46 can include the at least one limiter tab 132, and the upper endplate 44 can define the at least one limiter channel 134. Alternatively, the upper endplate 44 can include the at least one limiter tab 132, and the lower endplate 46 can include the at least one limiter channel 134.

The lower endplate 46 can define at least one pair of limiter tabs 132. For instance, the lower endplate 46 can include first and second pairs of limiter tabs 132 that are spaced apart from each other along the lateral direction. The limiter tabs 132 of each pair can be spaced from each other along the longitudinal direction L. Respective ones of each of the first and second pairs of limiter tabs 132 can also be aligned with each other along the lateral direction A. Similarly, the upper the endplate 44 can define first and second pairs of limiter channels 134 that are spaced from each other along the lateral direction A. The limiter channels 134 of each pair can be spaced from each other along the longitudinal direction L. Respective ones of each of the first and second pairs of limiter channels 134 can also be aligned with each other along the lateral direction A.

The limiter channels 134 can be open to the bone graft apertures along the lateral direction A. As described above, each of the limiter tabs 132 can include the first stop surface 131. The first stop surface 131 can be defined by a barb 133 that extends toward the upper endplate 44. The lower endplate 46 can include at least one complementary stop surface 135 that is configured to abut a respective one of the at least one stop surface 131 of the upper endplate 44 when the implant 20 is in the fully expanded configuration. The stop surfaces 135 of the lower endplate 46 can be disposed at respective ends of the limiter channels 134. In one example, each of the second stop surfaces 135 can define a respective end of the limiter channels 134. For instance, the second stop surfaces 135 can define the lower ends of the respective limiter channels 134. Respective ones of the stop surfaces 131 and 135 can be aligned with each other along the transverse direction T. Thus, when the implant 20 expands to its fully expanded configuration, the stop surfaces 131 can abut the stop surfaces 135 so as to prevent further movement of the endplates 44 and 46 away from each other. The abutment of the stop surfaces 131 and 135 can thus also prevent the wedge members 48 and 50 from further traveling toward each other along the actuator shaft 54. In this regard, it should be appreciated that the expansion limiter 129 can include the limiter tab 132 and the limiter channel 134.

In one example, the limiter tabs 132 do not extend beyond the upper surface 38 when the implant 20 is in the fully contracted position. For instance, the limiter tabs 132 can be recessed with respect to the upper surface 38 when the implant is in the fully contracted position. While the limiter tabs 132 are illustrated as extending from the lower endplate 46 into the limiter channels 134 of the upper endplate 44, it should be appreciated that one or more limiter tabs can alternatively extend from the upper endplate 44 into respective one or more limiter channels of the lower endplate 46.

Figure 7:
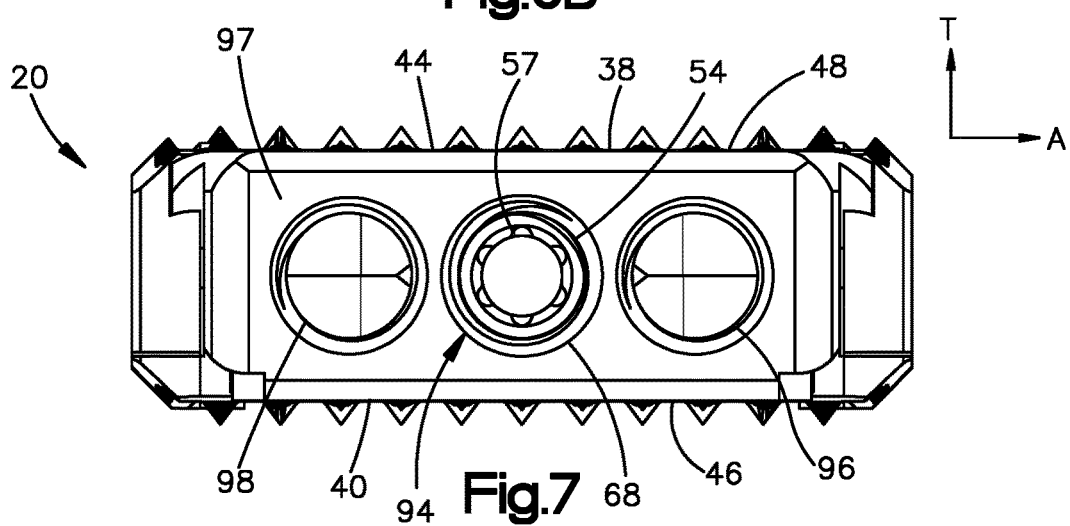
FIG. 7 is an end elevation view of the expandable intervertebral implant illustrated in FIG. 2A.

Referring now to FIG. 7, the upper surface 38 and the lower surface 40 can be substantially parallel to each other both when the intervertebral implant 20 is in the collapsed configuration and when the intervertebral implant 20 is in the expanded configuration. Alternatively, it should be appreciated that the intervertebral implant 20 can be configured to define a lordotic or kyphotic profile as desired. Thus, the side of the intervertebral implant 20 that defines the anterior side when the implant 20 is disposed in the intervertebral space can be taller along the transverse direction T than the side of the intervertebral implant 20 that defines the posterior side when the implant 20 is disposed in the intervertebral space. For instance, one or both of the upper and lower surfaces 38 and 40 can be sloped with respect to each other. In particular, the upper and lower surfaces 38 and 40 can be sloped along the lateral direction T. Thus, the slope can be defined along the upper and lower surfaces 38 and 40 in a plane that is oriented along the transverse direction T and the lateral direction A.

Figure 8A:
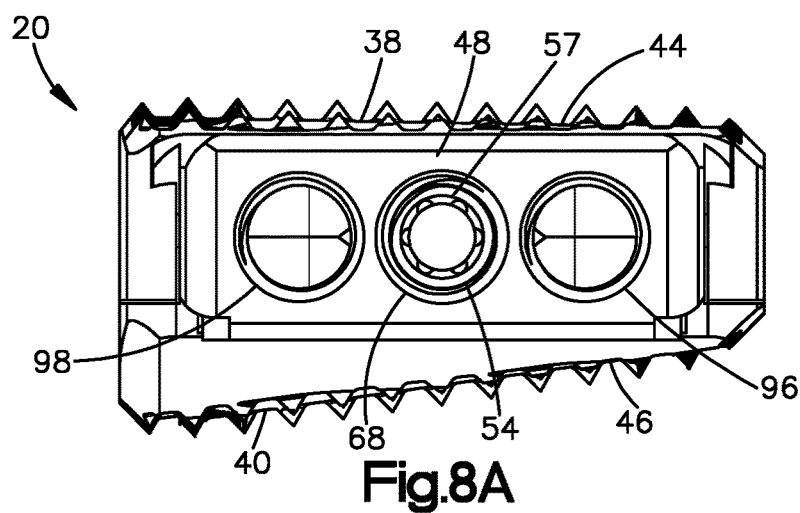
FIG. 8A is a side elevation view of the expandable intervertebral implant illustrated in FIG. 2A, showing a first lordotic profile.
Figure 8B:
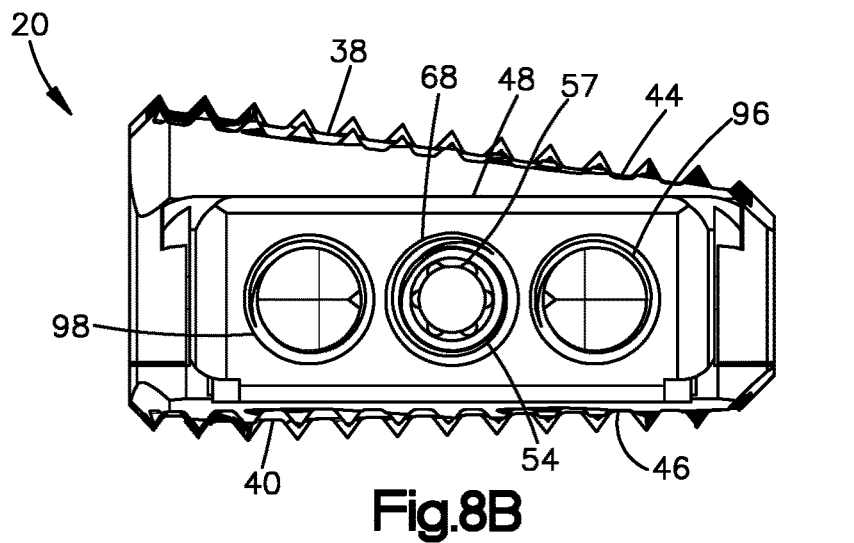
FIG. 8B is a side elevation view of the expandable intervertebral implant illustrated in FIG. 2A, showing a second lordotic profile.
Figure 8C:
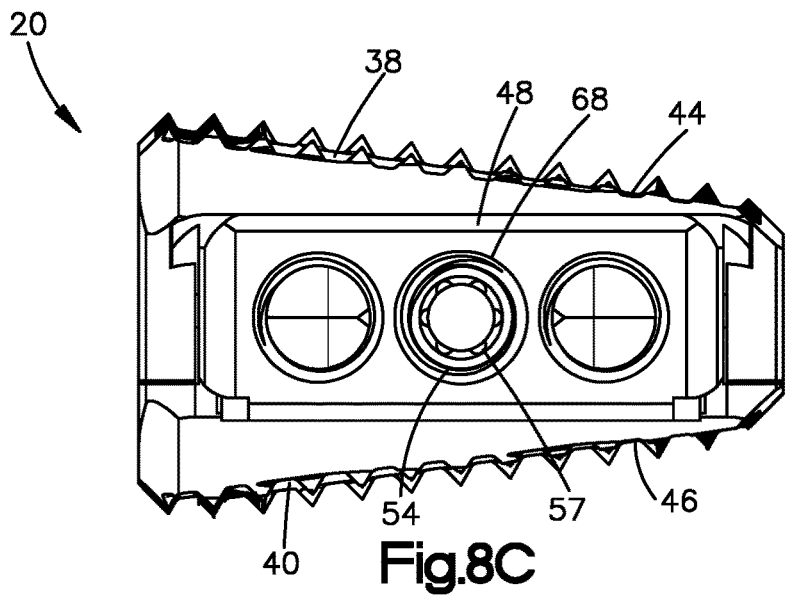
FIG. 8C is a side elevation view of the expandable intervertebral implant illustrated in FIG. 2A, showing a third lordotic profile.

As illustrated in FIG. 8A, the lower surface 40 can be sloped, and the upper surface 38 can be oriented substantially along a plane that is defined by the longitudinal direction L and the lateral direction A. Alternatively, as illustrated in FIG. 8B, the upper surface 38 can be sloped, and the lower surface 40 can be oriented substantially along a plane that is defined by the longitudinal direction L and the lateral direction A. Alternatively still, as illustrated in FIG. 8C, each of the upper and lower surfaces 38 and 40 can be sloped. The upper and lower surfaces 38 and 40 can define any suitable angle as desired in the plane that is defined by the lateral direction A and the transverse direction T. The angle can be substantially 8 degrees as illustrated in FIGS. 8A and 8B. The angle can be substantially 16 degrees as illustrated in FIG. 8C. It should be appreciated that these angles are presented by way of example only, and other angles are contemplated.

Referring now to FIG. 7, the first wedge member 48 can include at least one coupling member 94 that is configured to couple to an insertion instrument 152 (see FIG. 9) that is configured to actuate the implant 20 between the collapsed configuration to the expanded configuration. The at least one coupling member 94 can be configured as at least one attachment aperture. For instance, the at least one attachment aperture can include a first attachment aperture 96 and a second attachment aperture 98. The first attachment aperture 96 can extend at least into the first wedge member 48. For instance, the first attachment aperture 96 can extend at least into the first wedge member 48 along the longitudinal direction L. In one example, the first attachment aperture 96 can extend through the first wedge member 48. At least a portion of the first attachment aperture 96 can be threaded. Further, the first attachment aperture 96 can be open to a proximal end of the first wedge member 48. For instance, the first attachment aperture 96 can be open to a proximal facing surface 97 of the first wedge member 48.

The second attachment aperture 98 can extend at least into the first wedge member 48. For instance, the second attachment aperture 98 can extend at least into the first wedge member 48 along the longitudinal direction L. Thus, the first and second attachment apertures 96 and 98 can be oriented parallel to each other. Further, the first and second attachment apertures 96 and 98 can be aligned with each other in a plane that is defined by the longitudinal direction L and the lateral direction A. In one example, the second attachment aperture 98 can extend through the first wedge member 48. At least a portion of the second attachment aperture 98 can be threaded. Further, the second attachment aperture 98 can be open to the proximal end of the first wedge member 48. For instance, the second attachment aperture 98 can be open to the proximal facing surface 97 of the first wedge member 48.

The first and second attachment aperture 96 and 98 can be disposed on opposite sides of the first bore 68 of the first wedge member 48. Thus, the first bore 68 can be disposed between the first and second attachment apertures 96 and 98. In particular, the first bore 68 can be disposed between the first and second attachment apertures 96 and 98 with respect to the lateral direction A. Further, each of the first and second attachment apertures 96 and 98 and the first bore 68 can define respective openings at the proximal facing surface 97 of the first wedge member 48. The openings can be aligned with each other along the lateral direction. As will be described in more detail below, the instrument can couple to one or both of the attachment apertures 96 and 98, and can further extend into the first bore 68 so as to drive the actuator shaft 54 to selectively rotate in the first and second directions of rotation.

Referring now to FIG. 9, an implant assembly 150 can include the intervertebral implant 20 and an instrument 152. The instrument 152 can be configured to attach to the implant 20, and apply an actuation force to the actuator shaft 54 that selectively rotates the actuator shaft 54 in the first direction of rotation and the second direction of rotation. Thus, the instrument 152 can attach to the intervertebral implant 20, insert the implant 20 into the intervertebral space in the collapsed configuration in the manner described above, and subsequently rotate the expansion shaft 54 in the first direction of rotation so as to expand the implant 20 to the expanded configuration.

Figure 10:
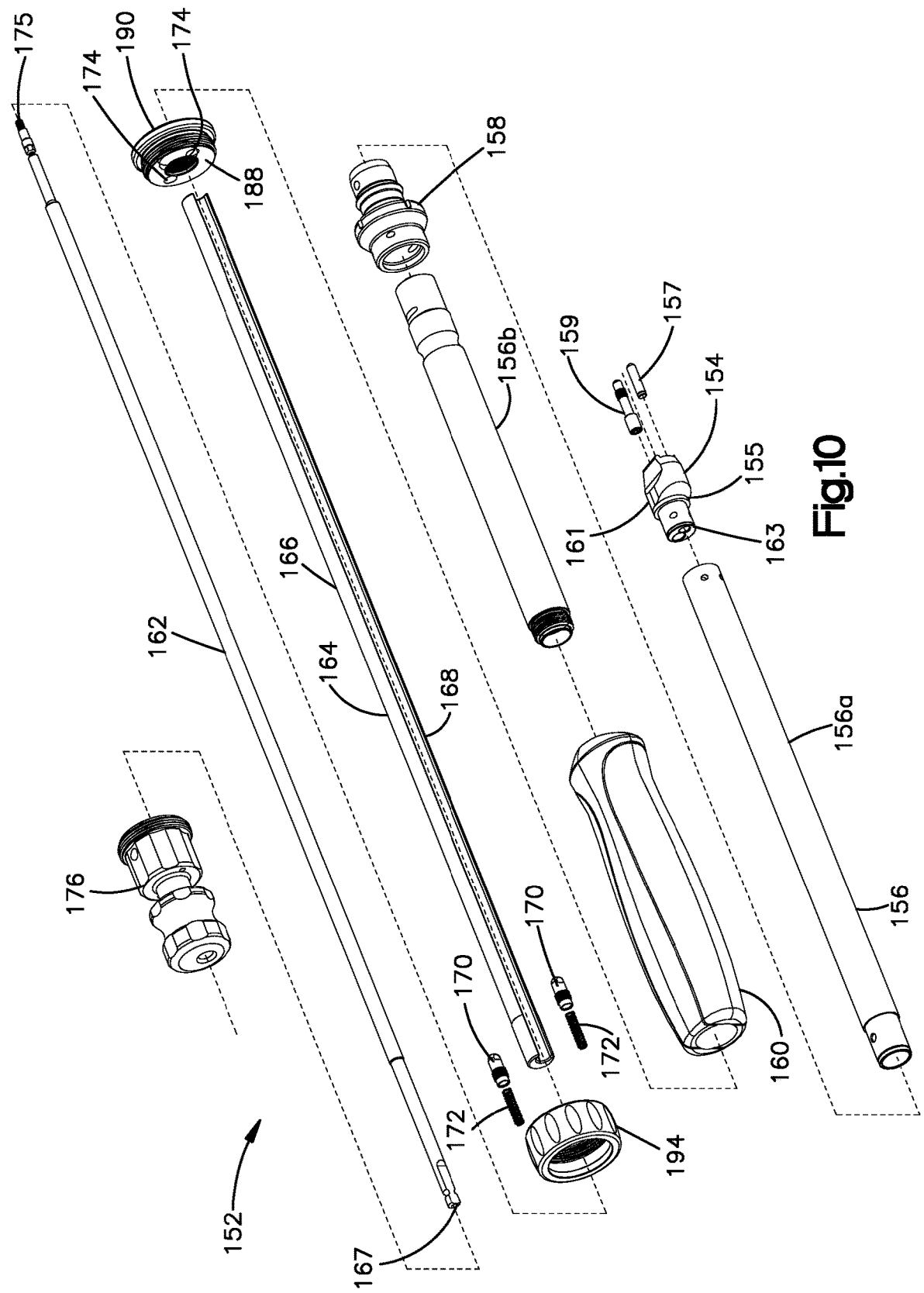
FIG. 10 is an exploded perspective view of the instrument illustrated in FIG. 9.

Referring now to FIGS. 9-10, the instrument 152 can include an attachment member 154 at its distal end that is configured to attach to and support the intervertebral implant 20. The attachment member 154 can include an attachment housing 155 and at least one attachment pin that is configured to be received in a respective at least one of the attachment apertures 96 and 98 (see FIG. 7). The attachment housing 155 can include an attachment head 161 and an attachment neck 163 that extends proximally from the attachment head 161. The at least one attachment pin can include first and second attachment pins 157 and 159 that are configured to attach to the implant 20. For instance, the first and second attachment pins 157 and 159 can be configured to attach to the first wedge member 48. In one example, the first attachment pin 157 and the second attachment pin 159 that are configured to be received in respective ones of the first and second attachment apertures 96 and 98 of the first wedge member 48. For instance, the instrument 152 can be oriented such that first attachment pin 157 can be inserted into either one of the first and second attachment apertures 96 and 98. The second attachment pin 159 can be inserted into the other one of the first and second attachment apertures 96 and 98. The first attachment pin 157 can be unthreaded and configured to be translatably inserted into the respective one of the first and second attachment apertures 96 and 98. The second attachment pin 158 can be threaded and configured to threadedly mate with the other of the first and second attachment apertures 96 and 98. Alternatively, the first attachment pin 157 can be similarly threaded and configured to threadedly mate with the intervertebral implant in the respective one of the first and apertures 96 and 98.

The instrument 152 can further include an outer support shaft 156 that is configured to support the attachment member 154. The support shaft 156 can be elongate along the longitudinal direction l. For instance, the support shaft 156 can extend proximally from the attachment member 154. The support shaft 156 can include a distal support shaft portion 156a and a proximal support shaft portion 156b that is joined to the distal support shaft portion 156a. For instance, the instrument 152 can include a coupler 158 that couples the proximal support shaft portion 156b to the distal support shaft portion 156a. The instrument 152 can include an instrument handle 160 that is supported at the proximal end of the support shaft 156. For instance, the instrument handle 160 can be supported at the proximal end of the proximal support shaft portion 156b.

The instrument 152 can further include a drive member that is configured as a drive shaft 162. The drive shaft 162, and thus the drive member, can be configured to engage at least one of the first and second attachment pins 157 and 159, and can further be configured to rotatably engage the actuator shaft 54 of the intervertebral implant 20. The drive shaft 162 can be oriented along the longitudinal direction L. The instrument 152 can further include a toggle member 164 that is configured to move the drive shaft 162 between a first position and a second position. In the first position, the drive shaft 162 is aligned with the at least one of the first and second attachment pins 157 and 159. In the second position, the drive shaft 162 is aligned with the actuator shaft 54 of the intervertebral implant 20. In one example, the toggle member 164 is configured as a toggle shaft 166 disposed in the support shaft 156. The toggle shaft 166 can define a channel 168 that is elongate along the longitudinal direction L and is configured to receive the drive shaft 162. The toggle shaft 166 is rotatable between a first rotational position to a second rotational position so as to move the drive shaft between the first and second positions. The toggle shaft 166 can be rotated about a central axis that is oriented along the longitudinal direction L between the first rotational position and the second rotational position. The toggle shaft 166 supports the drive shaft 162 in the first position when the toggle shaft is in the first rotational position. The toggle shaft 166 supports the drive shaft 162 in the second position when the toggle shaft 166 is in the second rotational position. The instrument 152 can further include at least one locating finger 170 and at least one spring 172 that delivers a spring force to the at least one locating finger 170 so as to urge the at least one locating finger 170 into a corresponding at least one detent 174 both when the toggle shaft 166 is in the first rotational position and when the toggle shaft 166 is in the second rotational position.

The instrument 152 can include a drive handle 176 that is configured to rotatably support the drive shaft 162 at the proximal end of the drive shaft 162. The drive shaft 162 can be eccentrically supported in the drive handle 176, such that rotation of the handle 176 along its central axis causes the drive shaft 162 to revolve about the central axis of the handle 176. The central axis of the handle 176 can be coincident with the central axis of the toggle shaft 166. That is, the drive shaft 162 can be positioned offset with respect to the central axis of the drive handle 165. The drive shaft 162 can define an drive member 167 at its proximal end that can engage a power tool that drives the rotation of the drive shaft 162. The drive member 167 can extend proximally from the drive handle 176. The proximal end of the toggle shaft 166 can be press fit into the distal end of the drive handle 165. Thus, rotation of the drive handle 165 can rotate the toggle shaft 166 between the first rotational position and the second rotational position.

Operation of aspects of the instrument 152 will now be described with respect to FIGS. 11A-11D. With initial reference to FIGS. 11A and 12A, the first attachment pin 157 can be inserted into one of the first and second attachment apertures 96 and 98. The first attachment pin 157 can be unthreaded and sized to be inserted into either of the attachment apertures 96 and 98 of the first wedge member 48. In particular, the first attachment pin 157 can be press fit into the respective one of the first and second apertures 96 and 98. When the first attachment pin 157 has been inserted into the respective one of the first and second apertures 96 and 98, the instrument is coupled to the first wedge member 48 at a first attachment location. As illustrated, the first attachment pin 157 has been inserted into the first attachment aperture 96. The first attachment pin 157 can be fixedly supported by the attachment housing 155, such that the distal end of the first attachment pin 157 extends distally of the attachment housing 155. In one example, the first attachment pin 157 can be press-fit into the attachment housing 155, and in particular in the attachment head 161.

Figure 11A:
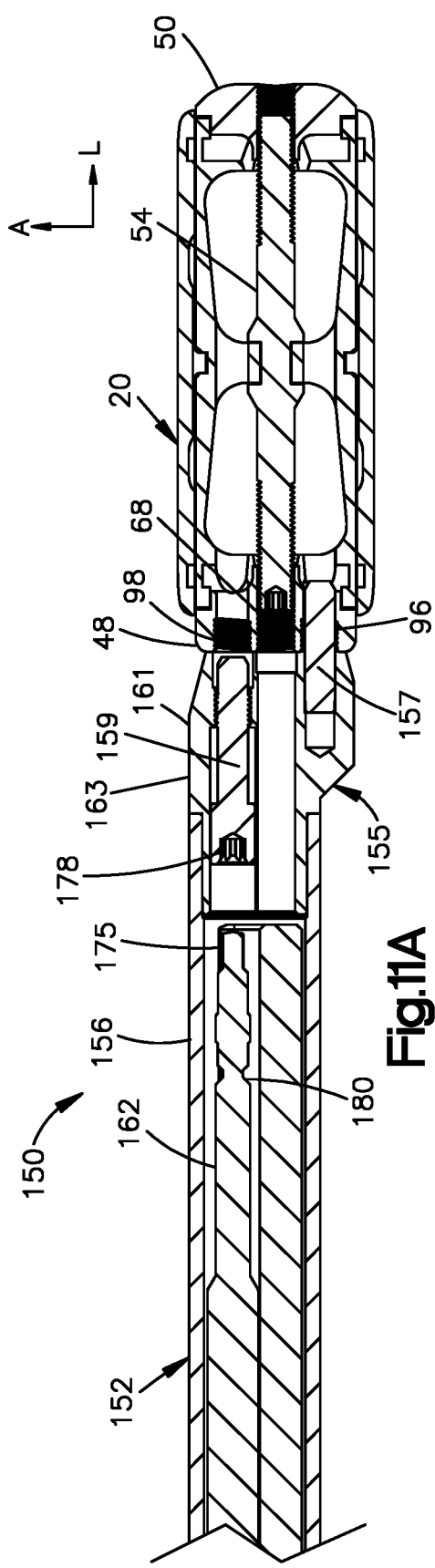
FIG. 11A is a sectional top plan view of the implant assembly illustrated in FIG. 9, showing a first attachment pin of the instrument inserted into an expansion member of the implant, and further showing a drive shaft of the instrument aligned with a second attachment pin.
Figure 11B:
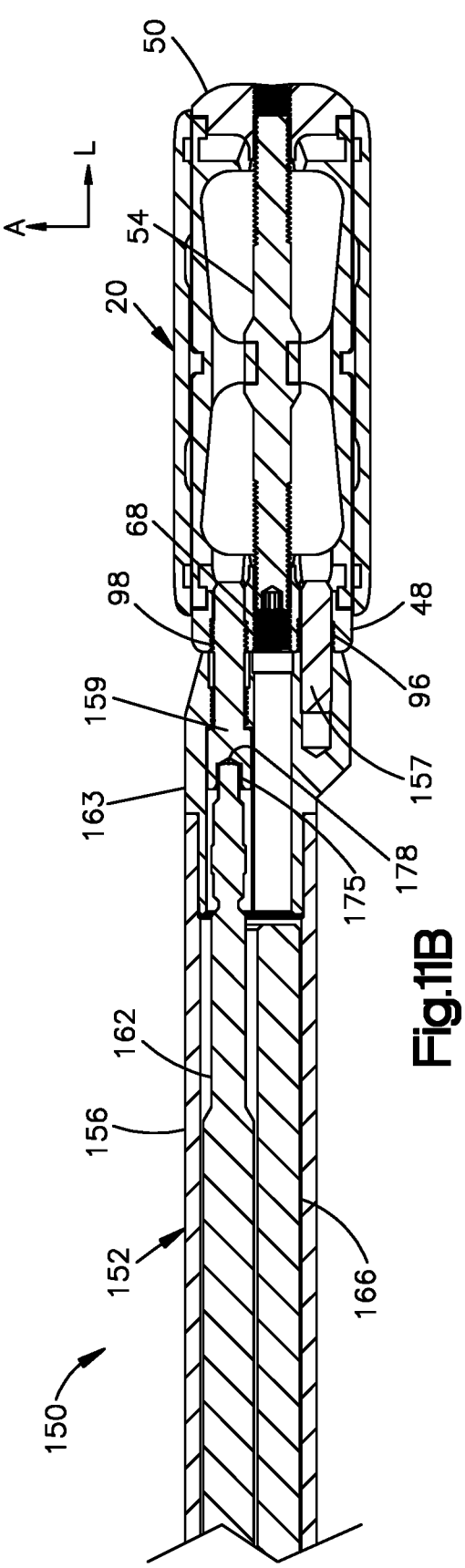
FIG. 11B is a sectional top plan view similar to FIG. 11A, but after the drive shaft has inserted the second attachment pin into an expansion member of the implant.
Figure 12A:
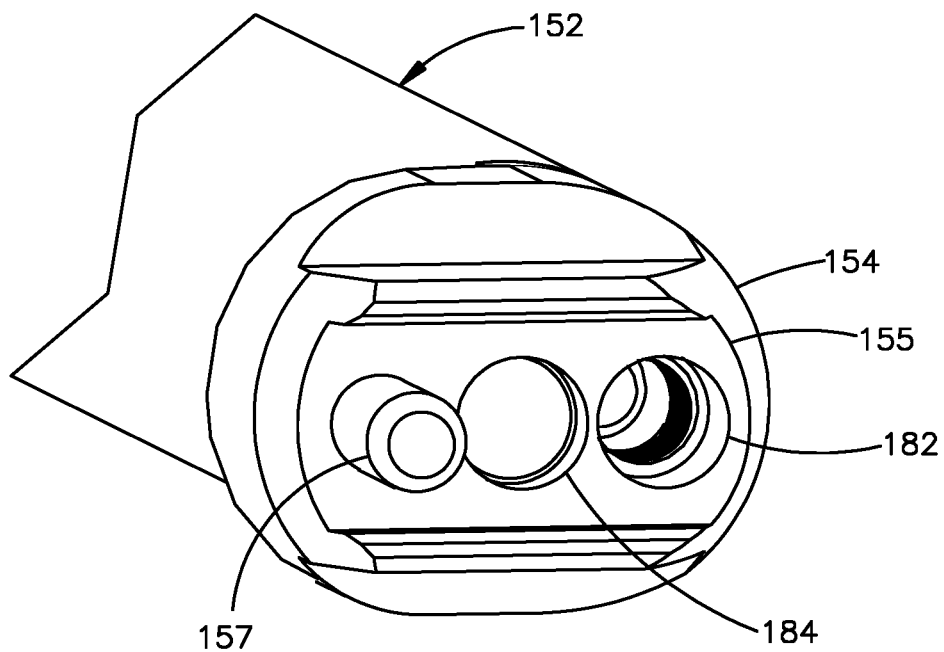
FIG. 12A is a perspective view of a front end of the instrument as illustrated in FIG. 11A.
Figure 12B:
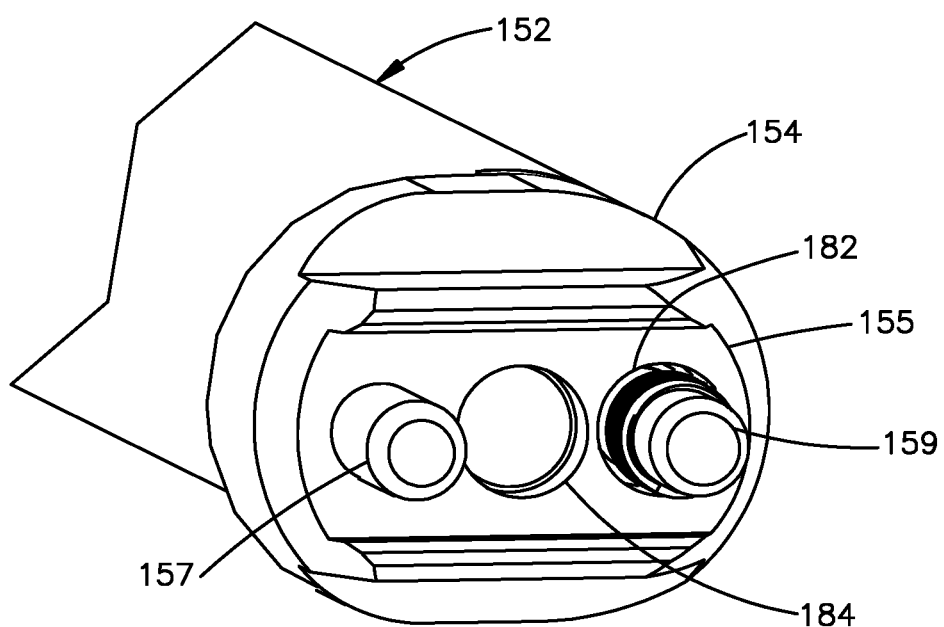
FIG. 12B is a perspective view of a front end of the instrument as illustrated in FIG. 11B.

Next, referring now to FIGS. 11B and 12B, and as described above, the toggle shaft 166 can be disposed in the first rotational position, whereby the drive shaft 162 is aligned with the second attachment pin 159 along the longitudinal direction L. If the toggle shaft 166 is not in the first rotational position, the toggle shaft 166 can be rotated to the first rotational position. The drive shaft 162 can be advanced in the distal direction until the drive member 175 of the drive shaft 162 engages a coupling member 178 of the second attachment pin 159, such that rotation of the drive shaft 162 causes the second attachment pin 159 to similarly rotate. The second attachment pin 159 can be at least partially disposed in a first or outer channel 182 of the attachment member 154. For instance, the channel 182 can extend through the attachment head 161. At least a portion of the channel 182 can be threaded, such that the second attachment pin 159 threadedly mates to the attachment head 161 as it is rotated by drive shaft 162. The thread pitch in the channel 182 can be the same as the thread pitch in the attachment apertures 96 and 98. Thus, the second attachment pin 159 can translate proximally and distally, respectively, in the channel 182 at the same rate as in the second attachment aperture as it is rotated.

Figure 11E:
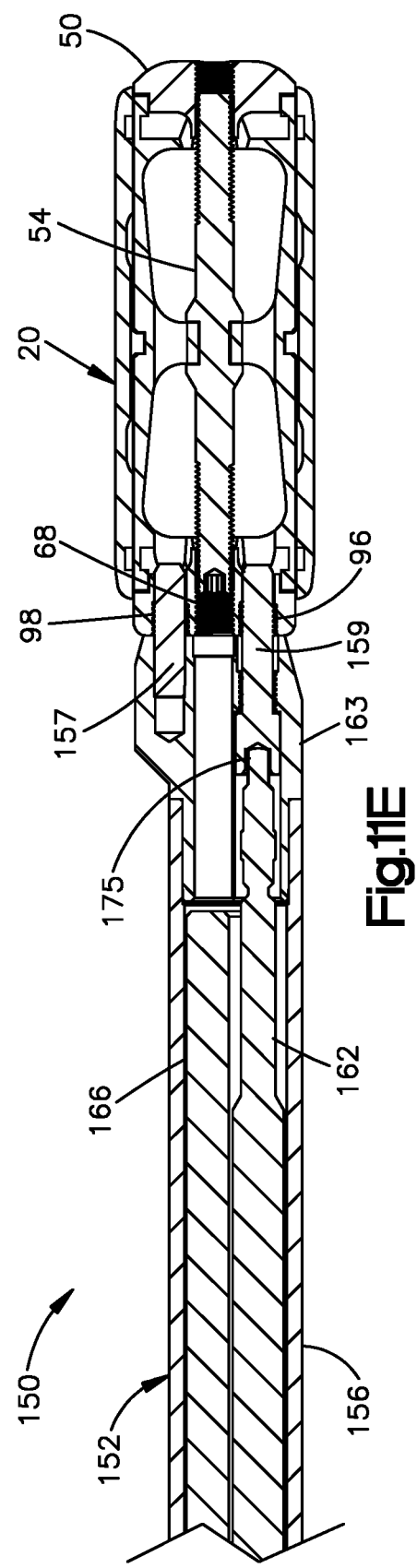
FIG. 11E is a sectional top plan view similar to FIG. 11A, but showing the instrument coupled to the implant in an opposite orientation with respect to the orientation illustrated in FIG. 11A.

The drive member and the coupling member 178 can define a hex head, a Phillips head, a flat head, a start head, or the like. The drive member 175 can be configured as a projection, and the coupling member 178 can be configured as a socket, or vice versa. As the second attachment pin 159 rotates in a respective first direction of rotation, the second attachment pin 159 can threadedly purchase with the intervertebral implant in the other of the first and second apertures 96 and 98. Thus, the second attachment pin 159 can be attached to both the attachment member 154 of the instrument 152 as well as the intervertebral implant 20. As illustrated in FIG. 11B, the second attachment pin 159 has been inserted into the second attachment aperture 98. Alternatively, as illustrated in FIG. 11E, the second attachment pin can alternatively be inserted into the first attachment aperture 96. When the first attachment pin 157 has been inserted into the respective other of the first and second apertures 96 and 98, the instrument 20 is coupled to the first wedge member 48 at a second attachment location. The drive shaft 162 can define a recessed break away region 180 that is designed to fracture if the torsional forces of the drive shaft 162 exceed a predetermined threshold. Thus, the actuator shaft 54 of the implant 20 is prevented from receiving torsional forces greater than the predetermined threshold.

It should be appreciated that the first attachment pin 157 can be referred to as a pilot pin that is designed to make the first attachment with the implant, and the second attachment pin 159 can be referred to as an attachment screw that is threaded and configured to threadedly purchase with the implant 20 in the second attachment aperture. As illustrated in FIG. 11E, it should be appreciated that the instrument 152 can be oriented such that the first attachment pin 157 extends into the second attachment aperture 98, and the second attachment pin 159 extends into the first attachment aperture 96. Regardless of the orientation of the instrument 152, the drive shaft 162 can be configured to drive the actuator shaft 54 of the implant 20 in the manner described herein.

Figure 12C:
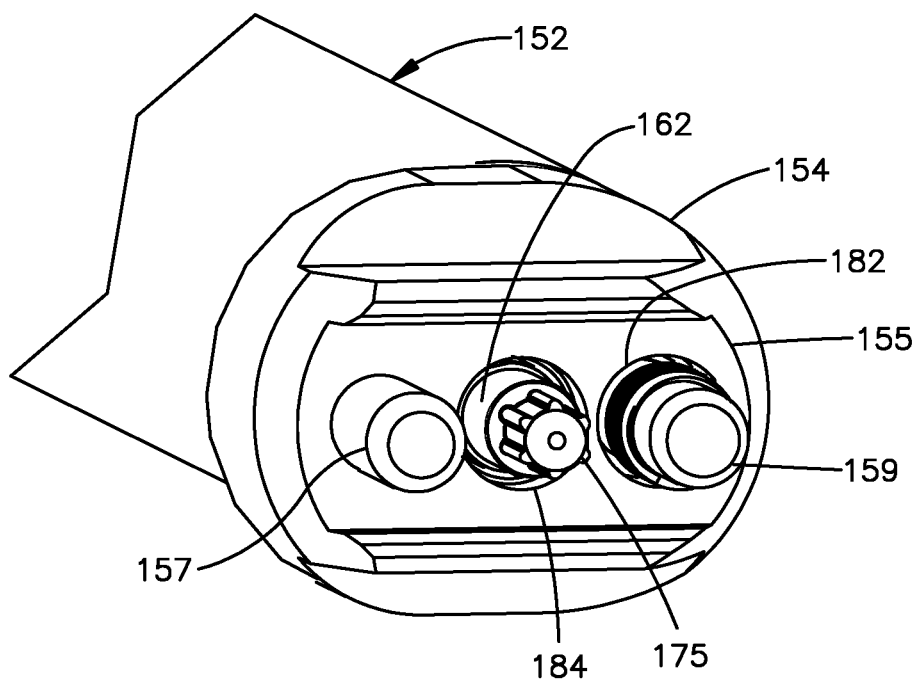
FIG. 12C is a perspective view of a front end of the instrument as illustrated in FIG. 11C.

Referring now to FIGS. 11C and 12C, once the second attachment pin 159 has been driven into the respective other of the first and second attachment apertures 96 and 98, the toggle shaft 166 can be rotated to the second rotational position, thereby aligning the drive shaft 162 with the actuator shaft 54 of the intervertebral implant 20. When the toggle shaft 166 is in the second rotational position, the drive shaft 162 can be aligned with a second or inner channel 184. Thus, the drive shaft 162 can be advanced distally and rotated to cause the actuator shaft 54 of the intervertebral implant to correspondingly rotate. It should be appreciated that the instrument 20 is attached to the implant 20 at the first and second attachment locations that are spaced apart from each other. Thus, the instrument 152 is sufficiently braced against the implant 20 when the drive shaft 162 causes the actuator shaft 54 of the implant 20 to rotate. In one example, the first and second attachment locations can be spaced apart from each other and aligned with each other along the lateral direction A. The instrument 152 can be oriented along the longitudinal direction L when the instrument 152 is attached to the implant 20 at the first and second attachment locations.

The instrument 152 can be configured such that after the drive shaft 162 has driven the second attachment pin 159 into the implant 20, retraction of the drive shaft 126 in the proximal direction allows the toggle shaft 166 to be rotated between the first and second rotational positions. In one example, the attachment housing 155 can define a first or outer channel 182 that can retain the second attachment pin 159. The drive shaft 162 can extend into the channel 182 when the drive shaft 162 drives the channel 182 into the other of the first and second attachment apertures 96 and 98. Thus, the drive shaft 162 can interfere with the attachment housing 155 in the channel 182 so as to prevent the toggle shaft 166 from rotating from the first rotational position to the second rotational position. Thus, the interference between the drive shaft 162 and the attachment housing 155 can prevent the drive shaft 162 from moving from the first position aligned with the second attachment pin 159 to the second position aligned with the actuator shaft 54. When the drive shaft 162 has retracted along the proximal direction out of the channel 182, the interference is removed and the toggle shaft 166 can be rotated from the first rotational position to the second rotational position.

When the toggle shaft 166 is in the second rotational position, the drive shaft 162 is in the respective second position, and thus aligned with the actuator shaft 54. Thus, the drive shaft 162 can be translated distally until the drive member 175 engages the coupling member 57 of the actuator shaft 54. Subsequent rotation of the drive shaft 162 in the first direction of rotation thus causes the actuator shaft 54 to rotate in the first direction of rotation, thereby expanding the implant 20 from the collapsed configuration to the expanded configuration. Rotation of the draft shaft 162 in the second direction causes the actuator shaft 54 to rotate in the second direction of rotation, thereby collapsing the implant 20 from the expanded configuration to the collapsed configuration.

As the drive shaft 162 rotates the actuator shaft 54 in the first direction of rotation, the first wedge member 48 travels in the expansion direction as described above. Because the first and second attachment pins 157 and 159 are attached to the first wedge member 48, the attachment housing 155 moves along with the first wedge member 48 in the direction of expansion. Thus, the attachment housing 155 translates distally along with the first wedge member 48 as the implant 20 moves to the expanded configuration. Because the actuator shaft 54 remains translatably fixed, the attachment housing 155 translates distally along with respect to the drive shaft 162. In one example, the attachment housing 155, the outer support shaft 156, and the handles 160 and 176 can translate with the first wedge member 48 both as the wedge member 48 selectively moves in the expansion direction and the collapse direction. The because drive shaft 162 is rotatably coupled to the actuator shaft 54, the drive shaft 162 can remain translatably fixed to the actuator shaft, and thus translatably stationary with respect to the attachment housing 155, the outer support shaft 156, and the handles 160 and 176 as the attachment housing 155, the outer support shaft 156, and the handles 160 and 176 translate with the first wedge member 48.

Further, as the drive shaft 162 rotates the actuator shaft 54 in the second direction of rotation, the first wedge member 48 travels in the collapse direction as described above. Because the first and second attachment pins 157 and 159 are attached to the first wedge member 48, the attachment housing 155 moves along with the first wedge member 48 in the direction of contraction. Thus, the attachment housing 155 translates proximally along with the wedge member as the implant 20 moves to the collapsed configuration.

The attachment housing 155 can define a second or inner channel 184 that is sized to receive the distal end of the drive shaft 162. The drive shaft 162 can extend into the inner channel 184 when the drive shaft 162 is translated distally such that the drive member 175 engages the coupling member 57 of the actuator shaft 54. Interference between the drive shaft 62 and the attachment housing 155 in the inner channel 184 prevents the toggle shaft 166 from rotating from the second rotational position to the first rotational position. Thus, the interference between the drive shaft 162 and the attachment housing 155 can prevent the drive shaft 162 from moving from the second position aligned with the actuator shaft 54 to the first position aligned with the second attachment pin 159. When the drive shaft 162 has retracted along the proximal direction out of the channel 182, the interference is removed and the toggle shaft 166 can be rotated from the second rotational position to the first rotational position.

Thus, referring again to FIGS. 11B and 12B, once the intervertebral implant 20 has reached its desired level of expansion or contraction, the instrument 152 can be detached from the intervertebral implant 20. In particular, the drive shaft 162 can be returned to the first position in alignment with the second attachment pin 159. The drive shaft 162 can then be advanced distally into the outer channel 182 so as to rotatably engage the second attachment pin 159. As the second attachment pin 159 rotates in a respective second direction of rotation opposite the respective first direction of rotation, the second attachment pin 159 can threadedly disengage from the intervertebral implant 20 in the other of the first and second apertures 96 and 98. In particular, the second attachment pin 159 can threadedly disengage from the first wedge member 48. Finally, the first attachment pin 157 can be removed from the first wedge member 48, and thus from the implant 20, thereby detaching the instrument 152 from the intervertebral implant 20.

During operation, the first and second attachment pins 157 and 159 can be attached to the intervertebral implant 20 in the manner described herein. The drive shaft 162 can be removed from the support shaft 156. The instrument 152 can receive impaction forces as desired to assist with insertion of the intervertebral implant 20 in the intervertebral space. Once the intervertebral implant 20 has been inserted in the intervertebral space, the drive shaft 162 can be inserted into the support shaft 156. The first and second attachment pins 157 and 159 can then be attached to the implant 20 in the manner described above, and the actuator shaft 54 can be rotated. The first and second pins 157 and 159 can then be detached from the implant 20.

Figure 13:
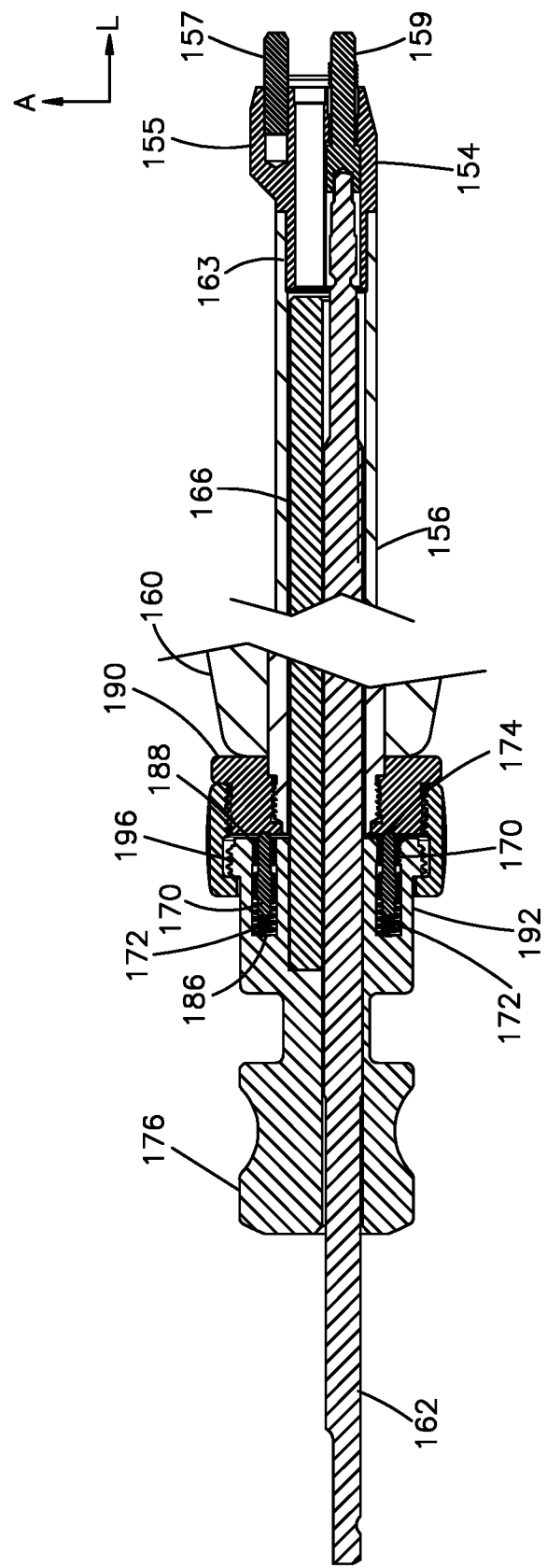
FIG. 13 is a sectional to plan view of the instrument illustrated in FIG. 10, showing a locating finger extending into a detent so as to provide a retention force.

Referring now to FIGS. 10 and 13, and as described above, the instrument can include a pair of locating fingers 170 and at least one spring 172 that can urge the fingers 170 into the detents 174 so as to provide tactile feedback when the toggle shaft 166 is in the first rotational position and the second rotational position. In particular, the instrument can include a seat 186 and a surface 188 that defines the detents 174 and faces the seat 186. The instrument 152 can include first and second springs 172 that are captured between the seat 186 and the first and second locating fingers 170, respectively. Thus, the springs 172 provide a respective force that urges the locating fingers 170 against the surface 188. When the toggle shaft 166 is in the first and second rotational positions, the fingers 170 can extend into the detents so as to define a retention force that resists rotation of the toggle shaft. When a torsional force is applied that rotates the toggle shaft 166 to a position between the first and second rotational positions, the torsion force overcomes the retention force before the locating fingers 170 ride out of the detents and ride along the surface 188. The retention force of the fingers 170 positioned in the detents 174 can initially resist movement of the toggle shaft 166 away from the first and second rotational positions. Thus, the engagement of the fingers 170 and detents 174 can provide tactile feedback when the toggle shaft 166 is moved selectively to the first and second rotational positions.

With continuing reference to FIGS. 10 and 13, the seat 186 can be defined by the drive handle 176. The surface 188 can be defined by a ring 190 that surrounds the support shaft 156. The ring 190 can be translatably fixed to the support shaft 156. For instance, the ring 190 can be threadedly mated to the support shaft 156. In one example, the ring 190 can be threadedly mated to the proximal support shaft portion 156b. The drive handle 176 can define the seat 186. For instance, the drive handle 176 can define respective pockets 192 that retain a respective one of the springs 172 and fingers 170. During operation, the drive handle 176 can be rotated so as to rotate the toggle shaft 166. Because the ring 190 is fixed to the support shaft 156, the drive handle 176 and the toggle shaft 166 both rotate with respect to the ring 190 and the support shaft 156. The instrument 152 can further include a collar 194 that attaches to each of the ring 190 and the locking handle 176 to prevent the locking handle 176 and the ring 190 from separating along the longitudinal direction L. In one example, the collar 194 can threadedly attach to the ring 190, and can define a flange that abuts a shoulder 196 of the locking handle 176.

Figure 17A:
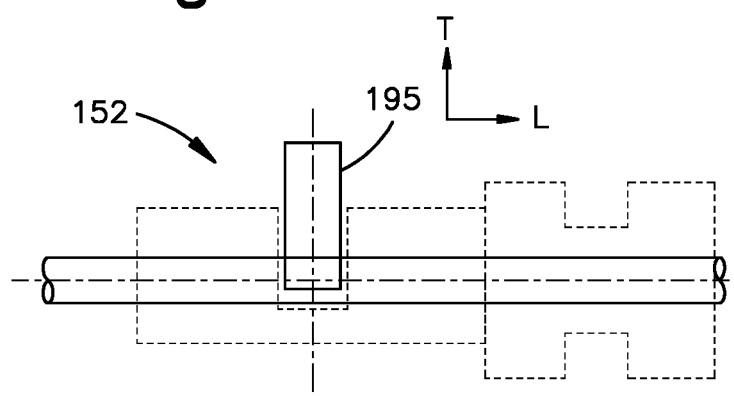
FIG. 17A is a schematic elevation view showing a portion of the instrument illustrated in FIG. 10 but constructed in accordance with an alternative embodiment.
Figure 17B:
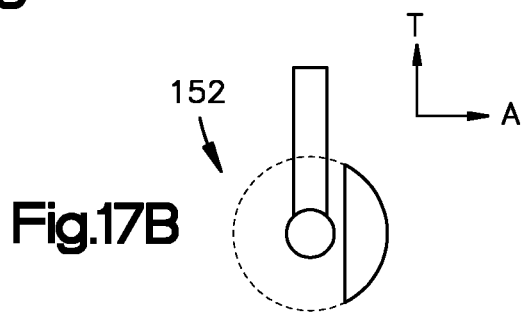
FIG. 17B is a cross-sectional view of the portion of the instrument illustrated in FIG. 17A.

Alternatively, referring to FIGS. 17A-17B, the instrument 152 can include an adjustment lever 195 that is coupled to the toggle shaft 166, and is coupled directly or indirectly to the toggle shaft 166. The adjustment lever 195 can extends radially outward to a position radially outward of the support shaft 156, along a direction angularly offset with respect to the longitudinal direction L. For instance, the adjustment lever 195 can extend from the toggle shaft 166 along a direction perpendicular to the longitudinal direction L. Thus, the adjustment lever 195 can be actuated so as to rotate the toggle shaft 166 between the first and second rotational positions. In this regard, it should be appreciated that the drive handle 176 can be eliminated in certain examples, thereby reducing the length of the instrument 152 with respect to the longitudinal direction L.

As illustrated in FIG. 9, the attachment pins 157 and 159 and the drive shaft 162 can be coplanar with each other. The plane can be oriented along the lateral direction A and the longitudinal direction L. Thus, it can also be said that a straight line extends through the central axes of each of the attachment pins 157 and 159 and the drive shaft 162. Further, the respective central axes of the attachment pins 157 and 159 can be substantially parallel to the central axis of the drive shaft 162. It can further be said that the central axis of the attachment member can be colinear with the central axis of the outer support shaft 156.

Figure 14A:
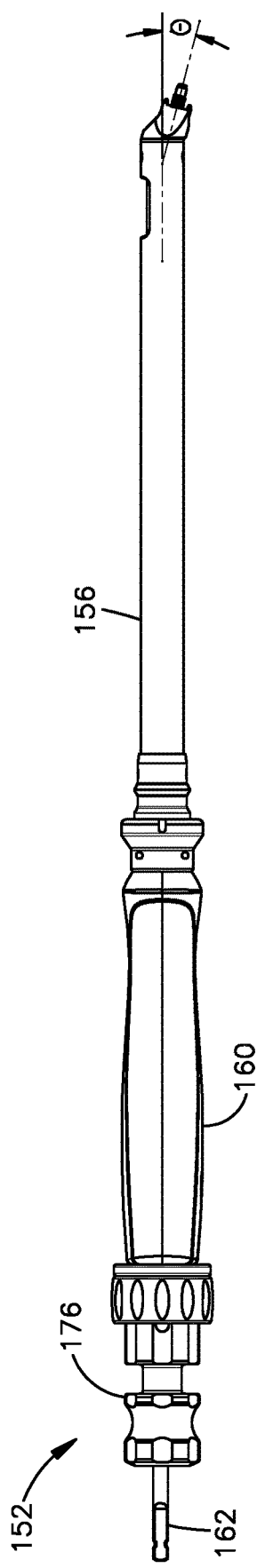
FIG. 14A is a side elevation view of the instrument illustrated in FIG. 10, but constructed in accordance with an alternative embodiment.

Alternatively, referring to FIG. 14A, the attachment housing 155 can be angled with respect any one up to all of the central axis of the drive shaft 162, the toggle housing 166, and the support shaft 156. In particular, the attachment housing 155 can extend obliquely along the transverse direction T at an angle θ. Thus, the attachment housing 155 can extend along the transverse direction T as it extends distally. Accordingly, any one or more up to all of the attachment pins 157 and 159 can extend along a direction that is angularly offset with respect to one or more up to all of the central axis of the drive shaft 162, the toggle housing 166, and the support shaft 156 at the angle θ. The angle θ can be in a range of greater than zero degrees up to approximately forty degrees. In one example the range can be from approximately five degrees and thirty degrees in one example, though it should be appreciated that the angle θ can be any suitable angle as desired. Thus, it should also be appreciated that the central axis of the implant 20, which can be defined by the actuation screw 54 in certain examples, can similarly be oriented at the angle θ with respect to one or more up to all of central axis of the drive shaft 162, the toggle housing 166, and the support shaft 156.

Figure 14B:
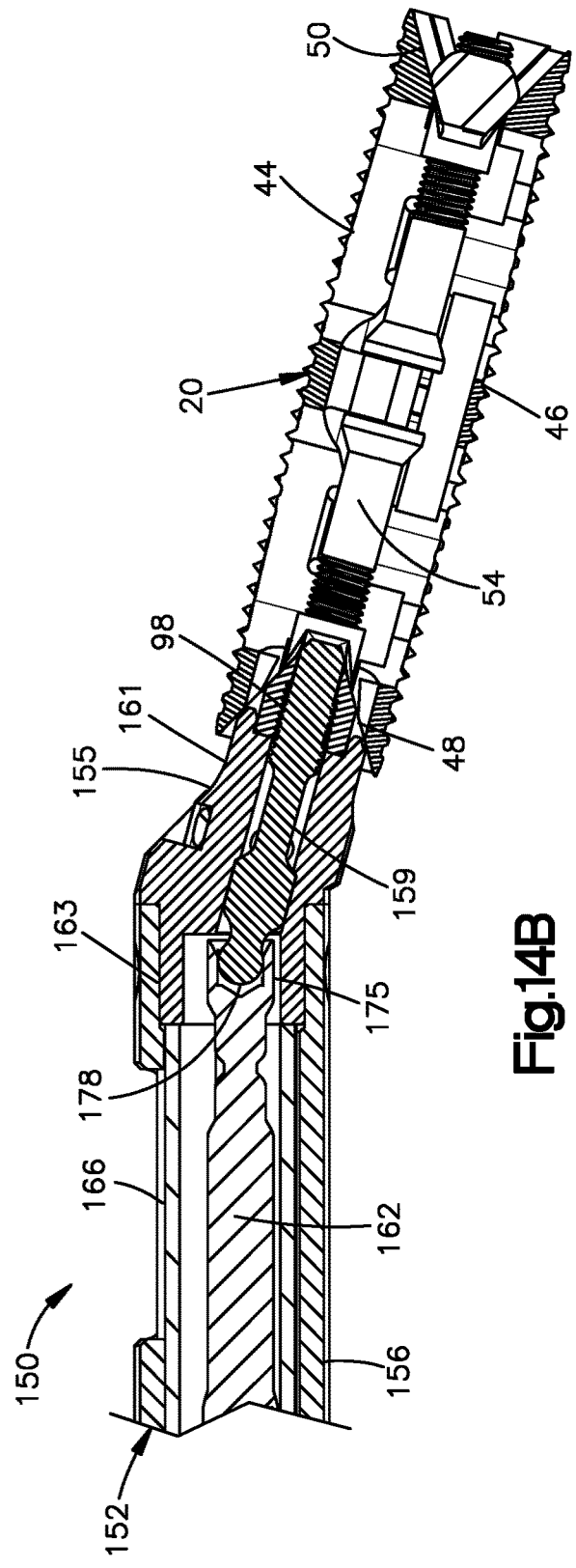
FIG. 14B is a sectional side elevation view of the instrument illustrated in FIG. 14A, showing the drive shaft coupled to the second attachment pin.
Figure 14C:
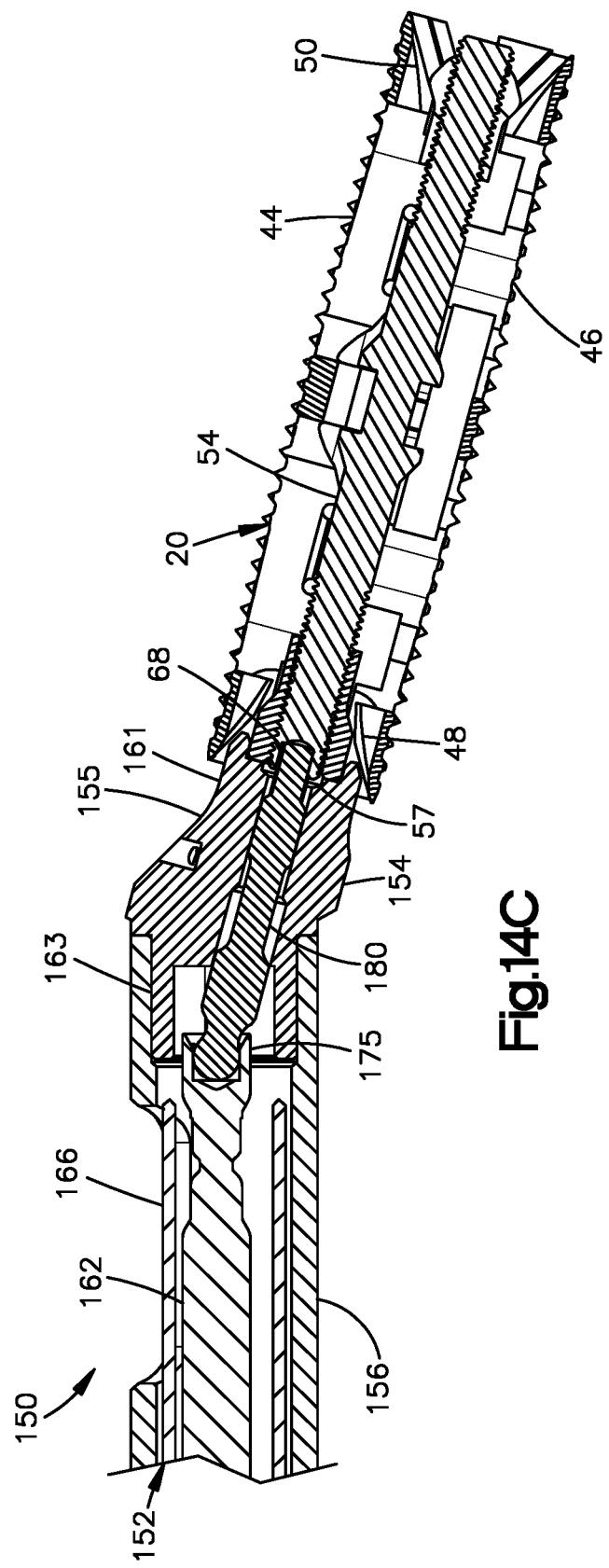
FIG. 14C is a sectional side elevation view of the instrument illustrated in FIG. 14A, showing the drive shaft coupled to the actuation screw of the implant.

As illustrated in FIG. 14B, the drive member 175 can define a universal joint that is configured to grip the second attachment pin 159. Thus, the drive shaft 162 can rotate the attachment pin 159 that is oriented oblique to the drive shaft 162 in the manner described above. As illustrated in FIG. 14C, the instrument 152 can include a coupling shaft 180 that is configured to be interconnected between the drive shaft 162 and the actuator shaft 54 of the intervertebral implant 20. In particular, the drive member 175 of the drive shaft 162 can rotatably engage the proximal end of the coupling shaft 180, and the coupling shaft 180 can include a drive member that, in turn, is rotatably coupled to the actuator shaft 54. Thus, rotation of the drive shaft in the first direction of rotation along its central axis causes the coupling shaft to rotate about its central axis in the first direction of rotation. The central axis of the coupling shaft 180 can be oblique to the central axis of the drive shaft 162 at the angle θ. Rotation of the coupling shaft 180 in the first direction of rotation causes the actuator shaft 54 to rotate in the first direction of rotation about its central axis. Similarly, rotation of the drive shaft in the second direction of rotation along its central axis causes the coupling shaft to rotate about its central axis in the second direction of rotation. Rotation of the coupling shaft 180 in the second direction of rotation causes the actuator shaft 54 to rotate in the second direction of rotation about its central axis. The coupling shaft can be disposed in the attachment housing 155, such that the drive member of the coupling shaft extends distally from the attachment housing and into the bore 68, where it can rotatably attach to the actuator shaft 54. Thus, when the drive shaft 62 is in the second position, it can be said to be operably aligned with the actuator shaft 54 via the coupling shaft 80.

The angled attachment housing 155 can be advantageous when it is desired to implant the intervertebral implant in an intervertebral space that is difficult to access along a pure lateral approach. For instance, the iliac crest, ribcage, or other anatomical structure can impede a pure lateral approach into certain intervertebral spaces. The angle attachment housing allows the outer support shaft 156 to be oriented along the lateral direction A and the transverse direction T while the attached intervertebral implant 20 is oriented along the lateral direction A as it is inserted into the intervertebral space.

Alternatively or additionally, referring generally to FIG. 15A-16B, the instrument 152 can be configured such that the attachment member 154 is angularly offset with respect to any one up to all of the central axis of the drive shaft 162, the toggle housing 166, and the support shaft 156 along the lateral direction A. In this regard, it should be appreciated that the instrument 152 can insert the intervertebral implant 20 into the intervertebral space along an anterior to psoas (ATP) approach. In one example, the attachment member 154 can be fixedly attached to the support shaft 156 such that the central axes of the attachment pins 157 are angularly offset with respect to the central axis of one or more up to all of the central axis of the drive shaft 162, the toggle housing 166, and the support shaft 156 along the lateral direction A.

Figure 15A:
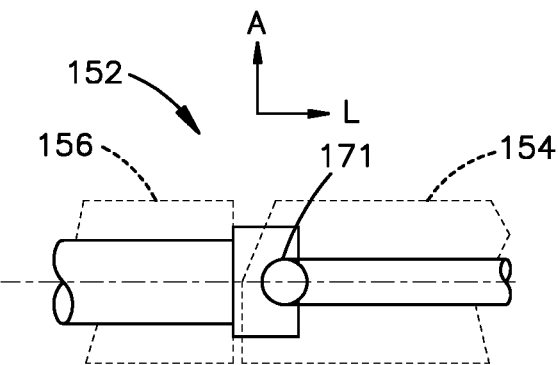
FIG. 15A is a schematic top plan view of the instrument illustrated in FIG. 10, but having an angulation mechanism in an alternative embodiment, shown in a straight orientation.
Figure 15B:
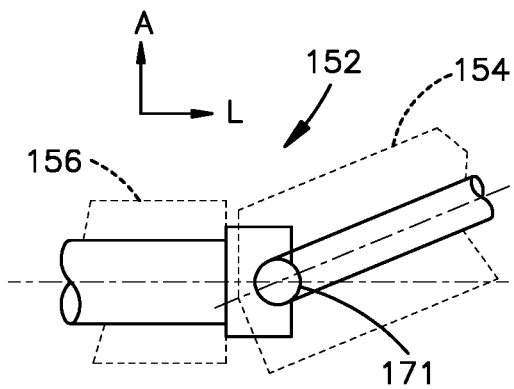
FIG. 15B is a schematic top plan view of the instrument illustrated in FIG. 15A, but having an angulation mechanism in an alternative embodiment, shown in a straight orientation.

Alternatively, as illustrated in FIGS. 15A-15B, the instrument 152 can define a hinge 171 that is connected between the support shaft 156 and the attachment member 154. The hinge 171 can allow for angulation of the attachment member 154 relative to the support shaft 156 along a plane defined by the lateral direction A and the longitudinal direction L. Thus, the attachment member 154 can be angulated from a straight or colinear configuration (FIG. 15A) to an angularly offset configuration (FIG. 15B) with respect to the support shaft 156. It should be appreciated in certain examples that the hinge 171 can define a universal joint that allows for angulation of the attachment member 154 relative to the support shaft 156 along any direction as desired, including the lateral direction A, the transverse direction T, and combinations thereof.

Figure 16A:
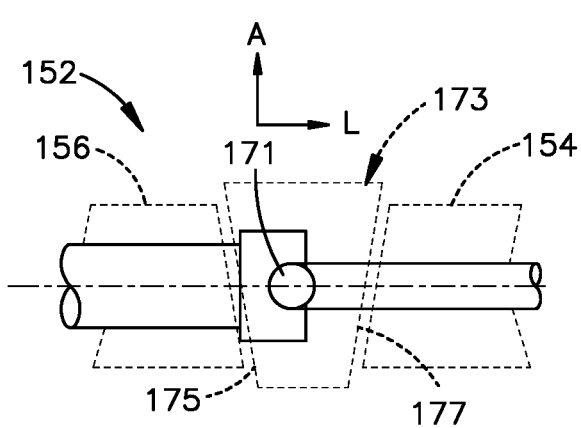
FIG. 16A is a schematic top plan view of the instrument illustrated in FIG. 10, but having an angulation joint in an alternative embodiment, shown in a straight configuration.
Figure 16B:
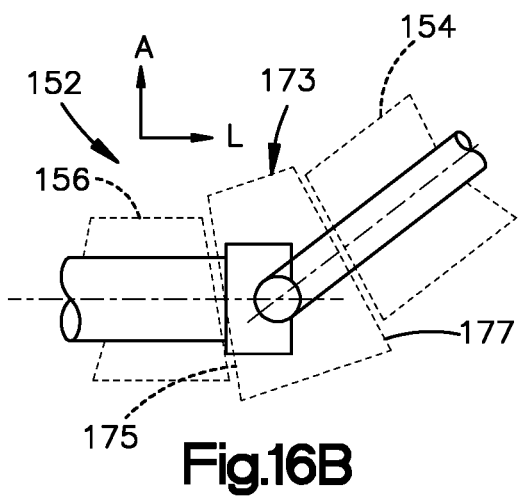
FIG. 16B is a schematic top plan view of the instrument illustrated in FIG. 16A, but having an angulation joint in an alternative embodiment, shown in a straight configuration.

In another example, referring now to FIGS. 16A-16B, the instrument 152 can include an angulation joint 173 that is disposed between the support shaft 156 and the attachment member 154. The angulation joint can define first and second surfaces 175 and 177 that are spaced from each other along the longitudinal direction. The first surface 175 can face the support shaft 156, and can be in abutment, such as surface contact, with the support shaft. The second surface 177 can face the attachment member 154, and can be in abutment, such as surface contact, with the attachment member 154. One or more of the surfaces 175 and 177 can be angled such when the angulation joint 173 is in a first orientation (FIG. 16A), the attachment member 154 is straight or colinear with respect to the support shaft 156. When the angulation joint 173 is in a second orientation (FIG. 16B), the attachment member 154 can be angularly offset with respect to the support shaft 156 in either or both of the lateral direction A and the transverse direction T. In one example, the angulation joint 173 can be wedge shaped. The instrument 152 can further include the hinge 171 to guide angulation of the attachment member 154 when the angulation joint 173 is in the second orientation.

Referring now to FIGS. 18-19B, it should be appreciated that the intervertebral implant 20 can be constructed in accordance with any suitable alternative embodiment. For instance, the expansion limiter 129 of the intervertebral implant 20 can include at least one stop member that is configured to abut a corresponding at least one of the first and second wedge members 48 and 50, thereby preventing the at least one of the first and second wedge members 48 and 50 from moving in the expansion direction. Because the first and second wedge members 48 and 50 are threadedly mated to the actuator shaft 54, preventing the at least one of the first and second wedge members 48 and 50 from moving in the expansion direction likewise prevents the actuator shaft 54 from rotating in the first direction of rotation. In this regard, the intervertebral implant 20 can be devoid of the limiter tabs 132 and the limiter channels 134 described above with respect to FIG. 3D.

The at least one stop member can include a first stop member 198 and a second stop member 200 that are configured to be supported by the actuator shaft 54. The first stop member 198 is configured to be positioned adjacent the first wedge member 48 in the expansion direction. For instance, the first stop member 198 can be positioned on the actuator shaft 54 at a location adjacent the first wedge member 48 in the expansion direction. Thus, the first stop member 198 is configured to abut the first wedge member 48, thereby preventing the first wedge member 48 from moving in the expansion direction. Similarly, the second stop member 200 is configured to be positioned adjacent the second wedge member 50 in the expansion direction. For instance, the second stop member 200 can be positioned on the actuator shaft 54 at a location adjacent the second wedge member 50 in the expansion direction. Thus, the second stop member 198 is configured to abut the second wedge member 50, thereby preventing the second wedge member 50 from moving in the expansion direction.

In one example, the first and second stop members 198 and 200 can be removably secured to the actuator shaft 54. For instance, the actuator shaft 54 can define a first shoulder 202 that is spaced from the first wedge member 48 in the expansion direction. Thus, in one example, the first shoulder 202 can be disposed between the first wedge member 48 and the recess 58 of the actuator shaft 54. Accordingly, a first gap 204 is defined between the first shoulder 202 and the first wedge member 48 along the longitudinal direction. Further, at least a portion of the first shoulder 202 and at least a portion of the first wedge member 48 can be aligned with each other along the longitudinal direction L. The first gap 204 has a length that extends from the first wedge member 48 to the first shoulder 202 along the longitudinal direction. Thus, the length of the first gap 204 decreases as the first wedge member 48 moves in the direction of expansion. The first stop member 198 can attached to the actuator shaft 54 in the first gap 204 such that a first or abutment surface 230 of the first stop member 198 faces the first shoulder 202 and a second or stop surface 232 of the first stop member 198 opposite the abutment surface 230 of the first stop member 198 faces the first wedge member 48. The first stop member 198 has a length that extends from the abutment surface 230 of the first stop member 198 to the stop surface 232 of the first stop member 198. It should be appreciated that the length of the first stop member 198 can determine the expansion position of the first wedge member 48.

The actuator shaft 54 can define a second shoulder 206 that is spaced from the first wedge member 48 in the expansion direction. Thus, in one example, the second shoulder 206 can be disposed between the second wedge member 50 and the recess 58 of the actuator shaft 54. Further, the first and second shoulders 202 and 206 can be disposed between the first and second wedge members 48 and 50. A second gap 208 is defined between the second shoulder 206 and the second wedge member 50 along the longitudinal direction. Further, at least a portion of the second shoulder 206 and at least a portion of the second wedge member 50 can be aligned with each other along the longitudinal direction L. The second gap 208 has a length that extends from the second wedge member 50 to the second shoulder 206 along the longitudinal direction. L. Thus, the length of the second gap 208 decreases as the second wedge member 50 moves in the direction of expansion. The second stop member 200 can attached to the actuator shaft 54 in the second gap 208 such that a first or abutment surface 230 of the second stop member 200 faces the second shoulder 206 and a second or stop surface 232 of the second stop member 200 opposite the abutment surface 230 of the second stop member 200 faces the second wedge member 50. The second stop member 200 has a length that extends from the abutment surface 230 of the second stop member 200 to the stop surface 232 of the second stop member 200. It should be appreciated that the length of the second stop member 200 can determine the expansion position of the first wedge member 50.

In one example, when the implant is in the collapsed configuration or in an intermediate expanded configuration that is expanded from the collapsed configuration but collapsed with respect to the expanded configuration, the length of the first wedge member 48 is less than the length of the first gap 204. Accordingly, the first stop member 198 does not prevent the first wedge member 48 from moving in the direction of expansion. Further, when the implant is in the collapsed configuration or in an intermediate expanded configuration that is expanded from the collapsed configuration but collapsed with respect to the expanded configuration, the length of the second wedge member 50 is less than the length of the second gap 208. Accordingly, the second stop member 200 does not prevent the second wedge member 50 from moving in the direction of expansion. The length of the first wedge member 48 can be equal to the length of the second wedge member 50. Further, the length of the first wedge member 48 can be substantially equal to the length of the first unthreaded portion 73. Similarly, length of the second wedge member 50 can be substantially equal to the length of the second unthreaded portion 75.

The first stop member 198 can be inserted onto the actuator shaft 54 at a first attachment region 212. The first attachment region 212 can be defined by the outer surface of the actuator shaft 54 at the first gap 204 that is defined between the first shoulder 202 and the first wedge member 48 along the longitudinal direction L when the first wedge member 48 is attached to the actuator shaft 54. Thus, the first attachment region 212 can be defined by the first unthreaded portion 73. Similarly, the second stop member 200 can be inserted onto the actuator shaft 54 at a second attachment region 214. The second attachment region 214 can be defined by the outer surface of the actuator shaft 54 at the second gap 208 that is defined between the second shoulder 206 and the second wedge member 50 along the longitudinal direction L when the second wedge member 50 is attached to the actuator shaft 54. Thus, the second attachment region 214 can be defined by the second unthreaded portion 75.

Figure 20:
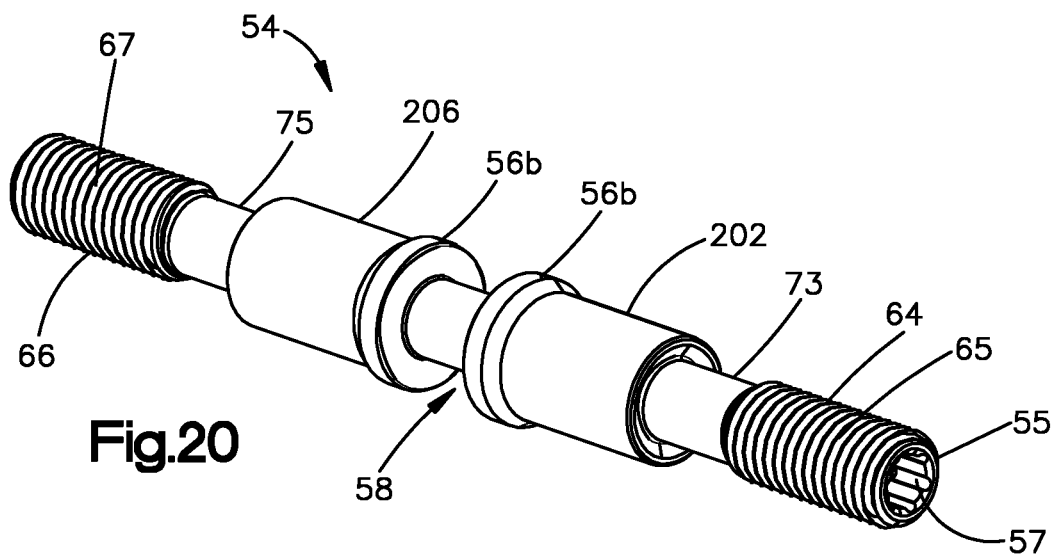
FIG. 20 is a perspective view of an actuator shaft of the expandable intervertebral implant illustrated in FIG. 18.

Referring now to FIG. 20, the actuator shaft 54 can include the first shoulder 202 that extends from the first unthreaded portion 73 to the first flange 56. The first shoulder 202 can define an outer diameter that is greater than the outer diameter of the first unthreaded portion 73. Further, the first flange 56a can have an outer diameter that is greater than the outer diameter of the first shoulder 202. Alternatively, the first flange 56a can have the same outer diameter as the outer diameter of the first shoulder 202. In this regard, it should be appreciated that the first shoulder 202 can alternatively define the first flange 56.

Referring now to FIG. 20, the actuator shaft 54 can include the first shoulder 202 that extends from the first unthreaded portion 73 to the first flange 56a. The first shoulder 202 can define an outer diameter that is greater than the outer diameter of the first unthreaded portion 73. Further, the first flange 56a can have an outer diameter that is greater than the outer diameter of the first shoulder 202. Alternatively, the first flange 56a can have the same outer diameter as the outer diameter of the first shoulder 202. In this regard, it should be appreciated that the first shoulder can alternatively define the first flange 56a. The first shoulder 202 can define an outer surface that is smooth or unthreaded. The outer surface of the first shoulder 202 can define the outer diameter of the first shoulder 202.

Similarly, the actuator shaft 54 can include the second shoulder 206 that extends from the second unthreaded portion 75 to the second flange 56b. The second shoulder 206 can define an outer diameter that is greater than the outer diameter of the second unthreaded portion 75. Further, the second flange 56b can have an outer diameter that is greater than the outer diameter of the second shoulder 206. Alternatively, the second flange 56b can have the same outer diameter as the outer diameter of the second shoulder 206. In this regard, it should be appreciated that the second shoulder 206 can alternatively define the second flange 56b. The second shoulder 206 can define an outer surface that is smooth or unthreaded. The outer surface of the second shoulder 206 can define the outer diameter of the second shoulder 206.

Figure 21A:
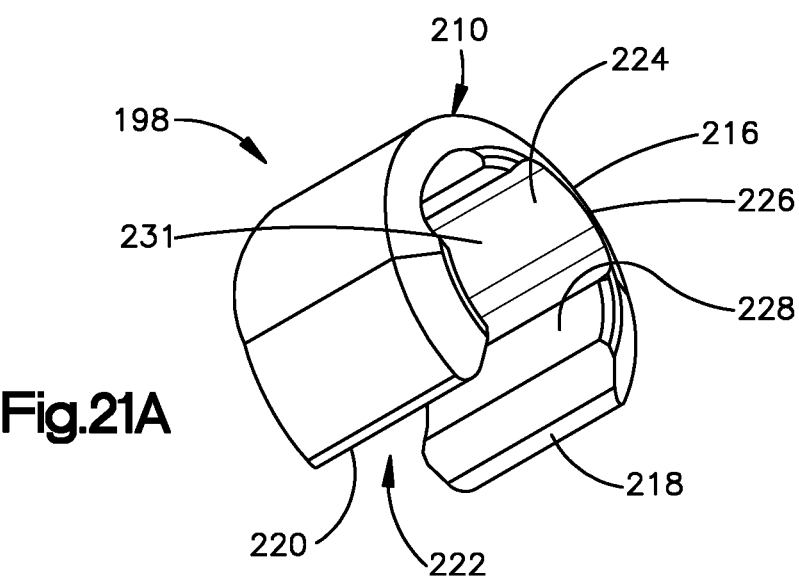
FIG. 21A is a perspective view of a stop member of the expandable intervertebral implant illustrated in FIG. 18.
Figure 21B:
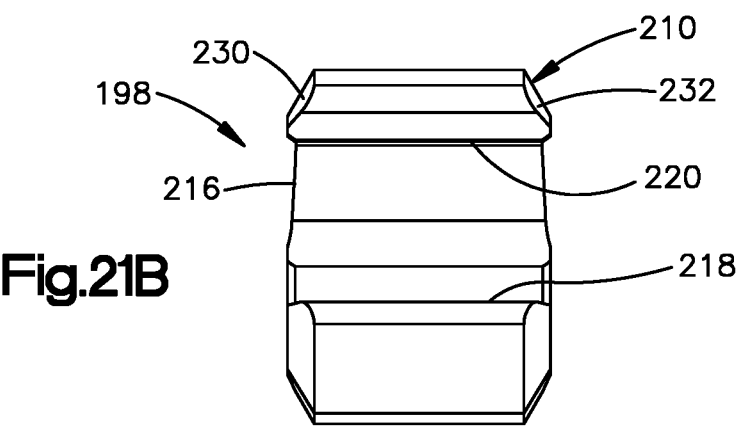
FIG. 21B is a side elevation view of the stop member illustrated in FIG. 21A.

Referring now to FIGS. 21A-21B, the first and second stop members 198 and 200 will now be described with reference to the first stop member 198. In this regard, it should be appreciated that the first and second stop members 198 and 200 can be constructed identical to each other. Thus, the description of the first stop member 198 can apply with equal force and effect to the second stop member 200, unless otherwise indicated.

The first stop member 198 can be configured as a clip 210 that can be configured to be clipped onto the actuator shaft 54 in the manner described above. In particular, the first stop member 198 can define a body 216 having at least a portion that is radially expandable. Thus, at least a portion of the body 216 can be flexible and resilient. The body 216 can extend generally circumferentially from a first circumferential end 218 to a second circumferential end 220. The first circumferential end 218 can be spaced from the second circumferential end 220 so as to define a circumferential void 222 between the first circumferential end 218 and the second circumferential end 220. A straight linear distance from the first circumferential end 218 to the second circumferential end 220 can be less than the diameter of the actuator shaft 54 at the unthreaded portion 73 when the first stop member is in a neutral relaxed configuration. It is recognized that the term "circumferential" and derivatives thereof as used herein can connote a circular shape, but is not intended to be limited to a circular shape. Thus, the locking members 198 and 200 can be circular in cross-section, or can define any suitable alternative shape as desired while still defining circumferential ends 218 and 220.

The first stop member 198 can define an inner end 224 that is configured to face the actuator shaft 54, and an outer end 226 that is opposite the inner end 224. The inner end 224 can define at least one contact surface 228 such as a plurality of contact surfaces 228 that are configured to contact the actuator shaft 54 when the first stop member 198 is coupled to the actuator shaft 54. The contact surfaces 228 can define a radius of curvature in a plane that is oriented perpendicular to the expansion direction. The radius of curvature can be substantially equal to the radius of curvature of the outer surface of the actuation shaft at the unthreaded portion 73. Further, the contact surfaces 228 can be spaced from each other by respective recessed surfaces 231 that face the actuator shaft 54 and are spaced from the actuator shaft 54 when the first stop member 198 is coupled to the actuator shaft 54.

Referring now to FIGS. 4A-5B and 22A-B, assembly of the implant 20 will now be described. In particular, the first and second wedge members 48 and 50 are attached to the upper and lower endplates 44 and 46. In particular, to attach the first wedge member 48 to the upper endplate 44, the first and second upper projections 108 of the first wedge member 48 are inserted into the first and second channels 112, respectively, of the upper endplate 44. Further, to attach the first wedge member 48 to the lower endplate 46, the first and second lower projections 110 of the first wedge member 48 are inserted into the first and second channels 114, respectively, of the lower endplate 46. To attach the second wedge member 50 to the upper endplate 44, the first and second upper projections 124 of the second wedge member 50 are inserted into the first and second channels 128, respectively, of the upper endplate 44. Further, to attach the second wedge member 50 to the lower endplate 46, the first and second lower projections 126 of the second wedge member 50 are inserted into the first and second channels 130, respectively, of the lower endplate 46.

Further, the first and second wedge members 48 and 50 can be threadedly attached to the actuator shaft 54, as shown in FIG. 19A. The first and second wedge members 48 and 50 can threadedly attach to the actuator shaft 54 prior to attaching the first and second wedge members 48 and 50 to the upper and lower endplates 44 and 46. Alternatively, the first and second wedge members 48 and 50 can threadedly attach to the actuator shaft 54 after attaching the first and second wedge members 48 and 50 to the upper and lower endplates 44 and 46.

Figure 22A:
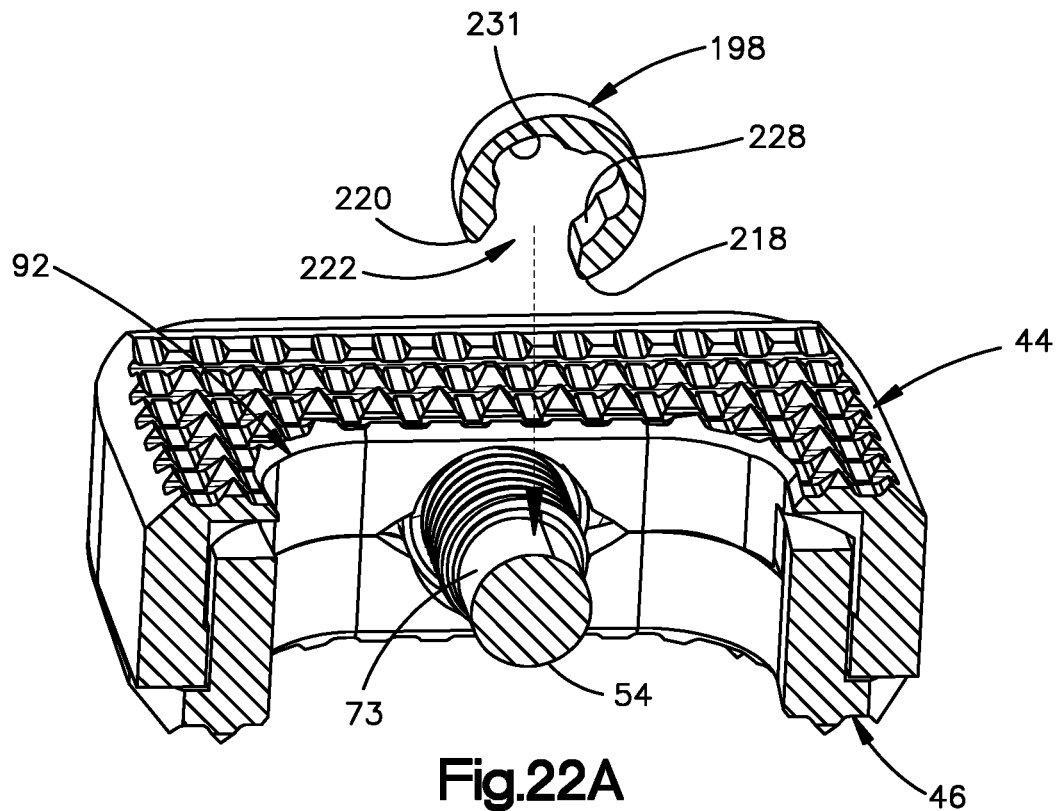
FIG. 22A is an exploded perspective view of a portion of the expandable intervertebral implant illustrated in FIG. 18, showing attachment of the stop member to the actuator shaft.
Figure 22B:
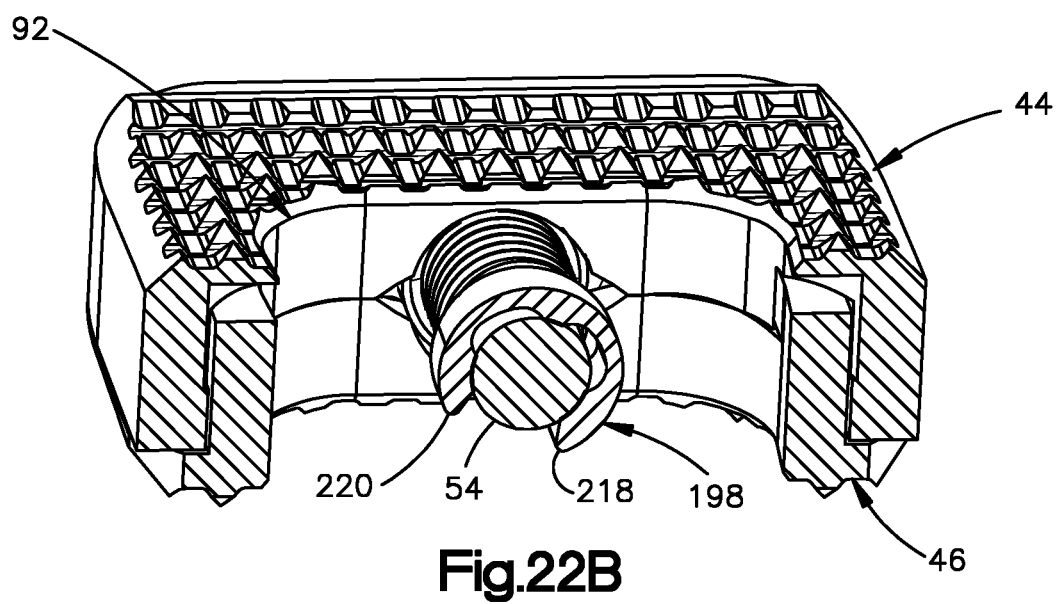
FIG. 22B is an exploded perspective view of a portion of the expandable intervertebral implant illustrated in FIG. 22A, showing the stop member attached to the actuator shaft.

Next, with specific reference to FIGS. 22A-22B, the first and second stop members 198 and 200 can be attached to the actuator shaft 54 as described above. In particular, the first and second stop members 198 and 200 can be attached to the actuator shaft 54 when the intervertebral implant 20 is in the collapsed position. Alternatively, the first and second stop members 198 and 200 can be attached to the actuator shaft 54 when the intervertebral implant 20 is in a position collapsed with respect to the expanded configuration.

For instance, the first stop member 198 can be inserted through the window 92 of the upper endplate 44 or lower endplate 46 and attached to the actuator shaft 54 at the first attachment region 212. For instance, the first stop member 198 can be attached to the first unthreaded portion 73 of the actuator shaft 54. In particular, the circumferential void 222 can be aligned with the actuator shaft 54. Next, the first and second circumferential ends 218 and 220 of the first stop member 198 can be moved away from each other. For instance, the first and second circumferential ends 218 and 220 can be forced apart from each other as they ride over the actuator shaft 54. Because the first stop member 198 can be flexible and resilient, the first and second ends 198 and 200 can flex from the neutral or relaxed position to a second position sized to receive the actuator shaft 54 therebetween. Once the actuator shaft 54 has been received in the first stop member 198, the first and second circumferential ends 218 and 220 can be biased toward the neutral position, such that the contact surfaces 228 apply a force to the actuator shaft 54 that captures the actuator shaft 54 in the first stop member 198.

The at least one contact surface 228 can therefore apply a retention force against the actuator shaft 54 that resists sliding of the first stop member 198 along the actuator shaft 54. Alternatively, the first stop member 198 can be slidable along the actuator shaft 54, it being appreciated that the first stop member 198 will ultimately be captured between the first wedge member 48 and the first shoulder 202. As an alternative to the first locking member 198 being resilient and flexible, one or both of the first and second ends 198 and 200 can be mechanically movable between an unlocked position whereby the void 222 is sized to receive the actuator shaft 54, and a locked position whereby the actuator shaft 54 is captured in the first stop member 198. As a further alternative, the first locking member 198 can be expanded and moved along the central axis of the actuator shaft 54 to the first attachment location 212, and then can be mechanically or resiliently collapsed so as to attach to the actuator shaft 54 at the first attachment location 212. In this regard, the first locking member 198 can be configured as a fully enclosed annulus. As described above, the second stop member 200 can be attached to the actuator shaft 54 as described above with respect to the first stop member 198, but at the second attachment region 214.

Figure 23:
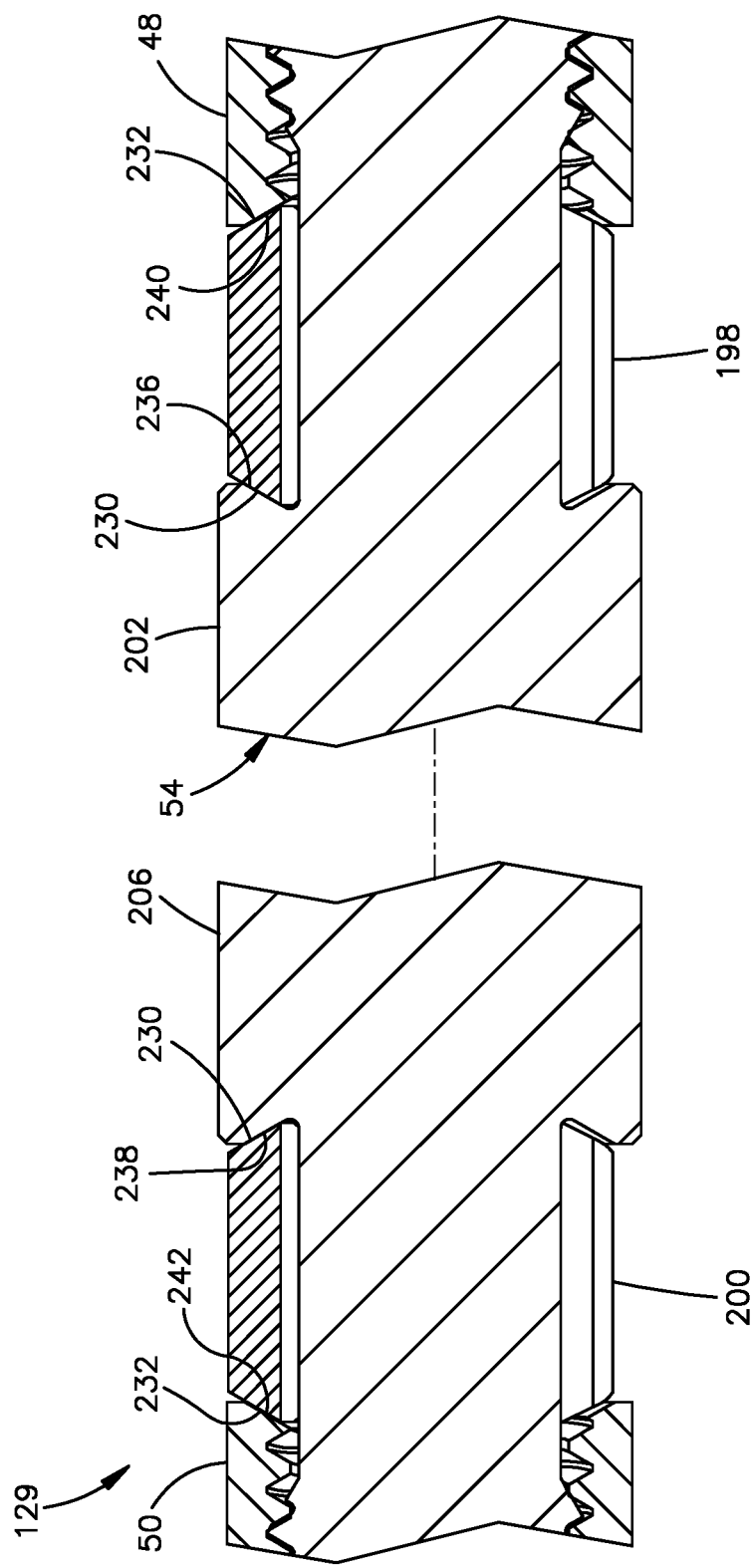
FIG. 23 is a sectional side elevation view of a portion of the expandable intervertebral implant illustrated in FIG. 18, shown in the expanded configuration.

Referring now to FIG. 23, the expansion limiter 129 can be constructed such that the first and second stop members 198 and 200 are urged radially inward against the actuator shaft 54 when the intervertebral implant is in its fully expanded configuration. In particular, the first abutment surfaces 230 can be sloped inwardly toward the actuator shaft 54 as it extends in the expansion direction toward the first shoulder 202. The first shoulder 202 can define a first abutment surface 236 that slopes inwardly toward the actuator shaft 54 as it extends in the expansion direction away from the first stop member 198. The first abutment surface 236 can at least partially or entirely surround the actuator shaft 54. The first abutment surface 236 can be sloped substantially equal to the slope of the abutment surface 230 of the first stop member 198. Thus, the first abutment surface 236 can be in surface contact with the abutment surface 230 of the first stop member 198 when the intervertebral implant 20 is in the fully expanded configuration. It is recognized therefore that as a force is applied to the first stop member 198 in the expansion direction, the sloped first abutment surface 236 will urge the abutment surface 230 of the first stop member 198 against the actuator shaft 54, thereby securing the first stop member 198 against the actuator shaft 54. In particular, the first stop member 198 is captured between the first abutment surface 236 and the actuator shaft 54.

The second shoulder 206 can define a second abutment surface 238 that slopes inwardly toward the actuator shaft 54 as it extends in the expansion direction away from the second stop member 202. The second abutment surface 238 can at least partially or entirely surround the actuator shaft 54. The second abutment surface 238 can be sloped substantially equal to the slope of the abutment surface 230 of the second stop member 200. Thus, the second abutment surface 238 can be in surface contact with the abutment surface 230 of the second stop member 200 when the intervertebral implant 20 is in the fully expanded configuration. It is recognized therefore that as a force is applied to the second stop member 200 in the expansion direction, the sloped second abutment surface 238 will urge the abutment surface 230 of the second stop member 200 against the actuator shaft 54, thereby securing the second stop member 200 against the actuator shaft 54. In particular, the second stop member 200 is captured between the first abutment surface 236 and the actuator shaft 54.

With continuing reference to FIG. 23, the stop surface 232 of the first stop member 198 can be sloped inwardly toward the actuator shaft 54 as it extends in a direction opposite the expansion direction, and thus toward the first wedge member 48. The first wedge member 48 can define a first wedge surface 240 that faces the first stop member 198. The first wedge surface 240 can slope inwardly toward the actuator shaft 54 as it extends in the direction opposite the expansion direction, and thus away from the first stop member 198. The first wedge surface 240 can at least partially or entirely surround the actuator shaft 54. Further, the first wedge surface 240 can define an opening to the first bore 68 of the first wedge member 48. The first wedge surface 240 can be sloped substantially equal to the slope of the stop surface 232 of the first stop member 198. Thus, the first wedge surface 240 can be in surface contact with the stop surface 232 of the first stop member 198 when the intervertebral implant is in the fully expanded configuration. It is recognized therefore that as the first wedge member 48 applies the force to the first stop member 198 in the expansion direction, the sloped first wedge surface 240 will urge the stop surface 232 of the first stop member 198 against the actuator shaft 54, thereby securing the first stop member 198 against the actuator shaft 54. In particular, the first stop member 198 is captured between the first wedge surface 240 and the actuator shaft 54.

The stop surface 232 of the second stop member 200 can be sloped inwardly toward the actuator shaft 54 as it extends in a direction opposite the expansion direction, and thus toward the second wedge member 50. The second wedge member 50 can define a second wedge surface 242 that faces the second stop member 200. The second wedge surface 242 can slope inwardly toward the actuator shaft 54 as it extends in the direction opposite the expansion direction, and thus away from the second stop member 200. The second wedge surface 242 can at least partially or entirely surround the actuator shaft 54. Further, the second wedge surface 242 can be defined by the second wall 71, and can define an opening to the second bore 72 of the second wedge member 50. The second wedge surface 242 can be sloped substantially equal to the slope of the stop surface 232 of the second stop member 200. Thus, the second wedge surface 242 can be in surface contact with the stop surface 232 of the second stop member 200 when the intervertebral implant is in the fully expanded configuration. It is recognized therefore that as the second wedge member 500 applies the force to the second stop member 200 in the expansion direction, the sloped second wedge surface 242 will urge the stop surface 232 of the second stop member 200 against the actuator shaft 54, thereby securing the second stop member 200 against the actuator shaft 54. In particular, the second stop member 200 is captured between the second wedge surface 242 and the actuator shaft 54.

Referring again to FIGS. 19A and 19B, as the first and second wedge members 48 and 50 move in the expansion direction, the first and second wedge members 48 and 50 can urge at least one or both of the first and second endplates 44 and 46 to move away from the other of the first and second endplates 44 and 46. The first and second wedge members 48 and 50 can move in the expansion direction until they abut the respective first and second stop members 198 and 200 while the first and second stop members 198 and 200 abut the first and second shoulders 202 and 206, respectively. Abutment between the first and second wedge members 48 and 50 and the first and second stop members 198 and 200, respectively, prevents subsequent movement of the first and second wedge members 48 and 50 in the direction of expansion. Thus, the actuator shaft 54 is prevented from rotating in the first direction in response to a torsional force applied to the actuator shaft 54 in the first direction. At this point, the intervertebral implant 20 can be said to be in the expanded configuration.

It should be appreciated that abutment between either one of the first and second stop members 198 and 200 and the associated one of the first and second wedge members 48 and 50 can prevent the one of the first and second stop members 198 and 200 from moving in the expansion direction. Further, because each of the first and second stop members 198 and 200 are threadedly coupled to the same actuator shaft, prevention of one of the first and second stop members 198 and 200 from moving in the expansion direction similarly prevents each of the first and second stop members 198 and 200 from moving in the expansion direction. Thus, the expansion limiter 129 can include at least one stop member, which can include one or both of the first and second stop members 198 and 200.

The first and second stop members 198 and 200 can abut the first and second shoulders 202 and 206, respectively, when the first and second wedge members 48 and 50 are in the collapsed position. For instance, the first and second stop members 198 and 200 can be attached to the actuator shaft 54 such that they abut the first and second shoulders 202 and 206, respectively. Thus, when the first and second wedge members 48 and 50 first abut the first and second stop members 198 and 200, respectively, when the first and second wedge members 48 and 50 are in the expansion position. Alternatively, the first and second stop members 198 and 200 can be spaced from the first and second shoulders 202 and 206, respectively, when the first and second wedge members 48 and 50 are in the collapsed position. For instance, the first and second stop members 198 and 200 can be attached to the actuator shaft 54 such that they are spaced from the first and second shoulders 202 and 206 along the collapse direction. Thus, as the first and second wedge members 48 and 50 move in the expansion direction, the first and second wedge members 48 and 50 can abut the first and second stop members 198 and 200, respectively, and urge the first and second stop members 198 and 200 to move in the expansion direction until they abut the first and second shoulders 202 and 206, respectively.

While the first stop member 198 can be attachable to the actuator shaft 54 in one example, the first stop member 198 can alternatively be monolithic with the actuator shaft 54 in another example. Similarly, while the second stop member 200 can be attachable to the actuator shaft 54 in one example, the second stop member 200 can alternatively be monolithic with the actuator shaft 54 in another example. If the first and second stop members 198 and 200 are monolithic with the actuator shaft, then abutment between the first and second wedge members 48 and 50 with the first and second stop members 198 and 200 can prevent further movement of the first and second wedge members 48 and 50 in the expansion direction regardless of whether the first and second stop members 198 and 200 abut the shoulders 202 and 206, respectively. Alternatively still, the first and second stop members 198 and 200 can be attached to the actuator shaft 54 such that the first and second stop members 198 and 200 fixed with respect to movement along the actuator shaft 54 in the expansion direction. Thus, abutment between the first and second wedge members 48 and 50 with the first and second stop members 198 and 200 can prevent further movement of the first and second wedge members 48 and 50 in the expansion direction regardless of whether the first and second stop members 198 and 200 abut the shoulders 202 and 206, respectively.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. An expandable implant configured to be inserted in an intervertebral space defined between a first vertebral body and a second vertebral body, the implant comprising:
   a first endplate defining an upper bone contacting surface, the first endplate having a first guide member;
   a second endplate defining a second bone contacting surface opposite the first bone contacting surface along a transverse direction, the second endplate having a second guide member;
   an insertion end and a trailing end opposite the insertion end along a longitudinal direction that is perpendicular to the transverse direction;
   at least one expansion member that defines a ramped engagement surface configured to bear against an engagement surface of one of the first and second endplates as the at least one expansion member moves in an expansion direction with respect to the first and second endplates, thereby moving the expandable implant from a collapsed configuration to an expanded configuration,
   wherein the expandable implant defines a first height from the first bone contacting surface to the second bone contacting surface in the collapsed configuration, the expandable implant defines a second height from the first bone contacting surface to the second bone contacting surface in the collapsed configuration, and the second height is greater than the first height,
   wherein the expansion member defines a first guide member and a second guide member configured to engage the first guide member of the first endplate and the second guide member of the second endplate, respectively, so as to guide movement of the first and second endplates away from each other as the expansion member moves in the expansion direction, and
   wherein the first guide member of the expansion member defines first and second outer projections, and the second guide member of the expansion member defines first and second inner projections, and the inner projections are inwardly recessed with respect to the outer projections along a lateral direction that is oriented perpendicular to each of the expansion direction and the transverse direction.

2. The expandable implant as recited in claim 1, wherein the first guide member of the first endplate comprises channels sized to slidably receive the first and second outer projections, respectively of the expansion member, and the second guide member of the second endplate comprises respective channels sized to slidably receive the first and second inner projections, respectively, of the expansion member.

3. The expandable implant as recited in claim 2, wherein the first endplate is an upper endplate, the second endplate is a endplate, the first and second outer projections engage the first guide member of the upper endplate, and the first and second inner projections engage the second guide member of the endplate.

4. The expandable implant as recited in claim 3, wherein the channels of the upper endplate are outer channels, and the channels of the lower endplate are inner channels that are inwardly recessed with respect to the outer channels along the lateral direction.

5. The expandable implant as recited in claim 3, wherein the expansion member is movable in a collapse direction that causes the implant to move from the expanded configuration to the collapsed configuration, and the guide members of the expansion member apply a force to the guide members of the upper and lower endplates that draw the and lower endplates toward each other as the expansion member moves in the collapse direction.

6. The expandable implant as recited in claim 5, further comprising actuator that drives the expansion member to move selectively in the collapse direction and the expansion direction.

7. The expandable implant as recited in claim 6, wherein the actuator comprises a threaded actuator shaft, and the expansion member is threadedly mated to the actuator shaft, such that rotation of the actuator shaft in a first direction of rotation causes the expansion member to move in the expansion direction, and rotation of the actuator shaft in a second direction of rotation opposite the first direction of rotation causes the expansion member to move in the collapse direction.

8. The expandable implant as recited in claim 7, wherein the expansion member comprises first and second expansion members that move toward each other in the expansion direction, and away from each other in the collapse direction.

9. The expandable implant as recited in claim 7, further comprising an expansion limiter that prevents rotation of the actuator shaft in the first direction of rotation when the implant has moved to the expanded configuration.

10. An implant assembly comprising:
the expandable implant as recited in claim 7; and
an instrument configured to attach to the implant and drive the actuator shaft to rotate selectively in the first and second directions of rotation.

11. The implant assembly as recited in claim 10, wherein the instrument comprises at least one pin configured to be received in an aperture of the actuator, and a drive shaft configured to drive the actuator shaft to rotate.

12. The implant assembly as recited in claim 11, wherein the instrument comprises a pilot pin and a second pin that are each configured to be attached to the expansion member.

13. The implant assembly as recited in claim 12, wherein the pilot pin is unthreaded and configured to be inserted into one of a first attachment aperture of the expansion member and a second attachment aperture of the expansion member, and the second pin is configured to be inserted into the other of the first and second attachment apertures.

14. The implant assembly as recited in claim 13, wherein the drive shaft is configured to be driven into a bore of the expansion member so as to rotatably couple to the actuator shaft.

15. The implant assembly as recited in claim 14, wherein the instrument further comprises a toggle shaft that supports the drive shaft and is movable from a first position whereby the drive shaft is aligned with the second pin, and a second position whereby the drive shaft is aligned with the actuator shaft.

16. The implant assembly as recited in claim 15, wherein the toggle shaft is rotatable between the first position and the second position.

17. The implant assembly as recited in claim 16, further comprising at least one locating finger that is movable into a detent under a spring force when the toggle shaft is in either of the first and second positions, and is movable out of the detent when the toggle shaft has rotated to a position between the first and second positions.

18. The implant assembly as recited in claim 17, wherein the instrument defines respective channels that selectively receive the drive shaft when the drive shaft is rotatably coupled to the second pin and the actuator shaft, and interference between the drive shaft and the instrument in the channels prevents the toggle shaft from rotating.

* * * * *